US009701943B2

(12) United States Patent
Nauclér

(10) Patent No.: US 9,701,943 B2
(45) Date of Patent: Jul. 11, 2017

(54) GENETIC VARIANT OF CYTOMEGALOVIRUS (CMV)

(76) Inventor: Cecilia Nauclér, Bromma (SE)

( * ) Notice: Subject to any disclaimer, the term of this patent is extended or adjusted under 35 U.S.C. 154(b) by 0 days.

(21) Appl. No.: 14/111,247

(22) PCT Filed: Apr. 13, 2012

(86) PCT No.: PCT/SE2012/050407

§ 371 (c)(1), (2), (4) Date: Feb. 18, 2014

(87) PCT Pub. No.: WO2012/141653

PCT Pub. Date: Oct. 18, 2012

(65) Prior Publication Data

US 2014/0178968 A1 Jun. 26, 2014

Related U.S. Application Data

(60) Provisional application No. 61/475,926, filed on Apr. 15, 2011.

(51) Int. Cl.

| | |
|---|---|
| ***C12N 7/00*** | (2006.01) |
| ***C12Q 1/70*** | (2006.01) |
| ***C07K 14/005*** | (2006.01) |
| ***G01N 33/50*** | (2006.01) |
| ***G01N 33/574*** | (2006.01) |
| ***G01N 33/569*** | (2006.01) |

(52) U.S. Cl.

CPC .............. *C12N 7/00* (2013.01); *C07K 14/005* (2013.01); *C12Q 1/701* (2013.01); *G01N 33/5091* (2013.01); *G01N 33/56994* (2013.01); *G01N 33/57407* (2013.01); *C12N 2710/16121* (2013.01); *C12N 2710/16122* (2013.01); *C12N 2800/24* (2013.01); *G01N 2333/045* (2013.01); *G01N 2800/50* (2013.01)

(58) Field of Classification Search

CPC .... A61K 39/0011; A61K 38/00; A61K 39/12; A61K 2039/585; A61K 39/245; C07K 14/005; C12N 7/00; C12N 15/86; C12N 15/1131; C12N 2710/161133

See application file for complete search history.

(56) References Cited

U.S. PATENT DOCUMENTS

| | | | |
|---|---|---|---|
| 6,194,542 B1 | 2/2001 | Kondo et al. | |
| 2005/0064394 A1* | 3/2005 | Liu et al. | 435/5 |
| 2008/0138354 A1 | 6/2008 | Zaia et al. | |
| 2010/0150968 A1* | 6/2010 | Spies et al. | 424/257.1 |
| 2013/0136768 A1* | 5/2013 | Picker et al. | 424/199.1 |
| 2014/0363469 A1* | 12/2014 | Meyers et al. | 424/231.1 |

FOREIGN PATENT DOCUMENTS

| | | |
|---|---|---|
| WO | WO 97/45437 A1 | 12/1997 |
| WO | WO 2007/038316 | 4/2007 |
| WO | WO 2007/041240 A2 | 4/2007 |
| WO | WO 2009/155535 | 12/2009 |
| WO | WO 2010/014567 | 2/2010 |
| WO | WO 2011143650 A2 * | 11/2011 |

OTHER PUBLICATIONS

Cosme RS, Yamamura Y, Tang Q. Roles of polypyrimidine tract binding proteins in major immediate-early gene expression and viral replication of human cytomegalovirus. J Virol. Apr. 2009;83(7):2839-50. doi: 10.1128/JVI.02407-08. Epub Jan. 14, 2009.*

Davison AJ. Human herpesvirus 5 strain Merlin, complete genome. GenBank Dep. No: AY446894.1. Dep. Dec. 21, 2003.*

Du G, Dutta N, Lashmit P, Stinski MF. Alternative splicing of the human cytomegalovirus major immediate-early genes affects infectious-virus replicationand control of cellular cyclin-dependent kinase. J Virol. Jan. 2011;85(2):804-17. Epub Nov. 10, 2010.*

Scholz M, Doerr HW, Cinatl J. Inhibition of cytomegalovirus immediate early gene expression: a therapeutic option? Antiviral Res. Mar. 2001;49(3):129-45.*

Human herpesvirus 5 strain Merlin, complete genome. Revision History. GenBank: AY446894.2. Latest revision Jul. 2, 2013.*

Dargan DJ, Douglas E, Cunningham C, Jamieson F, Stanton RJ, Baluchova K, McSharry BP, Tomasec P, Emery VC, Percivalle E, Sarasini A, Gerna G, Wilkinson GW, Davison AJ. Sequential mutations associated with adaptation of human cytomegalovirus to growth in cell culture. J Gen Virol. Jun. 2010;91(Pt 6):1535-46.*

Bradley AJ, Lurain NS, Ghazal P, Trivedi U, Cunningham C, Baluchova K, Gatherer D, Wilkinson GW, Dargan DJ, Davison AJ. High-throughput sequence analysis of variants of human cytomegalovirus strains Towne and AD169. J Gen Virol. Oct. 2009;90(Pt 10):2375-80. doi: 10.1099/vir.0.013250-0. Epub Jun. 24, 2009.*

Awasthi S, Isler JA, Alwine JC. Analysis of splice variants of the immediate-early 1 region of human cytomegalovirus. J Virol. Aug. 2004;78(15):8191-200.*

Puchhammer-Stöckl E and Gorzer I. Human Cytomegalovirus: An Enormous Variety of Strains and Their Possible Clinical Significance in the Human Host. Mar. 11, 2011. Future Virology 6(2):259-271.*

(Continued)

*Primary Examiner* — Rachel B Gill
(74) *Attorney, Agent, or Firm* — Foley & Lardner LLP

(57) ABSTRACT

The present invention relates to a genetic variant of CMV, said genetic variant lacking intron 2 of the IE region of CMV (CMV IEΔi2) The present invention also relates to various uses of this genetic variant as well as RNA splice variants transcribed therefrom, and proteins expressed from the RNA splice variants, such as in the diagnosis of a CMV related cancer disease, and identification of individuals at risk of developing cancer or risk of transferring the CMV IEΔi2 virus with a human sample and prevention and treatment through targeting of unique CMV IE proteins for immunotherapy and vaccination.

18 Claims, 20 Drawing Sheets

(56) References Cited

OTHER PUBLICATIONS

Munro SC, Hall B, Whybin LR, Leader L, Robertson P, Maine GT, Rawlinson WD. Diagnosis of and screening for cytomegalovirus infection in pregnant women. J Clin Microbiol. Sep. 2005;43(9):4713-8.*

Söderberg-Nauclér C. Does cytomegalovirus play a causative role in the development of various inflammatory diseases and cancer? J Intern Med. Mar. 2006;259(3):219-46.*

International Search Report and Written Opinion in International Application No. PCT/SE2012/050407, dated Aug. 2, 2012, 8 pages.

International Preliminary Report on Patentability in International Application No. PCT/SE2012/050407, dated Oct. 15, 2013, 5 pages.

Awasthi et al., "Analysis of splice variants of the immediate-early 1 region of human cytomegalovirus," J Virol., Aug. 2004, 78(15):8191-200.

Baryawno et al. "Detection of human cytomegalovirus in medulloblastomas reveals a potential therapeutic target," J Clin Invest., Oct. 3, 2011, 121(10):4043-55.

Bongers et al., "The cytomegalovirus-encoded chemokine receptor US28 promotes intestinal neoplasia in transgenic mice," J Clin Invest., Nov. 1, 2010, 120(11):3969-78.

Cinatl et al., "Molecular mechanisms of the modulatory effects of HCMV infection in tumor cell biology," Trends Mol Med., Jan. 2004, 10(1):19-23.

Cinatl et al., "Persistent human cytomegalovirus infection induces drug resistance and alteration of programmed cell death in human neuroblastoma cells," Cancer Res, Jan. 15, 1998, 58(2):367-72.

Cobbs et al., "Human cytomegalovirus infection and expression in human malignant glioma," Cancer Res., Jun. 15, 2002, 62(12):3347-50.

Dziurzynski et al., "Glioma-associated cytomegalovirus mediates subversion of the monocyte lineage to a tumor propagating phenotype," Clin Cancer Res., Jul. 15, 2011, 17(14):4642-9.

Geder and Rapp, "Evidence for nuclear antigens in cytomegalovirustransformed human cells," Nature, Jan. 13, 1977, 265(5590):184-6.

Hooks et al., "Human cytomegalovirus induced cyclooxygenase-2 in human retinal pigment epithelial cells augments viral replication through a prostaglandin pathway," Microbes Infect., Jul. 2006, 8(8):2236-44.

Johnsen et al., "Is human cytomegalovirus a target in cancer therapy?" Oncotarget, Dec. 2011, 2(12):1329-38.

Mangiapan et al., "Sequence capture-PCR improves detection of mycobacterial DNA in clinical Specimens," J Clin Microbiol., May 1996, 34(5):1209-15.

Maussang et al., "Human cytomegalovirus-encoded chemokine receptor US28 promotes tumorigenesis," Proc Natl Acad Sci USA, Aug. 29, 2006, 103(35):13068-73.

Maussang et al., "The human cytomegalovirus-encoded chemokine receptor US28 promotes angiogenesis and tumor formation via cyclooxygenase-2," Cancer Res., Apr. 1, 2009, 69(7):2861-28699.

Michaelis et al., "The story of human cytomegalovirus and cancer: increasing evidence and open questions," Neoplasia, Jan. 2009, 11(1):1-9.

Mitchell et al., "Sensitive detection of human cytomegalovirus in tumors and peripheral blood of patients diagnosed with glioblastoma," Neuro Oncol., 2008, 10:10-18.

Murphy et al., "Coding potential of laboratory and clinical strains of human cytomegalovirus," Proc Natl Acad Sci USA, Dec. 9, 2003, 100(25):14976-81.

Powers et al., "Cytomegalovirus immune evasion," Curr Top Microbiol Immunol 2008, 325:333-59.

Qiu et al., "Human CMV infection induces 5-lipoxygenase expression and leukotriene B4 production in vascular smooth muscle cells," J Exp Med., Jan. 2008, 205(1):19-24.

Rahbar et al. "Low levels of Human Cytomegalovirus Infection in Glioblastoma Multiforme associates with patient survival;—a case-control study," Herpesviridae, Mar. 16, 2012, 3(1):3, 7 pages.

Ranganathan et al., "Significant Association of Multiple Human Cytomegalovirus Genomic Loci with Glioblastoma Multiforme Samples," J Viral., Nov. 16, 2011, 86(2):854864.

Slinger et al., "HCMV-encoded chemokine receptor US28 mediates proliferative signaling through the IL-6-STAT3 axis," Sci Signal, Aug. 3, 2010, 3(133):ra58.

Soderberg et al., "Definition of a subset of human peripheral blood mononuclear cells that are permissive to human cytomegalovirus infection," J Virol., 1993, 67(6):3166-75.

Soderberg-Naucler et al., "Interferon-γ and tumor necrosis factor-α specifically induce formation of cytomegalovirus-permissive monocyte-derived macrophages that are refractory to the antiviral activity of these cytokines," J Clin Invest., Dec. 15, 1997, 100(12):3154-63.

Soderberg-Naucler et al., "Reactivation of latent human cytomegalovirus by allogeneic stimulation of blood cells from healthy donors," Cell, Oct. 3, 1997, 91:119-26.

Soderberg-Naucler, "Does cytomegalovirus play a causative role in the development of various inflammatory diseases and cancer?" J Intern Med., Mar. 2006, 259(3):219-46.

Soderberg-Naucler, "Human cytomegalovirus persists in its host and attacks and avoids elimination by the immune system," Crit Rev Immunol. 2006, 26(3):231-64.

Soroceanu and Cobbs, "Is HCMV a tumor promoter?" Virus Res., May 2011; 157(2):193-203.

Speir et al., "Aspirin attenuates cytomegalovirus infectivity and gene expression mediated by cyclooxygenase-2 in coronary artery smooth muscle cells," Circ Res., Jul. 27, 1998, 83(2):210-6.

Straat et al., "Activation of telomerase by human cytomegalovirus," J Natl Cancer Inst., Apr. 1, 2009, 101 (7):488-97.

Wolmer-Solberg et al., "Frequent detection of human cytomegalovirus in neuroblastoma: a novel therapeutic target?" Int. J. Cancer, Nov. 15, 2013, 133(10):2351-61.

Zhu et al , "Inhibition of cyclooxygenase 2 blocks human cytomegalovirus replication," Proc Natl Acad Sci USA, Mar. 19, 2002, 99(6):3932-7.

Davison, "The human cytomegalovirus genome revisited: comparison with the chimpanzee cytomegalovirus genome," J Gen Virol., Jan. 1, 2003, 84(Pt 1):17-28.

Paulus and Nevels, "The human cytomegalovirus major immediate-early proteins as antagonists of intrinsic and innate antiviral host responses," Viruses, Nov. 5, 2009, 1(3):760-779.

Stenberg et al., "Regulated expression of early and late RNAs and proteins from the human cytomegalovirus immediate-early gene region," J. Viral., Jan. 1, 1989, 63(6):2699-2708.

Zipeto et al., "Identification of human cytomegalovirus strain with immediate-early (IE) antigen-specific monoclonal antibody is prevented by point mutation in IE gene," J Clin Microbiol., May 1, 1994, 32(5):1402-1405.

Paulos et al., "The Human Cytomegalovirus Major Immediate-Early Proteins as Antogonists of Intrinsic and Innate Antivial Host Responses," Viruses, vol. 1, pp. 760-779, Nov. 2009.

Gibson, "Protein Counterparts of Human and Simiam Cytomegaloviruses," Virology, vol. 128, pp. 391-406, 1983.

* cited by examiner

```
MIE-refergen     1 agacttaccgagttctgtcaggacatcttttcggggttct-cgttgcaatcctcggtcacttgttcaaaggttttgagggattcttcgg
exon2-3ref.t     1 --------cgagttctgtcaggacatcttttcggggttct-cgttgcaatcctcggtcacttgttcaaaggttttgagggattcttcgg
CMV-MIE-I-3o     1 ---------gagttctgccaggacatcttt-----------------------------------------------------------
CMV-MIE-I-5o    20 -----------------------------------------------------------------------------------------
CMV-MIE-II-3     1 -----------------------------ctcggggttct-cgttgcaat---------------------------------------
CMV-MIE-II-5    22 -----------------------------------------------------------------------------------------
breastCA         1 ------------------------------ctcgggttgt-ggttgcaatcctcggtcactcgttcaaaagttttgagggattcttcgg
colonCA          1 -----------------------------ctcggggttgt-cgttgcaatcctcggtcactcgttcaaaagttttgagggattcttcgg
Glioblastoma     1 -----------------------------ctcggggttct-cgttgcaatcctcggtcactcgttcaaaagttttgagggattcttcgg
Neuroblastom     1 ------------------------------ctcgggttgt-cgttgcaatcctcggtcactcgttcaaaagttttgagggattcttcgg
OvarianCA        1 -----------------------------ctcggggttgt-cgttgcaatcctcggtcactcgttcaaaagttttgagggattcttcgg
MedullaCA        1 -----------------------------ctcggggttgt-cgttgcaatcctcggtcactcgttcaaaagttttgagggattcttcgg
CMVmononucle     1 -----------------------------ctcggggttttgcgttgcaatcctcggtcacttgttcaaaggttttgagagattcttcgg
healthy          1 -----------------------------ctcggggttct-cgttgcaatcctcggtcacttgttcaaaggttttgagagattcttcgg

MIE-refergen    90 ccaattctgggaacagcgggtctcccaggctcagctgactgttaacctccttccttaacatagtctgcaggaacgtcgtggc-c-ttggt
exon2-3ref.t    82 ccaattctgggaacagcgggtctcccaggctcagctgactgttaacctccttccttaacatagtctgcaggaacgtcgtggc-c-ttggt
CMV-MIE-I-3o    22 ------------------------------------------------------------------------------------------
CMV-MIE-I-5o    20 ------------------------------------------------------------------------------------------
CMV-MIE-II-3    21 ------------------------------------------------------------------------------------------
CMV-MIE-II-5    22 ------------------------------------------------------------------------------------------
breastCA        59 ccaactctggaaacagcgggtctcccagactcagctgactgttaacctccttcctcaacatagtctgcaggaacgtcgtggc-ccttggt
colonCA         60 ccaactctggaaacagcgggtctcccagactcagctgactgttaacctccttcctcaacatagtctgcaggaacgtcgtggc-c-ttggt
Glioblastoma    60 ccaactctggaaacagcgggtctcccagactcagctgactgttaacctccttcctcaacatagtctgcaggaacgtcgtggctc-ttggt
Neuroblastom    59 ccaactctggaaacagcgggtctcccagactcagctgactgttaacctccttcctcaacatagtctgcaggaacgtcgtggc-c-ttggt
OvarianCA       60 ccaactctggaaacagcgggtctcccagactcagctgactgttaacctccttcctcaacatagtctgcaggaacgtcgtggc-c-ttggt
MedullaCA       60 ccaactctggaaacagcgggtctcccagactcagctgactgttaacctccttcctcaacatagtctgcaggaacgtcgtggc-c-ttggt
CMVmononucle    61 ccaattctgggaacagcgggtctcccaggctcagctgactgttaacctccttccttaacatagtctgcaggaacgtcgtggc-c-ttggt
healthy         60 ccaattctgggaacagcgggtctcccaggttcagctgactgttaacctccttccttaacatagtctgcaagaacgtcgtggc-c-ttgga

MIE-refergen   178 cacgggtgtctcgggcctaaacacatgataaacaaagtcataagcacatggatcacatacaggaaatatgtatataacattaaagatata
exon2-3ref.t   170 cacgggtgtctcggg---------------------------------------------------------------------------
CMV-MIE-I-3o    22 ------------------------------------------------------------------------------------------
CMV-MIE-I-5o    20 ------------------------------------------------------------------------------------------
CMV-MIE-II-3    21 ------------------------------------------------------------------------------------------
CMV-MIE-II-5    22 ------------------------------------------------------------------------------------------
breastCA       148 cacgggtgtctcggg---------------------------------------------------------------------------
colonCA        148 cacgggtgtctcggg---------------------------------------------------------------------------
Glioblastoma   149 cacgggtgtctcggg---------------------------------------------------------------------------
Neuroblastom   147 cacgggtgtctcggg---------------------------------------------------------------------------
OvarianCA      148 cacgggtgtctcggg---------------------------------------------------------------------------
MedullaCA      148 cacgggtgtctcggg---------------------------------------------------------------------------
```

```
CMVmonocucle   149 cacgggtgtctcggg
healthy        148 cacgggtgtctcggg
```

Figure. 9

Positive Control

Viral stock

Infected fibroblast

VR
TB40
AD169
NTC
VR
TB40
AD169
NTC
C1
C2 bp
600
500
400
300
200

※Areas of significant similarity (in windows 20 bases in length)

MIE-exon2-exon4
IE1cds.txt
IE-9cds.txt
IE17.5-cds.txt
IE-19cds.txt
GBM48-5
GBM48-6
GBM48-7

B)

```
MIE-exon2-ex     1 ttactggtcagccttgcttctagtcaccatagggtgggtgctcttgcctccagaggcggtgggttcctcagcaccatcctcctcttcctc
IE1cds.txt    1476 ttactggtcagccttgcttctagtcaccatagggtgggtgctcttgcctccagaggcggtgggttcctcagcaccatcctcctcttcctc
IE-9cds.txt    249 ------------------------------------------------------------------------------------------
IE17.5-cds.t   483 ttactggtcagccttgcttctagtcaccatagggtgggtgctcttgcctccagaggcggtgggttcctcagcaccatcctcctcttcctc
IE-19cds.txt   519 ttactggtcagccttgcttctagtcaccatagggtgggtgctcttgcctccagaggcggtgggttcctcagcaccatcctcctcttcctc
GBM48-5          1 -------------------------------------------------------gcggtgggttcctcagcaccatcctcctcttcctc
GBM48-6          1 ------------------------------------------------------------------------------------------
GBM48-7          1 ------------------------------------------------------------------------------------------

MIE-exon2-ex    91 tgaggcaacttcctctatctcagacactggctcagacttgacagacacagtgtcctcccgctcctcctgagcaccctcctcctgttcctc
IE1cds.txt    1386 tgaggcaacttcctctatctcagacactggctcagacttgacagacacagtgtcctcccgctcctcctgagcaccctcctcctgttcctc
IE-9cds.txt    249 ------------------------------------------------------------------------------------------
IE17.5-cds.t   393 tggggcaacttcctctatctcagacactggctcagacttgacagacacagtgtcctcccgctcctcctgagcaccctcctcctcttcctc
IE-19cds.txt   429 tggggcaacttcctctatctcagacactggctcagacttgacagacacagtgtcctcccgctcctcctgagcaccctcctcctcttcctc
GBM48-5         36 tggggcaacttcctctatctcagacactggctcagacttgacagacacagtgtcctcccgctcctcctgagcaccctcctcctcttcctc
GBM48-6          1 ------------------------------------------------------------------------------------------
GBM48-7          1 ------------------------------------------------------------------------------------------

MIE-exon2-ex   181 atcactctgttcactttcttcctgatcactgttctcagccacaattactgaggacagagggatagtcgcgggtacaggggactctggagg
IE1cds.txt    1296 atcactctgttcactttcttcctgatcactgttctcagccacaattactgaggacagagggatagtcgcgggtacaggggactctggagg
IE-9cds.txt    249 ----------------------------------tcagccaca-----------------------------------------------
IE17.5-cds.t   303 atcactctgctcactttcttcctgatcactgttctcagccacaatta-------------------------------------------
IE-19cds.txt   339 atcactctgctcactttcttcctgatcactgttctcagccacaattactgaggacagagggatagtcgcgggtacaggggact-------
GBM48-5        126 atcactctgctcactttcttcctgatcactgttctcagccacaattactgaggacagagggatagtcgcgggtacaggggactctggggg
GBM48-6          1 ------------------------------------------------------------------------------------------
GBM48-7          1 ------------------------------------------------------------------------------------------
```

Figure. 15.
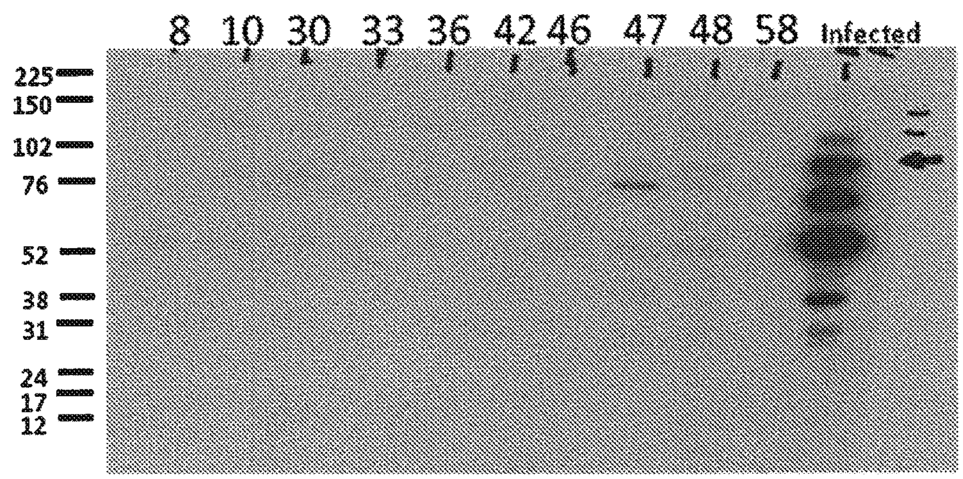
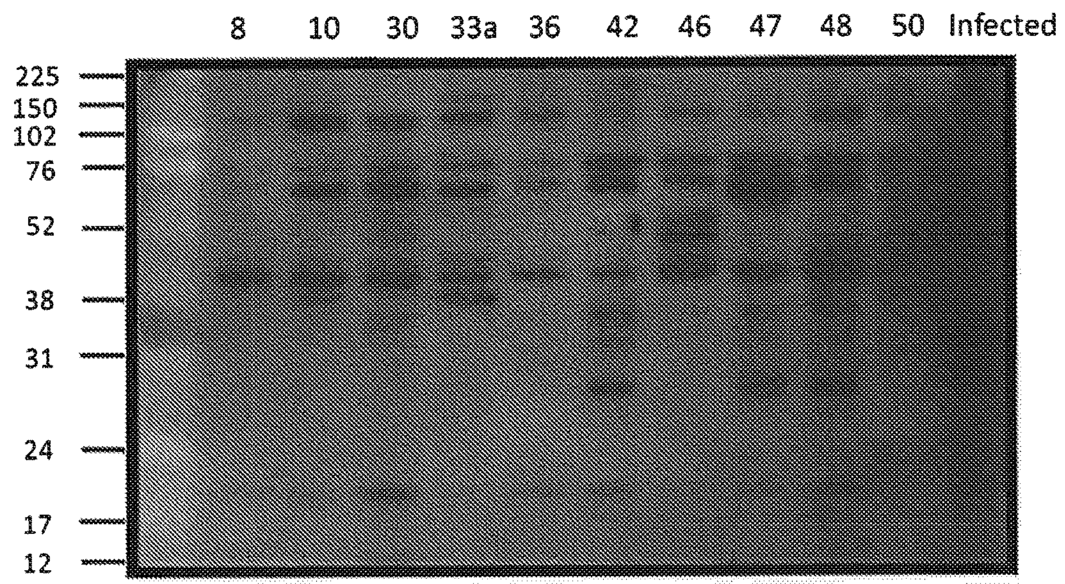

Figure. 17.
A)
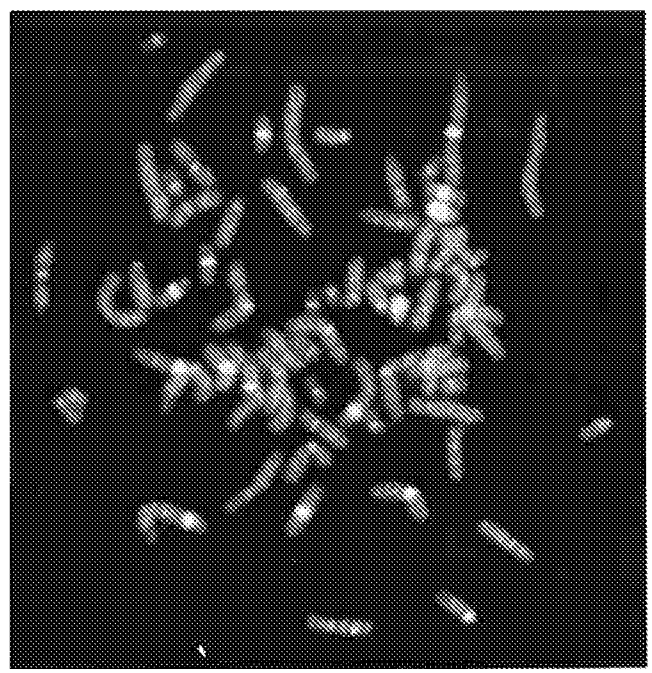
B)
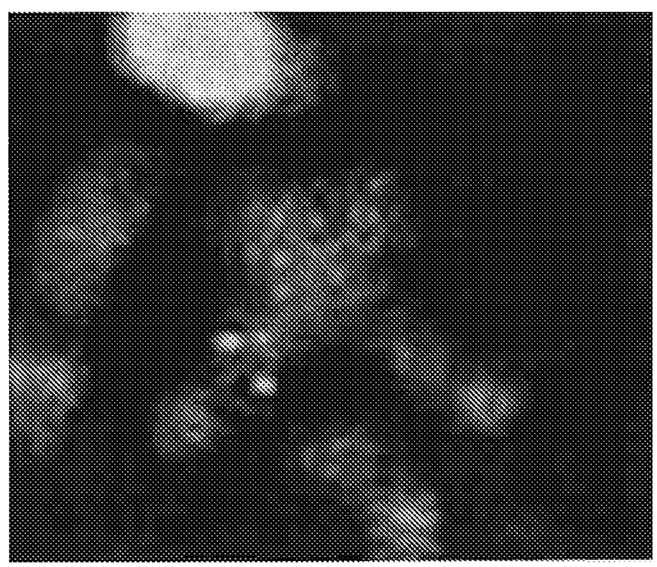

```
                          Exon 2                              Exon 3
IE19     MESSAKRKMDPDNPDEGPSSKVPRPETPVTKATTFLQTMLRKEVNSQLSLGDPLFPELAE
IE17.5   MESSAKRKMDPDNPDEGPSSKVPRPETPVTKATTFLQTMLRKEVNSQLSLGDPLFPELAE
IE9      MESSAKRKMDPDNPDEGPSSKVPRPETPVTKATTFLQTMLRKEVNSQLSLGDPLFPELAE

                                                    Exon 4
IE19     ESLKTFERVTEDCNENPEKDVLAEIESFVPATIPLSSVIVAENSDQEESEQSDEEEEEGA
IE17.5   ESLKTFERVTEDCNENPEKDVLAEI------------VIVAENSDQEESEQSDEEEEEGA
IE9      ESLKTFERVTEDCNENPEKD-----CG

IE19     QEEREDTVSVKSEPVSEIEEVAPEEEEDGAEEPTASGGKSTHPMVTRSKADQ
IE17.5   QEEREDTVSVKSEPVSEIEEVAPEEEEDGAEEPTASGGKSTHPMVTRSKADQ
```

B)

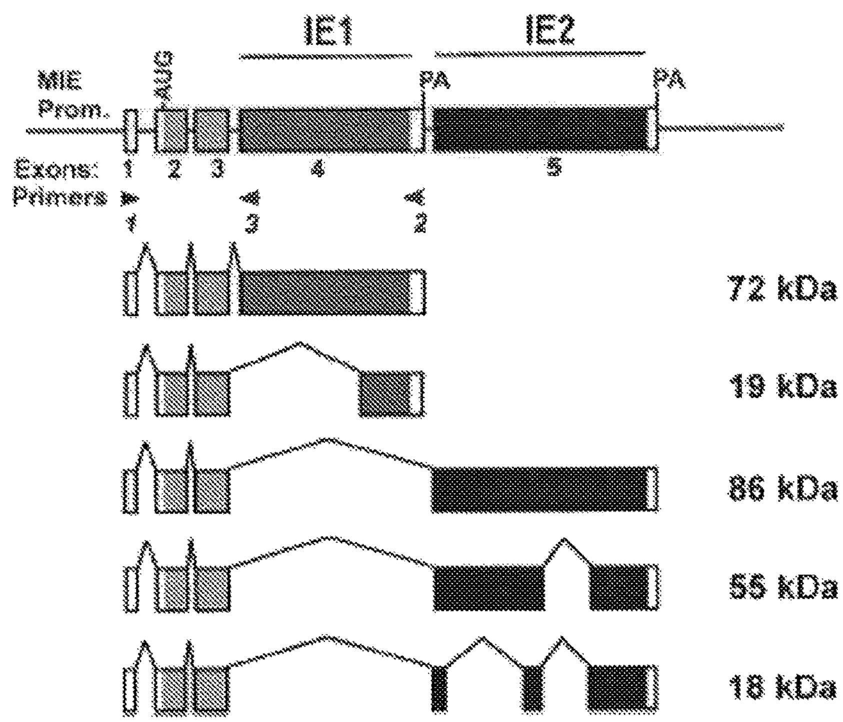

SEQUENCE LISTING

<160> NUMBER OF SEQ ID NOS: 41

<210> SEQ ID NO 1
<211> LENGTH: 251
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Deleted intron 2

<400> SEQUENCE: 1

```
gagttctgtc aggacatctt tttcggggtt ctcgttgcaa tcctcggtca cttgttcaaa     60

ggttttgagg gattcttcgg ccaattctgg gaacagcggg tctcccaggc tcagctgact    120

gttaacctcc ttccttaaca tagtctgcag gaacgtcgtg gccttggtca cgggtgtctc    180

gggcgtggca ccttggagga agggccctcg tcaggattat cagggtccat ctttctcttg    240

gcagaggact c                                                         251
```

<210> SEQ ID NO 2
<211> LENGTH: 298
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Tentative IE18

<400> SEQUENCE: 2

```
ctactggaat cgataccggc atgattgaca gcctgggcga ggatgtcgag ttctgtcagg     60

acatcttttt cggggttctc gttgcaatcc tcggtcactt gttcaaaggt tttgagggat    120

tcttcggcca attctgggaa cagcgggtct cccaggctca gctgactgtt aacctccttc    180

cttaacatag tctgcaggaa cgtcgtggcc ttggtcacgg gtgtctcggg cgtggcacct    240

tggaggaagg gccctcgtca ggattatcag ggtccatctt tctcttggca gaggactc      298
```

<210> SEQ ID NO 3
<211> LENGTH: 1269
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Tentative IE40

<400> SEQUENCE: 3

```
ttactgagat ttgttcctca ggtcctggat ggctgcctcg atggccaggc tcagggtgtc     60

caggtcttcg ggaggggtct cggtgggctt ctcaaactgc cccacggcgt aggccttcgc    120

ggccgtctcg tagataggca gcatgaaccc accctggttg gtggagaaga tgcgcaccat    180

gacctgtttg ggaaactttt gcatcagggg caggcacagg ttgagagcgc ccaacaggtc    240

cacgggggtg gcagcgtgga taatcatgtt gcggtaatca gaagagcggg ggcacaattg    300

gtgggtgtgc agttctttga ggttccacac ggccttgaca ccgtcgttac aagcatcggc    360

cgtgcgctgc gccacatcag gagggtgtgt cacaggcata gtgtgctcca tgaggaaggg    420

agtggagagg gccaggttgc acatgctacc caggcgacac cgtacctgat ccacctcatt    480

cttcacttca tgattgcggg tgtagatgat ctgaatgccc ttgttgttca cctgcatggt    540
```

```
tttgcaaact ttgatggcct cttctaacac ttggtgcata ctagggatca tgaatggcag    600

attcttgtac tcaagagaac gattggtgtg acggaacatg cggctcacct cgtcaatctt    660

gacgcgaccc cgccgagtct gcacgttggg tgtgcagaag ggggtgttct tatctttcat    720

gatattgcgc accttctcgt tgtccaactc ggagatgcgt ttgctcttct tcttgcgagg    780

tccggtgctc gccccgccgc tgctctgatg gccgcagctc agcagagagg aggaggccgc    840

gccaccaaaa ccgccgcgcc catggtggct cgaggtcacg gatgctcctc cgccactgct    900

gcatttcatc tcctcggact cactctccga gtccgaagcc gaactgcagg aggaggaaga    960

cgaagaggaa ctatcttcat cgggccggcc caaaggatcg ggaagaggag ggtggttcat   1020

ctgggagagc gggtgcgtgg gagaggtcac tcgcggcgtg ccgctgccgg tggaagggga   1080

agacgcggta gcaccgcggg tctcgacttc ttcaccctgt tcttcctcgc tatcagagat   1140

cacgatacag ccggcggtat cgataatctt gttgcggtac tggatggtaa agtcgggctc   1200

gggcttgatg tcttcctgtt tgatgagggg cagcatgata ggcgcgggag gcacgggcgg   1260

tttaataat                                                           1269
```

```
<210> SEQ ID NO 4
<211> LENGTH: 1591
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Tentative IE60

<400> SEQUENCE: 4

ttactgagat ttgttcctca ggtcctggat ggctgcctcg atggccaggc tcagggtgtc     60

caggtcttcg ggaggggtct cggtgggctt ctcaaactgc cccacggcgt aggccttcgc    120

ggccgtctcg tagataggca gcatgaaccc accctggttg gtggagaaga tgcgcaccat    180

gacctgtttg ggaaactttt gcatcagggg caggcacagg ttgagagcgc ccaacaggtc    240

cacgggggtg gcagcgtgga taatcatgtt gcggtaatca gaagagcggg ggcacaattg    300

gtgggtgtgc agttctttga ggttccacac ggccttgaca ccgtcgttac aagcatcggc    360

cgtgcgctgc gccacatcag gagggtgtgt cacaggcata gtgtgctcca tgaggaaggg    420

agtggagagg gccaggttgc acatgctacc caggcgacac cgtacctgat ccacctcatt    480

cttcacttca tgattgcggg tgtagatgat ctgaatgccc ttgttgttca cctgcatggt    540

tttgcaaact ttgatggcct cttctaacac ttggtgcata ctagggatca tgaatggcag    600

attcttgtac tcaagagaac gattggtgtg acggaacatg cggctcacct cgtcaatctt    660

gacgcgaccc cgccgagtct gcacgttggg tgtgcagaag ggggtgttct tatctttcat    720

gatattgcgc accttctcgt tgtccaactc ggagatgcgt ttgctcttct tcttgcgagg    780

tccggtgctc gccccgccgc tgctctgatg gccgcagctc agcagagagg aggaggccgc    840

gccaccaaaa ccgccgcgcc catggtggct cgaggtcacg gatgctcctc cgccactgct    900

gcatttcatc tcctcggact cactctccga gtccgaagcc gaactgcagg aggaggaaga    960

cgaagaggaa ctatcttcat cgggccggcc caaaggatcg ggaagaggag ggtggttcat   1020

ctgggagagc gggtgcgtgg gagaggtcac tcgcggcgtg ccgctgccgg tggaagggga   1080

agacgcggta gcaccgcggg tctcgacttc ttcaccctgt tcttcctcgc tatcagagat   1140

cacgatacag ccggcggtat cgataatctt gttgcggtac tggatggtaa agtcgggctc   1200
```

```
gggcttgatg tcttcctgtt tgatgagggg cagcatgata ggcgcgggag gcacgggcgg   1260

tttaataatc accttgaaag gacgcgtggt tttgcgcggt ttcttacgcg ggctgagctc   1320

gggagtagcg gatgccccgg ggagaggagt gttagtaacc gcgacgctgg tgggggtcgg   1380

cttgttaaga ggggcgctgc taacgctgca agagtgggtt gtcagcgtgg ggccggtgct   1440

actggaatcg ataccggcat gattgacagc ctgggcgagg atgtcacctg atggtgataa   1500

gaagacacgg gaacttagta cggtttcaca ggcgtgacac gtttattgag taggattaca   1560

gagtataaca tagagtataa tatagagtat a                                  1591


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

gagttctgcc aggacatctt t                                               21


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

gagtcctctg ccaagagaaa                                                 20


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

ctcggggttc tcgttgcaat                                                 20


<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

gagaaagatg gaccctgata at                                              22


<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

tgacgagggc ccttcct                                                    17
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ccttggtcac gggtgtct 18

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
aaggtgccac ggcccg 16

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gtgacccatg tgcttatgac tctat 25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ctcaacatag tctgcaggaa cgt 23

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ttggtcacgg gtgtctc 17

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gagaaagatg gaccctgata at 22

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

ctcggggttc tcgttgcaat                                                   20


<210> SEQ ID NO 17
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthesized intron 2 wildtype

<400> SEQUENCE: 17

ctaaacacat gataaacaaa gtcataagca catggatcac atacaggaaa tatgtatata       60

acattaaaga tataactttt tattaaaaaa aggggaacac aagtcccgac acgtac          116


<210> SEQ ID NO 18
<211> LENGTH: 51
<212> TYPE: DNA
<213> ORGANISM: Homo sapiens

<400> SEQUENCE: 18

gtggccttgg tcacgggtgt ctcggccgtg gcaccttgga ggaagggccc t                51


<210> SEQ ID NO 19
<211> LENGTH: 50
<212> TYPE: DNA
<213> ORGANISM: Homo sapiens

<400> SEQUENCE: 19

acgtcgtggc cttggacacg ggtgtctcgg cctaaacaca ttagaaatag                  50


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

tttttttttt tttttttttt                                                   20


<210> SEQ ID NO 21
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

agacttaccg agttctgtca ggacatcttt ttcggggttc tcgttgcaat cctcggtcac       60

ttgttcaaag gttttgaggg attcttcggc caattctggg aacagcgggt ctcccaggct      120

cagctgactg ttaacctcct tccttaacat agtctgcagg aacgtcgtgg ccttggtcac      180
```

```
gggtgtctcg ggcctaaaca catgataaac aaagtcataa gcacatggat cacatacagg    240

aaatatgtat ataacattaa agatata                                        267


<210> SEQ ID NO 22
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

cgagttctgt caggacatct tttcggggt tctcgttgca atcctcggtc acttgttcaa     60

aggttttgag ggattcttcg gccaattctg ggaacagcgg gtctcccagg ctcagctgac    120

tgttaacctc cttccttaac atagtctgca ggaacgtcgt ggccttggtc acgggtgtct    180

cggg                                                                 184


<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

gagttctgcc aggacatctt t                                               21


<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

ctcggggttc tcgttgcaat                                                 20


<210> SEQ ID NO 25
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

ctcgggttgt ggttgcaatc ctcggtcact cgttcaaaag ttttgaggga ttcttcggcc     60

aactctggaa acagcgggtc tcccagactc agctgactgt taacctcctt cctcaacata    120

gtctgcagga acgtcgtggc ccttggtcac gggtgtctcg gg                       162


<210> SEQ ID NO 26
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

ctcggggttg tcgttgcaat cctcggtcac tcgttcaaaa gttttgaggg attcttcggc     60
```

caactctgga aacagcgggt ctcccagact cagctgactg ttaacctcct tcctcaacat 120
agtctgcagg aacgtcgtgg ccttggtcac gggtgtctcg gg 162

<210> SEQ ID NO 27
<211> LENGTH: 163
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
ctcggggttc tcgttgcaat cctcggtcac tcgttcaaaa gttttgaggg attcttcggc 60
caactctgga aacagcgggt ctcccagact cagctgactg ttaacctcct tcctcaacat 120
agtctgcagg aacgtcgtgg ctcttggtca cgggtgtctc ggg 163

<210> SEQ ID NO 28
<211> LENGTH: 161
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
ctcgggttgt cgttgcaatc ctcggtcact cgttcaaaag ttttgaggga ttcttcggcc 60
aactctggaa acagcgggtc tcccagactc agctgactgt taacctcctt cctcaacata 120
gtctgcagga acgtcgtggc cttggtcacg ggtgtctcgg g 161

<210> SEQ ID NO 29
<211> LENGTH: 162
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
ctcggggttg tcgttgcaat cctcggtcac tcgttcaaaa gttttgaggg attcttcggc 60
caactctgga aacagcgggt ctcccagact cagctgactg ttaacctcct tcctcaacat 120
agtctgcagg aacgtcgtgg ccttggtcac gggtgtctcg gg 162

<210> SEQ ID NO 30
<211> LENGTH: 162
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
ctcggggttg tcgttgcaat cctcggtcac tcgttcaaaa gttttgaggg attcttcggc 60
caactctgga aacagcgggt ctcccagact cagctgactg ttaacctcct tcctcaacat 120
agtctgcagg aacgtcgtgg ccttggtcac gggtgtctcg gg 162

<210> SEQ ID NO 31
<211> LENGTH: 163
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
ctcggggttt tgcgttgcaa tcctcggtca cttgttcaaa ggttttgaga gattcttcgg     60

ccaattctgg gaacagcggg tctcccaggc tcagctgact gttaacctcc ttccttaaca    120

tagtctgcag gaacgtcgtg gccttggtca cgggtgtctc ggg                      163
```

<210> SEQ ID NO 32
<211> LENGTH: 162
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
ctcggggttc tcgttgcaat cctcggtcac ttgttcaaag gttttgagag attcttcggc     60

caattctggg aacagcgggt ctcccaggtt cagctgactg ttaacctcct tccttaacat    120

agtctgcaag aacgtcgtgg ccttggacac gggtgtctcg gg                       162
```

<210> SEQ ID NO 33
<211> LENGTH: 270
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
ttactggtca gccttgcttc tagtcaccat agggtgggtg ctcttgcctc cagaggcggt     60

gggttcctca gcaccatcct cctcttcctc tgaggcaact tcctctatct cagacactgg    120

ctcagacttg acagacacag tgtcctcccg ctcctcctga gcaccctcct cctgttcctc    180

atcactctgt tcactttctt cctgatcact gttctcagcc acaattactg aggacagagg    240

gatagtcgcg ggtacagggg actctggagg                                     270
```

<210> SEQ ID NO 34
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34

```
tcagccaca                                                              9
```

<210> SEQ ID NO 35
<211> LENGTH: 227
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
ttactggtca gccttgcttc tagtcaccat agggtgggtg ctcttgcctc cagaggcggt     60

gggttcctca gcaccatcct cctcttcctc tggggcaact tcctctatct cagacactgg    120

ctcagacttg acagacacag tgtcctcccg ctcctcctga gcaccctcct cctcttcctc    180

atcactctgc tcactttctt cctgatcact gttctcagcc acaatta                  227
```

<210> SEQ ID NO 36
<211> LENGTH: 263
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
ttactggtca gccttgcttc tagtcaccat agggtgggtg ctcttgcctc cagaggcggt     60

gggttcctca gcaccatcct cctcttcctc tggggcaact tcctctatct cagacactgg    120

ctcagacttg acagacacag tgtcctcccg ctcctcctga gcaccctcct cctcttcctc    180

atcactctgc tcactttctt cctgatcact gttctcagcc acaattactg aggacagagg    240

gatagtcgcg ggtacagggg act                                            263
```

<210> SEQ ID NO 37
<211> LENGTH: 215
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
gcggtgggtt cctcagcacc atcctcctct tcctctgggg caacttcctc tatctcagac     60

actggctcag acttgacaga cacagtgtcc tcccgctcct cctgagcacc ctcctcctct    120

tcctcatcac tctgctcact ttcttcctga tcactgttct cagccacaat tactgaggac    180

agagggatag tcgcgggtac aggggactct ggggg                               215
```

<210> SEQ ID NO 38
<211> LENGTH: 172
<212> TYPE: PRT
<213> ORGANISM: Human herpesvirus 5

<400> SEQUENCE: 38

```
Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Arg Val Thr Glu Asp Cys Asn Glu Asn Pro Glu Lys Asp
65                  70                  75                  80

Val Leu Ala Glu Leu Glu Ser Pro Val Pro Ala Thr Ile Pro Leu Ser
                85                  90                  95

Ser Val Ile Val Ala Glu Asn Ser Asp Gln Glu Glu Ser Glu Gln Ser
            100                 105                 110

Asp Glu Glu Glu Glu Glu Gly Ala Gln Glu Glu Arg Glu Asp Thr Val
        115                 120                 125

Ser Val Lys Ser Glu Pro Val Ser Glu Ile Glu Glu Val Ala Pro Glu
    130                 135                 140

Glu Glu Glu Asp Gly Ala Glu Glu Pro Thr Ala Ser Gly Gly Lys Ser
145                 150                 155                 160
```

```
Thr His Pro Met Val Thr Arg Ser Lys Ala Asp Gln
                165                 170


<210> SEQ ID NO 39
<211> LENGTH: 160
<212> TYPE: PRT
<213> ORGANISM: Human herpesvirus 5

<400> SEQUENCE: 39

Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Arg Val Thr Glu Asp Cys Asn Glu Asn Pro Glu Lys Asp
65                  70                  75                  80

Val Leu Ala Glu Leu Val Ile Val Ala Glu Asn Ser Asp Gln Glu Glu
                85                  90                  95

Ser Glu Gln Ser Asp Glu Glu Glu Glu Glu Gly Ala Gln Glu Glu Arg
            100                 105                 110

Glu Asp Thr Val Ser Val Lys Ser Glu Pro Val Ser Glu Ile Glu Glu
        115                 120                 125

Val Ala Pro Glu Glu Glu Glu Asp Gly Ala Glu Glu Pro Thr Ala Ser
    130                 135                 140

Gly Gly Lys Ser Thr His Pro Met Val Thr Arg Ser Lys Ala Asp Gln
145                 150                 155                 160


<210> SEQ ID NO 40
<211> LENGTH: 82
<212> TYPE: PRT
<213> ORGANISM: Human herpesvirus 5

<400> SEQUENCE: 40

Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Arg Val Thr Glu Asp Cys Asn Glu Asn Pro Glu Lys Asp
65                  70                  75                  80

Cys Gly


<210> SEQ ID NO 41
<211> LENGTH: 235646
<212> TYPE: DNA
<213> ORGANISM: Human herpesvirus 5

<400> SEQUENCE: 41

ccattccggg ccgtgtgctg ggtccccgag ggggcggggg gtgttttctg cggggggggtg     60

aaatttggag ttgcgtgtgt ggacggcgac ggcgactagt tgcgtgtgct gcggtgggta    120

cggcgacggc gaataaaagc gacgtgcggc gcgcacggcg aaaagcagac gcgcgtctgt    180
```

-continued

```
gtctgtttga gtccccaggg gacggcagcg cgggtccttg gggacacacg caaaacaacg    240
gccagacaag acgcgggcgc aagggaggag tcgcgggccc cggggcacac tgcacaaccc    300
gcgtcgagga cacacgcaga cacggcccgc caacacaccc cgacacaccc ctgacacacc    360
ccgccgacac acccggcaca cgcccgcgac acacccggcc aacacacccc gacacacccg    420
gcacacgccc gcgacacacc cggccaacac accccgacac acccggcaca cgcccgcgac    480
acacccgcgg cacaccctga cacacccgcc acacccggca cacacccacc ccgccgcgcc    540
cccgacacac cccgaccgcc gccggtgcgg gacagggcta agcgccttta tggcgccgca    600
agcgctccgc cgcttctgcg gcttgctgtc cacggcgctt tctgcgcgct gccggtgcgt    660
gtggctccac agcacttgtc gttccgccag tccgacactg gacagggctg agggagtgtt    720
gcgtgacata agtaagcgcg tcggcgtcct cagcgcgttt gcggcgtgct gtgtccggcg    780
ctttgtgcgc actgccgttg cgtggcgtcc cgcggtgttt tttttcgcgg accagcgccg    840
gggacggggt gttgcgggcg ctcgggggtt ggcggcgggt gtttctacgg tgtttgtgcg    900
gcgtttctac gcagcttttg cgcagcgctt cgcttttcgg ggcggcgacg gcgttgtttt    960
cgggcgtgct gggcgccggc gccggtaacg ggagttacgc tggggacagg gacgggggtt   1020
gcgccgggga cggggggtgt gcggggacgg ggggtgtgcg gggacggggg gtgtgcgggg   1080
acggggggtg tgcggggacg gggcgtcgcg ggatggcggg ctgttgcgtg ccggggacgg   1140
gggactcttg cggcggggac ggtggtgagg acggggacag gggcatttcg cggcggggac   1200
ggggagttgc gggatggcga gctgttgcgt ggcggggacg gggactcttt gcggcgggga   1260
cggggacggg ggcctttcgc ggcggacacg gggaacacag acggcacgca cacgcagctc   1320
gcctatttaa cctccaccca ctacaacaca cacatgccgc acaatcatgc cagccacaga   1380
cacaaacagc acccacacca cgccgcttca cccagaggac caacacacgt tacccttaca   1440
ccacagcacc acacaacctc atgtccaaac ttcggacaaa cacgccgaca aacaacaccg   1500
cacgcagatg gagctcgacg ccgcggacta cgctgcttgc gcacaggccc gccaacacct   1560
ctacggtcaa acacaacccc aactacacgc ataccccaac gccaacccac aggaaagcgc   1620
tcattttcgc acagagaatc aacatcaact cacaaatcta cttcacaaca taggcgaggg   1680
cgcagcgctc ggctaccccg tcccccgcgc ggaaatccgc cgcggcggtg gcgactgggc   1740
cgacagcgca agcgacttcg acgccgactg ctggtgcatg tggggacgct tcggaaccat   1800
gggccgccaa cctgtcgtca ccttactgtt ggcgcgccaa cgcgacggcc tcgctgactg   1860
gaacgtcgta cgctgccgcg gaacaggctt tcgcgcacac gattccgagg acggcgtctc   1920
tgtctggcgt cagcacctgg tttttttact cggaggccac ggccgccgtg tacagttaga   1980
acgaccatcc gcgggagaag cccaagctcg aggcctattg ccacgcatcc ggatcacccc   2040
catctccaca tctccacgcc caaaaccacc ccagcccacc acatccaccg catcgcaccc   2100
acatgctacg gctcggccag atcacacgct ctttcctgtc ccttctacac cctcagccac   2160
ggttcacaat ccccgaaact acgccgtcca acttcacgcc gaaacgaccc gcacatggcg   2220
ctgggcacga cgcggtgaac gtggcgcgtg gatgccggcc gagacattta cgtgtcccaa   2280
ggataaacgt ccctggtaga cggggtaggg agatctacca gcccagggat cgcgtctttc   2340
gccgccacgc tgcttcaccg atatccaata aacccatccc ctcgccacga cgtctccgcg   2400
tatctttgta gcctcaggaa tccgtcccca cgtccaccca tcccgagcac tccacacgct   2460
ataacagacc acgaacacgg caaaaaatgc atgcaaactt ctcatttatt gtgtctacta   2520
```

-continued

```
ctctgtgttg ctacagggag tgaagggggt gaaggcaaag aaaaaaaaaa ggaacaaaat   2580
aatagattag cagaaggaat aatccgtgcg accgagcttg tgcttctttt cttataagga   2640
ggcaaatata ctagggaaaa cataagaata ggaagaaacc gaggtttggg agaaaagctg   2700
agataaaata gcgcattttc catacagagg ttgttgtttt tgtggatcct aagaggtttc   2760
aagtgcgaat ctcaaagttc tcacgagaat attgtcttca agaatcgaca actgtggtcc   2820
aagatttttt tttggtcttt ttaggttctg cgagggacat cacgatggat cgttgcgatg   2880
aagtcacgcg tacgcctctg gtgtggcgcg gtgtcgtgac aggagagtgt gttttcagtg   2940
cagagctgtc ttgattccta tatccgagta tctgttttct cgtaaggacg gtaatcttct   3000
ttggtgtaag tacatctaaa agctgcaaac tatattttaa gggctgtctc taggtgtact   3060
ttgatgctgg agtttttcgc tgtgttgatg tgaataaatc tactactact attatatgca   3120
gaaagagtga ttatgccgag acaagattgc attggctgaa ctgtttcaaa aacgcctaca   3180
ctctacttat ccgtaaacct aaggtaatac tatgtgtaag ttgttttttt ttctttttgt   3240
agtaaaatgg tgatacgtgc aattaaaact gtattccatg tttccatcct ttcatttcaa   3300
ctttaaaggc ggctttgaga gcgaagaagt gcgaggataa aaatggatga ctccttcgtg   3360
tccagggagt cgactactgc aacgctgatt gattaaaaga tggtctccga tgatgatgtt   3420
gttattgatc gaatcatggt gcagaacggc gacggagagg agcgtgtccg ccgccgggaa   3480
ggtggtctct ttctctttc ttttttcaag aaatcttcca tgtgtttatc gtagtgatcg   3540
aaatcgactg atctcgggtt ctttttgttg gtttcttttc ggttaatcat gtattgtttt   3600
cttttttac agaaagatac ttttttcatg agcaattcct cgcccggcgc cggcatgccg   3660
aggtggggcc actgcgatca gcggcatgcc gacgccgacc cggggatctt ggattcaccg   3720
ttttctctct tctctctcta catacagacc gggtggcagg agcggtaagg aatcatcgtc   3780
gtctttcatt cttcgatgat tatggtaata ctaaatctta tctaggagca tatacatcta   3840
agattggagt actagtagtc gtttgtggtt tctatttttt ttttatattt atctatgaca   3900
gtttttctgt ttttcgtttt gataataata taataaaaac tcatggacgt gaaatctggc   3960
ttggttgtgg tgatttcatt ctcattattg ttgttttctt tccgtcttgc ggatgaagat   4020
gttgcgatgc ggttgttgtt ggtgttgcta tacaccgaga gagatgatct tttgttcttt   4080
ctggttcatt tcctatgatt gtttggctgc tgaccgacgc gtcaggatgt gcagggcatg   4140
cggggaatca ggaccggaca cgggataatt tcatctacct atacggagat cgcggtcctc   4200
gccatgagga tcgcgacagg cgcgtcgagg gggcaggaac acccttgcgg attgacattc   4260
ttggtggtat ttcgttgttg tcggtagttg ttgttgacga tgaggataaa taaaaatgac   4320
cttgtttttg ttctgtttc tcttgttggg aatcgtcgac tttgaattct tcgagttatc   4380
ggaaagctga ggtacccaaa tgtctgtagc ttttttcttt ttaccctctt gtttatcatc   4440
tgcgattcgt ggtaggtagg agagggaaat gataatccga gattaaggaa aggagaagat   4500
aaaaaataaa aaaaaaaata aaacagaagc cgaccggccg ccgacccgtt ccccaggacc   4560
agcctacgag gaacggataa cgcggtggcg acggcagcgg tggtggcgct gggggtggcg   4620
gtagtggtac tgctgatggt agtcgggacg gaggagagac gatgcataca tacacgcgtg   4680
catgctgcat gggtggatgg tccgaccggg agacgcggaa gagaaactca cataaaaagg   4740
tgacaaaaag agcggttgaa aaaagaaaac gagattcgac cagacagaag agaaggaccg   4800
gggcttggcg acccttccac gactgctgtt gtcatctcgg ctcctccgtc ttctcccggc   4860
cacgggcggc taagtcaccg ccgttctccc catccgtccg agcgccgacc gaccagccgg   4920
```

```
ccgattcgcc cgccggggct tctggagaac gccggagcag cagcgatctg ggaagccgc   4980

taaaccccctg cgtttttata tggtagctct gccgagcgcg ggctgacgcg ttgagtaagc   5040

ggaaagacgt gtgtgacgaa aaggggtccc atggtatttc acgtgacgat gaggagatgc   5100

ggtttggagc acatacggtt taaaaaaagg gagttgtcgt gacaagggct gagggacctc   5160

tgtctccatg tgtgtataaa aagcaaggca cgttcataat gtaaaaaaga acacgttgta   5220

aacaagctat tgctgtatca ttcggctgac tatgcttcat tcggactgat tttcttttcc   5280

taacggcgta acttaaagtg attaacgtat gatatttgtt ccccagagtt atactatagt   5340

catcatccta aaattcagat ataaatgaac acacgtcgta tgggattatt aagaaaccga   5400

aactctccac agttcaccat cttcttcgtc attcaaccga tgacccactc cgtacaacga   5460

atcagtctgc tgcgtcatat tgcaaagcac aagcgacgta tgcgaacaac ttgaaacaca   5520

ggctgttgta ttgatgaccg ttgtaccatt attagtcaca tcgtatagag actctccacc   5580

gtcatcccat gtttcccacc cgatggaaaa ccgtcttcta tcatcaactg tggtaagatt   5640

tcgaccctgc gaggtattca gtttcctcat atccataacc tggattttat cattaaaccc   5700

caatattaaa tactttttta gtacccccca cccaccaaaa aatgtgactg gaccggttcc   5760

tagcagctct gggagccatg ttcaggttga accacagcta cagcgaaacc gagtccagtg   5820

accggtaacc acgtccagcc cctgcgtatg taccagtcca agcacgtccg gtcattgttc   5880

tacacaggaa atctaactag gtcaacgcaa ttttattcca ccgttacgca gaatactaac   5940

aaaaaaacac acaaatttaa cgaattacac gtagtttatt acatgaaaac tgtaagaaca   6000

ccaattcact aagcgataca acatttagct gacttccaag tgccacacat caccactgta   6060

ttcatccatg ttttcaccga accaacgaga cagatcgaag aagccagaat ctcccgactt   6120

taaattacat aaatccaacg tattatgacc acagctcgac acacaaatag ttgcgttacc   6180

attcacagta gcattaccta tacccgtaac gttgcacaac cactgatcac cattgttacc   6240

aaaaacggtt ttccacttag ttgtcaacgg atctttccta tgcgtaatgg taaaattact   6300

cccagtcgtc gcttttagct cattacgagt attatccgca tccacatata tcaacgtcat   6360

agctaggcac gctataagta cccccccccc acaatggaat gttgccaaac cggttctttc   6420

ccgttatagc catagcgttc ccaggcaaaa gcaaacgcca aacctaatgc agtgaaaagc   6480

gcttgcagcc agaaccagct tatgtaccag ccacaatcac atccggttat tgtttccaca   6540

ggaaatccta ccaggcaaag ccccgcttgt tgtgttcctg accatcttgt ttagcaattc   6600

gtaaactgtc agcctagcga cgtccgttta gatcaaaagt cacgtatata gcgacgctgt   6660

ttccacccgt ttccccgtcc cgccgtttcc gaacaaccca cccgggttca gacaaccgac   6720

caccaacaga aatatacaca cagaccaccg ggagttcagt taaagatttc atcaggttta   6780

ttttggctgc tgctagtctt ttgcttctta gaaaaaaaat acccatatag agaaataatg   6840

atagtttgac aacacatatg gcagggattt cttcttcatc aataagatat gcaattcccc   6900

cagggagaga ctttcaacaa ttgaatttac aaaaacaaaa ttacatcagg agaaagagag   6960

gatacattaa taaatatatt atatctggtg tatatactga atgctgctgg ttcataaggt   7020

aacgatgcta cttttttttaa ttccaagatg gtttttcttt gttagtcttt tgttgacttg   7080

ctggttccta aaagttcgca aaaacgattg tgtgaagatt ttatgacgtt ggttgactag   7140

ttcatgagat tctgctgtac gtgtgatggt tattcgctgg ttcgttctaa gatgagtatc   7200

gtactgtgtc tgcgatggtc gtctcttact ggcattctct cggctgcctc ttgctttcat   7260
```

```
gattgaaaag gaaaaaagga ctccgagggc gcggtcatct tttacttttc ggttttctcg   7320
ttggcgggtc agaggtagtc agatcatgag actgtcgtgg tcgatgaaac tgtgtctgct   7380
caagtgacgt ccatttcttg tacggagaaa aaagtcatcg ggataaataa ggctatacaa   7440
ggcgttgtca agcgtgcggc tctaaacaaa ttaagcgata caaaattaca gtaatacgaa   7500
taataaatta ccccccctccc cctgtggtcc cccgagacga gagccaccca tcgtgtactc   7560
tcgcaccacc cacgaccaca gagggagacg ggacgaagag acgacgcaca gcgccatctc   7620
ctcctggagg ccggcgacgt taactgctac agctgcggcg gcgaagacag ctgcgatttg   7680
tcggccgaca tgccgatggt atgggcggcg gcggcagtgg ccgcggcagc ggggaggaga   7740
ggagagagaa gaggagcggg gcgtccgaag gcgaggatgg catggtctcg ccggagcgcc   7800
cggcttttat ggaacactcg cgtccggttg ggtatcaccc acaggaagat gagtcacaac   7860
ttccaaacca tcttgagacc cgagtaacgg tttacaggtc gcacgccagt ctcagctaaa   7920
aacagcggac agtcccacgc tgtttctgtt gtggctctct ccagtttcct catcaccgtc   7980
ccggtctccg tcgtcatcgg aagaatacca cccgctctca tgcggcagtc gatcggcctc   8040
gacgaacgag acgcggcgac gcctctccac ggccgactgg ttgtggtggt gaaagaagag   8100
caccagcaat cccaggagga gcaacaagcc ctcacatgtc caggaggtcg gggagagggc   8160
ctgtcggaga tggccgtgag gcatcacgta cggcagctga ggagaaacgg agaagaaagg   8220
aaaattaccg tcaggggccg gggttcttat tagagaaaca gcacgtaggt caggatccag   8280
atgctaatgg cgatcatgat gacgatgatc atgcaggcca agacgcggcg caccaatgcc   8340
gaatccaaga gccgccgtgc cgccggttgg tggctggcgg catctagaga catggtttgg   8400
gggggaccgg cggcgcgaaa agacagggag atggacagtg acacggtgtt ttgttatgat   8460
taggacatgg gaaccggaag ccgagacaga gtactacaga gtgttgaagg gtaacgtgag   8520
ggagatcatg tcatgggcgg gctgaagacc gtgcgggaag gattgacgtg tgcggtgctt   8580
gtggaacacg gtgttttaat atgtatccgc gtgtaatgca cgcggtgtgc tttttagcac   8640
tcggtttgat aagctacgtg gccgtttgcg ccgaaaacac ggttaccacc aactgtctcg   8700
tgaaagcaga aaatacccac ctgacatgta agtgcaatcc gaataccaca tctaatacca   8760
acaatggcag caagtgccac gcgatgtgca aatgcagggt cacagaaccc attaccatgc   8820
taggcgcata ctcggcctgg ggcgcgggct cgttcgtggc cacgctgata gtcctgctgg   8880
tggtcttctt cgtaatttac gcgcgcgagg aggagaaaaa caacacgggc accgaggtag   8940
atcaatgtct ggcctatcgg agcctgacac gcaaaaagct ggaacaacac gcggctaaaa   9000
agcagaacat ctacgaacgg attccatacc ggccctccag acagaacgac aactccccgt   9060
tgatcgaacc gacgggcaca gacgacgaag aggacgagga cgacgacgtc tgataaggaa   9120
ggcgagaacg tcttttgcac catgcagacc tacagcaccc ccctcacgct tatcatagtc   9180
acgtcgctgt tttgttcac aactcaggga agttcatcga acgccgtcga accaaccaaa   9240
aaaccccctaa agctcgccaa ctaccgcgcc acctgcgagg accgtacacg tactctggtt   9300
accaggctta acactagcca tcacagcgta gtctggcaac gttatgatat ctacagcaga   9360
tacatgcgtc gtatgccgcc actttgcatc attacagacg cctataaaga aaccacgcat   9420
cagggtggcg caactttcac gtgcacgcgc caaaatctca cgctgtacaa tcttacggtt   9480
aaagatacgg gagtctacct cctgcaggat cagtataccg gcgatgtcga ggctttctac   9540
ctcatcatcc acccacgcag cttctgccga gctttggaaa cgcgtcgatg cttttatccg   9600
ggaccaggga gagttgtggt tacggattcc caagaggcag accgagcaat tatctcggat   9660
```

```
ttaaaacgcc agtggtccgg cctctcactc cattgcgcct gggtttcggg actgatgatc   9720
tttgttggtg cactggtcat ctgctttctg cggtcgcaac gaatcgggga acaggacgct   9780
gaacagctgc ggacggacct ggatacggaa cctctgttgt tgacggtgga cggagatttg   9840
gaataaaaga tgcgtgttga ccgtcaaaaa cgcaacaact tcacgtatcg acaaacggta   9900
tatataatcc tgaccttcta cattgtatat aggggcaaat gtaacagcac tgataccaat   9960
aattctacgt ctacttcaga tagcaccgtc tctgatacta gtgtgtactc tactccaaat  10020
cttcccagta catttttttac aactcttgat acatctactg gctcacagat atcaaccacc  10080
tcaaacacca tatccagcac tacaaataca ttggccgcat cttctataac tacgttaaac  10140
acctcgacta acactacgtc ttatacagct tcaactctta ctgctctctc cagtacccac  10200
acaaattccc caatactctc caacaacgca acattataca ccacatcgtt ggataatacg  10260
actacagaca taacgtccag cgaaagttcg attaacgcgt caaccattca taacactacg  10320
tacagtcctg taacatcgat tgctgttaat tgtactgtcg cagctaatga aacaaacaat  10380
tcaagttcaa aaaattgcca acaagatatt ggaacaatac gtgttaaatc aactacatta  10440
acggcagaag aaggaaaaaa cattacgata cagggcaatt caacatggaa ctgccccaat  10500
gtagtttggt accgacatta caattggtct acacatggac accacattta tcccaataga  10560
cgttaccaaa cgccaacgta tcaacacaag atcttaacat cacatcccat atgtcatcct  10620
gacgtctcat cacctgcggc gtaccacgat ctatgccgtt cgtgtaataa gacagaacta  10680
cgtatatacg atttaaacac tacaaattca ggcagatata gtcgacggtg ttacaaagag  10740
tacaaccacg atggaccaca cgaggatgaa aatttcggac taactgtaaa tcccagaaac  10800
gacactgaca atcataccac cccactatgt cccagatacg taggaacaca atcagaagaa  10860
gacgaagacg acgattatac actaagcact atcacaaata ataacatgcg caaaacaagt  10920
caccgtgaca tctcacatgg cacgcgcact acatgggctc ttacactaat ctgcatagcc  10980
tgcatacttc tgttttttgt tcgacgagcc ctcaataaaa gataccgtcc attacgggac  11040
gatattagtg aatctagctt tgttgtacga tatcatcctg aacatgaaga ctgacgtttc  11100
cggacacgca acacatgaaa ttaagtaaca tatctaccat gaaatacagc aaagatatac  11160
taatgtctat ccatccaata gcggtaccat gcactggcat cttgcgatta catggacggt  11220
aatcatatta acgttttcgg aatgttacaa ccaaacttgt ccgtgcccct gcatttgtgt  11280
caattctaca acagttagca tatccaccag tgaaacaacg tctaaaaaca tcactccaac  11340
taccacgaca aattccaaaa aaacaacgtc aagtattgct accactacac cctcgttagt  11400
aacgactggc aaagtcgttt ctactgcagc gtcgtcaacc ataatatctc aaaccaaccg  11460
cagtcatacg agtaatgcta tcacaacccc gaaaacgcga tttgaatata atatcacggg  11520
atatgttggc caagaagtga ctctaaactt cactggatca tggaattaca ttcaatggtt  11580
ccggtacggt tctccaggct ggctttattc ctcggaacca atatgcaccg ttaccagcaa  11640
ttatcatcat actttccctc gtggtgctct ttgctttgat tgtgacatga caaaacttct  11700
aatttacgat ctgacgttaa acgattctgg aaagtacgtt gtcaagagaa cgcgccatga  11760
caatcaatac gaagaagcat gctacagcct cacggtgatt tttgccaaca cgacatccat  11820
agtcaccaac agaacgtgtg atagaaaacg aacagaaaat acagacacta ctaaccatga  11880
aatcgggaaa catattattg aaactattaa gaaagccaac attcctctgg gaattcacgc  11940
tgtatgggcg ggtatagtag tatcggtggc actcatagcg ctatatatgg gcaaccgtcg  12000
```

-continued

```
cagacccagg aaaccgcgtt ataccagact tcctaaatac gatccagatg agtcttggac  12060
taaaacctaa tatgcacatc aataaaattt tttatcttta gtcattaatg tttgggtgtg  12120
tttattctga gttaatcact tataagtcgg gatatccata gacatttaaa aacatgggtg  12180
tacaatgtaa cagtaaactg ctgctactag ccgtactaat aacaattatc ctatctagca  12240
ttctggtaca ggcaattcca cataaacaaa aaacatccta ccagcagctc ttgctgcaaa  12300
gtgaacatgt acaaataccc atcacagtag ccgaaggaga tacaatttgc tttaacgtta  12360
gtgataaccc ctgcaacttt tctagttact ggaatcacaa taactgcgaa ctttgcggtt  12420
ggacaccatt ttactcggaa tatgctggat attccgaaaa caagtcgtgt cacccacgat  12480
ttacctgtct tcacgatact aaaggtctga aactacacaa cgtaactaca aatgattcag  12540
gaatttatac ccgaaacgtt tattactgtg acattccatg caacatcagc gatgatcata  12600
aacataacgt agaggacttt gacaactgta acaccactat aaatagaact cactatatta  12660
ttactgtctc gtcttcacgt tattctaaac gcaccaattc ccacgtagcc actcacgttg  12720
gttggacagc caccgtggtg ataattatct gcgttttaac ttacgttaac gttacaacaa  12780
ccctgaagca cagactacga actagaaaca acgtcaacca cacaatgtga tcacaaagta  12840
ccaacgctaa tttatttagg gtacatttgt actactttgt gtagttctca aaaactgtaa  12900
ggtcccgctt ttccactccg tcatgaagga tcgcaataaa atacttctat gtatcatctt  12960
tatttgcatc atgtgcctca tttgtattta ctttaaacgt cattgtattc ctactccgtc  13020
tccggacaag gcggatttcc gagtagaatt tccttcgtta ctcccgtgta tcggcgtaca  13080
gtgcgctgca tagaaagacg cgtgacacat accgtacccc tggacggtac agtctatgat  13140
aacgtaattc aaataaagta caggttccta gtgacatgtt atcataaaac atagattttt  13200
ctacgtgttt ttacaaaaga gcgtctcgaa gcagcttgag ccacactgcg gtccaaatga  13260
caagcatgat caaaaaatatg ctgcgtagca gtcgaaagcc gtactgagcg tgcgaggcgg  13320
gtaggctgcc gaacgacgga tatgcgtcgt catcttcgac tataaggatc gtgaccgagt  13380
cttcggccat gctaaacgct accctgtgtg gctggtatgt agtgtatccg gtttggaatt  13440
gttctgttcc ggctcggggg atagtgagga attctcaagg gacaatacgg gacccaatga  13500
ctggatatga gaagggtttt tccccgtaag atgatcctgg tatcacatga ggtctggata  13560
tgtataaatg aggagtgaaa taggtaaagg gaatcagatg ccgccttcgt gatgcagccg  13620
ctggttctct cggcgaagaa actgtcgtct ctactgattt gcaaatacat cccgccttaa  13680
gcgataagtc cataaaacgc cgttgtccgg atacggtgaa ggtgacccgg attatagcac  13740
gttccttttt ttttgttttt gcatcactta tcgccactat cagtgcaata ttttgattgt  13800
gagactgaaa gagtatcgtt atgatgctta gaacgtggat atcattaccg atggtactgc  13860
ttgacgcgta ctgtttttgt atttttgtga gttgttcaat cagcacgacg actgctcccg  13920
tggaatggaa gtctcccgac cgtcagattc ctatgaatat tacttgcgct aattactcag  13980
ggaccgtcaa cggcaacgtt acatttcgag gtcttcagaa caaaacggaa gatttttttgc  14040
actggctgtt agggtggggt cataagtcca tttgttcatt ttttccgaaa ctccaaggca  14100
ataaagaaca acattatatg tatggaataa cgaatctcac gtataactgt acctatgacc  14160
gcctgacgtt gctgaatttg acgacggaaa acagcggaaa gtattatttc aaacgagaag  14220
atgtgaattc caccttttat tactcttgtt acaacctgac cgtgacctaa acgcatgtaa  14280
agttccacag agccgcgtgg ctgtagctat tgtgtttacg ttgcttttga aatgttaagc  14340
gtccctacgg cgctaacatg tttctaggct actctgactg tgtagatccc ggccttgctg  14400
```

```
tgtatcgtgt atctagatca cgtttaaagc tcatgttgtc ttttgtgtgg ttggtcggtt  14460
tgcgtttcca tgattgtgcc gcgttcgagt cctgctgtta cgacatcacc gaggcggaga  14520
gtaacaaggc tatatcaagg gacgaagcag cattcacctc cagcgtgagc acccgtacac  14580
cgtccctggc gatcgcgcct cctcctgacc gatcgatgct gttgtcgcga gaggaagaac  14640
tcgttccgtg gagtcgtctc atcatcacta agcagttcta cggaggcctg attttccaca  14700
ccacctgggt caccggcttc gtcctgttag gactcttgac gcttttcgcc agcctgtttc  14760
gcgtaccgca atccatctgt cgtttctgca tagaccgtct ccgggacatc gcccgtcctc  14820
tgaaataccg ctatcaacgt cttgtcgcta ccgtgtagct agttagccag ctgtgtgtag  14880
ttgtattttg cttttgcata tttgttttca gtcagagagt ctgaaacggg gtgggaggga  14940
cttttgcggg tagtgcatgc taagatgaac ggatgggctg gggtgtgctt gataactcac  15000
tgtttgaata cgcgctcacg cacatatgta gcactcaaca tgttagcttt tgcccgcacg  15060
ccccggggcg tgccgagctg ccttttttaat aaagtctggg tttccagata cgcgctggtt  15120
ctgattttga tggtttgtgc ctctgaaagc tctacgagct gggccgtgac atccaatgga  15180
ctgcctaact gtagcacggt aactagaaca gcgggtcaag acgctgaatt gcacggtccg  15240
gcaccgttaa gctgtaatgt gacccagtgg ggacgttacg agaatggaag cacacccgta  15300
ttatggtgca ctttacgggg atcacgcatg cgagtctcat taggacaccg tgtagcgttt  15360
ggctgttctt ggaaaacatt ttttatttat aacgtttctg aaagtagcgg tggcacttac  15420
tatcaaaaag gttacaactg caccgacaaa catataacac tatcttgttt caacctaacg  15480
gtggttcctc gagcggttca aagcacaacc accgtaatga cacccacgct ggttacaaac  15540
tccacattca gtgtgtcact tgttgcgttg agactgacga caaattccag cgcgtttgga  15600
cacgctattt atcaacgaca acagcgtgtt gaaaacggga cgttatccaa gaacataact  15660
aacttggcat tcacctatgg cagctggggc gttgcgatgc tgctgtttgc cgccgtgatg  15720
gtgctcgttg atttgggttt gcctcaatcg gcttggcgac gctggcgaag ccacgtggac  15780
gatgaagaac gtggtttgtt aatgtaggaa ataaaaggca gtttgagcat gactgtttcc  15840
aaaccgtaac gtggtaaata aatcatggct tctgacgtgg gttctcatcc tctgacggtt  15900
acacgattcc gctgcagagt gcattatgtg tacaataaac tgttgatttt aactttgttt  15960
gcccccgtga ttctggaatc cgtcatctac gtgtccgggc cacagggagg gaacgttacc  16020
ctggtatcca acttcacttc aaacatcagc gcacggtggt ttcgctggga cggcaacgat  16080
agccatctca tttgctttta caaacgtgga gagggtcttt ctacgcccta tgtgggttta  16140
agcctaagtt gtgcggctaa ccaaatcacc atcttcaacc tcacgttgaa cgactccggt  16200
cgttacggag cagaaggttt tacgagaagc ggcgaaaatg aaacgttcct gtggtataat  16260
ttgaccgtga aacctaaacc tttggaaact actccagcta gtaacgtaac aaccatcgtc  16320
acgacgacat cgacggtgac cgatgcgaaa agtaacgtta cagggaacgt cagtttagca  16380
ccacaactac gtgccgtcgc tggattctcc catcagacgc ctttggaaaa caacacgcac  16440
ctggccttgg taggtgttgt tgtgttttta gttctgatag ttgtttgtat tatggggtgg  16500
tggaagttgt tgtgtagtaa atcagagtta tagtaatgtc ctttttatca gggagaaggt  16560
tttgttccca caatgactag ctcgagacta tctgcgtcgg aaaattatga cggaaattat  16620
gaattcacgg aaactgccaa tacaacgcgt acaaatacca gtgactggat aacgttagga  16680
agcagtgcat cgctgttgaa aagcacggag actgcagtca acctcagcaa cgcgactacg  16740
```

```
gtcatcccac aacctgtaga atacccggct gggggagtac aatatcaaag agcggcaacg  16800
cattattctt ggatgctaat cattgtcatc attctcatca tttttattat catctgtcta  16860
cgagcacctc gaaaaatcta ccatcactgg aaagacagta aacagtacgg acaagtgttt  16920
atgacagaca cggaactgtg acagtgatgt ctaagcgttt gcaggtattt ccatggataa  16980
caattttatt ttacacatca aaatcccagt attggaacta tatgacaata ccatgtaccc  17040
ctacagttgg atacggcagt cataatatta gcttgcatcc gcttaataac tcattatttc  17100
aagacgatgt ttttgaatgg tacatagaca aaccaatggt tactaacaag ttatgtcttt  17160
atcaaagtaa tgaacgcata aaatccaatc tagactctcc aaatattatg tggcagtgca  17220
cagataatcg tacactaatt ctcatgaact taaccacaac atacagtaga aactattatt  17280
ttcaatcttt taaatatctc ggacaaggag taccaaaacc gaataacttg tgttataacg  17340
ttagtgtaca ctttacccac caaacacatt gccatacaac tacatcatcc ctgtatccac  17400
ctacatctgt acacgattca ttagaaatat cacagtcatt cacctcaacc aacttcacac  17460
ataccgcggt ccactacgcc gccggtaacg ttgaagcaca acacgacact gccacttcac  17520
atacaatgtg gatcataccc ctagttatcg ttataacaat catcgtttta atttgtttca  17580
agttccccca aaaagcttgg aataaattca cacaataccg atacagcggt atgctcgccg  17640
ccgcttaaag aatcaacgcc aaggaaatca aaacgtaaaa agaatagata tgtacgttta  17700
tttttcagct cactgtttga ataccgtaaa cataatgacg tacatatacg tggttataca  17760
acaggtgttt gtgttatgcg gcaactgatt aaccatatcg tgaaccatga tcttttccga  17820
tggtccgtcg tgaccgcaat gatattttac agatattccg aaacctgtat ggaggtcact  17880
gtcagagtag gtgatccagt taccctcggt agtggacatg gttatcatcc aggacaaaaa  17940
gtacactggt ataaccagtc atgcgtcggc atcggcaacg gcgaaaatac gcatcctatc  18000
tgcacctacg accctcctaa acctggtaga caaaagacaa tgaaaactac tccgttgcca  18060
tcaccattgt tgtacgagtg tcacaattcc acattaagca ttcttcatgt aaacgtctca  18120
gatcccagaa actattgcag gcgaaaatgt ccaccaaagg gtaactgtga gtttcccaca  18180
tgttttacat tatcgctgat ttctagaact acgaccagaa aacccgaaca aaaaactacg  18240
ttgttgcgat taaaaaccac gccaaataaa catacgcagc acaaaagatc cacgcggaga  18300
acgtcaccta aagattacaa tgtaacgggt cttccaaaag gctttgcgga ctcgtttacc  18360
ggtaacgtag aggcacatcg aaccaaagat gccgcacaca gcgcatggat tctcattatc  18420
atcatcatta tcatagtcgt cattctattc ttcttcaaga ttcctcaaag actccgagag  18480
aaatgggaca ccaagggata cctttacaaa ggaaccgatg gcctgcccac tacggactaa  18540
ttatcgtgag cggacggata tgttcggttt caaactcact gtttgaatat agggacagtc  18600
cctacggaac ctgagaacat gtggaaatca cctgtggtag aatgctgttc aggtacatta  18660
cctttcatcg cgaaaaggta ctttacctaa cggctgcatg catctttggt gtctacatca  18720
gcctccacga tgcctgcata ccggtggtcg gcaaaatagg taccaacgtt acgttaaacg  18780
cggtagatgt tcttcccccct cgcgatcaag ttcgttggtc atacggtcca ggtgggcaag  18840
gctacatgtt atgcattttc actggcacat caacaacaac atttaacaat acgcgcttta  18900
atttttcatg tctaagcaat tacagccttc tcctcattaa cgttaccacg cagtatagca  18960
ccacctatcg tactatgaca tcactagacc attggcttca ccaacgacat aaccatggtt  19020
ctcgatggac tttagacaca tgttacaatc tgacagtgaa cgaaaacggt acattcccca  19080
ctaccaccac caaaaagccc actacgacta cgagaacgac aactaccaca acacaaagaa  19140
```

```
caaccaccac gagaacaacc accaccgcca agaagacgac gataagcact acccatcata  19200
aacaccccag tcccaaaaaa tccaccaccc ctaacagtca cgtagaacat cacgttggtt  19260
ttgaagccac agcagcggaa acaccgttac aaccaagccc acagcaccaa cacttggcta  19320
cacacgccct ctgggtttta gcggtcgtaa tcgttattat catcattatc attttctact  19380
ttcgaatacc gcaaaagctg tggctgctct ggcagcatga caagcacggc atcgtgctca  19440
tcccccaaac cgatctgtaa gcaagtcgcg taggaaatga ttgcatgaaa tcactgtgaa  19500
acgccaactc cgtgccagct ggcgcggcgg acaggccttt gacgtatttg aagccaggcg  19560
cgctctcgat accgaaagga tccaaggggg ctttccaaag ccgacgtccc tgattccctt  19620
cataaagctg ttgaccggcc ctagaaagac caagagcatg ctgtgggccc actgcggtcg  19680
cttcttgcgt tatcatctgc tcccgctgct actgtgtaga ctgccattct tactcttttt  19740
tcagcggccg cagtgggccc acggcttgga cattgtcgag gaggacgagt ggctacggga  19800
gatacaagga gcgacgtacc agctgtccat agtacgccaa gctatgcagc acgccggatt  19860
ccaagtcaga gcggcgtcgg ttatgacacg gcgaaacgcc gttgacctgg accgaccgcc  19920
gctttggtct ggatcgctcc cgcatttgcc cgtctacgat gtgcgttccc cgcggccgtt  19980
gagaccgccg tcatcacagc atcacgccgt atcacccgaa ctgccgtcgc gaaacgggat  20040
acgttggcag taccaagagc tgcagtatct ggtggaagaa caacggcggc gaaatcagtc  20100
gcgtaatgcg attccgagac cctcgttccc ccctccggat ccaccatcgc agccggcaga  20160
ggatgcacga gacgcggacg cagaacgtgc cgaatcacca cacactgcag aaagcaccgt  20220
cagccacgac gcgagtgaca acgcagtgcg gcgacggcac gaaagacggc gctataacgc  20280
tctgacggtc cgcagcaggg actcgctgct cctaacgcga atacgcttct ccaaccaacg  20340
gtgtttcgga cgcgggcgtc tgagacatcc cgcgggaagc ggtcccaaca ccggcggacc  20400
gcgacccggc ggtgcgggac tccgtcaact acgccaacaa ctgacggtcc gctggcagct  20460
gttccgccta cggtgccacg gttggacaca gcaagtctct agccagatca gaacccgctg  20520
ggaggaaagc aacgtcgtga gccagacggc cacgcgagta cgtacgtggt ttgtgcaaag  20580
aaccacgttg tggcgtcgca cgtgggttcc gggacagaac ccggcggccg aagcgcaaga  20640
actggcgatc ataccgccgg cacccacggt gctccggcag aacgaggaac cacgtcaaca  20700
gcttacggga gaggagacaa gaaattcaac gcacactcaa cgtgaagaag tggaggacgt  20760
ttcgagagag ggcgcgagag aagggaatga tgggagccga gcaagtggaa acgacgagag  20820
aaggaataat gcgggaagat atgatgatga tcatgaggtt caagagccgc aggtcactta  20880
tccagcggga caaggagaac tgaataggag gtcacaggag gagaacgagg aaggtggacc  20940
gtgtgaatcg ccgccaatga cgacaaatac gctgaccgtg gcctgtccgc cccgcgaacc  21000
cccgcatcgt gccctgtttc gtctatgctt aggactgtgg gtctcgagct acctggttcg  21060
acggcccatg acgatttaga atacaccgag ccattccttt atttcccccc atccccggtc  21120
gcttatgcgt gtcaaacact accaataaag ataatctgcc aatcgcacct tatatataat  21180
atgtggtcgc gtgtggtctt tttaaggagc tctgaaacac agacaggtat ggggggtggc  21240
cggctgccgc cgctgtggct gccgctgctg atcgcctgga gcgagtgggg caactgctgt  21300
ctcgatgcgc ctccggtggt gcgttcgccc tgtctgcagc cggtgcgcga ccgcaaccgc  21360
gagcggaacc cgggctcacc gcagttgctg ccttacggcg accgtctgga ggtggcctgc  21420
atcttccccg cgcacgactg gccagaggtc tctatccgag tccacctctg ctactggccc  21480
```

```
gagatcgtgc gttcgctggt ggtggacgca cgcagcggtc aggtgttaca caacgacgcc  21540
agctgttaca tcgccggcgg gcgctggcgt ttcgaggacg gcggcgcggc gcagcggctg  21600
agcctctcgt ttcgtctcat caccgagacc gcgggcacct acacctgcgt gctgggcaac  21660
gagacccaca gcctggcgac cgagaccacg gcgctggtgg ccgacgtgca cgacctgcgc  21720
cactcggacc gctcctgcga cctggctttc ggatcgcgct cacagacgcg gtacctgtgg  21780
acgcccgatc cctccaggtt gcgcagtata aactgcggtt gggagggtga acggcaccgc  21840
gtagtccact acatccccgg cacctcgggt ctgctgccct cgtgcgagga ggacgagcgc  21900
gaactgtgcg tgcccttcat cagccagagc atcgcggaca acaactgcag ccgccggcat  21960
cgggtagacg gcgctaggcg gcgctatcat ctgcggaggg attactggct gacggatccg  22020
aagatcgggc tgctggccgc gggatcggtg gccctgacct ccctctgcca cctgctgtgc  22080
tactggtgtt ccgaatcgta ccggcgtctg aacaccgaag aggaaaacga ggcggcggag  22140
gaaactgccg cgggagaagc ctctgcggta gcggcggcgg ccgtctctga ggaagagcag  22200
cagcgggagt aaacgaggag agccatgaag cggatgattc gcagtcacgg caggaaaacg  22260
gagtgtcaga tgacgggcgc cggcgagcga cgcggctccg ccgtcggtgc gctcatctgc  22320
ggcagcggta cccgacgcgg cagcggcgcc aacgaacgcc gcgactccga cgtcggtccc  22380
atcgcccaca gtagcggtac cagacgcggt tcggcgaatg aaacgtccgc ctgtacgcgg  22440
accgatcacc agaaggcgga cattgggctg tggttcatgt ttctggtttt tggactgtgt  22500
tcgtggttgg cgatgcggta tcgcgcacaa taaattttga atcgatgtca aggaacgcgt  22560
gttttgtatt ttattgggaa tattggcggg gacaaaccgg tttcggatgt ttacccttaa  22620
tcttaccggg gacctcgttg tcctctcctc cttcttcctc ggacacgggg cttcatgctg  22680
acgtaggtac cgactggggt caaaagcctg ggtacttatg gggagcgcgc acaaaggacc  22740
gtcaggcgcc ggcatggagc gtcgccgagg tacggtaccg ctgggatggg tgtttttttgt  22800
tctttgctta tctgcctctt ccccgtgtgc tgttgatctg ggtagcaagt cctccaactc  22860
gacctgccgc ttgaatgtga ctgagttggc ctcgatccat cctggggaaa cgtggacgtt  22920
acacgggatg tgtatttcta tctgctacta cgagaatgtg accgaggacg agataatcgg  22980
cgtggctttt acttggcagc ataacgagtc tgtggttgac ctgtggttgt accagaacga  23040
cacggtgatc cgcaatttca gcgacatcac cactaacatc ttgcaagacg gactgaaaat  23100
gcgaaccgtc cctgtgacta aactgtacac cagccgcatg gtcactaatc ttaccgtggg  23160
ccgctatgac tgtttacgct gcgagaacgg tacgatgaaa ataatcgagc gcctctacgt  23220
ccgattgggc tcgctatatc cgagaccgcc cggatccggg ctcgccaaac accccctccgt  23280
aagcgccgac gaggaactgt ccgcgacctt ggcgagagac atcgtgttgg tctcagccat  23340
cactctgttc ttcttcttgt tggccctacg gatcccccag cgactgtgtc agcggctgcg  23400
cattcgcctg ccgcatcgat accagcggtt acgcaccgag gactgaacgg ataaccgcaa  23460
aggccacgtg caacgttcac gctgctataa gaaggccatg tcccccgtgg acgggtctct  23520
ttgacacgag cgcggcacgc cgttgccacg agcatggatc acgcgctctt cacacacttc  23580
gtcggccgac cccgtcactg tcggttggaa atgttgattc tggacgaaca ggtgtctaag  23640
agatcctggg acaccacggt ttaccacagg cgccgcaaac atctacctcg acgtcgcgct  23700
ccgtgcggcc cccagaggcc cgccgagatt cccaaaagaa gaaaaaaggc ggccgtcctt  23760
ctattttggc acgatttgtg ctggctgttt cgacgacttt tctttcctcg ggaggactca  23820
gagccactga tgtcggatcc ggcacggtct cccgaagagg aggagtaaac aacacacggc  23880
```

```
taagaggata catcatcaaa gaagatagga ggggtcaaaa cgcggactga aagtatataa  23940
cgccgatcat gttcgaggaa ctgttaataa aacgccatga tgacaatgtg gtgtctgacg  24000
ttgtttgtgc tgtggatgtt gagagtggtg ggaatgcacg tgttgcgtta cgggtacacg  24060
gggattttcg atgatacatc gcatatgacg ttgaccgttg tggggatttt tgacgggcaa  24120
cactttttta cctatcacgt taattccagc gataaagcgt caagtcgggc caacggtacc  24180
atttcttgga tggctaacgt ctcggcggcc taccccacct acctggacgg ggaaagagcc  24240
aaaggtgacc ttatttttaa ccaaaccgag caaaacctgt tagagctgga aattgcgttg  24300
ggttaccggt cacagagcgt gctgacgtgg acgcacgagt gtaataccac ggaaaacggt  24360
agttttgtag ccggttacga gggatttggg tgggacgggg aaactttaat ggagctcaag  24420
gataacctga cactatggac gggccccaat tacgaaatta gttggttgaa gcaaaacaaa  24480
acgtacatcg acggtaaaat taaaaacatc agcgaggggg atactacaat acaaaggaac  24540
tatctcaagg gtaattgcac tcaatggtcc gtcatttata gcgggtttca aaccccccgtc  24600
acccacccag tggtaaaggg cggtgtccga aaccagaatg acaacagagc tgaagcattc  24660
tgtacatctt acgggttctt tccaggggaa attaatatta cttttatcca ttacggtaat  24720
aaggcgcccg atgatagcga gcctcaatgc aatccgctac ttcccacctt cgatgggact  24780
ttccatcagg gatgttacgt agccatcttt tgcaatcaaa actacacctg ccgcgttaca  24840
cacggtaatt ggacggtgga aatccccatc agcgttacct cacctgacga cagttcctcg  24900
ggggaggtcc ctgatcaccc gacagctaac aaacgctata acaccatgac catcagcagt  24960
gtcctcctag ccctgctttt atgcgctttg ctattcgcgt tcctgcacta ctttaccacc  25020
ttgaaacaat acctacgtaa cctggccttt gcgtggcgct atcgcaaggt ccggtcgtca  25080
tgaccagcaa cgccctgtat gagctgtttc gacgtcggtt accgcgtgcc cccgtcaaca  25140
cggtcatgtt tctcacgcga cgcactcgtg atgggttctg cggtcggttg acgtccatcg  25200
ccacgaattc ccactacact atgttcgtgt tagatcacgg atccgtgcgc atcgagcgac  25260
cgagtcagtc agaagtggat tgcgccagtt taatggaaac gctgaagcgg attcggttac  25320
gaaattcgtg ggtagcgtca gaagacgagc tagatgtgag tcgcagggac gcgtgacacg  25380
aaacgcgttc aggattaacg taggttttcg aaataaccta cgtccgtgag tgacgcggtt  25440
tcgtgttgaa acccgcgccc gcttctcacg gcggtttatg atgaaaccgg cgttgcggat  25500
ccacgcgggt tcctcattca acctgcgaaa agaggaagtt gcggtaaaac cacgtcaata  25560
aagacgtcaa tgacacctca atgttgcgtt ggaacggtct ttatatatac aaacgccgtt  25620
atgatcagtg tccggcaaga tgctcgggat acgggctatg ctggtgatgc tggattacta  25680
ctggatacag ttgataacga acaatggcac tcgaagcaac aataccgata ccatctttgt  25740
atctctcctt accgggccca acggagttac tcgcacagcc atcggaggtc tgtattcaaa  25800
ctacaccaac ttaactggag catttggctt cacttcaaca aatatgtcag caaccaactc  25860
ttccgctgag gataattgga gcgtaaccaa cctgacggag agttgcatca accgcggtga  25920
gtcctatgtg actaccatct ggcttctgga ctgcactaaa aacgatactt attggtacta  25980
tggaaatgcc tacaatcata catgtgaagg tacaatttcg ggatatctcc tgggcatgtg  26040
caagctatgg aaaagttggg tcaataatat tacttcttat aacactgtca gagtcgaatc  26100
gctgggaaat gaaacacggt gcatgctgct ccctagacag tatactctca acgccacggt  26160
ggaatggtac aacaaatctg aaggtgacgt accagaagaa ttcatggact atgttatcct  26220
```

```
gaccccccttg gctgtgctta catgcggact gcaggaagct tatatactcg acaaaggtcg  26280
tagatacatg tatttgtttt ccgtgtcctg cgtgggaatc acaggtaccg tatctattat  26340
actcgtctcc ctatcgctgc tcatcctcat ctgttactat cgctgtggcc ggcttctgat  26400
atgcccacgc ggctttgaac tcttgccaga attcactgag gaagaggagg aaaaagaaaa  26460
attgttaacg cataatgaca ttgaagtcca agtgcctatt cgcacgcggc gactactcgt  26520
cccttggatc cgggagagca aaatgtgggt actaccaccc ccgttgcctc cacgacctcc  26580
ccacttaata gaattcccgc cgtctcctcc gccatcgcct gggcccatgc acatggtggt  26640
ctgcatgcca gcatgacgaa ctttggactc tgagccccaa gcggtacgaa ctacatattt  26700
tccataaatc tacactgaac ttgagcacaa agatactgac aatagactgg atatacagac  26760
ttttatatga tccctgtaca gatgtaaata aaatgctttt atttaaaact ggtcccaatg  26820
ttcttcggga atcatggggt ggggacgggg gacgcggtag ggagcaaaac cgggtacatg  26880
ggggggaaca tcgtccagca gtagcaccag cggattgggt aggggttgct gcggaggtcg  26940
gtcgatgacg atgtcgatct ccatcggcag atccggcaac atctcttcat ctccctcacc  27000
gaccagcact cggcgctgtt ctggatgtat atgattctgg aaaagcctcc gacgagctcg  27060
cggcgcgtag aaagccaagc ggcgcaaggg ccggcgagcc cgaaagtcca tgcgcacaga  27120
tggcatgagt ccttgagtga cggtggtgag ctggggaaca gggctacctc ccatcgcgac  27180
ggtgacagtg gatccatgag agaggcgccg cacgctgcat ggctaaatac cgtgaatccc  27240
ctgacgtcgt ctttcgtccc gaacgcgtca tgttgggggc gaggcgtaaa ccgtcgaggt  27300
tgaaaaaccg cgtatctgcg acccgtccgg actacgttgt tttttagaag cggccacatg  27360
acctcgagat gtcgtcaccc aaggtattta acggcacaca gccagacgcg ttcgtcagca  27420
gcgacgccga caagacctca gcatggctcg gaggctatgg atcttgagct tactagccgt  27480
gaccttgacg gtggctttgg cggcaccttc tcagaaatcg aagcgcaggt aaacggaatc  27540
tggggaattc aacacaggta agaaatacaa aaaaataacg tgattgtgaa cgcggttatc  27600
gtgttttgca gcgtgacggt ggaacaaccc agtaccagca ctaactccga tggtaatacc  27660
acccccagca agaacgtaac tctcagtcag ggggggtcca ccaccgacgg agatgaagat  27720
tactccgggg gagactatga cgttttgatt acggatacag atggaggtaa ccatcagcaa  27780
ccacaagaga agaccgacga acacaaggga gaacacacca aagaaaatga aaagacccag  27840
tagcagcagc agatcccaag ggttaaagac catgttgact attttgtttt ttattaaaaa  27900
gctgtaaggt tttgctctaa aaacaccccg cctccggtct tttttctttt gtattcggca  27960
cgcgaaacac ggtttcttcc catagcctgt ctaactagcc ttcccgtgag agtttatgaa  28020
catgtatctc accagaatgc tagtttgtag aggctatgcg ggatgctgcg gcggcgcgac  28080
cttccctctc cacccagccc cgtcaaaaca cacgcgactc gagcggttcg tatgaaaaat  28140
aaaaaacagc tttttattta caggaacggg gaaaaaaaaa ggcacacggt ccgtgggaga  28200
cgcgggttca cgcgtcgtca aaaagttggt ggtccactcc gtaaggacag gtaggcttat  28260
ttagcttccg catgctcctg gttccgtaat aaatgccgtt ttcgtggcag cgtgtcatgc  28320
cgcgagtcac aaactccatc aaactgtcgg ccacgatgca aacgtgctga ttgttggcag  28380
caaagacgcg catacagtcg tccacgaaga ggttgatcac gtcgtagggg ctcaccaacc  28440
agcctaaagg ttccacgtgg ttactgccga ccatgaccct ccagtcgtta atctcgctcc  28500
agtcgtacag ccgaatcgtg gagacgcgaa tgacgctgta atcacccatg accatgagtc  28560
ggccgcgata cgtagcacgc cactgcgcga acgcgtggat gtgcatgcag ccggccagcg  28620
```

```
ctctaagcga ggcggtgtgc ggcagctcct ctgggacggt gatgaagttg cagcgtcgca  28680
aaccgatgtt gagaaattca gtgatgctct cggccacaaa ggtcaacgag tcagagtaga  28740
tgtggtcggt ccataggtac atggcgcccg aggcgcccag gtacagttca gacggcacgt  28800
tgtgatcgcc cttgtgttta agaaagttgt aggtgcagat gctgccgacg aaacgcagcg  28860
gctcggggca gcagaggtag ctggccagac gctgtgcatc ccgtccttcg tcgcgcacca  28920
agcgccagcg acgccggata acgaggcagc ggtctttggg ccagaccagg gccacgcgtt  28980
gcccgggttt ccacggtcgc gacgtcttag gaggcctcca gcggtcgagc agattgagaa  29040
aacagtcctt gattaccgac atcgcggtcg cgcgtcggtg gacaaaaaga aatcgggccg  29100
atccggaaaa aaaaaacgac ggcaaaacac cgccgtgctc gagcgaaggg tggcggaggg  29160
ccagaagagg cggccttgac ggcgttggca gcgaaaaaat tggcacgcga gtcaaacggg  29220
aagtagcgtc ggtgttttat gccccaagca gcgtcgtcgt cactcgtggc gtcacagtca  29280
acggtgctga cgtcctttgg ggcagtcggg cacgcgatcg tagatgccgt tgtggccgct  29340
gaaacgtcgg ttttcaaaca gcaggttaag tcccagacac atgaacgtgt tgagattatc  29400
tcccacccgg atgtagcggt cgtcgcgcac gtcgcaggcg tagacggccc cggtataggc  29460
gacgacgatg gggataaggt cgacgggcca gcgcaagtga ggaaagggcg cgttctcgcc  29520
cttgaggctg acggttccca ggccgagaac gcgcattccg aaagcggttt tgatgttgcg  29580
cagcaagtga ccgccttcca cgctgttttc gaaacacctg aggttgcata gacgcagttc  29640
cgttcccggc gggtacgtca acggcatgaa ctgcccgtgg tggcggatga tgaatcgcgc  29700
catggtatcc aaaccgaggc tccaggcgcg caacagcggg cgaaagtagc gcttaaccaa  29760
cgacgaggtc aggtagcgca tgcagtgcag ggtctcgacg gcgcgcagcc cgacgcgcgc  29820
aaactccatg aggttgcggg ccaggtagta gacggcggtg tcctcgcgta catagcaaaa  29880
aacatagccc tcgtccgaga tgaggcacac agcggtcttc ttctgctgat ccggcgacaa  29940
cacgccctcg ttcacgaagc gacccacgaa ggccaggcgc gtctggcaac acaggtagtg  30000
actccaagcc ttcacgtcct ccggtttgaa gtcctcgtcc gtctcgatct cctgcagcac  30060
taggttccag cccggcggcc agaccacggg caacacctgg cctgcgttga tgcgcacgta  30120
agcttccaga cagcccaggc cgaactcggc cgtgagcgcc aggctagcca gatcgctcat  30180
gtgacgcgcc gagtcagtgg gcgagcccgg gggcccgtcg cacaccacgc tccgtcttct  30240
tgtcctcacc gcggccagcg tggcgaggac actttccgcg cccgaggctg tatcttcggt  30300
ttgcccgccg gagccggccc tcactatata acgtcccgcc cgggtctcct ccatgtatgc  30360
aggtaagcaa ctgagccgaa cgcacctcag cagacgagag gatgtcgtcg cggcgtcgca  30420
gctcgtcacg tcgctctggc gaaccctcga cggtgattta tatcccctcg agcaacgagg  30480
acacgccggc ggatgaggag gcggaggaca gcgttttcac gagcacgcgg gcgcgcagcg  30540
ccacggaaga tctggatcgc atggaggccg gtttgtcgcc ctacagcgtc tcctcggacg  30600
ctccgtcgtc cttcgagctc gtgcgcgaga ccggcggcac cggcgccgcc aagaaaccga  30660
gcgaaaagaa acgatcgtcg tcgcgtcggc aaccgcagat cgcagcgggc gcgcctcggg  30720
gctcgccggc gacacccaag gccggcaagt cgcctaaagt ctcgcgaccg cctagtgtgc  30780
cctcgctgcc cgagaacggc gccggcggcg gtggcgacga taacagcagc agcggcggta  30840
gcagcagtcg caccaccagt aacagtagca gaagtaccag tcccgtggcg ccaggtgagc  30900
cgtccgctgc cgagggcgat gagttttcct tctgcgacag cgacatcgaa gactttgagc  30960
```

```
gcgaatgtta ccgggtcagc gtggccgaca atctgggctt cgagcccagc gtggtcgcgc  31020
cgcagcacgt cgagtatctc aaattcgtgc tgcaagactt tgacgtgcag cacctccgcc  31080
gcctcaacga atgcataccc atgccggcct tcgcgctcac cagcctcgtc gaccccgtct  31140
taaacaacgt agcgcctggc gagcgcgatc tcacgcgtcg gataatcacg cacgcggtga  31200
tcatcaacta ttactacgtg gcgcaaaaga aagcgcgcca catggtggag gccatacgga  31260
ccaccgtgcg gggcgacacg gtacgccggg tagccgcgca ggtcaacaac cagagccgtt  31320
cggggcgtgc ggccgcgcta gcgcttcact ttctcacgtc acgaaaagga gtgacggacg  31380
gccagtacgc cacgtctctg cggcggctgg acgaagagct gcggcatcgc ggcacgcccg  31440
aatcgccgcg gctcaccgag gtctaccaga cgctacgcga ttacaacgtg ctcttctata  31500
ccgcccacta cacctcgcgc ggcgcgctct atctctatcg gcaaaacctg cagcggctca  31560
acgagaacca ccggggcatg ctccggctgc tttcggtcga agagatatgt gaagagcaca  31620
cgctcaacga tctggcgttc ctagtaggcg tcgagcttat gatcacgcac tttcaacgca  31680
ccattcgcgt gctgcgctgc tatctccagc accagctgca gagcatctcg gagctgtgtt  31740
acctcatcta tgtacaactg ccgtcgttgc gcgaagacta cgcgcagctt agtgacgtga  31800
tctactgggc cgtcagtcaa aactacgact acgcgctcta cgcgagcacg ccggcgttgt  31860
ttgacttttt acgcgtcgtg cgtcagcagg acgccttcat ttgcaccgac tacgtgtact  31920
gcgccctgcg tctgctggcc tgtcccgaca gacctattat cggtgacacc ggcggcagca  31980
gtagctccca acgcctcgta ggcgagttta tggtgcgcga tccgctgttg cgcgacccgc  32040
gcgccaccca cctgcgccag aaactcatca cccgcgacat atgcgtggcg cggttgcaag  32100
cgcagccctc gagtcgacac attccggtcg aacacacggg tgtctcctcc gtcaccctgc  32160
tcaaaatctt tagccaggtc ccccccgacg aacgcgaaga agacacgtta cgcgagatgg  32220
ctcttaaagc gtttatggaa gcgaacggta atcaccccga acaaatctgc cgatccccac  32280
cacccccgct gccaccgcgc gactatcctc aacgcgacga gcgggaccgt caccgtcgcg  32340
accgccgcga cagcggggaa tactgttgct gatggtggga cgaaacagca gggcggaaca  32400
gtttatgata gaaagtcaca ggaaagtatg tgttgttttt ttttttaatg taccaagaat  32460
aaaaagtgcg tctacgacca aagcggtgtg tggacgctcg tcctctgtct tctccggttt  32520
tttttttatg tgtgtgtttt tcttttcctt cctattttgt tacggcaaca gcgctgatgg  32580
cacgttgccg gcttcgaaca tcgcgtcggt gatttcttgc ttgcccggcg tcacacggtg  32640
acgcagcagc gcgcggctca cgtagcaggc cgactcacgg atgacctggc cgtcggcgtc  32700
gcgtcgcagg cccgagcggt tgccgtgacg cagtctgccc tgcgcagcgc gctccacgtc  32760
ttcaaagtag ctgtgtagca ggccgcgctc cagcaactgc ggcagcgagt cggcggcgcg  32820
caccacaaag ttctcacggc tgatctcgta gcacagcacg ctgccgtcgg ccgccacgcc  32880
ggccacgctg cggtcccaac tgaaaaggtt ggcgagtccg atggtgccga tgacgcgcaa  32940
ctgaccctgg gtcaccacca gcagcttcca gtattctacg tcgcgcgggg tgaggatggt  33000
ctcctccacg tcgcagacaa acaacgtgta gccgcgcgga tagggcagat ccaggtggcg  33060
accgcgctgg cggcgcataa aatcgtctaa attcaaaccg ccgtcgggtg cgcgcctgct  33120
cgtcatcgcc gcgcctcgtc ggtcgatgac cccacggtgc ttataacgcg ccgccgcggc  33180
ttcatgtggc gtgacctccg acctcgtgag gccgaaaacg gcgtacatga agacgctcaa  33240
acttttgaat gtgggcccgg tagcgcaccg agggccccgg ggcggcgacg acggcgggtc  33300
cgagttccag cggggccttg cggcggcagc ggttggcgtg gttgctcagc tcggcgtccg  33360
```

```
agagcgccga gctgaactgc ggcagccgcg tgcgatcctg cggcgcgtcc ccgtgtcgca  33420
gcgagtgcca gagtaggcgc tggacgcgca ccgcctcggg cgtcggcggc gcgcgacagc  33480
cccggcgcag cttgaaaacg tgcaggcaca gcagctcgcg cttgatgcgc agcgacacgc  33540
tgcggtagtc gggaatccgc tgcaccagct cgagaaagtc gcagaaggtc tccacgaacg  33600
tgtcctcggt gaagcgaatg cgcttcagat cgtggacgtg tttgcgaaac cgcgacagtt  33660
ctcgacgttg cacggggttc tgagcgagtc ccttgcgcag cagcgcagcc tcgcctttaa  33720
acagcctgat gagccgctgc acgtccccgc tcaacatacg tatacacgcc gtgtactcgt  33780
gacgtatact ggcgcgcagc agccgaatga tacgcagggc cagcacggcg ttggaggcca  33840
ggtacatggc gtagccgcga cgcgggttgg cacaggccca gcccgcgggg agcagaaagt  33900
agtcgtcgac cagcgtctgc gaccagtcgg cgaagcccag gtcacgtgat acgctgtcct  33960
ggacgcgggc cacgtcgccg gctgtgaggt ggcggatcgc cggcaggtga aacgcgccca  34020
ggtgtcgatt gcgctccagc ctcagctcgg cgtgctccaa acgggaatgg tgggacgcca  34080
ccgcggaggg cgacaaagag gagtggtcgc cgccgccgta gttaccgttg tgattaccgc  34140
cgtcgtcgcg cccgtcgccg cactcgcaaa aggccgcgta gaggtccttc aacgccgctt  34200
cggctcgcgc cataaacgtg gcgtggaaaa aaacggcggc gcggtgcgtc cggtacttga  34260
cgggcaaccc gcggcacagg gccgccggca ggcagcggcc gatgagttcg cgctcctcgg  34320
gctccagaaa caggcacagg gtgccgtcca ggcgcaggta cagctcctcg gtcatcgagc  34380
atagctgccg caagtaatgg gtgcgcgtcc caaaggtctt gtaatcgagc aacgtgcaca  34440
ccacgtattg ccccgtggcc acggccagag cgatgcgttt ggcggcgcga ctgatctctg  34500
gcaagtactg cgcctcgtgc accagacggc ggaaagcgcc ggcgttgagc cagcgaaaat  34560
gctgcggatc gggcggcaag ggcacgcctc gaagcgcggc ccagacagcg aggtccgact  34620
cgagcgtcag accgcggatg tcgtacttgc cgtgcgccgt agcgcaggct gaatggacca  34680
gacagctgcg gcgaatgtac accatggcgt gcttgggatg tttgggcgcc ggcgttttcc  34740
ttttctgacc gccggcggcc gccagatcct cgggcgtgcg acacaacagg ccggcgcgca  34800
cagcctcctg tcgattacga atcggcgtca ggtaggcgcg caggaactgg tgacaaaact  34860
cctcatcatc acgacagtcg tcgagatact cgtacgtggt gagcggatcg cgaaataggc  34920
gctcgtcacc gtcgtcatgg tcttctttag cctgctcctc cggctgctgg gttagcggtg  34980
gaggtggcgg ctgatccacg gggttcatga ctgagaggaa gaagaaggtg gcggcgaagc  35040
gacgcggagc gacggcggta aagccagaca gcggctatat agctagtcat cacagtctcc  35100
tccttcacga cgcccccgtg ccgctcacgc tatccagcac gctacgaccc gaaaacacgt  35160
actcgctgac gtcgtacgcg ggcgatgtat ggctgctcac cggtttcgcg gcaacggttg  35220
cgctcgagtc caacggcgag aagcaaaaac gccgtgggca acgaaaccag aaggagccct  35280
gacggataaa accgcgcagc gtctcggcca acttaaccag catcgtaccg tacagcagta  35340
cgtgaatgcc gccatgcgcg tccataaata cggctttgtt cacgggttcc atccatccga  35400
tgactacaaa atgggcctgt tctagcacgc cgatcacgaa attgttggcc tcgtcggcct  35460
cggccacgtt ccacgagccg aaagtgaaag tacaagcggg cgagccgccc aggcggatct  35520
tgctaccggc gtggagctga catacgcgca gcagattggc gcggtcgtgc agtatctggg  35580
agagttcgta catgcccgca aaggtgtgct taaaccacgc gccctctacg atctcatcca  35640
cgtagtcgcg ctcaaagaag ctgtacacgg caaagaggcc gttctcaaaa aactcgccga  35700
```

```
acgagagccc cagcacgtac accttgtcct cgccgggcag gtacgcaaag gcgtgcccgt  35760
gcccggagac ccagatctcg ggcgccgtgt ttgcgtccgg cacgcattcg tacacactga  35820
cgaggccgat aaagtacaag cggccagcct ggcgcaggca cgagaagcgc cggtaggtct  35880
tgtgatcgcg caccacccca aagtactgag tgtcgcccag catgatgccg tgcagcggcg  35940
gccagcacag cgggagccaa cgacccgccg tggcgcgcac gtagcgctgc aggtgaaccc  36000
cgctcgcacg ctcgcgcggc ttcgggcgct tgtgggtcca ggcatcacgc agaccgcgcc  36060
agatgctgct gaacttgggc tgcccgcgca gatagagcga cgagagcgag tcaaagtagc  36120
ccacgacgag cctgtcggga gacacaagag cgcgaaaatc aaacctagag cgacgacggt  36180
gaaaaaaccg accagaagcg cgtgtctcaa acacgctact ttcggttata aaaacaccgt  36240
cgccctattt ctgggcgcgt gtacactgat gactcaccta cgctttttga acggcagtct  36300
cagctcggga ttggcctcgt acagcgagct gcggtccacg ggccgatgc tctcgtagcg  36360
aaagtcgtcg atgagcagcg ccagccccac gcgcacgaag cccctgaggt cgcgcgacag  36420
ccgcaccaac ttatcctgcc ccaccagcgc cgcgtacacg gtgcccgtgt cgccgcagag  36480
aatccgcacg cggtgaaaga aggtcttgtc ctcggcgccc tcaatttcgc ccagcggcat  36540
gacgggctcg cgcgtgtaca acgaacgttg aaagcggcgc agcatcgagg ccgagagccc  36600
cagatcgcgc gccgtgcgca gcactaggga atgcttctcg ggccagatga gggtcagttg  36660
cgcctcgcgg tgcgcctcta cgtaggcgca acgagcggcg gtgtcctcgc aggccagcaa  36720
ctcgcggaaa gccagcagcg aacgtaggta gcggccgcga gcggaggcgc gcgagcggcg  36780
gcacagctcg gcccgatggt cgggatgcac caagggcacg ttaggttgca gacgcgcgca  36840
gatggattcg tgcaccgggt cgcagcggat catgcccttg gcaaaaaatc cggccagatc  36900
cgaggccaac tcgtacaggc agtcctcttg cgcgtcgtag gcgaacacgg cgccgtacgc  36960
gtccacgaac acctggtacc ggcaggtggc gtgcgagacc gtgccaatga gatgcagagc  37020
tcggaattcg ccgaaaaagt cgttctggca gtgctccaga tcgatctcag tcagcgagtg  37080
cggcgaatgc tcgcccccga ccacgtagat gcactgcgag ggccagccca gcgacacgca  37140
cgagccctcg aagcgccgca agtaacgccg caggccctca tagtcgcgtc gcacgcacag  37200
gtcggccaag tcgcgcgtgc aaaagacctc gggtaccaag cagcgtttgc gacgcggccg  37260
acgcgcgtgc ccaggcagag gaaggcgcga cggcggcgac gacgaggagg aagacgccgt  37320
ggccgccgag cagcccttgc gacggccgga catgccggca gtccgcgacg atccacagga  37380
gacaaaaaag cagaagcagt agtagtctcg gcgacccgct ccaccccgtc ctccacacgc  37440
tcagccgcga ctgagcgccg gggcgcgccg ctacttgggt ttttatagcc atctgccccc  37500
cgtctcgggc acccgggagc gatctacgga gacctgacag cagttgggca acacaagaca  37560
gggaaataca aagacacttt taataaaaaa cgagactact ttgtgtgtgt gctccgtaaa  37620
ctgtttattc tccccctccg tctcgctctg gatgggctcc gggtccgtca acacgcgacc  37680
cgcgcggcaa aaggcacgct gttgacggcg cgagagcccg tcgtgatagt ccatcatgcc  37740
ccggagatcg tgcacaaagc agctgtcgcc gcgtagaaac cgacgcagcg tctccacgtg  37800
ctgcagctgt cggcgcgtat caggagccgt catcgccgat gtcgtcatcg ccctgacagg  37860
cgcgtagatg gctccgcgag atcatgcgcg ttttcaaccg ccgtgacaca tcaggtccat  37920
cttgagctgg cgccgggcct cgcgcaggtc tcgcacgcgt tgtgagcggg aggcgagttc  37980
ggcttcttgc tcgaactcct gctgctcact gtccgagagg gtgcgataaa aggcggcaaa  38040
gtcctccaag tcggctacat gcgccctggg tctgacgctc caaagcgtac gcagtctgat  38100
```

```
gaagcggacc catcgagcgt cacggcacgc cgtcttgaac gcagggcccg ggaagagatt  38160
cttctccccg gcgcgctcgg gccggcgagg ccgacgcggt ttatatacac cgtctcggac  38220
ggcgggacgc cgagcccgcg ccgcggccgc tcatccggag acggcggaaa ccgcggcgcc  38280
ggaggaaacg gggaccggca acgacggcgg tggcggcgac cagattatgg gggacaagcc  38340
cacgcttgtg accctgttga ccgtcgccgt gtcgtcgccg ccaccgtcgt cgccgctgcc  38400
gctcgtcagc ttcacggagc tgctgttacc gccgccgtcc gtcgccgccg ctgcggtggc  38460
ggcaacagcg acgagcgagg tgggcgagaa aaccgcggag caagaggtag cggctgcggg  38520
tccggagacc aggaatgaga gaagagaaaa cagggaggac gaaggagggg agacgaggac  38580
gacgggcacc accgcggtca aaaggtcgca cgacggtatc cctcgccaac tggcagagcg  38640
cctgcggctg tgccgccaca tggaccccga gcaggactat cgtctgccgg cgcaggacgt  38700
ggtgacctcg tggatcgaag cgctacgcga cgcggaccgc gacaactacg gccgctgcgt  38760
gcgccacgcc aagattcacc gttcggcctc gcacctgacg gcctacgagt cgtacttggt  38820
gtccatcacc gagcagtaca acacggcctc gaacgtgacg gagaaagctt cgtacgtgca  38880
gggctgcatc tttctctcgt ttcccgtcat ttacaacaac acgcagggct gcggctacaa  38940
gtacgactgg tccaacgtgg tgacgcccaa ggcggcgtac gccgagctct tctttctgct  39000
ctgctccacc agcgagagct ccgtggtgct gcaaccgctc atcaccaagg gcgggctctg  39060
ctcgtccatg gcggtttacg acgaggaaac catgcggcag tcgcaggcgg tgcagatcgg  39120
ttttctgcac acacaactgg tcatggtgcc cttcgtgccg cacgcctgcc cgcattacgc  39180
cgtgcctttc acgacgccgg gaaagccggg ctgcggcggt gctccgagcg gcgttgcggg  39240
gttggaggag acggcgccct ttggacgggt cagcgtcacg cggcatggcg cgacgctgct  39300
gtgtcgcgtg gaccatctga cctggatcag taaacgcgta accacgtacg gacacaaaaa  39360
aattacgcgc tacctcgcgc agttccgcgg cacgatggac gacgacgagg cggcgctacc  39420
cggcgaggac gaggcgtgga tcgcgtccaa aaacgtacag tacgaattca tgggtctcat  39480
tttcaccgtc aacgtggatt cactatgcgt ggacgcggaa cagcgccaac tgctgggcac  39540
cgtggccacc tccttctgtc accgcgtctc ggacaagatc acggcgcgca acatgccgcg  39600
cgccttttcc ttctacctgc tgacgagcgc gcagcgcggg tacgacctgc gatttagccg  39660
caacccgtca ctctttttta gcggcgacgc gctcaactgt ccgcttctca acgagcccaa  39720
cgtgttttcg ctcacggtgc acgcgcctta cgatatccac ttcggagtgc aaccgcggca  39780
gacggtggag ttggacttgc gctacgtgca gatcacagac cggtgtttct tggtggccaa  39840
cttgccacac gaggacgcct tttacacggg gctcagcgtg tggcgcggcg gcgagccgct  39900
caaagtcacg ctgtggacgc gcacgcgttc catcgtgatc ccgcagggca cccccatcgc  39960
cacgttgtat caaatcaccg agggcgacgg taacgtgtac tcgtacaatc accacacggt  40020
gtttcggcag atgcacgccg ccggagcaac cacgttcttt ctgggcgaca tgcaattgcc  40080
cgcggacaac tttctcacgt ctccccatcc ctgaccctcc gtccgtcctc ctttcccgac  40140
acgtcactat ccgatgattt cattaaaaag tacgtctgcg tgtgtgtttc ttaactattc  40200
ctccgtgttc ttaatcttct cgatcttttg gaggatgttc tgcacggcgt ccgacggcgt  40260
tttggcgccc cccatgccgg cagaacccgg ttgcggcccc gtaccgctct tctggggcga  40320
cgataagtcg aaagccaccg ttttcatgcc cgtcgtgctc ttgacggggg aacctacggc  40380
ggcgatcccc gtcgagcggc gtgattgcaa agccgcgctc gcccccggtt tcaggatgga  40440
```

```
gggggaggcc acaggcggcg cattcgatac gctgcttttg gccgtagacg acggtgggta  40500
aacggtggtt accgcgggat acgtcggcgt ggtcgaggcg gcccggctgc tgccggacag  40560
gcgacccggc gcgctaccgc tcacggggac cgagggcggt cgacctacca ccgccttgcc  40620
gcccaaagta ggtttcaagg aaggaacacc gacgcggctg ccccggcctt tcaccggaga  40680
cggggggggca ctcttggccg gggacggaga ggctgacgaa agcatggaca gcggcgatgt  40740
ggcaggggac acgacatcat cctccgtggg cgacaaaacg gacgccgagg ctgacggctg  40800
tcgagccgaa gaagcggaag aggttcccgc gccagaagtc acgttccttg atgacgtcgt  40860
tttagacgaa gccggttgag gttgcaacag cgtggcgggt accgtcgacg gcgtgcccga  40920
cacctgtttc tctagccttc cctgaaccgg cgtcgacgtc accgtctgcg ctcgggcgga  40980
cgcgtgcggc gtcgcgactc gcttgcccag caccggtttc tggctcgtgg atgtcgtcgt  41040
cattggagac gataacttag ctttacgtat tctggacggc gtcgactgct cgggcgtctg  41100
actgggaggc gaaatgacgt cgttgttgta atcggacgac ggtgttgtgt gtcccaggct  41160
gacgacggag ccggtgtccg aggagtcgtc gtcttcctcc tcgctgtctt cgaccggtga  41220
ctctgcagtt tggtccctta aagcccaaac ctcatcagcg gcgtcccgag acgctgtttg  41280
tgtcaccgcg gcgcgtggag tcgacggcct ccgaggggtg gtggacacgg tgttttgaga  41340
agccgtggaa gtcgtaggca tcctgaaggg attgtaagcc aggtgaggat tcttgagggc  41400
ccacgcgcgt tcgcgcggcc agttggcggg gttcatatcc ccgggcaacg gcgccgtcgg  41460
agcccagggc gagttaccgt tgaccggggt ttgggtaccc gcgaaggtag gtgtcggggc  41520
cggagcgggg gccgtggaag gattgacagg cgtcggcgtg aggatggcag cgccggcgcc  41580
agcaggaacg ttaactccgg cgccgaacgt caacgtcggt tgctcgaact tgtacgcggt  41640
ggtgacgggc ggtttggcgc tcgtctcggt atccgtgatg tccaccagcg tgtcggtgaa  41700
acgcggatct tgacggttgg ggggatagcc atccgagctg tcggaatcct cgtcgcccga  41760
gaaaagatcc cctctggtct ccgtgagcgg cctcacgtcc cacgcgctgt cccgacggac  41820
ccttcccggg ctggccttgg tcacctgcgg ggaaacgaga ctgaaagccg cgtgacgctg  41880
ttgttgctgc gggatgttca agggaccgct ggtcggtttc tgactgcccg aggataacag  41940
gccgctgaaa atgctggaaa caccgccacc actagcggcg cccttgccgc tagttcccgg  42000
tttcttgatg ggcgtaaaga tgtttttctc gtcatcatca tcgtcgtcgt cgtcctcatc  42060
ggcactggag ccaaagagcc tccgggaggc gcccggttta cgtgtcgggg gcggcggttg  42120
ctgctgacgt tgctgcaggt tctgctgcct ctcctcccaa gccttcagct gctgtttctc  42180
acgctgcacc acctcgtcgt ccacccgttt ctgccgctcg cgacgctttt cctcttcgtc  42240
gtaatagccg acggccgccg aacgggcagc gtgggcttcg gcggccggtg ccagagaacc  42300
atgggcctcg aagcggaacg gtttgtgtcc cttccaggga ctggcgatcc agctccagcc  42360
gtccagcggc tgcgtgggga catgtttctt gggtaccgac gagaaggctg aaccgccgcc  42420
gagcgagagg agattggcgt catcatcaaa ctccaacgac ggcgagcgcg cgcccaaaaa  42480
ggtgtgcgcc gactgcggga agctgtccac gtagatgtca aagtcctcga tgagcagctc  42540
cagcagcgtg tcggccgagt cgccgttttc cacggcgtgc ttgaggatat tgcgacagta  42600
gttggaatca aaggaaaggc acatgcgcag ctccttgacc agcagcttgc aacgctcctg  42660
aatgcgcgcc agacatttgc gctccagctc ctcccaagac ctgcgcacgt tcatgatgag  42720
acggcccgtg tacacgagct tgttgacggc gttgaccagc gccgtgttgg cgtgccggtc  42780
caggttaagg tcgagcggtt tcgcacagaa catgttacgg cgcacaccct ccaggttttc  42840
```

```
ttcaatgcgc tgcacctccg tatccttgag gtgcacaaag gcgatgggtt ccgtctggcc  42900
gatggctgtg accagcgtct cgcgcaccga catcttggcc agaatgaccg cgcttacgag  42960
cgcgcgctcc acgatctcgg catcgtggcg cacgtccgta tcgaattcgg tacggtctag  43020
cacagccagg tggtcacgcg ccttaccacg atcaccgaac gggtaagtgt agccgcgacg  43080
cgccacggcc gcgcaacgca cctcgaactc ctcgagcacc gaggaaaggt cggggttgtg  43140
gaaacgcagc tcgcggtagt atcccaacca aagcatgagc tcgttgaaca gcaccgtacg  43200
ccggtgcagg cgtttttcgc cgcatttttt caggatcttg ggtgtgcct cgagatccac  43260
gtcgggcttt tgcgtgagat ggcgcagaaa gttgaccagg gctaccacat cgcgccgctg  43320
tagaccgata aactgcaaac tcatgctggc ttttctccag aacccggaag cgtcgtcgcc  43380
ccggactgcg cccgcggtct gctattcgtc cacgatggac accatcatcc acaacaccac  43440
ggtgagcgcc ccacctagag ggaggggggg tagtttaata gcggaggcgg atacgcggtt  43500
ttcacccggg cgccgctgac ttgtttcttc tgttttttac tccgtatgct gttccgccca  43560
gaaccgcagt accgatactc cgcatgtcaa catcacctgt aacataacgg agccgctatc  43620
cgccatccgt accacagaag ccgtgatcaa cacgttcatc attttcgtag gcggcccgct  43680
caatgccata gtgttgatca cgcagctgct cacgaatcgc gtattgggct attcaacccc  43740
caccatctac atgaccaacc tctattccac caacttcctc acgctcaccg tactgccatt  43800
tatcgtgctg agcaaccagt ggctactacc cgctagcgtg gcttcgtgca aattcttgtc  43860
ggtgatttac tactcgagct gcacagtagg ctttgccacc gtagccctga tcgccgccga  43920
ccgataccgc gttcttcata agcgtaccta cgcgcggcag tcgtaccgct ccacctatat  43980
aattttgcta ttgacctggt ttgccgggct gatcttttcc atgcccgcgg ctgtctacac  44040
tacagtagtg atacataatg gtacaaatgg acaaagtagc aatggacacg ctacctgcgt  44100
attgtacttc atagccgacg aggtgtacac ggtactactc tcgtggaaag tgctgctgac  44160
gctagtgtgg ggcgccgcgc ccgttatcat gatgacgtgg ttttacgcct tcttctactc  44220
aaccgtacag cgtgcgtctc aaaaacaaag gagtcgcact ttaaccttcg tcagcgtgtt  44280
actcatctcc ttcgtggcgc tacagacgcc ttacgtgtcc atcatgattt tcaacagtta  44340
cgccacggcc gcatggccca tggactgcga acacctgaca ctgcgacgca ccattggcac  44400
gctgtcacgc ctggtacccc acctacactg cctcatcaat cccattctgt acgcgctgct  44460
gggtcatgac tttctgcagc gcatgcggca gtgtttccgc ggccagttgc tggaccgccg  44520
cgctttcctg agatcgcagc agaatcagcg agctacagcg gagacaaatc tagcggctgg  44580
caacaattca caatcagttg ctacgtcatt agacaccagt agcaaaaact gcaatcagca  44640
cgccaaacgc agcgtgtctt tcaattttcc cagcggtacg tggaaaggcg gccagaaaac  44700
cgcgtccaac gacacatcca caaaaatccc ccatcgactc tcacaatcgc atcataacct  44760
cagcggggta tgagctttcc tgttacttta ttcagaaagc accagaaccc gtcgccattt  44820
cccctcatat acggtacacg tccccctgat ctgtcatcac ggtacacaga tttcgcccga  44880
ctgcggacgc cgacggccaa tcgcgtggcg taggagtggc gccccggctt cattataacg  44940
ccacgtcgga gcccctgcgc gccacaacgc cgtccggcgc aacttctgtc tcggcacggt  45000
acgataaaaa cgacgtcccc cgtcgacgtt gttttctccg agcggtgatc gttcccgtcc  45060
ctctcctccc tccgcggccc ccacggcggc ggcctgctcg cacggaccta tactattacc  45120
gccccaccgc cgtcgtcgtc atgaacttca tcatcaccac ccgagacttc tccaacgacg  45180
```

```
attcagtcct gcgagccgcc gagatgcgtg acaacgtggc aggctcgatt tccaaagcgt  45240
acaagggcac ggtacgcgcc gaaggcaaga agaagctgct gctgaagcac ttgcccgtgc  45300
cgcccggcgg ctgctcgcgc cgcaacagca acctcttcgt tttctgcacc gagcgcgact  45360
accgcaagtt ccaccagggc atcgcacagc tcaagcgcgc gccggccgaa ctggaccccc  45420
acgagatcca gcaagtcacg gccagtatcc gctgccgcct gcagcccagt ctccgcgagc  45480
cgcccacgcc ggccgacgag ctgcagacgg ctgtgtcgcg cgtgtgcgcg ctcttcaacc  45540
agctggtttt cacggcccag ctgcgccact actgcgagca ccaggacaag gtggtgagct  45600
acgcgcgcga cgagttgacc aaacgctgcg gcgaaaaatc ggcgctgggc gtagaggtgc  45660
atcaactggt agccttgctg ccacacgagc gccaccgcga actgtgccac gtcctcatcg  45720
gcttgttgca ccagacgccg cacatgtggg cgcgctccat ccgtctcatc ggacacctgc  45780
gccactacct gcagaacagc ttcctacacc tgttgatgaa ctcaggtttg gatatcgcac  45840
aagtcttcga cggctgttac cacagcgagg cctaccgcat gctcttccag atcggtcata  45900
cggactcggt gtcggcggcc ctggaactct cacacagcgc ggcggccggg ccgcccgagg  45960
ccgatgagaa caacgacgag ggagaggagg acgacgacga gctccgtcac agcgacccgg  46020
cgccgcttca cgattccaag aagccccgca acgcccgtcg tccccgcaca cgcgtgccgc  46080
ctcacgagca aaagcccgaa gaaaacgagg aggaagaaga ggagctgttt ccctcctgca  46140
aggcaaccgc agcattcctg cgggcagaac cctccgtctc caacgacgac ggcaacggtg  46200
gcgaacgctg cgacacgcta gcgaccgccc tgcggcatcg cgccgacgaa gaagacggac  46260
ctctagccag ccagacctct gtgcgagtcg ccgcgacccc ctcaccttca gtcacctcag  46320
cccttacccc cgtcacgtcc cccataaccc cgttgtgtat ttaacgtcac tggagaacaa  46380
taaagcgttg atttctcaag ttccgctctg gttttggttt cgttttcaaa gggggcccca  46440
tcatggccca gggatcgcga gccccatcgg gcccgccact gcccgttctc cccgtggacg  46500
actggctcaa ctttcgggtt gacctgtttg gagacgagca ccggcgcctg ctgctcgaga  46560
tgttgaccca gggctgctcc aactttgtgg ggctgctcaa ctttggcgtg cccagccccg  46620
tatacgcact cgaggccttg gtggacttcc aggtgcgcaa cgcttttatg aaggtgaagc  46680
ccgtggccca ggagattatc cgtatctgca ttctcgctaa ccactaccgc aacagccgcg  46740
acgtattgcg ggacctgcgc acgcagctcg acgtgctgta ctcggagccg cttaagacgc  46800
ggctgcttag agggctcatc cgactctgcc gcgctgcgca aaccggcgtt aagcccgagg  46860
acatcagcgt gcacctgggc gccgacgatg taacattcgg cgtgctaaaa cgagcgctgg  46920
tccggctgca ccgggtacgc gacgcgctgg ggctgcgcgc gtctcccgag gccgaggcgc  46980
gctatccgcg cctcaccacc tacaacctgc tgttccaccc accgcccttc accacggtcg  47040
aggcggtgga tctgtgcgcc gagaacctgt ccgacgtaac acaacgtcgc aaccgaccgt  47100
tgcgctgcct cacctccatc aaacgcccgg gctcacgcac cctggaggac gcgctaaacg  47160
acatgtatct gttgttgaca ctgcgacact tgcagctgcg acacgcgctg gagctacaaa  47220
tgatgcagga ctgggtggtg gaacgctgca accgtctttg cgacgcgctt tacttttgtt  47280
acacgcaagc ccccgaaacg cggcagactt tcgtcacgct ggtgcgtggg ctggaacttg  47340
cgcggcaaca cagcagtccg gccttccagc cgatgctgta caatctgttg caactactga  47400
cgcagctgca cgaggccaac gtgtatctct gcccgggata tttacatttc agcgcgtaca  47460
agctgctgaa aaagatccaa tcggtctcgg acgcccgcga gcgcggcgag ttcggggacg  47520
aggacgaaga gcaggagaac gacggcgagc cgcgcgaggc ccagctcgat ctcgaagccg  47580
```

```
atcccacggc gcgcgaaggc gagctctttt tcttctccaa gaacctgtac ggcaacggcg  47640

aggttttccg cgtgcccgag caacccagcc gctacctgcg tcgacgtatg ttcgtggaac  47700

ggcccgaaac cctgcagatc ttctataact tccacgaagg caagatcacc accgagacgt  47760

atcacctcca gcgcatctat agcatgatga tcgagggcgc ctctcggcag acgggcctga  47820

cacccaagcg cttcatggaa ctcctcgaca gagcgcctct gggccaggag tcggaacccg  47880

agatcacaga acatcgcgat ttatttgccg atgtttttcg ccgtcctgtg accgacgcgg  47940

cttcttcgtc gtccgcgtct tcgtcgtcgt cctcagcatc tccgaattct gtttcgctgc  48000

cgtctgccag gtcgtcatcc acacgaacca ccacgcccgc gtccacgtac acctcggccg  48060

ggacttcttc taccacgggt ctcttactct cctcttcttc tttgtcgggg tcgcacggca  48120

ttagctccgc ggacctggag cagccgcccc ggcaacgacg ccgcatggtc agcgtgaccc  48180

tcttttcgcc ctactcggta gcctacagcc accaccgacg tcaccgaagg cgacgcagcc  48240

cgccacccgc accccgaggg ccggcccaca cacgcttcca gggacccgac agcatgccga  48300

gcactagcta cggcagcgac gtcgaagacc cgcgggacga tctggccgaa aacctacggc  48360

atctctgaac gcggtttttc ctctttttct acgtgtctgt ctcaggacga gacgtcgata  48420

tcaataaaaa taccgtcgac gtggttttct aacagcgtgg ttttctttat tgaccagcgg  48480

agtacacagt ttacgagtaa aaaagacagg gaaaggttat ataaaatgct gtgttatata  48540

caaaaacatg cacatagaca gacagaacca ccgtgctcgt cgtcccctcc ttaatcagtt  48600

gttcatgtag gcgtgtggcg gggtgagggg cggcatgccg ttggcggcgc cgggaataat  48660

gtgccgtcga ccgacgtcgc acaccttgaa acgccgtcgg cgcacgcagc ggtcgcagga  48720

cgggatatcc cagaggaagc ccatgtaggt ctcggggtcc tcgtcgtgaa agcggtaaga  48780

gagttcaaag tggtgcaacg agcccgtccg agctcgcagc ttctggcgaa caccctccac  48840

gtcatcggtg cacagcgaca gtgctgggct gtcacacagg gcctgaagct cctgcggcca  48900

caggtgcgta gccaggggcg agtccgtcgt caccagtttg acgcagtgca tcaggttctc  48960

ggtgatggcg tcgtacaggc gactctcggc ctcctcgtgc gtcatcacgt ttcgaggcag  49020

cgacagctcg tcgtcgtcat cctcgtcaaa catgatcatg gggtcagggg tttttttggg  49080

atgttgacag gtgggtgtct tttccagacg cacgatggcc tcacgccggc cgctgaaacg  49140

gtggtttcgg tgtcccttct ttcccatgac gcaggtgaac ataaccacgt cctcggccag  49200

acggtagacg gcgtccatgg cggggtcgta gccgtagacg acgccgaaag tgtccaccaa  49260

gacgtactgg cgtacgagga actctttgcg ttctggcacc tcgtggccca gcgcgcccaa  49320

caactggtgg taacaggtga tgcgcggcac ggtacggatc atgagctcca tggtctggat  49380

gctgccgccc gcgcggacga cgctgaaaga tgtttccttg aacttcataa cctctgtgtt  49440

gtgggtccag aaggcgaaat gggtgtcggg acactcatcg aaagggtcgt cgatgctgta  49500

ggaagcgtag ccccgcttgg tcacctcggc cgacaggctc tccacgtcgc cgcggtagag  49560

cataacggcg ttccagtagt cgtcatactg caccatgggc cgctggtagt cgcgcatagt  49620

gtggaagtgg tcgcagtgac gaaagccatg ccgcagaaaa tccttcatgg tgggcgccag  49680

ctcgtagatg cagtcgcgca ggtcatcgta gcagtagatg ccgccgcgct gcccgatgag  49740

cacgatgagt tggtagcgca taaagcccgg accctcgacg aagccaaagg ggtgcaggta  49800

ctcctgacag cagacgtaag cacctggtag agaatagaaa aaatccacgc acgttgaaaa  49860

cacctggaaa gaacgtgccc gagcgaacgt cctctttcca ggtgtcttca acgacgtggg  49920
```

```
gcttaccttg cgaacagacg gtgcccatct tgcccacgaa gggccccagg gcgctgcgcg  49980
aacggagctg gatgaagcag cgttcgggcc aggccacgtg cagccgggtg ccgcattcct  50040
gctccagaaa gtcgttgaga ccgttgaagt ccccggctcg gatggcgatg cagccgtagg  50100
ccatcagcgt gtcccgtagg tcgtccatga cggactcctc taccttcgct cgccgacgct  50160
gcgcttctcc agccaccgct gcggtcgaca gactcctccg tccgccttcg gagaactacg  50220
gcgcggcggc acggccttta tagacactat cagcgttgac gtcagacgat ccaatgaacg  50280
tcgtttttttg tgctggaact tccctcgtcc cgacaaatgt agcggaaatc ttcaagcaaa  50340
tcgcgacgaa gtccgatgag gaggatgcag aagaggctga gcaacgcgat gctgcccgcc  50400
gccacagtac atatgctcaa caacgcccag tgtcccaacg cgcgactttt ggctcggagc  50460
agagccgaac ggcggttttt ccacatgatg gataacgtag tccaatattt ccacccctgg  50520
cattgttgta gtgtccactc gggaagcgac gtcacgttag ttcccgtaaa agttgtgttt  50580
cttctgttgt ttttcgcaag cttaacgctc ctcttaagaa accgcggaca catgtcttgt  50640
agaaaaatgt aatcactttc cgcatatacc gttaagactg acatcacggt gacggtgttg  50700
ttttccgaag acgtcgcgtt gtcggtgacg ttggtttcct cccaatttac ggatgactca  50760
aacggactcg tgcgcgccag tgcccgtaat acgtaactgc ggccggtaag gttaagcgtc  50820
agctgtccca tggtaatgtt agtgtcattt gtaaaacacg caacctcccc gtagacctcg  50880
gtgacgttga tatcgcggct ctcgttcagg atgcgcaggg gaaaccagcc ttccaggtgg  50940
tactgaaaac caaacgtgag catgacgctg tgccactgcc gacgtgattg ccgaaacgtt  51000
acgttcaagg gcagtttgga ttcggctccg gcgcaggggc cgttgtagat ttgcgtatga  51060
ttgcacgtgc agtttaaccg gcagttcata ctcgtggcgt tggaagtgac gttaatgtcc  51120
gtaccgtggt acgtacatcg aacagaaaca ccgtatcccg tgctccaaaa cagcgtcaac  51180
aacagccaca cagacaccta cgtggggacg acacgggact ttttattgac ggagactcac  51240
gtttctgccc tccccttcc cgtaggtaaa aacccacgtt tatcacacac gttgttttta  51300
cctgaaaccc gcgcagcccg tggacgcgac aaaaaaccgc ggcactagaa agaaaatgaa  51360
acaagtatgt ttattaagca gcatgtgggg ctaatagggg ggataactga ggtatagcaa  51420
ctatgaaaaa atactacaaa aaaaaagctg aacatggtca tctagcagca aagttctcct  51480
tctagaccac gaccaccatc tgtaccacgt cgccctcccc ggccgtgtac atcacatcct  51540
tcaccacgac cggcggcaac ggcggcgacg aggacaactc gctctcgacg gaggccggga  51600
cgacagagga cggggggtg gtggcggcgg aggacggagg ggtggcggcg gcagcggggt  51660
cttcttccga cacgggcgac ggcaggctcg gcggcgcgga cagcacccgt tgcgccggag  51720
cgtgagaagg ctgagccccg gtggcctgga tgtgggccaa cgaattggct cgcagcgagt  51780
cgcgatccac gaaggtcata ggaattttcc cttcgcggat tcgccgctca gattccagga  51840
tggcgcgcac gtagctgttc accgacttgg caaaagtgcg cggcccctcc gtattcttgt  51900
cgcgacgcgc ttccagcacc tgcttttcgt agtccagctg gtggaagacc atcaccaggt  51960
cgtccatagt gtgcgcgtgc tgacggacgt gggagcgcac ctccaccggg aacaaagcgt  52020
tccaatactc cagcactatg gcaccgtgcc agaactgcgc catgctgggc gccaggaaaa  52080
acaggatacc ggagtcgtag gcgaacacgt cccacttggg cgtcatgaac aacaccagct  52140
gacgcgtggg ccgcaccgaa gcttcctccc aggcctcgat gaccccgaac atgatgagct  52200
cctggtccaa cgggggcag tgtcgctcca gccaactgat cttgctcagg ttcatctgca  52260
gaaactcgta agaggggtcg cagatgcaca cgtagagacc cgagtcgtgc cgcagcctgg  52320
```

```
ctccgcgctt catcagtttc ctcaccgcgt agcgaagcgc caccttgccc aacgccgacg  52380
cctggatcag tccccccacg tccatctgcg tctgtcgcca ctcggcctcg tccagcaggc  52440
tcatgatagc ggcggtgcta tgcgtggtcg tagtcatcct ttctatcctt ctctatgaat  52500
agcagcaata gcggtaaagt cccttcttat actatcccgg agtctgtggt ttttttgttt  52560
acccctgctt actggtgaga ctgctggggg ccgttgtgct gcagcagccg agctcgtcgc  52620
cgccgttgcc acaggaaccg gtgcctccgc agggcctttt tgagagcctc gcaggcttct  52680
cgcgcaagtc ctgagaggcc ctcggcgtcc atggggttca cctcgggcgt ccgagcctcg  52740
ttttcttctt cttcatcctc cctttcctcc tccgtgtcct cccgctctgt gtcctccgtt  52800
acgctctcct ccccggcctc ggccaagagc gcggccacca agtccacgga ccgctcggtc  52860
tccgagttct caccgtcaat tacgccatgt tggcggcgta accggtgccg agaacgccgg  52920
gtgagcgcac atgctttttt ctttcttaac caaggcggga gaggatcttc aaggcgtttt  52980
cgctggatcc agcggtagct aaagtaccaa aaggccagca ggcccacgct acctaacaga  53040
ttcacgtaga ctggagacat aattaaagaa agaagtgaaa cccgcgtgtg ggtctcacgt  53100
cgtcttgaaa caccgtctta tatacatgaa gatgccggac atgacgcgcc caagacacgt  53160
ggggttttcc ccttaggcga cccggtttct taagatgttt ttcatcttcg cacgcgatgt  53220
actacatcaa agggtcggct gaccgaccgc attgacgcac agtttccgag tacgcgcgtc  53280
tcggagcacc tgacggtgaa ccacccaact cacgcggata ggggacaaca ctgacgtgag  53340
gggcgattca cgtcactgac ggctgacggg aataagacgg gtgagggatt tccacatttt  53400
tcttaagtgt gactctcctt acggtaaatc gcacctgtga cttcttaacc cctcctccct  53460
ggtacccgat aacagtgaaa aacacacacc acacgtcacg acaccgatcg attttcttta  53520
ttcttagtgt gatgataggt aagggcactc gtgaggatgt gcagttatca ttatcaagcc  53580
ttcttcaagg cgtagtgatg atcgttgggc agaacccccca ggctcctagc gatctgggaa  53640
tagaaggagg agaacgaccc caaggccaga atgcccacag tgtacatggc ccaggtctcc  53700
agaccgaacg tggcgggtcg cagcttcaga tggtaggcca cccgctccga gagttgtgaa  53760
tgctcgttca ggcaacagga ctgcaggtgg gtgagcccaa aagcgctttc gtttacgccg  53820
cgcacgtgca ccgtctgggc cgggcaatcc tggtgttgcg cgcgaaaatg gtcctgacag  53880
gagattccgt ctacgtggcg acgcgtgttg ttacccactt cgatcagcaa cgtgttatcg  53940
gcaggatgat gcgagaacgc gacgacggtg ttgctggagg tctggcggca gcagtacacg  54000
tcgagcgtca tgaggaccat gtcgccttgg tggtacacgg cgtacgccca accctggaac  54060
acgagcggac atagcggacc gtgagcggac gtcacgccgg cggttgttac cgtcgtctcg  54120
acaggagaag acaataaact cctgatcctc atacacagga gtccaaccgt cagaattaaa  54180
gtccgcggag ccataaccgc gcaagtgaag ccgatacgag tgttgctgaa tttgttcatt  54240
ctgccgactg ttgctcacga gcgttcggag gcggtgccac aggctgttgg ccattaaaaa  54300
gtcctggccc gaatgacgac gagacagagc ccgaggcgaa gaaaaaggcg cccgtcatga  54360
agacgtaggc aggggaattc ccatattttt atggcttctt ttaaaagtct gtatccgact  54420
ccatccggcg cttttcccaa accgtggtct cctcgtcgtc cgactcggta cccaggaggt  54480
ggtaagtctt ttgccgcacg tagaaagctt tcaacgtgga gcaaaagatg agaataaaga  54540
ccccgaaaac gaaacaaacc acgccgatca tgccgatgca gacgttcatg tcgacgtagc  54600
cggcggtgct gttggcggtg cggcaaaaga gtgtcatgtc gtgcgtgcac aaaaaacaac  54660
```

```
acacaccaca ggccaggtcg tagcgtagtt attattccgt agcagcaatg atggtacagt  54720
caagcacatg ctctatcccc gttaccccga tgatgcttgc gtccccgttg ttatattggc  54780
actgtcccgg ttaatcacca cggtgaacac cacggccaag aaaatgatcc ctaatatagc  54840
gaccactaag agagcaaaag tccatttcca gccgttgtca aagtacgccc ccgtggtggg  54900
atgcatggtg gcgggcattt ccatcatatc catgtcgaac gtgtgtcgcg gcgacggcga  54960
actaaccagg cagtacgggg gtcgataggg cggtgggctg cagtcgggtg gtggcggcgg  55020
tggcgtggaa accgtcgtcg ggcacagacc catggcctgc tcgtaggtgg ggggcgcgtc  55080
gtcgtgatcc cggtcgcgga gcatcggcgt gggctccatg tcggtggcag tgacggcgac  55140
ggtggtaact gtggtggaga cggtaccgac ggcgtccgcg gctcaccttc gagcaaagag  55200
ccccttcttt ttgcgcaaac gacgacaaaa cagttctctg ggacagccgg tggcgcggta  55260
agcgggtgcc acgctttcag ggtgggtaaa acagtcgcgg gcgaagcagt agttgttgca  55320
gaaccgcaag aacccgacgc gaaagaagcc caggagtccg cgcgccagaa agtgcgcctg  55380
ccgcgtatcg ggatgcacgc cgaagacggc gccgctctcg ttcaccagta tggagatgtc  55440
caggcgctgc tgcgactcca ccggcacggc ccgcaccaca aatacctgca gcacgttcag  55500
cgagcacgtc tcttttaacc agttgccgtg ggccggatcc tcgtaagtct ggctcccgtt  55560
caagacgacc gtcgtcagcg cctcgttacc gtctcgccag ctgaagatag aaccctcgcg  55620
cttcatgcac aggcgccaca gggccagcag gtcgcgcgcc aacatgaact cgcgacccac  55680
gtcgccgccg gtctcgaagc ggacatagcc cagttcttcg cgcagcggcg cgtagttgcg  55740
caggccctcc tgcacgaagc cgcggaaacc ggaccgcgac accaggtaca gcgattccac  55800
cacaggcgag tagacgtaga cgcgaccgcc ctcgccgatg agtacgggta gcggtgggcg  55860
gccgatggct tcgcaacgac tcacagtgcc caccggcagc aagaacttgt cgcagcacag  55920
gaaggtcttc tccaaacctt taatattgag atgtccaaag tagccgacgc gtaacaggtc  55980
gcagtaggtg aagaaccaac cgtttggcca gctgagacgc agcaccgtgc cgctgacgcg  56040
acgaaccagc ttctgcaagt ccttgcgggc gtcggaggtg acagagcagc ggaaggtctc  56100
gttgaccagc tcgacagcca gcgcgtcctc cagcgtgcgt tccttcatct cgtcgttgat  56160
gctctggcgg cgccgccgga tttcgtcgaa acgggccgcg gaggcggcga ccgacgcgga  56220
ggtcgtccga acgccctctg tgacgctgtc gtccggccag tcaagaaagc taaggctggc  56280
gctgcgccgc ctaaagtgtc cgatccgcgc gggacgtcgc tgagggacgg tggctggtct  56340
gctggggcgg gtacggccgc gggtgtccgc ggacacgtta gttatacacg gaattgagtc  56400
acgtggcacg ttgccagctg aaaccgccgt cgtctccgcc ggcgttttct ccatcgcggg  56460
accgcgccgt gcgcacgttc ccaggcacgc ggcccacgct ctagccgcac ttttgcttct  56520
tggtgttagg gacgaactcg aacgttacag aatcctcgct gtcgctctcc tctttcgcgt  56580
cgttgaagta attgccggag ttgcgatcca aaccgccgcc tcctcctccg ccgccgccgc  56640
ccgatccacc tttggacgtc aggtagctgg tgatcttgtg ctgctcgtat ttttccttgg  56700
aggaaagacc gtggtcgtga tcaccgccgc cgccaccgct gctcattttc cgcgtaccgg  56760
aaccaccgcc gccaccgcgg tcgtgcttct tgccgccacc gccgccacct cctcccagac  56820
cgccgagacc catgggctcg ttcataatat cgttatccag acccgggccg tcgtcgtgca  56880
gaccgccggc attagccagc gaagagaggc tgccgctacc accgccgccg ccacgcgatt  56940
tgccgctgtt cccgacgtaa tttttgtcga agggatcgcc acgctggaaa ggttcctcgg  57000
tgagaaaatt ctccacggcg aacagaccgt tgcggctggc cacgtacaac agcgtgtcgt  57060
```

```
gctccgtaac tatacgcaac gtgcacggca gtttggtgac ggcgcaattg agcagcgtct  57120
ggtagaagtt cttcagctgc acgttgatac gcatgttttt cacgccgtgg aaactgacgc  57180
ggttattggc tgtgaattcc agctcgctgc cgttggtcag gataaacttg atggccggtg  57240
gaccggcgtg caccagaatc tgcacggtgc ccgtagggca gggcgctttt ttaacgttac  57300
gcttgacgcg ggtatgcggc ccgatccact taagcaggtc ggccaccacg ccgaaatcta  57360
gatccacgtg cacggccgaa ttctcgcttt cgcgcacaat gtcttggccg tgcacgcagg  57420
ccgagctgaa ctccatattg aaatcgggcg cgcacatgga gatcttggcc gacaggtccg  57480
agatgtcctg cacgtagaac ttggtcaggt ccttgctgga agtcaggtac atgaaattac  57540
ccagcagcgg cgtggaattg ttaatggtct tgggctgaaa cgacttgtca gtgatgtaga  57600
ggcatgagct gttaaaagtg atttttgaca cgcagtgact gcgtaccgtt tgcaagataa  57660
gcgacggcgt gggcaagaag gtaaccgtgg tgttctcctt gagcgcacgg atcacagatc  57720
gcagctgctg gatagccgtc ttgtacggct tcagccgcag cgccagcgtc ggcggctccg  57780
agaggcgcgt cttgcgatcc atcccggaca gcgtgcaagt ctcgactaag gagcgggcgc  57840
gagcgagcga aagttttata gagagcacac acgacgaccg ggaacgctgc gaagacgccc  57900
ggcgtctaat aatacagccg cgccgagcca gcgggccccc gactaagagg cacagtactt  57960
atatactccg accttaaagc gccagtggta ccacttgagc atcctggcca gaagcacgtc  58020
gggcgtcatc cccgagtcat agtagaaaac cagggccacg cactggtcca caaacacgct  58080
caggttcacg gccgccattt ccacgtcgtt ttggatcgcc ggtgccgcct ggaacagaca  58140
ctgcgtcgcc ttgccctcct cctggtgctg ctccaaccac gcgtaattca ccacgggcac  58200
gcgcagcggc ctccgcacca cggtggggaa gtaacactca cggttgggcg ggcacaatga  58260
ccacaccgtc tcctcctcga acacggtgcc gcgcgaagcc cacactgacg gcgtcacgcc  58320
ccacagatgc gccacctcgt cgtcgggacc caccgccaga aactgacagt tgcgcaatcc  58380
gaactcgagc atgtcggcgc gcagcgcttc ccagcgcgcg ctggcgatgg agagccgcgg  58440
caaccgatac aattcgaaaa tgaatttgcc ctcttgatag atggtgcgtt cgaaccactc  58500
gcagcgcggc aaacccgact tgcacaaatc gacgctagcg cgcaccgcgg caaagtacat  58560
gtgctcaaag atgcgctcga tcaagtccca agaggcaaag tacgtgaacc ctaaccgcat  58620
gagcgccgtg tgcaagccag ccacgccgat gtgcagcgga cgcagttttt ccagcgcgct  58680
ctctacccac cattcggacg ccgacattag cgcgtccaag cgcgcgttgc cccaaaccac  58740
cgcctcggtc accaactcgc gcagcacgct caaatcaaag taacgtcgcg tgttccccaa  58800
aaccacgtcg ggtagatgca gcttctgctc gtcgctacgc gcaaacacgc agcgagccac  58860
gttcaccgtc agccgctgca ccggcatgtc acactcgcca aagtggcacg acgccatatc  58920
gggactcaag cacggcggca ggcacacgct gtcggccata atcgagtact tgactacgtg  58980
atggacaaag accaccgagg cacggccctt gagcgcgcac agcaacatct ttttcagaaa  59040
atcgtccgtg ttcacgacca ccttggggca cgattgctcg cagcgcgaat actctttctc  59100
gaaagccgac tcctgaccca ggtccgagag ccgccgggag acaggccgcc caaacagcga  59160
gtagcgctgc tcacgcgcac ggtagcgctt cattaacacg ctaggcacgt tgaaagcgta  59220
gcaaaccccc gtcaactccg acgtgctttc tttgagaata aagttaatca cgcggatagc  59280
ggccacgtcc cacatgtcca caaacacacg taccacgggt cgatgcacct ccttctcgcg  59340
tatcaaatcg cagtatcccc ccaggcaacg aatcacgctg ttcacatcgg cgttaagtcg  59400
```

```
cgttacgttc accgacacag aaacgccgca actcaaggta ctcatccact tgcacatggc  59460
cgcccaactg gcgtcacgcg agaaagggtc ggccgagatc agaaagtcgt actgcggcac  59520
gcgatcgaaa cccacggtag acatggtgaa ggtggacagc gacagctgcc catcgcgaca  59580
gcgcttcaac accgattcca acacctcgcc ctcgaaacgc gcatccagat ggaaacgata  59640
gatgcgcgag tgcctactgt tctcgatagc ggccgtcaac gccacggcga tgcgcaaaaa  59700
cacgccgccc gggctctcgt cctgtccgtg cagttggcga cacaccttat ccaaacacaa  59760
aatggccgcg tacaagcccc agcaaccggc caattccaca aaacgcgccg tctcctcggc  59820
cagcttgggt agatcctcca tgtgacgcag cacaaaacgg cgcaccgact catcgcacag  59880
ctccgaagcg taacacagtg gcgtgcggct ttcacgcgcc cagttggctt tgaaataaaa  59940
gcgacccaac agcaggtcgc aacgcggcga gtgacgaatc agacagggac cgtggcgcat  60000
aatgagctga aatagcctga aactgcccaa accggcactg tgccgcgaca cggtgtccat  60060
ctcgcgccac agcgcgttcc tgtcggacgg cagctcccgc gccggctcct gtacgccgca  60120
aaagcgaaac ttgccccagt agccgtgaca atgacacttt ttgcccatca acatgcgcat  60180
agcttgtatc ggcggcgata ctttgcagag cgaagccccg aaatcgtcct cctcctcgac  60240
actgtccagc tccatcctgg tcgcgccggc cggattaaag gtgctcagac cgctactcac  60300
gcgtccaccg cgactgggca cggcgggacc gctgtcacgc gtcaacgaca gcacagacgg  60360
cgtgccgtcg ggagacggcg actcgggacg ccaactgacg acgccgccac cactcgtaaa  60420
acccgctaca catgctacac cgctcgatac gttggtattt ccagcggacg cttccttgtc  60480
acccccgggc agcggcccct cctcgagctc gctgtcatct cccccgatag tatcagcggc  60540
gacctctgcc gacgattcct ccgtctcggt ttccgcgctg cggcttggaa tcctacctgg  60600
ccggcaccga tgtgcgggca ccgaggacac ccgctgttcc tcgtccgcgt cagccggatt  60660
cataagttta cgaggaaaat aacaaagaaa tcaggtagat ttcaataaag tgagtctaga  60720
tggcgccgac aactacggtt tataaagtct gtgtgcgatg tgttttttttc ttctgtgtct  60780
cctccccgta tgctgtcagc gccgctcaga cgaattctcg aaagtctccc aattcgacgc  60840
taaagttgtc caaacggacg acggacagtt tgagttcttt gtgtaccagg aacgaggtgt  60900
gaatgtcgtc agccaggcac cagcccagct tttgtatgac cccggtacac agagggatct  60960
ggcgcgggcg cgtgatgcga cggttgacaa agctacagcg ctcgcgggcg aactttccgc  61020
gtgcaacgtc gaccaaggtc tgccagtgtg cgatgctgga ggtgagcacg tagatgccgg  61080
gacgtgtttc gggcccgtca tagtcataga cgatgattaa atacacgtat tgcagccgtc  61140
cccgggtctc ttcccacgtc aggtacatgt ctttcggtat catcaacgcg aacacctccg  61200
ttttgagcgt gttgtaaagg tagccgcgca tgacgcaggt gagcaacgag gtgatgccca  61260
gcgagacggt cttgacgcag cccagcgtct cgaggcggcg gtgcagcaga tgcgggccca  61320
ggtccagcca ctgcagcgcg gcgcgcgcgg ccgaggccgt gtacacgctt tcgagcaggc  61380
agcgcgtgct ggccgagacg ttggaggcgc gaatgcctaa caggtaaagg ctaatgtaga  61440
ggtgtcgcgg cgagtcgcaa cccgtctcca tgcggatgag cagcgcgccc ggctgcgcct  61500
cgaactctac caggccctcg ggcacgaaga aacgcgccgt gagcgcctgg tgatcggcgt  61560
ggtagagata gcgaaccgat atagtattta cctcgcgttt ggctttgagc gccgtcacta  61620
gttcattgtc ctcgtcggcc gggtcgcgcg gccgtttggc caccgcgcgc gcgtccatga  61680
tggcgaggcg cacggtagat ttcaaaaagt tgatagagca gctgcgggca cgggccacgg  61740
acaaagcgga ggcgttaaat accgtgagcc aattggagat cggcgcggtg gatgcccagg  61800
```

```
acgtgaccgc gagcgccgtg cgcgccttcg tgggtgcgtt gccgagctcg ggctaccact  61860
ttggcttcgt gcgtcagaac gtggtctttt acctcctaag ccacgccacg gtacagacgg  61920
cgcgcgaccc gctgtacgcc gccgagcagt tgcacgaaca gctggaccgc ttcctgcgac  61980
accagcacga cggcggcgga gacgaggacc ggttgccgtt ctaccacaac ggggccacgc  62040
tgacggcttt ccagaagctg ttgcagaccc tgcgcgagat ccagaccgta atagccgaac  62100
agagcggcgg caccgcggcg gcggcggact tgatcgccag taacaacgcg tcgaccgagc  62160
gccgcggcaa gaagggcggt tcgagttccg ggggccagca gccgctggtc cgccgggtga  62220
tcacgcagct ggaaacggct gccacggagg cgcggcccta cgtcaattgt cgcgccgtgg  62280
ccgaactcct ggacctgacc taccagcggc tcatctactg ggcctgcacg ctcatgccct  62340
acgtgttgtt tcggcgcgac accgacaccg aactggacac ggtgcttctg atgcattttt  62400
tttacacaca ctaccgttcg gttaacggcg atttggccgt ggagtttcaa aactacgtca  62460
agaacagcgt gcggcacatg agctctttcg tcagttccga tatcgacggc gaccagaagc  62520
ccggtgccga acacatgcgt gacgtcagct acaagctgtt cgtgggtaat ctgcaagcgc  62580
gtgacgccag cggcctcatg tttcccatca ttagcacgcg catctccacc gtgaaccttt  62640
acctgtcgcc cgaacgtatg tttttccacc cgggtctgat ctcgcgtctg ttgagtgagg  62700
aagtttcgcc gcgcgccaac ctagacgctt acgcgcgcgt gtgcgatcgc gtgctggaag  62760
accacttgca tacgccgcga cgcgtgcaac ggctactaga tctgacgcag atggtaatgc  62820
gactggtgga actgggtttc aatcacgata cctgcgcggc ctacgcacaa atggcgctga  62880
tccagccggc cagtcagaag agctcgctct ttgtcagcga gattcgcgag aaactcatac  62940
agatcatcta caatttttac acgtttttca tgtgcctcta tgtgtacagc cccacgttcc  63000
tgttcgacca ccggcggcgg ttgattttgg agcagcatcg atccacgttg atcggctcca  63060
aggaggaact acagcacgtc tggagcaacg tgacactgaa cgtcaatacg cactttgcgg  63120
ttcagtacac ggaagaagac tttgaggcac atacgaaggg tgccacggag gcggagcgcg  63180
agtacctgta tcgggacctg cacagcaagt ggggcgtgca cctgtttacc ttgcgtccgt  63240
ctcgcggcgc ggccggcgcg gcctcgcctt tgcctccgct tgacggcgtc acacgctccg  63300
acatcttacg cgaatgcgcg ctcgttaatc tgaacgaagg ccgcgtcaac tacgcctccc  63360
tgctagcctt cagccatcat cccgagttcc ccagcatctt cgcgcagttg gtggtggtaa  63420
ctgagttctc ggagatcttt ggtatcccgc agggcctgtt tcaagccgtg ggttcgccgc  63480
gtcttttcgc actcattcag ctgtgccgtg tattgttgcc cgagcaggtg acgctgtacc  63540
agaacctggt ctccatctac aacctgacca ccttcgtcaa gcacatcgac gccgcggttt  63600
ttaagacggt acgcgattgc gtcttcgaca tcgccacgac tctcgagcac ctcagcggtg  63660
tacccgtcac gcccaatgtg gacctgctgg ccgagctcat ggcgcgctcc gtagcgcata  63720
acctgtacac caccgtcaac ccgctgatcg aggacgtgat gcgcagcagc gccggcagtc  63780
tgagaaacta tctgcgacat acgcgactct gtttcggtct ggcgcgtggc cgggcgcgcc  63840
tctcggagga cggcgtgacg gtgtacgtgg aggtacaagg tcaatacgga ctacgcgtac  63900
ccaccacgcg tttcgtagaa cagttgcgcg agctggttcg ccgcgatcgg ctgttggccg  63960
agaatctgcg cggcttgaac gagcgcctgc tgagtgttcg cgtgcgcgta cgtcagatca  64020
gcagcgacac agaggaagta agccgacacg ccaagggtca ccgcacggtg gcccagatga  64080
gcaaggcgct caaaaagacg gcctccaaaa tcaaaatgtt ggaaacacgc gtgacattgg  64140
```

```
cgctcgagca ggcgcaacgt tccaatggcg ccgtcgttac cgcggtgcaa cgcgcgctag  64200
ccgtctttga cgtactaagt cgcgagaact tggaacgccg cggcgcacag ctctgtctga  64260
cggaagcgac gagcctactg caccgacatc gcgcgctagc gccgatgacc tggcccgcgg  64320
gcacgggcgt tgcggcggcg gccgaagcgg atggcgcctt acgcgagttc ttggaggcgc  64380
cctgggaatc ggcgccccaa ccgccgcgac tccgcatgac gcccgacacc gatcacgaag  64440
aatcaacggc aggcgcgacg tccgtaccgg aggtcctggg tgcgcgctac gaacccgcac  64500
acctggccgc gagcgaccta ttaaactggt acatcgtccc cgtaagccag gcgcagcagg  64560
acatcttgtc ttcgatcgac ccgcccgccg gctcgacatc ggtgtccctg ccgccggcct  64620
cgccatgaaa gtcacacagg ccagctgcca ccagggcgac atcgctcgct ttggagcgcg  64680
agcgggcaat caatgcgtct gcaacggcat catgttccta cacgccttgc acctgggtgg  64740
aacgagcgcc gtcctgcaga ccgaggcgct ggacgccatc atggaagagg gcgcgcgtct  64800
ggacgcgcgg ctagagcgcg agttgcaaaa gaagctgccc gccggcgggc ggctgccggt  64860
ctacagactg ggcgacgaag tgccgcgccg cctggagtcg cggttcggcc ggaccgtgca  64920
cgcgctctcg cggcccttca acggcaccac cgagacgtgc gacctggacg gctacatgtg  64980
tccgggcatc ttcgactttc tgcggtacgc gcacgccaaa ccgcgtccca cctacgtact  65040
cgtcaccgtc aactcgttgg cgcgcgccgt ggtcttcacc gaggaccaca tgttggtctt  65100
tgatccgcac agctccgcgg aatgtcacaa cgccgccgtg tatcactgcg agggtctcca  65160
tcaggtgctg atggtgctca cgggcttcgg cgtgcagctg tcgcccgctt tctactatga  65220
ggcccttttt ctctacatgc tggatgtggc gaccgtacca gaggctgaga tcgccgcgcg  65280
tttggtctcc acctatcgcg accgcgatat cgacctcacc ggcgtcgtcc gagaaagcgc  65340
ggacacggca gcgacaacga ccaccgccgc accttcctta cctccgctgc ccgaccccat  65400
cgtcgacccg ggttgccctc ctggcgtggc gcccagcatt cccgtctacg atccctcgtc  65460
ctcacccaaa aaaacacccg agaaacgccg caaggacctc agcggtagca aacacggagg  65520
caaaaagaaa cccccgtcca cgacgtccaa aacactggcc accgcctcct cctccccctc  65580
agcgatagcg gcggcctctt cttcgtccgc ggtaccaccg tcctacagct gcggcgaagg  65640
ggccctgccg gccctgggcc gctaccaaca gctggtcgac gaggtagagc aggagttgaa  65700
ggctctgacg ctgccgccgt tgcctgccaa caccagcgcc tggacgttgc acgcggcggg  65760
taccgaaagc ggcgctaacg cggcaacggc cacggcgccg tccttcgacg aagctttcct  65820
caccgatcgt ctccagcagc tcatcatcca tgccgtcaat cagcgctcgt gtctgcgtcg  65880
cccctgcggt ccgcaatcgg cggcgcagca ggcggtacgc gcctatctgg gcctatccaa  65940
gaaactggat gcctttctgc tcaactggct gcaccacggc ctggatctgc agcgcatgca  66000
cgactacctg agccacaaga ccaccaaagg cacgtactcg acgctggatc gcgcactgct  66060
ggagaaaatg caagtcgtct tcgatcccta cggacgtcag cacggcccgg cgctcatcgc  66120
ctgggtggag gagatgctgc gctacgtgga aagcaagccc actaacgaac tgtctcaacg  66180
actgcaacgt ttcgtaacca agcgaccgat gcccgttagc gacagcttcg tctgcctgcg  66240
acccgtagac tttcagcgtc tgacgcaggt catcgaacag cgacgtcggg tgttgcaacg  66300
tcaacgcgag gaataccacg gcgtttacga gcacttggcc ggcctcatca ccagcatcga  66360
cattcacgac ctagacgcca gcgatctgaa ccgacgcgaa attctgaaag cgctgcagcc  66420
gttggacgac aacgccaagc aggaactctt tcgcctgggc aacgccaaaa tgctagagtt  66480
gcagatggac ctggaccgtc tgagcacgca gctgctgacg cgcgtgcaca atcacatcct  66540
```

taacggcttt ttgccggtag aggacctgaa gcagatggaa cgcgtcgtcg agcaggtact 66600
gagactcttt tacgacctgc gcgacctgaa actgtgtgac ggcagctacg aagagggatt 66660
cgtcgtcata cgcgaacaac tgagctacct catgacgggc actgtgcgcg acaacgtacc 66720
gctactgcaa gagatcctgc agctgcgaca cgcgtaccag caagccacgc agcaaaacga 66780
gggtcgcctc acgcagatcc acgacctgct tcatgtcatc gagacgctgg tgcgcgaccc 66840
gggcagccgc ggctcggcgc tgacactggc cttggtacag gagcagctag ctcagctgga 66900
agcgctaggc ggcctgcagc tacccgaagt gcagcagcgc ctacagaacg cgcaactcgc 66960
gctaagccgc ctctacgaag aggaagagga aacgcagcgt ttcctcgacg gactctcgta 67020
cgacgatccg cccaccgaac agaccatcaa gcgacaccca caattacgcg agatgttacg 67080
tcgcgacgaa cagacgcgtc tgcgactcat caacgccgta ctgagcatgt tccacacatt 67140
agtgatgcga ctggcgcgcg acgagtcgcc gcgaccgacg ttttttgacg ccgtcagtct 67200
gttattgcag caactgccac ccgactcgca tgaacgtgag gatctgcgtg ccgccaacgc 67260
cacgtacgcg cagatggtca agaaactgga gcagatcgag aaagccggta ccggcgcatc 67320
cgaaaaacgc ttccaagcgt tacgggagtt ggtttacttt ttccgtaatc atgaatattt 67380
ctttcaacat atggttggac gactgggcgt cggacctcag gtaacggaac tctacgagcg 67440
atatcaacac gagatggaag aacagcacct ggaacggctg gaacgtgaat ggcaagaaga 67500
ggccggcaag ctcacggtaa cttctgtgga ggacgtgcag cgtgtcttgg cccgggcacc 67560
gagccatcgt gtcatgcatc aaatgcaaca aacgttaacc accaagatgc aagacttttt 67620
agacaaggag aaacgtaaac aggaagaaca gcaacggcag ctactggacg gctaccaaaa 67680
aaaggtacag caggatttgc aacgcgtggt ggacgccgtt aagggcgaga tgctctccac 67740
catcccgcac caaccactgg aggccacact cgagctgctc ttgggcctag atcaacgcgc 67800
ccaaccgcta ctggacaagt tcaaccagga cttgctgtcg gcgctgcagc agctgagcaa 67860
aaaactagac gggcggatca acgagtgtct gcacggcgtg ctaacgggtg atgtagagcg 67920
gcgctgtcac ccgcaccgag aagcggctat gcaaacccaa gcctcgctaa accacttgga 67980
ccaaattttg ggtccacaac tcctgatcca tgagacgcag caggccctgc aacacgccgt 68040
ccatcaagcg cagttcatcg agaagtgtca acagggcgat ccaactacag ccatcacggg 68100
tagcgaattc gagagcgact ttgcacgcta ccgcagcagt caacagaaga tggagggaca 68160
attacaagag actagacaac agatgaccga gactagcgag cggctagatc gctcgctgcg 68220
ccaggatccc gggagcagct ccgtcacgcg tgtacccgag aaacctttca agggtcagga 68280
gctggcgggt cggatcacgc ccccgcccgc cgacttccag cggcccgtct tcaaaacgct 68340
gctagatcag caggccgacg cggcccggaa agcgctcagc gacgaggccg atctgctgaa 68400
tcagaaagta cagacgcagt tgcgacaacg cgacgagcag ctgagcacgg cgcagaacct 68460
gtggactgat ctggtcacgc gccacaaaat gagcggcgga ctggacgtga ccaccccccga 68520
cgccaaggcg ctgatggaaa agccgctgga gacacttcgc gagctgttgg gcaaagccac 68580
gcaacaactg ccgtacctgt cggcggagcg cacggtgcgc tggatgctgg cttttctgga 68640
ggaagccctt gcgcaaatca ccgcggaccc tacgcacccg catcacggaa gcaggaccca 68700
ctaccggaac ctgcaacagc aagctgtcga gagcgccgtg acgctagcgc atcaaatcga 68760
acaaaacgca gcctgtgaaa attttattgc acagcatcaa gaggcgactg ccaacggcgc 68820
gtccacgccg cgggtcgaca tggtccaggc ggtggaagcg gtctggcagc gactggaacc 68880

```
cggacgcgta gccggcggcg ccgcgcgtca tcaaaaagtg caggaactgt tgcagcgctt  68940
gggtcagacg ctaggcgacc tagaactgca ggaaacgttg gcgacggaat actttgcgct  69000
gttacacggc atccagacct tcagctacgg gctggacttt cggtcgcagt tggaaaagat  69060
ccgcgatctg cggactcgtt ttgcggaact ggccaagcga tgcggtacac gtctctccaa  69120
cgagggagcc ctgcccaacc cacggaaacc gcaggcgacg acttcgctgg gcgcctttac  69180
acgcgggttg aacgcactgg aacgacacgt ccagctgggt caccagtatc tgctcaacaa  69240
gctcaacggc tcatcgctag tctataggct ggaagacatt cctagcgtgc ttccgccaac  69300
acacgagacc gaccccgcgc tgatcatgcg cgaccgcctg cgtcgtctat gcttcgcgcg  69360
tcaccacgac acctttcttg aagtggtaga cgtcttcggc atgcggcaaa tcgtcacgca  69420
ggccggcgag cccatttacc tggtcaccga ttacggcaac gtagccttta agtacttggc  69480
gctgcgagac gatggccgac ccctggcatg gcggcgccgc tgtagcggcg gaggactcaa  69540
gaacgtcgtc accacacgtt ataaagccat cacggtagcc gtggccgtct gtcagacatt  69600
gcgcactttc tggccgcaga tctcgcagta cgacctacgg ccctacctca cgcagcatca  69660
gagccacacg caccccgcgg agactcacac gttacataac cttaagctct tttgttatct  69720
ggtgagcacc gcctggcacc agcgcatcga cacgcagcag gagctgacgg ccgccgatcg  69780
cgtaggcagc ggcgaaggtg gtgacgtagg ggaacagaga ccgggccgcg gcaccgtgct  69840
gcgtctgagt ctccaagagt tttgtgtact catagcagct ctgtaccccg agtacatcta  69900
caccgtcctc aagtacccgg tgcagatgtc gctaccctcc ctcacagctc acctacatca  69960
ggatgtaata cacgcggtag tcaataacac acacaaaatg ccccccgacc acctccccga  70020
acaggtcaag gctttctgta tcacccccac ccaatggccc gccatgcagc tcaataaact  70080
gttttgggaa aataaactgg tgcagcaact gtgccaggta ggcccgcaaa aaagcacacc  70140
atccctaggc aagctatggc tctacgccat ggccacgctg gtctttccac aagacatgct  70200
gcagtgtctg tggctagaac tgaaacccca gtacgccgag acctacgcct cggtgtccga  70260
attggtacag acgttgtttc agattttcac gcaacaatgc gagatggtga ccgaggggta  70320
cacgcaaccg cagctcccca ccggagagcc ggtgcttcag atgatccgcg tgcgacgcca  70380
agacacaacc accacagaca caaacacgac cacagagcca ggacttttag atgtttttat  70440
tcaaacagaa accgccctag actacgcgct gggctcctgg cttttcggca tacccgtgtg  70500
tctcggcgtg cacgtagccg acctgctgaa aggccaacgt gtattagtag cgcgccacct  70560
cgaatacacg tcgcgagacc gcgacttcct ccgcatccaa cgctcccggg acctcaatct  70620
cagtcaactg ctccaggaca cgtggaccga aacgccgctg gagcactgct ggctacaagc  70680
ccaaatcaga cggctacgcg attacctgcg tttccccacc cgcttagagt ttattcccct  70740
agtcatttac aacgcacagg accacaccgt tgtacgcgtg ctgcgaccgc cctccacgtt  70800
cgaacaggac cacagtcggc tggtgttgga cgaggccttc cccaccttcc cgctgtatga  70860
ccaagatgat aacacatccg cggacaacgt cgctgcgtct ggcgccgctc caacaccgcc  70920
ggtacctttc aaccgcgtac cagtcaatat tcagtttctg cgtgaaaacc cgccacccat  70980
cgcacgagtt cagcagccgc cgcgccgaca tcgtcatcga gcggccgcgg ccgcagacga  71040
cgacggacag atagatcacg cacaagacga tacatcaagg acagccgact ctgcattagt  71100
ctccaccgcc tttggcgggt ccgtctttca agaaaaccgg ctgggagaaa caccactatg  71160
tcgagatgaa cttgtggccg tggcacccgg cgccgccagc accagtttcg cctcgccgcc  71220
tatcacggtg ctcacgcaga acgtcctcag tgctctagaa atattgcgac tagtgcgatt  71280
```

```
ggacctgcga caactggcgc aatccgtaca ggacactatt caacacatgc ggtttctcta  71340
tcttttgtaa ccgacactga cagtagcggg caataaaaac aagaggattg ttatcgtttt  71400
ttatgataca aaacaacgtg tcactttcac ggtgatttat tcttgctatt acttttcccc  71460
atgggctgtc agcgtcgggt gcgcgacacg gctatcatgc gcaacaggtc cagcttaaag  71520
gcgcacttgt cgttaaacag actggacatg cgcgtatact tgctcagcat ggtggccagc  71580
accgggtggg tggcctctga gatctcggtc ggcaactcca aaacgacgtt gacgacgtga  71640
cggtgttttt cgtcccgctt gttggccacc gtgggtcccg gcgcggtgtt agacatgggg  71700
caggccgtgg ggggaggacg aggaggacgt cgctgctaaa ccgccgcgcg cctgctgcac  71760
aatgtggccg ccgacgtggc aggcggtctg tttaaccagc gcgcagcctc gacacagcgg  71820
ggcgccgtct tcgctttcca aacagctgtc gcggtactcg cccgtctgac agcgcgcgca  71880
cagcaggccg tgcccgtgcg aagtgagacg caggagacgc gggaccgtca cgccgcgtac  71940
caccacagtg gagtcgcagg tgcgtgccgc gcagggcaga atgacgtcga aagccagccg  72000
gtgatcgtac acggcacaag ccgcgttgag gcccagcacg gctttccagc ccacgcgtac  72060
gcagcgctgt ccaaagagcg tctcggagac gagctcgtag acgcgctgcc gcactacccg  72120
ctgactgccg cagagcgagc agtgtacgag ctcggcgtgc gtgttgaaga tgacgctctt  72180
ttcttgacgg tcccgataat agaacatcga gttgagcgga aaattttgct ggcagtgtag  72240
cttttcctta cccaggttga ggcagtgtcc gcactgccga cagaccacgg ccaccagcga  72300
gcgcgcatcc agatggcgct cgcacttgag tcgacacaga caccagagcg gcaggtcgat  72360
gacgctgccg atgaggccgc cgcgcagcgc ggcgctgagt gcaaagagga cgatcttggt  72420
gggctctacg tgatgcgcct gctgtccggc gcccgcgtgt cctaccgccg cagctgccgc  72480
cgtcgagcct cctccgcgcg tctcgtcgtg cagacccagt gcccgcaacg gcaccaggta  72540
tcgcggacac gtgtcgcaaa acgtctgcac cgcttgtcgg gccagtacgt agagcgggtt  72600
tccgcagggt accttcccgg cgtgccgacg caaggctgcg atgaggcccc gcagctgcgg  72660
cgaccgcggc tgccgttggt gacaccactg gttacggtgg tatacggcca aatcagcgcg  72720
ggcgtcgaag cgcttggcgc gtagtagtgc taggcacggc gagctggtgg ggtgaagcac  72780
gggcagccga aggtccaccc cgaaaaggaa acggtgaagg tcacctagca gcgagacggt  72840
gacaccgtcc aacaacgcgt gcagccgctc gggcgggtag agccgcagac ggcgcagcag  72900
gtagtcggtg tcgtagcgtt cgaaacgcag aaaggccatc gtgcggacgg ccacggtgtg  72960
cagacagtcc atgctgtaga cgtaagcgag aaacacaaag tagggcttgg tcataaccat  73020
acgctgaaag agcgccgtca ccgcctcccg ctcggcctgc cgacacacca gccattcgcg  73080
caggaagcgt tggtagagac ggtcgcccag ctcgcgattc agaaagcgct tatccgtcac  73140
gaagagatga aggacgcaag aacgtggcac gtgatgcacc agctgctgct ggaggaccgc  73200
cgacgtctgc gccgcaaact gcgccggtgg ctgcgacgtt tctaccgccg cttcctccgg  73260
ctgcagcgca ccgcggccga tcaccagctg cacatggaaa tggtcctcgt gaacgcagag  73320
gggcgcgaag agacggcgca gagcctggtg gaactcatca gtcgcggtgt gcggagcgtg  73380
tcggagacga cgattggcca tgaccgcgcc acagcagagc cagcaccagc agaagagcca  73440
gcaccagcgg gcccagagtc gcaaagcgcg cgggcagcca cggcccagac tgcggtcgcg  73500
atggcccgga gcgcgctcgc caccacgatg acggtgccca acgataacca gtccgctcca  73560
aggacggcgt gcacggcgga gacggcggat gacggtgatg ggtcgacacc cctcgccgac  73620
```

gactcacgtg ctcctccaga ggccgacgcg cggaccctcc gatgtcctgg cccgccgctg 73680
ccgctgccgc cttcccttct cccgccagag ccagcaactc ctcctcctct tcatcagcgt 73740
ctccctcgct tgcgcatccg catcgtccca tacaggcctc acaacgacac agccgccacg 73800
accccgccgc catgggtggc ggcggcggcc gaggcccggc agcggcgccg ccagcggcga 73860
ccatggtggg agagcaactc ggatgacgag gaggaggagg agggggagat gcggtccgag 73920
gggaccgctt tcccgccgtt cgcgtgagcg cggccgacat gcgggcgcgc cacagagatg 73980
gaccactgcc gctgtgactg cttacggtga cgtggttccg gaccgccaac gacgtcgacg 74040
cggctttctt ggcgtacagc tcgcgcagca gattctcgta ctcgccctcg ttttcgggtc 74100
cgaaggcgat gagctcgatg ttgaacaccg acgccgaatt ggatttgcgc accacgcact 74160
tcgtcagcac tccgtaggcc gagggcttga tctcctcgat gtccttgagc gtgacgatga 74220
gcgactcgtt caccttaagc acattgaact cacctacgtg gcgcgccggc gagacgagct 74280
tgacgggcgc tcgcacaaaa cagcagaggg agacggcgca gccagtgttt ttaaagataa 74340
aacaaggcac gtggtctgtg cggctctccc agtagctgag cagatattcg acacaataga 74400
ccgtgtctgt cttgagcatg gcgtcgcaca ccgagtaatt gggattttta cagataaggc 74460
cggcgtcggt gacgcgcagc tcgctaggac ccaacttgag gatacgccgc gtggcctgca 74520
ccagatcctg atggagaacc ttgttcatct ccatcgcacc gacgccaccg ccgatttatt 74580
tacccggcgc cggctcgtct tttccctcca ggattccgtt aatgtccatg agcttgctga 74640
cgatcgccgt taatagttgc gtcttctcac ggaggatctc tccgtgactg caggtcgcgc 74700
agtcgccgtg cacgtacttg aggaaggcgg cgtacttctg acccgcgttc acgaaattta 74760
agcgcgcgtc cagagagggc agcaacagat cgtagacgcg cggcagcatc ggctcgaact 74820
gtaatagcag atcgtcgtca agatcgggta gcgcgtgtcc gtcttcaccg tcctcgtcgt 74880
caccacctcc cccctcgagc ccaccgctcg taccagccgc gggctccgcg tcctcgtcga 74940
tcaccagcgg tcgcgtcggc accggagaat ccacgtcatc ctgcacgtcg ttttcctcct 75000
ctccgtcgtc atcgtccaga aacggcaccc gctgcttagc ccaggacatt ctttttccgc 75060
gtcctcaatc agcggcgccg atcgccatga atccgagtac ccacgtgagc agtaacggcc 75120
caacgactcc ccctcacggg ccccacacca cgtttcttcc cccgaccagc ccggccccgt 75180
ccaccagctc cgtcgccgcc gctaccttgt gcagtccgca acgacaggcc gtttcgcgtt 75240
acagcggctg gagcaccgag tacacccagt ggcactcgga cttgacaact gagctgctat 75300
ggcacgcgca cccgcgtcaa gtacctatgg acgaagcgct ggccgccgcg gcggccgcct 75360
cataccaggt gaatcctcaa caccccgcca accgttaccg tcactacgaa ttccagacgc 75420
tcagcctcgg cacctcggag gtagacgaac tgctcaactg ctgtgcggaa gaaaccacgt 75480
gcggcggcac gcaatccacc gtactcacca atgcgaccaa caccactagc tgcggcggag 75540
ccgtcgccgg cagtagcaac gcaggacccg ccggcgcttc ggccgcctgc gacctagatg 75600
cagaactggc cggcctcgaa acctcggcgg ccgactttga acaactgcgg cgactgtgcg 75660
cgccgctggc catcgacacg cgctgtaacc tatgcgccat catcagcatc tgcctcaaac 75720
aggactgcga ccagagctgg ctcctcgagt acagcttgct gtgcttcaaa tgcagttacg 75780
cgccccgtgc ggcgctcagc acgctcatca tcatgtccga gtttacgcat ctgctgcagc 75840
agcacttttc cgatctgcgc atcgacgacc tgttccgaca ccacgttctc acggtcttcg 75900
atttccacct gcactttttc ataaatcgtt gctttgaaaa acaagtgggc gacgcggttg 75960
ataacgagaa tgtcaccctg aaccatctag ccgtggtgcg ggccatggtc atgggcgaag 76020

```
acacggtgcc ttacaacaag cctcggcgcc acccgcaaca gaagcaaaaa aacaaccctt  76080
atcacgtcga agtgccgcaa gaactgatcg acaactttct agaacacagc tcacctagcc  76140
gcgaccgctt cgtgcagctg cttttctata tgtgggccgg caccggcgtc atgagcacca  76200
cgccactcac ggaacttacg cacactaagt tcgcgcgact agacgcgtta tccacggcct  76260
cggaaagaga agacgcaagg atgatgatgg aagaagagga ggatgaagaa ggaggagaaa  76320
aaggaggaga cgatccgggc cgtcacaacg gcggtggcac cagcgggggg ttcagcgaga  76380
gcacgctaaa aaagaacgtg ggtcccattt acctatgtcc cgtacccgcc tttttacca  76440
agaaccaaac tagtaccgtg tgtctgctgt gcgaactcat ggcctgctcc tattacgata  76500
acgtcgtcct gcgcgagctg taccgccgcg tcgtctcgta ctgtcagaac aatgtgaaga  76560
tggtggaccg cattcagctg gtattggccg acctgttgcg cgaatgcacg tcgccgctcg  76620
gcgcggcgca cgaggacgtg gcgcgctgtg gactcgaagc gcccacctcg cccggaggcg  76680
actcggacta tcacggcctg agcggcgtcg acggcgcact ggcgcgaccc gacccggtat  76740
tttgccacgt cctgcgtcag gcgggcgtca cgggcatcta caagcacttt ttctgcgacc  76800
cgcagtgcgc cggcaacatc cgcgtcacca acgaggccgt gctcttcgga cacctgcacc  76860
cccaccacgt ccaggaggtg aaactggcca tctgtcacga caattactat ataagtcgac  76920
ttccgcgacg tgtgtggctc tgcatcacac tcttcaaggc ctttcagatt acaaaacgca  76980
cctacaaagg caaagtgcac ctggcggact ttatgcgcga tttcacgcag ctgttggaga  77040
attgcgacat caagctggtg gaccccacgt acgtgataga caagtatgtc tagcgtgagc  77100
ggcgtgcgca cgccgcgcga acgacgctcg gccttgcgct ccctgctccg caagcgccgc  77160
caacgcgagc tggccagcaa agtggcgtca acggtgaacg gcgctacgtc ggccaacaac  77220
cacggcgaac cgccgtcgcc ggccgacgcg cgcccgcgcc tcacgctgca cgacctgcac  77280
gacatcttcc gcgagcaccc cgaactagag ctcaagtacc tcaacatgat gaagatggcc  77340
atcacgggca aagagtccat ctgcttaccc ttcaatttcc actcgcaccg gcagcacacc  77400
tgcctcgaca tctcgccgta cggcaacgag caggtctcgc gcatcgcctg cacttcgtgc  77460
gaggacaacc gcatcctgcc caccgcctcc gacgccatgg tggccttcat caatcagacg  77520
tccaacatca tgaaaaatag aaacttttat tacgggttct gtaagagcag cgagctactc  77580
aagctctcca ccaaccagcc gcccatcttc caaatttatt acctgctgca cgccgctaac  77640
cacgacatcg tgccctttat gcacgccgag aacggccggt tgcacatgca cgtcatcttc  77700
gaaaactccg acgtgcacat cccctgcgac tgcatcacgc agatgctcac ggcggcgcgc  77760
gaagactaca gcgtcacgct caacatcgtg cgcgaccacg tcgttatcag cgtgctgtgt  77820
cacgccgtct cggccagcag cgtcaagatc gacgtgacta ttttgcaacg caagattgac  77880
gagatggaca ttcccaacga cgtgagcgag tcctttgagc gctacaaaga gctcattcag  77940
gagctgtgtc agtccagcgg caacaaccta tacgaggagg ccacgtcgtc ctacgcaata  78000
cggtctccct taaccgcgtc gccgttgcac gtagtttcca ccaacggctg cggcccctcc  78060
tcctcgtctc agtccacgcc gcctcatctc cacccgccgt cgcaggcgac gcagccccac  78120
cactactctc accaccagtc tcagtctcag cagcatcatc accgtcccca gtcaccaccg  78180
ccgccgctgt ttctcaacag cattcgtgcg ccttgacact gtacggcaga aaagccggct  78240
ccaagtgcaa gcgccgcggc agcaccatgt gcaaaaactt gtccttgcgc gcggtttcgc  78300
cgccgggaaa gacgggcgac agcacgttgg ttacagcctt gagaacctgc tcaaagtact  78360
```

```
tgtcggcgtg aatgggcacg ccgtgctcgc gcacgtagct cggatcttcg gctacctcgt  78420
agttgcacac ggccgacggt ggtttccgcg ccctcttctt tgccggctct cctcctctcc  78480
tgttgctctc ctctaccccg ccgccgtcag cgtcgtcgtc cgtgccatca atcgcgtccg  78540
accgggaaac cacgccggtg gttacagaat caccgttgtc ggaggaaccc tgcggcgccg  78600
cccggacacc gggcgccgtc aggacgtaaa agacccgatc cccgaccgag ggtagctcct  78660
cagaacgggc cgccaatcgc ttaatgacgg caatgtgcgg caggttagat tgacggtaca  78720
acgagatgtc cttagaaagc accgacgaaa gcaccaggtc ctcaacacgc acacggtgca  78780
ggtacagatc gtcgcgggcc tgcaccaggc ggcgcaagat acgccagaaa ccgcgtggca  78840
caccgtattt cttaacttca tcgagtgaga ggcgcgacag gcgcacggct gcttccgaga  78900
cctcgcgatc ctcaaagagc agcgagagga cgtcacgcgt gacgcccttg acgaactcgc  78960
aggccgtctt gcgcaccaga tccacgccct tcatgctcag acccgaggcg ccctccactt  79020
tgccgatgta acgtttcttg cagatcatca taagagagac gaagaccttt tcaaactcca  79080
gcttgacggg ctccacaaaa agacaagccg tcacgtagtg cgccaggctg ggcccacgcg  79140
ccaccagagc ctgcggcgtc aggccacgaa agcggacaaa cacgctgtcc gtgtccccgt  79200
agatgacccg cgcctccacc cgccgttcgt ttaagccccc tgatgatgtt tcgagcccct  79260
ccggtaacgt gctgctctcc tccgaatccc cctcccgcgt tcctactaca tagtcttcct  79320
gattaaaaaa attgtgcaaa aaacacggct ctgaaaagtt gtctttgatg aaccgcgccg  79380
tgcgctctag catgtcgcga ccgatgcgcg taatgctggc ggcgatgggc agacacggca  79440
tcatgccgtt gaccacgccg gtaaaaccgt agaaagcgtt gcacgttact ttgagcgcca  79500
tctgttcctt gtcgagcagc atacggcgca cggggtcttg acactcgcgc atgcattcgc  79560
gcacggcacg ccgctgcgaa acccacttgt tgagcagttc cgaaagcacc gagacgcgca  79620
ccgaagcacg cacaaagcgg tgtgtcacgc cgttctctag cgtgacgctg tatacgtcgg  79680
cagggtccac ggggtactcg ccacccggca ccagcagggt ggagtagcag aggttgtgag  79740
ccatgatgat ggaagggtag aggctggcaa agtcgaacac ggccacgggg tcgttgtagt  79800
aacccacctc gggctcaaac accgtggcgc cctggtacga aaccgccgca gtaccaccgg  79860
cgccgtgatt gtcgttggaa acgccgacgc cgccactact gccggagccg acgctgaaaa  79920
cgccgacgct gctactactg ttactgccgg agccgggtga aacgccgtcc tgactggacg  79980
gcgcagattg caagggcggc gacatctgaa acatagccgc cacagaaccc gcgtcgccgg  80040
gcacggcggc ggtagagatg atagcggcgt taggtgacac ggcaacacta ttcgtttcgg  80100
gcaccgtcgt acctttgctg tagtggttgg gcaggataaa atcgcggcag gcgcactcgt  80160
ccagcagcga ggtgtagata cggatctgct gtccgtcaaa gatgacacgc cgcaacggaa  80220
ttttagccag ccgcgcgatg gccccggcct cgtagtgaaa attaatggtg ttgaacagat  80280
cgcgcaccaa tacggcgtcc tgcagacagt aacggcctac ctgggcgcgg ccctcggcat  80340
tagccacgaa acaacgcggg atgtccttgt aggacaggtc atccttgcgt tgccgcaggt  80400
aaagctcggc catagtgttg agcttatagt tgggcgagtt agtcttggcc atgcatacgg  80460
ggtacatgtc gataaccacc gaacccgcaa tatacacctt ggtggcggcc gtgctggccg  80520
gattgttgtg agaagccgag ggaaaggcgg cggcgtactg ccgcttaaaa cccacggcgg  80580
ggctgtgtaa aaagaaacgg ccgccctgcg ccgtaggcaa cttgcagaag cgctgcgagt  80640
ccaccttata caggtactcg aggcgcgtga ggatgtactt caagtcaaaa gagttgatgt  80700
tgtaaccggt cacaaaggcc ggcgcgtacc gttgaaagaa aagcataaag cccagcagca  80760
```

```
gctcgtattc ggaagggaac tcgtagacgt ccacgtctgg gcccacctgc ccgcaggtgc  80820
cgatcgtgaa gagatgaaga cccgagtgcc caaagatcac accctccgaa gtgcagcccc  80880
ggccatcgtt cccgtttggg atcccctgat ccacggcggt gtttcccccc gtctcgtagc  80940
acacgcacga gatctgaatg acaatgtcat cggacttctc ggcgcaggga aaaccaccct  81000
cgccgctcat gcactcgata tcgaaggaca ggcatcgata gcgcggccac gagctgtcgt  81060
cgggcacggc caccaggtca gagacatcgc agtcgacctc gatatcacaa gtcgacgcgc  81120
gaccctgctg ccgccagtcg taacgattca cggagcacca gccgaacgtg gtgatccgcc  81180
gatcgatgac caaacgcgtc agcggatcca cacggacctc gtacacggga aaaccctgct  81240
ccagcagata ctcgccgatt tttctggcca tggtccagtt gctgatagac acacactgca  81300
aatcgggcac gggtcgcgtc ccgtacccgt agatcgaggt tttggtggcc ggcgtgacag  81360
acacggcgta tggcgtccgc ggttcgggca ctagttcgcc cacgctggca atgacctcac  81420
gcagcctatc ggtgtcgctg tactcacagt aaaagtagct gcgctgcccg aaaacgttga  81480
cgcagatact gtagccgtgt tctgtggccc cgaagaaacg caacacgttc cccgaaggca  81540
ccagatgctg acgatagcgc ggcgacacgt tttcgggcga gtcgaagaag agcacggcgt  81600
ccgtctgatc gtaggtgtga aaacgaatag gtcccaccac gcgacccacc agggtctcgc  81660
gccaaggaca cggccaaacc atgtcatgac tcaacaaatg tttaatctct cgatagaaca  81720
tgagaggcag ccgtcccgtt ttatgcttga tcaaccccgt ctgaccgtcg aacatgacgc  81780
ctcgcggcac gatctgcaaa aactgtttct gtggcggccg cttgcccgag ccctgcgcgg  81840
agccgggctg cgaacgctga cgccggccac ccgcgaccgc accgccggtc acgccgccgc  81900
tcagatacgg gttgaaaaac atagcggacc gtgagaggct gacagcttac gaagcaaaat  81960
cacaaagaaa atacacatgc agcacctaga tatccagttt aaccccgtat atcacaagtc  82020
tctgtgtcac tttttttttg tctgtttttt ttttcttctc ctggttcaga cgttctcttc  82080
ttcgtcagag tctttcaagt gtcggtagcc gtttttgcga tgtcgcagtc ggtctagtag  82140
gttgggcttc tgtcccttgt cctgcgtgcc agtccgtccg tccaaagaat ctgtaccgtt  82200
ctgctgcgct cgctgctctg cgtccagacg ggccagggcc agaagcatct ggtaagcctg  82260
ctcgttggtg taaggcggag ccgccgtgga tgcatcagac gacggtggtc ccggtccttt  82320
gcgaccagaa ttataaacac tttcctcgta ggaaggcgga gcctgtaacg acgtgtcttt  82380
ggtgctgccc gacgtcacgg tggtcccgtc ggcggacacc agatagggaa agaggttctg  82440
cagcggctgc gtgcacaaac gccgctgtcg agtatagatc aaataagtga taatgactac  82500
agctatggcc acgaggatga tggtgaacgc tccgaagggg tttttgagga aggtggcaac  82560
gccttcgacc acggaggcca ccgcgccacc cacggcccca atggctacgc caacggcctt  82620
tcccgcggcg cccaggccgc tcatgaggtc gtccagaccc ttgaggtagg gcggtagcgg  82680
gtcgactacc ttgtcctcca cgtactttac ccgctgcttg tacgagttga attcgcgcat  82740
gatctcttcg aggtcaaaaa cgttgctgga acgcagctct ttctgcgagt aaagttccag  82800
taccctgaag tcggtatttt ccagcgggtc gatatccagg gcgatcatgc tgtcgacggt  82860
ggagatactg ctgaggtcaa tcatgcgttt gaagaggtag tccacgtact cgtaggccga  82920
gttcccggcg atgaagatct tgaggctggg aagctgacat tcctcagtgc ggtggttgcc  82980
caacaggatt tcgttgtcct cgcccagttg accgtactgc acgtacgagc tgttggcgaa  83040
attaaagatg accacgggtc gtgagtagca gcgtcctggc gactccttca cgttcatatc  83100
```

-continued

```
acgcagcacc ttgacgctgg tttggttgat ggtcacgcag ctggccaggc ccaagacatc  83160
acccatgaaa cgcgcggcaa tcggtttgtt gtaaatggcc gagagaatgg ctgacgggtt  83220
gatcttgctg agttccttga agacctctag ggtgcgccgt tgatccacac accaggcttc  83280
tgcgatttgc gccagcgccc ggttgatgta accgcgcaac gtgtcatagg tgaactgcag  83340
ctgggcgtag accagattgt gcaccgattc catgttggat aaatgagttg cattgttgcc  83400
atctgtactt cttttggttc tattatgagt aagattcaga ctggagcggt tggccaaacg  83460
ttcgagttcc accagagatt tttgcttgat accttgccag aacactacca aaccaccagt  83520
ggtttcaaag acggacacgt ttccatattt ttcatatgtt tgattgtatg aagtattgaa  83580
aatctgctgt aacttattta tagcctcatc acgtacgcag tccagcgcag agtcggacat  83640
gttcacctct tgcttcttag ataagaaagt ggcggtcatt ttggcagaag aaaagtgata  83700
cgagtcctcg gcttcggaac gaatggtgcg ttccgaggct tcccagaaag tgagttgaca  83760
agtgacattc ttttcgtcct gtatatccca ggagatcacc gagtccgcac gttcaagaaa  83820
agccaccaac ctgtgggtct ctaacgcaga attcggtctt ccaaagtcgg agacgatagt  83880
gtagttcgga aaaatgaaaa acttgtcggc gttttctcca aagtagctgg cattgcgatt  83940
ggttccgttg tagaaaggag aaatgtcaac cacgtcaccc gtggaagtgg cgaaaaaatg  84000
ataaggatat ttggagcgcg cagtagtgat ggtcaccata caattcagat tacaggtctc  84060
acgatagagc caggtgctgc cgcggctgtg ccattgatcc ttgaccgtca cgtaacgggt  84120
actgtgggtg ttggaataat cgtcgggcat taattgcatg gttttgtttt catagctgtc  84180
cctatgataa gccacgaaaa ccgtgcctgc tataacgcgg ctgtaggaac tgtagcactg  84240
actgtggctg ttgatatgat gaatctccca cataggaggc gccacgtatt ccgtgttgct  84300
gcccagcaga taagtggtgt ggatgtaagc gtagctacga cgaaacgtca aaaccttctg  84360
gtagactcgt accttaaagg tgtgcgcgac gatgttgcgt ttgtagacca ccatgatgcc  84420
ctcgtccagg tcttcattga tgggcttcat cgaggtgcag acgatattac gttcaaagcg  84480
aataagatcc gtaccctggg ccatagaaca cacgcgatag gggtacttgg tggtattgac  84540
ccccaccaca tctccgtact tgagggtagt gttgtagatg gtctcgttaa caccatggct  84600
gaccgtttgg gaagaagtta cgcgttgaga gactgaaccg gatcgagagt gagcagcaga  84660
cgtcgtatga gaggaatggt gactgtgagt agcagaagtt ccacgagtag aagatgagga  84720
aaccgcagca cccagacaga cgatacacaa gttaacgcag actaccaggc accagatcct  84780
ggattccatg ttcgtcgcgg gccaaatcca gcagcgatga ggcgcgtcgt ggtctcttgc  84840
gtgttgcgcg gaccctccgg gaaacgcccg cggtcgagga ggaggggtac ggacttggca  84900
gccaaggtcg gtccggctcc ctgaaggcac ccgagacggc cgcggcggcc gtcagggtgg  84960
agggcttggc cacgggagct gttggcacgt cgccactctc atccggtctg gacagatgcc  85020
tgtagaggag gagatataga tctttggact tataaagact tccttcgtga cgaagcagca  85080
gcggccactc tttgttatac gtgagaatca catctctgtc cgggtgcagt tcgtcgcgca  85140
ggcacgcgat cgagagttgt ttcccgaaag tttcattata tagtgcgacg gagagcacga  85200
gctcccgcac gtgcatccac atctccttct gcagcacgtt taggtcctga cagtccgaaa  85260
aattgaaaaa acccatgtac ttcaccacca tccactcact gggatacacg gtaccttccg  85320
cgcatttgac caaatcgtcc ttgacgtggg gtagtacgcc cgcgttgtcg caggcatagg  85380
ccatgtccac attgtgagag aggggatagc gatcggtaca gtgtgtgaag aggggcccgt  85440
tacacaactc gtagatctgc tgacccagta gcgggaggga ttccacaggc agactcttgt  85500
```

```
ggatcaggtt attgaccaca tacaggtgct catcgtacgt gaactgattc cccacgtcca  85560
ccacgtcttg gtcctggtgg tattggctgc ggtatagaaa cccattcatg agcttagaga  85620
taaagtccag acacaagggc cccactaggt tgacatcgat gagtttgcta gtcagacgct  85680
cctgcgtttt gatgcaacgg atcaccttgc catagcccac ctccgagacc ttctgcaggt  85740
aggcgcgttt gcgcacgttc acctcgcggg tgacgttgtg gatgcgggaa cgcgcgtcca  85800
ccaagtcgag agcttcgtgt tcgtcgcagt tgcgcacccg taagccgttt tcgctgccgt  85860
cgccgtcctg cccattcgcc cctcccccta cagctttctt gcctcctcca cgggcccggc  85920
cgccgccacc gttattcctc tgactgtgag tactgctgtt gctgctgttg ctggccgtca  85980
tcaaagtcgt acccgtcccc gacatcgcct cccgtccacg caggtgaata acctcgccct  86040
cggggccgtc gccccccgtg ccatcgggca gcggacgtcg aatctcctcg agaatatgct  86100
tgattttggt gtacatctcg ttgctttcgt ggagcttgtt gaacaccggg ttgtcctcga  86160
aagcttgaat gctgagggat gtgatgaggt cgatgatcct gttgggggcg gcaaagaccg  86220
accccacgaa catgcgctcc tccccgtcca acgccttttc cccgagcacg aagatgtcct  86280
ccacgtcctc cccgtacaga tggcgactga tgccgttcat gagcgcccgg cacagctggt  86340
gatacacatt tagctgctgg atggtgatgc ccacccgctt gacgataacc tccgaggtac  86400
gggaccagta ggtaaaatcc gacaaggaat atattcgttc cggtatatcc gtaaacaggt  86460
tgtactccct cagcgcctcc tccgcctcct ggatgtagct gtggtaggcc gatgaagaag  86520
agaataggct tttgagggcc gaaaggactc cagccaagtg ggggatgcgc gttgtcaggt  86580
ccagcaggtc ctgctccacc gtctggatat tcacatcgga ctggcttgac ggacggtgga  86640
ccgctatatg gttgcacagc aagccctgca gccgcttgtt cagcgagcgg ccctgattcg  86700
ggatgatggt cagctcctcg tagcattggg cgcatgtcgt cccttcgacg tacacttcct  86760
gacgcgccac cggcgagatg ccgcataggc gacggaggag ctccagcagc tgcgcgcaga  86820
cctccaggcc ggcctccggc gccaggatcc cgtacacgta gttcattttg cacaggaagc  86880
gctcgatgtc gttgagtgtg gccagactga cgctgaaacg gacgttgtcc gtaaactgga  86940
gctccacggt gtgatggcga tcgcagcgat ccaaacggag gacggtacgg tagaaggccg  87000
cccggtccgg ctggcgcgag taggccatca gcgcccgatc cagcaaagcc gtatcctcgt  87060
gcagcgcctt cagcagcatc tccagataga gagtcagcag cgaactctgc gtacgattct  87120
gcgccaccac ctccgggtag atcttccggt acagatacac tatagccgcc gcgtttctct  87180
tgaacggcgt ggactccgcc agtaacacgt tcggatcgca gtactttaga cactccagct  87240
ccatggcgta ttcgttgcat ttcgaacaca ctacgcatag tttctgtaac aaattcatct  87300
ccatgactcg actcgctcac gtacgagacg ctgtcgtccg gtctggcgcc ggccagagac  87360
atggagtcgg tgcacaaata actcgcgggc cgctcgctat gccgactgac gttgacgtta  87420
atatataacg acgtcgtcga cgacgcgggt tctgctcccg aagctgttgc cgccgcttgc  87480
ggcgcaacct cctccaccac cgccgccgcc ggctcctccg cctcgggcga cgggggctcg  87540
gagatgaccg gctgtgtctg acactcctcc ccttcctcag gcggcccggg cgccgacgcg  87600
aatgtcggag tttgccagcg cggcggcggt ctctgtctct ggtgccgcgg cgctaacctt  87660
cggggctgtt gctgctgttg atgatgcgac gccgtccgtc gccgctgttg cggcggtagc  87720
tgatacggtg tcgcctggtg ctgctgtgtc ggtggctgct gttgctgctg ttgttgcggt  87780
ctgaaaagcg gccacggggg ctgcgactgt tgctgctgtt gttgcgatgc tcgtggctgc  87840
```

-continued

```
ggcggccgtt gtcgcggcgt ttgctggcgg ttacaaccgg ctgcgtttgg ccggcaataa  87900

cccgctgccc ccgccgcccc cgctgctccc gccgacgccg ccagcctcgt cttcgccggc  87960

gttcacgaga aagcagccac ctcccgtctc gccgggcacg ccgaagcaaa tggagttgcc  88020

cgcgacggac tcgccgagaa gaagaccgcc acccccgacg ccggacgccg cgccgacgcc  88080

actgggcgcg aagagcgccg acaggtcgtg cacctccccc ccggcggcgt ccgttaatcg  88140

ctgggcgtcg gcgtccagca cgcgtcgcaa gttctccagc gaaaagtcct ccacgccctg  88200

ctcctgcaac gcggcaaact tgtccatcag cgacgcggcc agcgcctcgc agccatccac  88260

gaagaagagc acatcgtcgg acgcggggat ctcctcacgc acgctcaaaa tctcgtacac  88320

ggccatcact tcggggtcgc aatccaagtt ctcggcgtcc agcgccagca tgacgcggtt  88380

ttttataaga tccgcgtcaa aaagcacgtt ctcgcggcgc gagcgtttga tgagcacgtc  88440

ggccagacgc gtagccaaga gatagcgctg gcgcatgaaa cgataatctt gaccgctcat  88500

agagctcacg ttaaggctgc gttccacacc gttgcccgaa aaatagccga tctgcccaaa  88560

ctgatagatc tccttgctgt tgttgatacc agcatatttt tccacgctca cgggcacggt  88620

caccaaggaa cgatgctcaa aaacgctccg taccaacgat tcacgcgcca cagtggcggc  88680

catgggcgcc ggcacgcctg cggtcttcaa gcccttgaca tgcaacgcaa attcggcggg  88740

cgacgagaaa cgcggactag cacctaacac gtgaggaaac tgcgcgtggt tctgcgtcgt  88800

taagcgcgtc gttaacccgt gcagcgagcc gatgtagtcc ttgaagccgt agtagcagag  88860

gaatttgtta tggaaacggc tttccacgta actcagcaca cagtctggcg ccacatccag  88920

cagatcgtgc tcctgatagt cagccgtcac agccaccaga aatttgacga aagcattgaa  88980

ctcgcccatg tcacctatgg gcacattctt gggcaacgcg ttggaacaaa ccttctgcca  89040

aaactgtaag caggggagac cacattcagg aaagagtcgc tcgtgatgtc gatacagcag  89100

aaatcccaag cagcccttag ccggattacg acgcggaacg tgatcgcggc gaaaaaacac  89160

gctacccgcg ttgcccttgc ccgcgcggta gatgggtcgg tttttcaccc gcaccatgat  89220

caacgtgggt accgatagcc gcgagagctt gatctccatg ggcaccacgg cgtacgtgcc  89280

ctgcgcgtac agcctaaagt ccagcaggcg gtcgtgatcc gaattcttgg acgacttgat  89340

ctgcttggtg aagagaaagc ccttgcgcga cgacgtggtg gagaacgcgc cgtgaatgga  89400

ttgaaaatgc tgcgtcatcc atttggatac caagttggtg gtcaacggat tgtccacaat  89460

gtatgaggta gcggtaataa gcgccacgtt ctggatcacg taaaagacgg atctgaaata  89520

ggcgtaggcc agcagcggct ggaaggccac ggcgtaggga ttcagatcca ggttgaaggc  89580

ctgcgtggcg cccgccacct cgtcgcggct gctcttgagg cgcacctccg aaacgaaacc  89640

cagggcctcg tcgtccacaa acttgttgag cgccgaaaag acggccacaa agtcgctttt  89700

gccgtgcgcg ctaaaggtat cctcgcccgt cacggggtcg atgagccgca tcttgcggca  89760

gtaatccaag atgcgattga gccgataggt acggtccacg ctagcgccca gcatgcgacc  89820

gccgcgcccc atcattcccc cggaatcccc gccaccccca ccaccacgac cgccgcccag  89880

accgtcgctc gggcccccgc tcacgtcccg tccaccaccc ccgccagcac cgccgcccgg  89940

aaccccgtcg tcacctttgc cgtccaaacc cccgtccttg gcgtcgacgt tgtaacgccg  90000

accgaagctg cccaaaatat ccacgtcgtt gagaaaacgc gactgcacgg tgatcacgca  90060

gggctccttc ttgggctgct tgggcaccac gggcaagcgg gtgcgcaccc gcacgaaggc  90120

cgtctgataa cacgtgtggc aacaagtacc cccacaggcc tcgcacagcc ccgcggcgca  90180

gcccaccagg tgattcgtga gcgtcgacga acccgacaag cccgtgttat acaccgagac  90240
```

```
acgatttaga taccagacga agcccgaaac tagctgcgga cacgtgccac acaccaacgc  90300
caaatgctgc ggcccatagc gttcgtcctt gagcggcgcg ccttgaaact tgagcacctt  90360
gcgcgcgtcg ttgtagacgt cttcgcaggc cgccgacaac ccgttggtga actgaatagc  90420
cttgagcaac gtctcctgac tggccgtacc gccggcgctg ggatgccgcg ccgacgactg  90480
gagatacacc agcctgtgct ggtagagcac cgaattagcg ctgaagacca aggcggccac  90540
gtgcgtcgag agatgcaact tgagctcggt cagcgcgcgg atcagatcgc ggtgatcggt  90600
tgcgttggtc actaaaggcc actcggaaaa gagcatagac tcggcaggtt ggtaggccga  90660
atcgaaaaat accgaggcaa aactgaaggc caactcgcaa accaccgcgt cactcagcat  90720
cagatgatcc ttttccagac tgctgagtcg ctggctcatg taccccaagt agcgcttatg  90780
tggcgccagc ttcaccgact gctgactgtc gtgcacaaac tgccgcaacg ccgcctcgat  90840
cagcacacgc ggctccgaga agcgcagcga ttgacaccat gacgtgtaca cgtagtagaa  90900
aagcgtctcg cttacggccg gcacgtagag ccctcgcgcc tccacaaaag cgctgcgcgc  90960
atccagcgag acctcgtcgg cttcggcgtc aagctgcagc gaattaaaga gcgtaggcgg  91020
gtacaacggc acgcgcaccg cctcgccgcc gtgcagtcgc accgtggtcg cctcctccac  91080
gcatggaatc agctgaccgg caaagagaaa ctccttcaag ccgttgccca ccaccacgtg  91140
cacagtcgtc tcggacgcct gacagcccac cgccgcgcac aacgccgcca gatcggtagg  91200
cacgcgatcc gcctcgggcg tgtaggcctc caacgcgtac ttctggcggg cgtcctcgca  91260
cagccgatgc acgtctccgt gatcctcggt aaaagccacg atgccttgcg tatgatgaaa  91320
gtagagcgca aaaggacaga aggacgtgac tttcgtgagc accccgccgt cgtaacaaag  91380
cacaggcgta cgcacagaga cgccgaaatc cgcctccacc gtgagccccg ccaacagagg  91440
agcgatcacc acgctcgagg aacggtcgca tagcgagaga gtggccagaa tctcctgcgt  91500
ttctgcgttc aacctgctga agtagagaaa agccgcgggc cccaccggcg ctagcgcggt  91560
tagttcctcg tggctcatgg tggatgaacg gaagacaatg gctacgccgc cactgagtga  91620
attttatacc aaggaaaagt tcagcacgtc atgtttgacg cacgacgtct gagacaccac  91680
cgtggccacc actgcggtct ggctgcggtt gcggaccacc aaaggcgaca accgcaacga  91740
tcccagcaat tcgtaagaaa agctaaccgc tacggtcggg tagcctctcg cagccagacc  91800
gctagccgac gcacccgccc gcgaaaatag cgtgatgttc gggacggctt tgcgtcaccg  91860
ccaactaacg tcggtagtcg agcacgtcgt ttatcctcag cacaccgtcc gatcacaatc  91920
cgttttccca ctcagtcgca caagcagcac ataaaaaccc cacacagggc acgtgaaaac  91980
accgtcccta gaaaacggtg ttttctgtcc taccgtcacc ggtatacaca ggcaaatccc  92040
aagcccgatc cccgaaaaca ccgtacggtg tttgtgacct ccaaaatcac atcagctaac  92100
aaaccgtgaa aagtcacgtt tcacgaacac ggtgttttta aatcacaaag aaccgcctaa  92160
cggtttacaa gcagaaacac cgcaccacgg tggtacaagc gcgatgaatc tggtctcgca  92220
acctcaatcg ccgctatcac caccgatttt cgctgcgctc cgccgacaaa acgtcgtaca  92280
agctacacac cccaaaaacc cgcgcgccta cgggcgccaa acctgtgtat tatctcaacg  92340
tcacaacacg acacaaaccg cgtaacgtgg tttcccgaac acgtacgcgg cacagacccc  92400
cgacacgtac tcgaagacct tacagtttac gagtcaataa aacaggaaaa gatccgaact  92460
ttaaaattgt gtatttttat tttcccatcc ccctcttttt accaaaaaac acatttttcg  92520
tcttgtaaaa agtaactttc gcccattgcc atgaaacacc gtgatgggga acggtgttgt  92580
```

```
gtgtcgactg acgtcactac ggcgatcagt atcgacgtcg tgtatacata acggtgcccg  92640
gtgtttttat tcggggcgtt gtcgcgtctt gatgtagtgt aacctgaaac cgccgtgccc  92700
aagaatgcgg aagccagcgt gtaatcataa cggggttttg ggtacaatct gacgacatct  92760
ggcggcgagc gtacaccatc gaatgtggcg atcgccggct ctacgtcaca atgacgcaaa  92820
aacacactgt aaaacccgcg tagacagctt tcctggtcaa cgagcgccat ctggtgtcgg  92880
cataagaaca ggcatcaacc ccgtggccgg cgaggcggtg agcacttttc ctggtcacgt  92940
gaccatcagt gcaggaagcg aggcccgtag aaccgcccaa gaggcggtgc cagatgccaa  93000
cgtcataatc acaaggtgat ttgttacgtc acgcgtgtgc gcacacgcgc acgcgcgcac  93060
acgcgcgcgg tagaatacag cgatccctag tgaagccaca cccattacgt gtagccatat  93120
ccgcttacgt atacaaccac accccctaggt acgccacctt atctaccaat cacagaaacg  93180
gatatacaat gagccctccc tagactccac cccttgtacg gaaatttcag ataggtggaa  93240
cccgttaggg ttccaccgtc ctcggtgtac gtacaggctt ctccgtctac cggaaatata  93300
cacctgctga cgtagacgct actcccggat acgcgtcata agctactgga ccctaggggg  93360
gagtgtctac agggctacgt gcacgtcccc ttacctaggg tatccgcccc cttccgctgt  93420
tttggcctag taaacttaac gccgccgctt ctcacgtgac ccctgacaag cccacgtcac  93480
actcgcgtag ccacacccac tccggatata cgtcatcctg tggacttccg gacatacggt  93540
gacgtagcga gcgtagcgag ctacgtcacg tatgcgtacg tcatctccgg cggaaatcat  93600
ctctgatgac gtagcgagcg aagcgagcta cgtcatcagt ccgttttacg tataccggat  93660
gctaggcgac gccccgtagg ggcggagcct agcttccacc cctaggatgc ataccctata  93720
tagcataatt cttctaacga aacgttctac gaaaacggac tggcggaacg ggaaccaccg  93780
taaccccccc ccctcacccc ccccctctc ctccggaacc gggggggca aatttttacc  93840
aaatttgggc aaccatgatt tccaatggga cggcgtttcc gtgcgcatgc gcagtcgggg  93900
cgaattttcg gttgttaggg cgttgccacg cggattatgg gatgtggcct cgagtgcgca  93960
tgcgccgggg atgtcgtata aaaagcctat atataaagag gggtgaacca ggggacccgg  94020
tgcgcatgcg cgggccagga cccgcgggag gcgcgccctg cgcatgcgcc ggtaaaattc  94080
cactgggcat gcatcgtgcg catgcgccgg tatttttcca ctagaggcgg tcagtgcgca  94140
tgcgtcggta aatttccact ggatgcgcgt cgtgcgcatg cgccggtatt tttccactgg  94200
gcggccgcac ctagggagcg cgagccccgt gccgggcatg ggtcgcggcg gtggaaaatt  94260
accgctccgc ccacctaggc ggggcctctg aaaacctata aaacccggcg tgcccgccgc  94320
cccccggcgc agtccgcggc agggttccgg ccgtgctgcg gtccgcacgc tgcgcccgct  94380
cccgcctgcc tcccgcccta ccccccaccc tccccggccg aggcccggcg ccggtccgtc  94440
cgcgggcccg tcccaccgcc ctggagcacc atccggggcc gtgggccggg caccgggcgc  94500
ggcccgctcc ggacctcggc cgggggtccc tgccctcccc ccgctcgacc ccccatccga  94560
cggcccggcc gggctgggac cccgcaccg gggtcccggt tcccgtccgc ggcccggggg  94620
gacccgagcg ggggcttccc acccccaccc cgctcctccc cgggctccgg cccgggatcc  94680
ctcgctgctc ccggcgacct ccgccggctt cccggtccac ccgccgcgga acggacggga  94740
cccggggtcc gcgcccttcc cctcccccca cggggggctg ggtcgcggac cccggttcct  94800
aggctcgttc cgcggtgggc gaccggggat cccccaccca gctcccccttc ccggcccgcc  94860
ccgctggctt ttgggcccct ccgggctttt tttttccggc tgggggtcgc ggcggtcggc  94920
cgacgacgac ggtaggtggg ccgggtggac ggtggtgggg acgggcgacg ccccggctcg  94980
```

```
acggcagtcg gtcccggaag gttgggggct gggggcccgg tcaggagctt cgggagcggg  95040
gtcgaccgcg acggcttccg ggtctcgcgg cggctccctc tcggcggctc cggttgggct  95100
cccctccccc ctctcgaggg tccggccgcc agtcgtgacc gggggtccct cggcctagcc  95160
gccggctctc ggtccgcctt atcctgggcg ttggccggtc ccgtgacgct cccctccccc  95220
actgctcccc aaaaaaactc cgcccgaacc gtcgcggctt gctggccctg ggcgtggtcc  95280
cccactcccc tccccccatc ggccgcccag ccggggtcgg cgcctcggac cccaccaggc  95340
tgtggcgtgt gtgctggccg atgcggcggc gaggttgggt gtggccggaa gcgctcgggg  95400
tcgacggtgg gccgccatga cacctcaatt gccgtcagta cgcccctcca caatcaccgt  95460
ccccacacga tgggcccggc aggtcaccca acgttggttc aggcccagtc gagtttttcc  95520
ccggcacgaa cgcacgtccc cgtgggctcc acgcgttttc caccctttcc tggaggggtc  95580
cggaacaccg tgaatccacg gggagggtcc cggcacgggc cgaggagacc acgaccgtcc  95640
cacccggcgt gtcgactcgt ccgagacccg ggaagggaac aggccccacc tttttttccc  95700
ttctccgatt ttgccgtgga aaacccgtga accgatacgg gtgcagacgg ccgaaaaaaa  95760
tcgagacgac aatatgacgg cagggcgcga tcttctcccc catccgacaa aaccgtgtcc  95820
cttaaaattc cccacctttc tctgttcaaa tgggcccgaa actgtaaaac accgtttgac  95880
cgcaccccaa ccggcgccat cttggtgact ttctcgacgg ttctctcgct cgtcatgccg  95940
ttctgagctc cgacatggcg gacgagagaa aatggcgtcg agagcctagg agcgttttcg  96000
ctccaggcgg gtaaaaaaat agcacgataa cttttctgtg cttttttttg agacgtttta  96060
gaagagcttt tttctgctca gagcgaaaaa atgatagccc tgaaaatctc gacgagtctg  96120
gccgagcggc gccatcttgg aggaggggcg agtcgcgggc accgcctcgg taccccctgg  96180
ccgaggcgag tccgcggtcg ccgcctgttc cgtgatgcta cctagagggc gctgtcgagg  96240
cgactcttcc tgttttcgcc ctgagggcta acggtcgctg acgtcaaacc atctcgtgct  96300
cgctgagtca catccggttg ttgacaagcg atggaggacc gcacccaaag tgcgccctct  96360
agtcatcgcg cctgacccct tttataaact gctcgaagaa aagaacacct tatgtgaaaa  96420
aatacagaat gatgacaagt tcatccaaca caaccgctca acaacgccat atctatcagt  96480
gtccaaaaac tatcttctat cctttgaaac tataaatgct gcctatatac atatttagta  96540
tccaagactc ttaccacgta gacgaaaaga agtgatacaa tgatcttgac gtgtatcgtc  96600
tatatcgtgc tagatatatt cagataagac gcgcaaacca tagatttctc atcagtatca  96660
tgaaagacct atagctctat atacgaacct agtcatttta ggacagccgc cggagaagcc  96720
gacgagggat cgggcgggtg cagccagaac ctcacgcccg atcccgcctc cggtaggcga  96780
tttgcatctg tttggtaaaa agctcataag tctgtatgtg acctatatat atattatacg  96840
ctatgtacac cgaactgtcg ctgttgtata agaagaaaaa actctccata tttatatcgt  96900
ctgaattttt gcttgataga cacgtgtttg gaactctgtc cccccacgtt ttcactgtgt  96960
ataacaaaaa tatgtgtttc tcaaaagatc ttgaggtgtt tgaaaacggg ggaaacctgc  97020
gtttgggtgc gctaagcccc ggactgggac gtagccggcg tccggcacct atatttttct  97080
atttttttac aaaatatatg atgaaccaag aataaaactc tagctctcgt ctatttttaa  97140
tatgctctac ttagaacctt tttaatgaca gaatgaactc catgttatac gctctttata  97200
tagtttctct gcactaacct ttaaaaccgt atccttccct gttgtacaaa tcatcttttg  97260
atacacaatg atgacctgat atccctccat atatatgatc ggatattatt ccgttagact  97320
```

```
tgtcctcctt ttttttcctc atctcctata tctggagata tatgttgacc accaccgcca  97380
tgaccaccaa aaagctagcc gtcacgacta gaaatgtgta ggattcggac tttccgttcg  97440
agaagaaaga gaccgcgtct ctggacgctc tttttgtcgg tctgaatcga cccgggatac  97500
gtaagagagc ggccctacat cggggggcgc tcgagaccga cgacgttcca tctgaccaga  97560
aaaaaaggca cccctcggta gcgacctctc accatcgttt gcccgtccgc ccgtccttcg  97620
tagccatcat catcatctca ggctctatcg gtaccatcgt tgtcatctga aaaaaaaaac  97680
tgcctcaccc acctgcgtaa aaacaccatc tttccggagg tgcggtaaga cgggcaaata  97740
cggtcgtgcc gaggcaaaaa aaaacgcacc atcgacacca caccctcatg agcaccacct  97800
gtcggtgttg gtcgtcctcc atcgttctct acgaacatct cgacgcccgg gtgacggacg  97860
acggcaagac gtcccggaga agacggtgtt ctctcgggcg gtacgctctc tggatctata  97920
atatctatag tagctaaacg agactgtgag tacgacgaac cacatcatct tttttttatg  97980
ttgcttcttt agaaaatgac ttatgtcgac gacactcggc atcagccatc tcgtgaaaca  98040
cgctcgcttt tcgtctctcc aaggaacact gggtccgctg aaagggaccg tgtaccgacc  98100
aaagcaaaaa acacacacgt agtaacatga tcaaccacgt ctgaatgaca cgaaaacaca  98160
atcgtataac gctctattca tggaacgaac ttggaataaa aaaaaccatc gcaggccaga  98220
ggctaagccg aaaccgtccg gggaagcggg cgcgagtttt ccgacttagc ctttggtgct  98280
cgttgagcct cttttttttt ttctgattct ctgaagaatc accgtcacag ccctatgacg  98340
cgaaatcaat tgctagaaca taaacgttct caacaggtat gaaatgaaca aactagatga  98400
tgctataacc ttatattgtg tgtatataga taggtgtgaa atttgtagga taaaaagtgt  98460
cgttgtatga tgcacaacga tcgtgaaact ggagactgta gctctctacc gaatgcaaat  98520
acacaaatga catcgattcc cgtccccaca taaagaaatg tgctttactg tgaaagaatg  98580
aagaagattc ttgttcctcg tacgacgggg ccctcgctcg tcgtgcctct tccccctcc  98640
gggagagggg acgtcggggc cctccgtcgc accgggccga agccagtgaa atgtttacta  98700
cactgtcatc agaatatatg atgtatatta tttcctccaa actcctcacc atagccacca  98760
attcgcatca cttaagaaag tagtagcaac cgcggcggcg gcgaccggcc ggtcgtcgtc  98820
tcctcgtcct caaatgttgt acatgtgcag aaaaatgtgt aaatacgtgt tatttatccc  98880
atgcgtcttg tacatagata tatgttttta tatacgctat ttatacttta tatatccttt  98940
tgcataacca tagacagtca aggattttaa tgatttgctc atccgccttt gagccatcgc  99000
ttaggagtta gttcctctat gttctcggcc cacctttttcg actacagtag caaacccttg  99060
tactaccacc ccgataaaaa ccacatcatc atcgtcacca cgacctggaa acgacacacg  99120
ttcccccca atcttgggca tgtgtatata tatataaaga atgggaggga gaggacgtgg  99180
ggctcgagaa gaaataaacg ccaagctcga ttcgaaccaa aaaaccacat gtgtattgtg  99240
ctttgttttt tttttttacg gtggggaaaa ggagggggcc gtcattaacg gaaaccgtgt  99300
atggggtccg gacacgaaca gtacacagct tatggggaaa aaagctcaca gagagaaaaa  99360
aaaacaccaa gctcaggcac gcgtacatca ttatcatcat cggatatctc accacgagtc  99420
atagtagtac caaggagtgt gtaacaccat tttttctttt ttctttgtaa cgggataagg  99480
gacagcaatc atcacgcaca acacccttca ctctcttttt agtcatccat atcatcgctg  99540
taacacagca tgtcctcgta atcgggcgtc tggcagcgca ttaccaccga gtcgtcttct  99600
tgcggtaccg gtggtggcgg cggcggctgc tgctgttggg ttgccgtcgt actgtgatta  99660
ccgttggcgg actgcaccgg gatgatgggc tgcttgtggg gaacctgggg tggactgccg  99720
```

```
ccgtgagaag gcgacggcgt catcaagtta agctcaccac ggtgactccg gacaccggcg  99780
aggggcgccg ggggactggg agggaccgcg gtcgtcttgt agacgacggt gtccccgtgt  99840
cgatccgtgg ctcgtaccag atcttgactg ctagcgtcgt cactgtcttc gtcctcttcc  99900
agctcgccct cagagtagtg ctgctgtggt tgcgacggtg gctgggcggg aggagcggcg  99960
gcggcgatca ttggagaggg atgtcgatga ctcccttctc tgtccttttt atcgtaggct 100020
gtcagcgttg ctgggtccgt cctgctttcc atacttgcgc attgctcatc ggtgggatga 100080
atttggtctc ctccccgctg ttgtccgccg gcagtggcgt ggttgctggc ggttgtcgtt 100140
gtcgtaccgg caaagacggt gagatccaat agcgactgct cgtcgaaggg acagtacgct 100200
atcatgaaac gatagggtgc caacgcgcgt tggatgcgca gttcgcacat ctcgttctga 100260
cactcgtggc actgcagggc gcctaggatc aggtccgaga cagcgccgca gcggtaggta 100320
cccatggcgt tgttagtatc gaactggtca aaaaattggg gcgtaccggt gacttgcaac 100380
gcgcgacggc gtagcgagac ggccacgcgc gagaaggagc acacgtaggc catggcgcgg 100440
tgcatgggtt gcgagaaggt ctcgggcgga cgcttctgca gatcgcagac gtcgtcgcgt 100500
agccaggcgc tcatttgacc gggcttcttg actagccgtt tgagcgtgct gcaatggtcg 100560
ccccagccgt cctggtggtc caggatgcag cccaggtcca ggttgttgag tttgttgaaa 100620
agcagctgac gcatgccgcc caccgtctcc agatagggat cgtgcgggtt gacgggtagc 100680
ccgtgcaggt ggtggtactt catgtagctg agcgtttcgt cgatgatggc cagcaacgtg 100740
tgcaagttgg gagcgttgta tacggcgaag atcttttcca ccaccagctt gcgcagcaac 100800
ggttcctcca gccaatcgaa ctgttgacgg atgtgcaaca ggtagtcggt gtgcatgagc 100860
tcgtcgtgtg acagcaggat gcgaccgcgc ggctgatgat cttgcgggaa ggcggtgggg 100920
accttgaggt cggcggggta gggtgccaga cgtagactct cggccgtgta gcgctgaagg 100980
tcgtagacgg gcgaggtaga actcggtgag gtacccgacg aggcggcgcc gcgctgcaga 101040
cgcgctcttt ttttcttttc gatcaaacgg ctgagttgct gtagttcgtc ctcgtccatg 101100
gcgtccagtt cgtcgtcaat aagcgccagc atctgttgtt gttgcggtcc ggcggacgat 101160
ccgtgatgat tattggctga ggaggggtga gaagaaccga aagtcgtagg acaactggga 101220
actcggcgac gaagatgcgt cgaatcgccg ccgtgatggt gcggttcgcc gtcatcgttg 101280
tcgtaagact taccgtagtg gggggttaagg ggcaccgagg cggacgcggc cacgcgtcgc 101340
ttgaaagagg aggacgccct atgtccgcca cggaagcccg cagtgcccat gatgatgtgt 101400
ccgccggtgc ccccgagtgc gtggcgggag gagggtggaa ggggaggagg atagtggtcc 101460
ggatcgcctt cggtatcatc gtctttgctg tagcggggtc gtcgtgcggg gacgcagggt 101520
cggtgatgat gcgaggcggc gccgacggta tcttccgcga gatggtattc gctggcggct 101580
gctccgttcc gtgtcgacgg cgaggttgga cttcgctcgc gtcggaactt ccgtggcacg 101640
ggttcgtaat ccagacagaa gcgccgtgcg cgacgggcgc ggcgttcgcg ctcgctcagg 101700
gaagataacg acggagcgtc gtgacggccg cgtgagtgca gctccatggc cgccgtcgct 101760
aggaaggtca cgttctggca cgctgatgta tatatagatg agaccgctgc cggggggcgg 101820
gtcaccggcg ccgtggaaag tgaggctcag acggcggtcg ccggcggcat gggcgcgtcg 101880
ggcggtctga ttttgatgga aatgtggacg tttttggcgt tggagtgaca ctttttggtg 101940
aaacagcggc tccagaggct ggcccagagc gcgtagctgt gctcggtgcg caggtcgatg 102000
aacacctgca cggtctcttg cgggttgcgg tgcgtgtagt tgagacagcg aaaatcccgc 102060
```

gtgcgcgcgc cgtcgcgtcg cttgacggcc acgcagcagg cgccgtgggg ctgaaagagg 102120
aggacgtggg gcgcggtaaa ctgctcgctg acgtgcggtt cgtagtgttg cgtgaggtgc 102180
tcgagcagcg gcggccacac gcgggtgacg acgagccgct gcaagtccgt gtcggaaatc 102240
gcagcggcag tggcgccgtc gccaccgtac aggtgatagg cgagcacctc ggtgagaccg 102300
cggcgtcgat aacgcgtcac gttaagcgag cgcgtctcga taaagttggc ttcggtcgag 102360
gggcagattt tgtcgcgtac gctgagaatg acgcgtggcg gcggtgacag gggcaacgcg 102420
ggcaggtcgt gcggcgggtg gtggtgaagc aggttacgca gatccagttg ggcgcgcaca 102480
aagcctagcg ggtgttcgcg gtaggcgtcg ggcacgatga acagcggcaa cagacggcga 102540
tgcatgaaat agccgtcgtc ttggtccatt ttatacatgt agggcagacg tacagagcgt 102600
ccatggtggt agatgcctgt gtctaggctg ctctcgggat gcgagatggg gtccagcagc 102660
gtgtgcagtt cggcgtcgag acagacggcg tgattgagca cctgcgccac ggcgcgtaaa 102720
acgctggggt gtacggctat ggtacaggcg gggaacggcg tgatgatgcg cagccccagt 102780
ttgcccttgc agcggcagta agggggtgac gtgtcaacag aggacgttgt tttttggaaa 102840
acgccgttac ccgggacgtt atttttatcc tctttcccgt cttcgtcttc ctctgtgtcg 102900
cgctcgtccc ggtaatcgag atagtcgtcg tcatcgaaag gcgcgccggc cgcgtccacg 102960
ggcacgctgt tgggtgggca cgcgcttttg aagaaataga ccgggtgccg gtcggggtgc 103020
gtgtagccaa agaggctcgc ccatacggtc atccagacgc gtcgtagtcc gcgacataac 103080
tcaaagacgg tgtgtcgcgc cagaccggag acgccgtcgc gcagccgtaa atcaaagtcg 103140
gccacaaaat tgaagacggg cagacgttcg ttgaagactt cgtgtcgcgt gtagtagaac 103200
tgtgtctcgg ggctggtgct ggccacgtcg tcgtcgtgta gccacacggt ctcggtcagg 103260
gcctcgtccg agaaacggct gtcgggtacg tgacggagca ggtcgcgcgg aaagaggctg 103320
cgatgccagg tttcggaggc cacggcgcag aagacgtgct ggtcattggg caggtgtacg 103380
cggtagacgg gcagcggtcg ctccagcagc ggtgccagcg cgggctcggg tagcaggtag 103440
cgacgttgcg agtaacgcgt tagcgtgccg gtggtgtagg tctgagctgt gcgcagcgag 103500
gcgcatagac gtaacaagcc ggacagggag cgttccagcg gcgagaagac agactcggaa 103560
agcgtgttga tgcgttcgag ctggcgcgcc agctgcgtgg aggtgccgaa gaagcccgcc 103620
aggtgcgtgc cgtcgatgcg gccgccgtag ccggccagcc ccaggccgtg cgggctggtc 103680
gccgagtggg gggattcgtc gagacgtagt agatgcgtct ccacgtaatc gtgtagaaag 103740
ttgtcgagcg agaagtattt ttgcatgacg tccagcagct cggtggaaag ccggcggccc 103800
agaaaacccg gttcgcgcgt acactgcgct tcgggcgccg cgtcagcgtc gtaagccacc 103860
acgcgccggt actcgagcaa ccgcgcgcgt gccagcgccg tgcggtaggc caggtagacg 103920
tagtgcacgc agaccgtgtc gggcagacgc gcacgttcgc ggaacgcgtt gatctgcgtg 103980
tccacctgct ctagctcggt gtagtcgcgg cggttgcgcg ccacggcgta cgccacgaaa 104040
gcggacacgc gctgacggaa gggcgagccc agtagcagac gcgcgaactc gcccatggag 104100
gcgtgcgtgg ggatgatggt gcccaggtcg cgcgtgcaga agctgcgcac gtactcctcc 104160
acggtggaga tggtgctgta ctggccctcg aataggtagt aggccatggt cagtagcacc 104220
tggccctcgg tgtgcccgaa gacgctgatg aaccacgagg gcgaggtggg gcagaggaag 104280
acctggttga gatgacgtag cacggccgcg tggtgaaagt acaccaggtg cttgaattcg 104340
cgcacctcgc cgccgtgttc gggcgagagc acgggcgtgc ggaagagatg ccggtagagc 104400
ggccgcgtct cggcctcgtc cagactggcg atgagcgccg agagggggat gggctggcgc 104460

```
gcggccaggt agcgcgagag ttgcagcgtt tcgttgttca cggcgaagac gggcgccacc 104520
cgccgcgagt ccgagcactt ttgcgtctgt aggcagaaat aaacacgtcg cgagacctgg 104580
tgtttgacca gcagggggaa gacgcagtgg tccgtcggtg tctgcgagag tacgttggcg 104640
actatatgag cagaatcata ctctgttgcg aacagaacga gcgtcatcgt cgcgccggca 104700
cgatgcagct ggcccagcgc ctgtgcgagc tgctgatgtg ccgtcgcaaa gccgcgcctg 104760
tggccgatta cgtgctgctg cagcctagcg aggacgtgga gctgcgcgag ctgcaggcgt 104820
ttctggacga gaactttaag cagctggaga tcaccccggc cgacctgcga accttttctc 104880
gcgacacgga cgtggtgaac cacctgctga agctgctgcc gctctatagg caatgccaga 104940
gcaagtgcgc gttcctcaag ggctatctct cggagggctg tttgcctcac acgcggccgg 105000
cggccgaggt ggagtgcaag aaatcgcagc gtatcctaga ggccctggac attctcatcc 105060
tcaaactggt ggtgggcgag tttgccatgt ccgaggccga cagtctggag atgttgctgg 105120
acaagttctc cacggatcag gcctcgctgg tggaggtgca gcgcgttatg ggcctggtgg 105180
acatggactg tgagaaaagc gcgtacatgc tcgaggccgg cgcggctgcg acggttgcac 105240
caccgacgcc accggcggtc gttcaggggg aaagcggcgt ccgcgaggac ggggaaacgg 105300
tcgccgccgt gtcggccttt gcctgttcct cggtttcgga ctcgctgatc cccgaggaaa 105360
cgggggtcac gcgtcctatg atgagtttgg ctcacattaa caccgtctcc tgtcccaccg 105420
ttatgaggtt cgaccagcgg ctgctggaag agggcgacga ggaggatgaa gtgaccgtga 105480
tgtcgccgtc acccgagccc gtgcaacagc agccgccggt cgagcccgtg cagcagcagc 105540
cccagggacg cgggtctcac cgtcggcgct acaaggagtc ggcgccgcag gagacgctgc 105600
ctacgaatca cgaacgcgag attttggatc tcatgcgaca cagccccgac gtgcctcggg 105660
aggcggtgat gtcaccgacc atggtcacca tacctcctcc ccagataccc tttgtgggtt 105720
ccgcgcgtga actcaggggc gtgaagaaaa agaaacccac ggcggcggcc ttgctgtcct 105780
ccgcgtgaac agcctggcac gttttggaaa acgtacgtga tcacgaacac gacgagtacg 105840
aggtttctca tagacgtact ttattaggtc agggatgacg gggaggtttc ggaccgacgt 105900
caaaaataac gtcactcgtg ttgacagggc tttctgcgtc ggagctcttt tcatcttctt 105960
ctgtctcgtc gacgtcatcg tctaccggcg agggtgtccg ttgcagcaac gcgtgctcgg 106020
gtgtgtgggt gaaaccgatg tcgggggtgg gcggcacgat catctgtcct agggggtgac 106080
tgcccaccgg cagataggta aagcggtggg tggtaaaaac cgctttggct acggtggtgt 106140
gtggggagat gcagacggtg gtgtgcgaag tgttgaccac cgtcacgccg gccgcggtac 106200
ccgggagcca gatggtgggt cggatgatga gatccgattg actaaactgg cgcacgccca 106260
ctatgagggc gcagataccg ggcgcgtgca cgtaggccgc gtcaaaatag acggtttgcg 106320
tgtgacccgg accgatcacc agcgtctgac gggtacgtaa tgaaaagaaa cggtgttcgt 106380
tgggcggcgg caagttcatg agctgccagg gttctggcac aaaacagggg aaaacgccga 106440
tatcgccttc gatggtgccc ggaaagatgg actgaaaagt gtcgttgagg ttgacgacat 106500
ccaactgcgg gacttgcagc ccggattcca gcagctcggg catgcaaacg aattgcgcgt 106560
ccaggcattt gtaaaaggta atgccgaaaa aaccttcggg gatatagagg ctgacgccca 106620
gcgaggtggg cactttgcgc tcgcgtgata gccaaatgat gtgtttattg taaaaggcca 106680
gctgcgtgtg gcattgtttg acgatgaaac tggaaggcat ccacttgtag ggaactttga 106740
gcggcgacgg taatggcgac gacgcttcat cctctcccgg atgctgctct ttgtcgtatt 106800
```

```
tctcctcggt cgattggggc agcgtaaatg tggtttgaaa atcgctatcg ctagcgaaac 106860
gcacgcagta acgcatattg acggatttct cggctaggat gatggagcct gatgacggtg 106920
cggactcttc cttcattatt aacgtagggg tctcccagaa tcgctgaaaa cgggagcgcg 106980
gcagccgcga cagtaccagt tgagagtcga ttcggtcggt taacatcgta agcatcgtgg 107040
cggtggtgtg atggagtgga acacactagt attaggtctt ttggttttat cggtagtggc 107100
aagttccaac aatacgtcga ctgctagcac accgcgtccc tctagttcta ctcacgcctc 107160
aacaaccgtg aaggcaacga ctgttgcgac aactagtaca actacggcga caagtacttc 107220
atcgacgact agtgccaaac ctggttccac tactcacgac cccaacgtga tgagaccaca 107280
tgctcacaat gatttttaca atgcgcattg tacatcgcat atgtatgagc tttcactgtc 107340
cagctttgca gcctggtgga ctatgcttaa cgctctcatt ctgatgggag ctttttgtat 107400
cgtattacga cattgctgct tccagaactt tactgcgacc accaccaaag gctattgagg 107460
gtggatagat ttgcagcccg gcggtgttcc ggcggggtaa gatttccata cgcgggtaac 107520
tggaggctaa agttacggat tttatctaga aacagcagcg agtctagata gtcccatagg 107580
ggatctatga acgttctctg aaacctcgtc gatggtgacg taggtgtagt ttcgttatta 107640
tcggaagccg tttcgttttc cacggacatg gtttcgttgt aatataagga gctcatgtca 107700
agagtgccat aaatagtgta cggcgtttcg ttacgaatca gtacgtgcgt gtttttcata 107760
aattctgaca cggcggtacg gttacggtct ggtttacaaa agggttcatt ccgataccgc 107820
agagtagtat atacccatgt tgcgagatct cttaactgcg tggccataat ggatttcata 107880
aagttactat caggacgata acctgtcgta gatgtggcaa cccgcgttac agcagcggta 107940
gcactataag tcacgttagt ggtgacgttg aaagcggtag acgttgtata ggaaagatat 108000
ggcgtagtag tactttgaga tttcttattc tttttttgtg gttgttcttt gacaagcgct 108060
tgtttacgtt tgagttttcg catagtgttt ttcaacttgg tgccgttaat atacttggga 108120
acgcggaata aatttcggct catggcgtta accaggtaga aactgcgagt gcagttacgt 108180
tgcgcgtatc gtaaaagtag ggcggttagg cccaaaaagt agattgtctg actatccacg 108240
ttgactttgt tggaacctat gtacagtttt gtgttccaac gtggtacgtt gaaaaacata 108300
ggattaaacg tggtgaaatt accgcaacct ttttcgccgg tatcattgcg tttggaaaca 108360
tttaacattt cggataggca gttcatagaa ggcactgtgc cgcaaggtgg gggtcgtaac 108420
gttattttgt gggccgtgtg attatattcg gaatatacgt acttggctgg ttttcggagt 108480
tgagtactgt aaaagtcaaa ccacatatgg gtaatgctat catttctaat gggacccgct 108540
aaaatgtagt cttgaggaaa tttatccatg ctaataacga tggcatgaaa tttttgctga 108600
ctggggtaca ttaaaaaccg gtatccgtca gatgatgtag acatcaatcg ttttaagata 108660
tcttccttct gtttcttcag aatctcttta cctcgataag atagcacggt atacggccag 108720
gaacgtcttg ttcctctgga gtttaccaat acattacaat ttatgaggga aaggagcaag 108780
aacgttatag agatcaggag cataatttta ggaatgcctt tcaccattat catctctttt 108840
ttccccatta cagaggagga gacccccgcac cgtccgtctg ccttgtggtt tggtttgcct 108900
gcgtgtactc actgctgatt ctggtcgttt tgctgctcat ctaccgttgt tgcatcggct 108960
tccaagacga cctagtctcc cgcaccttgg ctgtgtaccg agcttgtata cagggcccga 109020
tatgtaacca aacccacaac agtacctcgt aaataaagac gcacaaacct cacgcatata 109080
gtatcatcac accgtgtggc gtgtacttta ttacaatgag caagagtgcc cctaagtatt 109140
ggggcccgta ccgttttaga aggttttgtg cgaatgtctt taacttctct gtcccttttt 109200
```

tcataaactg tcaggtccta caatcagcat gtcttgagca tgcggtagag cagatagatg 109260
ccgatgatgg ccgatagcgc gtagacggac atcatgagga gacgactgtc ggtggcgtcc 109320
acgacgacgt cagttacttc tagtaccgta ccgtttttca aaagcatgag gtagtgagtt 109380
cgcggagatg agaccaccac ttcgttgtag ggatccaggg cgaaaaggac gtcgtccgag 109440
tcgtgcatgt acatgatgtt gatgacgcct tgcgtgtcgt cgtattctag cagggcgctt 109500
tggcaaaagg cgcagttttc tagcgaaatg ttgagcgcca ctgtgatgct gtgtgtggta 109560
tgcatgttgc gcgtcagttc gcatttagtt tgactgtccg tctgggtgat gatgaggctc 109620
tggcctacga cggtggtgga gacagggtag gagatacctt tgatcaggta ctggtttgtt 109680
acgatataac tgacgtgttc ggagacggtc agcgcggaga aggattcgcc gagcggcaag 109740
caaaacaggt cggggaaggt ttccagcgtg cttggttgca tggtagatag gatggagagg 109800
gcggcgggaa cggtagcggg gacggtggca tcggggaaga gacgcgtgag gcgttcgagc 109860
gagtgatcgc gtcgcccgct actggaacag ggtgtgtaca ggtcgctgag gtattcgtgg 109920
tgtggatgag ctaacaactg cgtaaagtgt gatagctcgg ccaatgaaca gaggcccgtt 109980
tctacgatga agatttcgcg tctctccgtc gtatgtacca gcatggagtg gacgaggctg 110040
cccatgaggt agagttcttg gcgtgcgaag gctgaaagaa aagaggccag gtgcgttttg 110100
tgtagtttta gggcaaagtc ggcgatctgt cgtagtgccc attgggggat gagatgttgc 110160
tgattctgtt tagagagtat gtagaccagg cgtacgaggc tggtgatgtc ggtgatctga 110220
ttcggtgtcc aaagggctcg tttggccagg tccacggccg tgggatacag cagcaacgtg 110280
gtgcgtggtg gtgtttgtga gaggcaggtg atcataaatt cttgtatttg taagagtgcg 110340
gcctggcggt ctagggcccg tgggacggag acttgggcgc cggcctcttc ttgtcgggct 110400
gctgcgaaca gtgctaatgc gtaggcgaag gccatttcta ccgtgcggcg gtccagcatc 110460
tgacatcgac cgctcttgag tacatccacg gcgtaacggt gaaagctgtt acgtagtagt 110520
gcgctgaggt ctaggtagtt gaagtcaagt gcggcgtcaa gaaagtccgg gtctttgaga 110580
taagagtgac ggttcagttg atctttctta actagcacca ggagctcgtg tttttcagtt 110640
tgtcgtagta taaagttgtc gcgttgatag ggcgctttga aaagtacgcg tggaagatgg 110700
ccgaagataa gcagcatggg tgtgtcgtcg tctatggaca ccgtaactac gaagaagtcc 110760
tcggtcagtg ttattttaac gtaacgtagt tcgtcgatga ggtaaaagcc ttggtgcaaa 110820
caaggtgtga cggtgctgaa tagtagatcg tgtccatcaa agaggataca ggtctggtta 110880
aagtgtggtc ggtgtagtcc tgaggtggta tgtgattctg tccagccgtg tggagtggtt 110940
tgcggtggca tccaaacgtg aggtattgac aggtcaatgg gcggtggcac agtggtgggc 111000
tgttcaccta ggctgtcttg tgcctttagc tgctgcgaaa aagatcggta gctggccagg 111060
tctttggata ccagcgcgta agtgttaagt ctctgttggt atctttccag ggtttcggtc 111120
agatctacct ggttcagaaa ctgctccgcc agaggacccg caaaaagaca tcgaggcata 111180
tggaatacat agtattgatt atagctttgg aaaaagttga aactgatggc gttttccctg 111240
acgaccgtgc tgttacggag gctgctgttg taggtacact gggtggtatt ttcacgcagg 111300
aagcggatgg gtctcccgta ggtgttgagc agtaggtgaa acgctttgtc cagcggttcg 111360
gatacggctt ctgcgccata tcgtgacgaa agtaggtggc tgaagagaca gacggcgagg 111420
atgatgaggt aggaggggag gcctggccgc atagcgcggc cgcgccgctg ggttcagcgg 111480
cgtgatccag gtggtggttg gcgttacacc cgagagaagg agagaaagga tcccaggaag 111540

```
gagcacccgg gtgtggcgct acgggttaca aaagtcgcgt ctccgtctat ttaatacgat 111600
gtcattggcc gctgcgaagg gagaagaggg gacacgcgag taagccatgc cgtccgggtg 111660
tggggacgac gctgattcga cggggaacgc tctgcggaga ttgcctcacg tgcgtaagcg 111720
gatcggtaag cgcaagcacc tggacatcta ccgtcgcctg ctgcgggtct ttccctcgtt 111780
tgtggcgctc aaccgcctgt tgggaggcct tttcccaccc gagttgcaaa agtaccgtcg 111840
ccgtcttttc atcgaagtac gattaagtcg gcggattccc gactgcgtgt tggtgttttt 111900
accgccggac tctgggtcac gcggcatcgt gtattgctac gtgattgagt tcaaaaccac 111960
gtactcagac gccgacgatc agtccgtgcg gtggcacgcc acccacagcc tgcagtacgc 112020
cgagggcctg cgccagctca agggcgccct ggtggacttt gattttctgc gtctgccgcg 112080
cggtggcggt caagtctgga gcgtagtgcc tagtttggtt ttttttcagc aaaaggccga 112140
tcgcccatct ttttaccggg cttttcgctc gggccgtttc gacttgtgta ccgattctgt 112200
tctggactat ctgggacggc gtcaggatga gtctgttgca cacctttttgg cggctacccg 112260
tcgccgtctt cttcgagccg cacgaggaaa acgtgctgcg ctgcccccgag cgcgtgcttc 112320
ggcggttgct ggaggacgcg gcggtggcaa tgcgcggcgg gggctggcgc gaggacgtgc 112380
tcatggaccg ggtgcgcaaa cggtatctgc gtcaggagct gagggatctg ggtcacaggg 112440
tacagactta ctgcgaggat ctcgaagggc gcgtgtccga ggcggaggcg ctgttgaacc 112500
agcagtgcga gctcgacgaa ggaccgtcgc cgcggacgct gctacaacca ccgtgtcgtc 112560
cgcgttcgtc gtccccaggg accggcgtgg caggagcttc cgccgtccca cacggtcttt 112620
atagtcggca cgatgccatc acgggacccg tcgccgcccc gtctgacgcg gtcgccgcgt 112680
cagcggccgc cggtgcttct tctacctggc tggcgcagtg cgccgagcag ccgttgcccg 112740
ggaacgtacc taactacttt ggaatcacgc agaacgatcc ctttatccgc tttcacaccg 112800
attttcgcgg cgaggtggtc aacaccatgt tcgagaacgc ctccacttgg actttctcct 112860
ttggtatctg gtactatcgg ctcaagcggg ggttgtacac gcaaccacgg tggaaacgag 112920
tgtaccatct ggcgcagatg gacaactttt ccatttcgca ggagctgctg ctcggcgtgg 112980
tcaacgcttt ggaaaacgtg acggtgtatc cgacgtacga ctgtgtactc tccgatttgg 113040
aagccgccgc ctgtctgcta gtcgcctacg gacacgcgct ttgggagggc cgcgatccgc 113100
cggactccgt gacggcggtg ttgagtgagc tgcctcagct gttaccgcgt ctggccgacg 113160
acgtgagtcg tgagattgcc gcttgggaag gccccgtcgc cgcgggtaac aactattacg 113220
cgtatcgcga ctcgcccgat ctacgctact acatgcccct aagcggtggt cgccactatc 113280
acccgggcac ttttgatcgt cacgtgctgg tgcggctttt ccacaaacgc ggcgttcttc 113340
agcatttgcc gggctacggg acgataacgg aggagctggt gcaagagcgt ctgtcgggcc 113400
aggtgcgcga cgacgtgctt tctctctgga gtcgacgtct gctggtcggc aagctgggtc 113460
gcgacgtgcc cgtctttgtg cacgaacagc aatatctgcg ttcgggcctg acctgcctgg 113520
ctggcctgct gttgttgtgg aaggtgacca acgcggatag cgtcttcgct ccgcgcacgg 113580
gcaaatttac gttggccgac ctgctgggtt cggatgccgt agccggcggc gggttgcccg 113640
gggggcgcgc gggcggcgaa gagaagggct acgggggacg gcacgggcgg gtacgtaact 113700
ttgagtttct ggtacagtac tacatcgggc cgtggtacgc gcgcgacccc gcggtcacgc 113760
tgtcgcagct ctttcccggc ctggctctgt tggccgtgac cgagagcgtg cgcagcggct 113820
gggatccctc acgtcgcgag gacagcgccg gaggtggcga cggcggcggc gccgtgctca 113880
tgcagctcag caagagcaac cccgtggccg actacatgtt cgcgcagagc tccaaacagt 113940
```

```
acggcgattt acgtcgctta gaggtacacg atgccctgct ctttcactac gaacacgggc 114000
tagggcggct gttgtcagtg accctgccgc gtcaccgtgt gtccactctg ggctcgtccc 114060
tctttaacgt caacgatatt tacgaactgt tgtacttttt agtgttgggg tttcttccga 114120
gcgtggcggt gttgtaattt ccaccacgtg tcgctcgctg cataaagggc gaacgtcctc 114180
ggagagggta tattcgttcg gcgagagcgg gcggcggtgg tgggtatgtc cccttctgtg 114240
gaggagacta cctcagtcac cgagtccatc atgttcgcta tcgtgagttt caaacacatg 114300
ggcccgttcg aaggctactc tatgtcggcc gatcgcgccg cctcggatct actcatcggc 114360
atgttcggct ccgttagcct ggtcaacctg ctgactatca tcggttgcct ctgggtgttg 114420
cgtgttacgc ggccgcccgt gtccgtgatg atttttactt ggaatctggt acttagtcag 114480
ttttttttcca tcctggccac catgttgtcc aagggtatca tgctgcgtgg cgctctaaat 114540
ctcagcctct gtcgcttagt gctctttgtc gacgacgtgg gcctatattc gacggcgttg 114600
tttttcctct ttctgatact ggatcgtctg tcggccatat cttacggccg tgatctctgg 114660
catcatgaga cgcgcgaaaa cgccggcgtg gcgctctacg cggtcgcctt tgcctgggtt 114720
ctttccatcg tagccgctgt gcccaccgcc gctacgggtt cactggacta ccgttggcta 114780
ggctgtcaga tccctataca gtatgccgcg gtggacctca ccatcaagat gtggtttttg 114840
ctgggggcgc ccatgatcgc cgtactggct aacgtggtag agttggccta cagcgatcgg 114900
cgcgaccacg tctggtccta cgtgggtcgt gtctgcacct tctacgtgac gtgtctcatg 114960
ctgtttgtgc cctactactg cttcagagtc ctacgcggtg tactgcagcc cgctagcgcg 115020
gccggcaccg gtttcggcat tatggattac gtggaattgg ctacgcgtac ccttctcacc 115080
atgcgtcttg gcattctgcc gctctttatc attgcgttct tctcccgcga gcccaccaag 115140
gatctggatg actcctttga ttatctggtc gagagatgtc agcaaagctg ccacggtcat 115200
ttcgtacgtc ggttggtgca ggcgttgaag cgggctatgt atagcgtgga gctggccgtg 115260
tgttactttt ctacgtccgt ccgagacgtc gccgaggcgg tgaaaaagtc ctccagccgt 115320
tgttacgccg acgcgacgtc ggcggccgtt gtggtaacga caaccacgtc ggagaaagcc 115380
acgttggtgg agcacgcgga aggcatggct tccgaaatgt gtcctgggac tacgatcgat 115440
gtttcggccg aaagttcctc cgtcctctgc accgacggcg aaaacaccgt cgcgtcggac 115500
gcgacggtga cggcattatg agcggcggcg ctgtacggca gcggggagaa aagtggcaga 115560
taaatcacgt caggttcaca cgtcgttagc cagcgtcggc atatgaaggg cgcgggcggc 115620
cagtacggcc tctgggctga gacaggacga ggcagggtga gaaagaggag gatgggggg 115680
accggggtgg tggtgctgct gctgttgtgg gtgcggacgg tgcgggtgcc gggacagcgt 115740
gccggcgaac gttctgtaat cttccataat aaaagtaaaa atgcccgtct cgtgtcgact 115800
ccgctggatg tcgaaggcgt cgggggtaat gcgcatcttg ccggtgccga tgagataaaa 115860
gtaccacatt ttttgacaga tgatgcgaat caagggttcg tacgcttcgg caccccagtg 115920
gcgcgtgaag aaggccgcca gacgaaacaa gcggtgtccg tagagcgtgc ctagggagaa 115980
gaggatgttg ccgttgcgcg ccaggtcttc ggggaaaacg accggcaggc cggtgtggcg 116040
ctgcacaaag cgcgtcagca gtccgccgct caagcgcggg tgacataggc gctggctgag 116100
acgggcggcg cgcgtttcat cgaacacggc cgcctcaaag tccagccccg ggaaggcctg 116160
gcgcagttcg cggtacagat gaggccagta gggttgcggc gtcttgcgac taagcacggc 116220
gtggtccgag acacccaggt tgttcatggt ttcgcgcagt agcagcgttt cgagaccgcg 116280
```

gtgaaagagg aggacgcaga tgaggcgtac gatcttgagt tcttccaaac gcagcgagct 116340
cagcggctgt ccgcgcgaca tcttctcgct aatctgtaat attagatgat tggcgcaagt 116400
aaaggagaat ttgcccgtgc ggacccgcgg gacggcgggg ttctcttcgt cgcgggccat 116460
catcgttcgc tcggtgagcg ggtagcgacg gtgacgacaa tgacgatgga cgagcagcag 116520
tcgcaggctg tggcgccggt ctacgtgggc ggctttctcg cccgctacga ccagtctccg 116580
gacgaggccg aattgctgtt gccgcgggac gtagtggagc actggttgca cgcgcagggc 116640
cagggacagc cttcgttgtc ggtcgcgctc ccgctcaaca tcaaccacga cgacacggcc 116700
gttgtaggac acgttgcggc gatgcagagc gtccgcgacg gtctttttttg cctgggctgc 116760
gtcacttcgc ccaggtttct ggagattgta cgccgcgctt cggaaaagtc cgagctggtt 116820
tcgcgcgggc ccgtcagtcc gctgcagcca gacaaggtgg tggagtttct cagcggcagc 116880
tacgccggcc tctcgctctc cagccggcgc tgcgacgacg tggaggccgc gacgtcgctt 116940
tcgggctcgg aaaccacgcc gttcaaacac gtggctttgt gcagcgtggg tcggcgtcgc 117000
ggtacgttgg ccgtgtacgg gcgcgatccc gagtgggtca cacagcggtt tccagacctc 117060
acggcggccg accgtgacgg gctacgtgca cagtggcagc gctgcggcag cactgctgtc 117120
gacgcgtcgg gcgatccctt tcgctcagac agctacggcc tgttgggcaa cagcgtggac 117180
gcgctctaca tccgtgagcg actgcccaag ctgcgctacg acaagcaact agtcggcgtg 117240
acggagcgcg agtcgtacgt caaggcgagc gtttcgcctg aggcggcgtg cgttattaaa 117300
gcggcgtccg ccgagcgttc gggcgacagc cgcagtcagg ccgccacgcc ggcggctggg 117360
gcgcgcgttc cctcttcgtc cccgtcgcct ccagtcgaac cgccatctcc tgtacagccg 117420
cctgcgcttc cagcgtcgcc gtccgttctt cccgcggaat caccgccgtc gctttctccc 117480
tcggagccgg cagaggcggc gtccatgtcg caccctctga gtgctgcggt tcccgccgct 117540
acggctcctc caggtgctac cgtggcaggt gcgtcgccgg ctgtgtcgtc tctagcgtgg 117600
cctcacgacg gagtttattt acccaaagac gctttttttct cgctacttgg ggccagtcgc 117660
tcggcagcgc ccgtcatgta tcccggcgcc gtagcggccc ctccttctgc ttcgccagca 117720
ccgctgcctt tgccgtctta tcccgcgtcc tacggcgccc ccgtcgtggg ttacgaccag 117780
ttggcggcac gtcactttgc ggactacgtg gatccccatt atcccgggtg gggtcggcgt 117840
tacgagcccg cgccgtcttt gcatccgtct tatcccgtgc cgccgccacc atcaccggcc 117900
tattaccgtc ggcgcgactc tccgggcggt atggatgaac caccgtccgg atgggagcgt 117960
tacgacggtg gtcaccgtgg tcagtcgcag aagcagcacc gtcacggggg cagcggcgga 118020
cacaacaaac gccgtaagga aaccgcggcg gcgtcgtcgt cgtcctcgga cgaagacttg 118080
agtttcccag gcgaggccga gcacggccgg gcacgaaagc gtctaaaaag tcacgtcaat 118140
agcgacggtg gaagtggcgg gcacgcgggt tccaatcagc agcagcaaca acgttacgat 118200
gaactgcggg atgccattca cgagctgaaa cgcgatctgt ttgccgcgcg gcagagttct 118260
acgttacttt cggcggctct cccctctgcg gcctcttcct ccccaactac tactaccgtg 118320
tgtactccca ccagcgagct gacgagtggc ggaggagaaa cacccacggc acttctatcc 118380
ggaggtgcca aggtagctga gcgcgctcag gccggcgtgg tgaacgccag ttgccgcctc 118440
gctaccgcgt cgggttctga ggcggcaacg gccgggccct cgacggcagg ttcttcttcc 118500
tgcccggcta gtgtcgtgtt agccgccgct gctgcccaag ccgccgcagc ttcccagagc 118560
ccgcccaaag acatggtaga tctgaatcgg cggatttttg tggctgcgct caataagctc 118620
gagtaagaga gacgctatat ttagggcttc cctctctttt ttttctacac cgtgataccc 118680

```
taataaagca caccgcggtt attatcaacg tctctgtgtt tttattattt agaaataaat 118740
acagggaatg ggaaaaacac gcgggggaaa aacaaagaag tctctctcta gatgcggggt 118800
cgactgcgtg gggtgctgga agtggaagcg gtgctgatgg gtgagggtcg tggcgcgggc 118860
acggaccgca acgtgctgct gatgtctgcc gcggtacgca cgtcgccgtc catgtcgctg 118920
cgcagataag aggtaggtcg tagtgcggcg tgctgcacgc tcaccgttaa tggtaccaag 118980
tcgtcaaggc tcgcaaagac gtgccacgag gggatgacga gcgtgagagc cccgttgtta 119040
ccgcttcgac gtctttgtcc ggtcaggatc agtgcccggg acagtccggc ttgggtgtcc 119100
gagtcctcgt cgccgctggc ttcctcgaag ccggcaaaca tggcttcgga caggggggtc 119160
ggcgtcggtg tggaggagag gtcatcttcg tcgtcctctt cctcttcttc ctcctcttcc 119220
tcggtgggtg gtaatccggg ggactgcggg agaaactcgg agacggcgcc gcgcatgacg 119280
ttgctccgtg gaaagagacc ggcgcgcagc tgcacctggg gacgcttgat tttgtccggt 119340
ttaccgggtg tgagagtcca aaacccacgg cggaaaaagt ggatgcggcc tagcggctgt 119400
cggtgttcca aatgaacggc ctgatcgccg gtcagcgtga cgcggagggt gattcgcaca 119460
cgatcgggta gcgggccggc ttctatggag acgcccggga tgttttccgg gaaaaagatg 119520
gtgtcgtgag tctgattggt ctcgaaagca ttctggatct gcacgatgta ctcgggatgt 119580
atgcgcgtca gcgtaaaact tttgggaatc aacagctgga agccgttgtc cggcaagcgt 119640
cgtaggtgcg ggtacggatt gtgtcgcgcc accacctcgg cgcgatgcgt gtaaaccgaa 119700
aagtgcagaa acacgctggt cggcgggtgc ggtgagtcgt gatgcagaaa cagcatgatc 119760
cattggcctc gttcgtccgt ctccgttttg tggatgtacg tgttagggtc cgaacaggcc 119820
agctgctcca gggcgtctac cagcgtcagc gggatggcgc cggcgcgaaa ggcgaactgg 119880
ctgacaaaga tctgccctgc ctccaaactg ctgtcggttc tgcggcgcca gttcggcgtt 119940
acggtcagtc gcacggccca gtggtgagcc gtgcggcgga tgatggcgcg cgcttccatt 120000
cgcggccgat tttcttcgcc gccgcgccgc tggctctgaa agaggtgcag tccgctaacg 120060
ggcacgcggt ccagcggcag cgcaaaggcc agtaccgaga ccgtgttgtt ttctgagcct 120120
ggcgtcaggc gtcgtgggcc aaagttgttg aggtccacca gcagtcggtc ctgttcgccc 120180
accacgcagc ggcccttgat gtttaagtcg gtcaggtcta cggtgtcgtg cggagatttg 120240
ttctcctgaa aacagcagag aaccgagggc cggctcacct ctatgttggt acgcaggtcc 120300
aggagtcgca gacgaccggc ttccagcgag ccgccttcca cgttggtgat gagccgaagc 120360
acctggcagt gcaggcgacc aaagcttccg ctggcggctt cggcctcgct gatcgcggcc 120420
gcttccgacg agggtccctc accgggcgag gacgatgcct gagacattgc gaaggcggga 120480
tggggggagg gtcaggggat gcgcaaaggt gaacgggtct tcgtgggagg tcgggaaggg 120540
ttccggcaac tgtcgcaaat atagcagcgg tgacaggtgt ggcggccaaa agttgcgtgt 120600
ctgagtggac gtgggttttt atagagtcgt cctaagcgcg tgcgcggcgg gtggctcaac 120660
ctcggtgctt tttgggcgtc gaggcgatgc atggcccggg caaggcgtct tgccggtggc 120720
ggcgacgttt gggttgcgca gcgggctgcc atacgccttc caattcggcg aagatgcggt 120780
agatgtcgtt ggcgtcccag aagaactcct ggtacttcag attctgaccc tgaaccgtag 120840
ccaccatggg caccaggttg cgggccagga tgccggcctg ccagggcggc caggtgaaca 120900
cggccggatt gtggatttcg ttgtcggaat cctcgtcggt gtcctcttcg ggcgcgacgg 120960
tggactcggc cttaaggcgg ccgcgtgtca taacgcccgc cgtgcacgcc gtcgccgagg 121020
```

atgctgattt gcgtttgcgg cccgcggaag tggaggcgct cgccatggcg ccgccgccgg 121080
tgacgcgggg cgtcttacgc tcggtggtta cgagttcttc gtcggagtcc gatccgctgg 121140
tccagacgtc gtcgtcgccc tgggcggcac cctcgtcgtg ccggtcccag gtgtgtcggt 121200
actcaagctt gccctggatg cgatactggc tggtgaaggt ggggtgctcg ctgtactgag 121260
gcccgcgctg cagcaacaag tcgatatcga aaaagaagag cgcagccacg ggatcgtact 121320
gacgcagttc cacggtctcg cgtatcgctt gtacctccag gaagatttgc tgcccgttca 121380
tcaacaggtt acctgagatg ctcaggcccg ggatgctctt gggacacagc agcccaaaat 121440
gctcgtgtga ggtaaaagcc acatccagca tgatgtgcga gatcttgccc ggtttgatta 121500
tcatattttt gggacacaac accgtaaagc cgttgcgctc gtgggggcgc atgaagggtt 121560
gcgggttgcg ggtcatcgtt aggtcctctt ccacgtcaga gcccagcgtg acgtgcataa 121620
agagcttgcc ggagggcacg tcctcgcaga aggactccag gtacaccttg acgtactggt 121680
cacctatcac ctgcatcttg gttgcgcgcg tgttctccat ggagcaaacc agctcgtgcg 121740
cgcacaccac gtgccgcagt gccacgtcct tggtgggaaa cacgaacgct gacgtgtagt 121800
agacgtcggg ctctttccac tggttctgct gacgcgtcca ggccagtccc gagaccgtga 121860
gacgcgcctg ccacatctgc ttgcccgacg cgtgaataac agcgtcggct acgggcaggt 121920
gtcggtgttt gcgctcggcc gccgacgggt agtggtgcac gttgatgctg gggatgttca 121980
gcatcttgag cggcagcgcg tacacataga tcgacatggg ctcttggctg gggcagatgc 122040
ttcggcccgt ggggttgtgc acgttgaccg acacgttctc cacctcgctg cccgtaaagt 122100
acgtgtgctg cacctgcagc tgattgtcgc cgcggtggca tggcgtcgag tcgggcgtgt 122160
actgcgacac caggatcagc gagggctggc tcacgcgtac gtggataccc gtctgcagga 122220
gtcgcgtctc gtgcggcagc accggcgtat cgccgcgact aaacacggct ttcagcacgt 122280
gccccgaaat gggacccagt acggatatca tttcgggaca acggcgaccg cgcgactcca 122340
tgctgcctgc gcgtacgggt gtaggcgact gagcggcgcg ccctctgcgg ccgccgcctt 122400
acataggcag gcgaccaaac gcggaacccg aaataaaaac gttatacaca gagacaaccg 122460
cggattattg agtgtctttt tttattacaa aaaaaaagag gcaaagcccc accgtcacca 122520
caccccatca cacaccacca ccgatttttt ttgttttaat cccgtattgc gcggacgcct 122580
agtgtccgtt ttccatcacc agggtcctct gtttagagat cgccgcagac catggctaga 122640
gtgacaggac tcgttttctc tgtcgtattt tccgtaagct tacagtcttg cggttccgtc 122700
tccggggacg ccagtcgcat gggcagcagg tcctccagcg cgatggaagc gcccagcacc 122760
gagagctgct gttgcgacgg cgaatgggac gtggaccgcg agtgtagcgt ggatttgact 122820
tggtgcgtca ttgctgacag gcaaccgcga ttcagcgtat gctttgacga gataaaatag 122880
aggcgtccca ggagcgcgtc ccgtgggaac gtggcgccgt tctcgtcgct taccagtacg 122940
gttaattcca accaggagcg cggtagccag accgtaacgg gcattttgag tccctgacgg 123000
ttgtgtggta caaaaacacc cagataaggc ccgtaaaagc ggcggtagat acgtaacgtg 123060
tgcgagtttt tcagcgtcaa ttcgtaaggg acgcgcacct ccagtccctc gtccgccgcg 123120
ccggagcgtg gcggtacaaa gtaaggcagt ggcgcgtccg aaaagaaggg tcgtcgcacc 123180
gtttcgcgtc gcagccgcag gcgaaacgcc actgggtcgg ctggcgcctc ggtgcggtcg 123240
caggtcacgt tgaaacgtaa tatgccgtct tggtatagcg tgagtgacga cagcgtcagg 123300
tccggcggtg attcgttcgg gtctagctcc aatcgtccaa agacggaggg tcccaatgtc 123360
ttggcagtgg tttccgagag gcgcgccgaa atacggctgg tgagtccacg cggccccgag 123420
atgccgcctt ccactcgatg ccagcacagc gcgtgtcgta cgcgcaccgt cagtgtgggc 123480
gtcagatccg cgtccgttga ttccgcggta tcagcgacgg aagccgcgtt ctccgttacg 123540
ttgtttatat ccagcgtcgg ctcgaacgtg agttctggca gatgcagcgc cagacagtcg 123600
tgtaacgccg tgtgatgcgc ggctttacgt cgtagcggta gccgtttcag cagcggcgtg 123660
atgatacgga gcgcgaagag attgagtgat aagcgcacga tggccatgcg cgtcagttgt 123720
tggtcaatta ccgagcgcag gatatggcag cctgggcgtg cgggaaagag agagaaggcc 123780
gggcgcacgt cagaatcctc gttagagacc acgcatagaa tgccgcgttc acgatcgtcg 123840
ttgcggtcat cctcgtcctc ttcttctttc ttctcttctt tttccttttt tttctcgggc 123900
tcgtgggaag ccgccgtttc ttcttcttgc gacgtcgcgg gggcggtttg agactcgccg 123960
ttcgcttccc ccaattgcag cggcgtagag agcaaaatct ggaagggatc ccgcaattct 124020
tcgggtcgga ggtcgaggtg caactggatc agatggtagg tgccgcggtg cacccgaggc 124080
tgacggatgt cgtgtttatc cgtcagtgtg aggatggtct gcggtgagcc gctgtgcttg 124140
tccagctcgt ccggcgtttt caggaggaga ctgtcgtcgt cggtactggc gacacccatc 124200
atggtcgtgg tggtagtggt ggcgaggaaa gtgagcggcg gcgtcgacag agctcggcgt 124260
tggcggcggc atttgccgct gtgtcggctg ctattgctgc caacgccacc gccgccgcct 124320
cgtctggctc gtggccgacg ggcccgattc cgaaggttgg ggtcgacgcg tggcatgctt 124380
ggtgtctgcg ggcgcgagag ggccggctca gcctttaaat atgcaggtcg cggatttgtt 124440
atcgggtgaa acgtcacaca ccgtgaagac gacctgttcg cggatgaggt catccagctg 124500
tcgcagcatg acgaaaagcg ccgacagccg cgcgatctcg tcgtcgggcg acacgtgctg 124560
cggccgcgcg ggcgtgcgcg gctcgccgac gctgcgctcg cggtccagcc gcatcagcag 124620
ctcctggcac ttgacgagca gcatggagct gtcctctagc gctaacttgc gcacgtaggt 124680
catggtcagc tccgaggcta ggttagccac catggacatg gagaggcagg cggtcttcat 124740
gtcgatcagc aggtgctggt cgatgaccgg atcggggatg gtgaaggtgg cgtcgcgaaa 124800
agtaatggtc tgcagctgct gcacggcagc ctttacctcc tcgtacgaac ggtcgagcga 124860
gaagaggccc atgatgagta gtcgctggtt gatttccagc gccagtggca tgggtacgat 124920
ccagggcagc accagctccc actggcccag cgtcagcagg ttctcgcgcg ccagcggtcc 124980
gtggaagagc ggcggcagca cgcatagcgc gtcgcccttc tcccaagtca cgggtcccgt 125040
gttgaggacg gtgtagagca gtccgtgcgt cggtacgtgt aggaggatct ggttgccttc 125100
tacgcgccgc atcaacgtca gcgtcatatt gcgcagcagg ccgcgcagtc gtacgtagcc 125160
gcgggtgtga tctacgaact ggtgtaggcc cagctggtag tgcttgatga gatgtagacg 125220
ctgcggaatg ggcacaacgg ccgctactag tttggtcagt ttgcctacgt cggcgatgct 125280
gagcttgtgg tcgaaagtgc agaagatgtt ggcctccatg gccgccatag cggcggtgaa 125340
atcctggccg cgacggagga gaagcggaga cgaacaacgt ctgcaccggg cgcggcgtca 125400
gagcgagcgt ggcgcgtccg ggcccgcgtt tgcgtctagg tgactcgccg ctaacctgcg 125460
gtcgtcgccg tcctcctcac cggacggcct cacgagttaa ataacatgga ttgctgcagc 125520
gggatgattt cgcctacgac gtagttacca aagtgcgttt cggacgtagc aaaagccccg 125580
gcgccaccct tgagtttggt ctccatcagc gccagcgtgg tggtgctgag gatcggtagc 125640
gcttcctgcg tcagacggca cgggttttcg atgagttgtt ccgtgccttc gacgcagacg 125700
tactgcgtgt ccgtgtcgcc gcggatgcag tccttggcgc gtagcaggta ctcgtcgatg 125760
gttttgaaga gcgttttgtt ggccgcgata atctcttctg tgttaaagta ctgcgcgcaa 125820
gggctgtaga atttggagtt gtagcctaga cgttcgcgat gtcgggtgtt gtagagtacg 125880
tcgctcagac agccggcttg cgaggcccag gggttgtgtg tggccgcgaa agtctgtgcg 125940
tccgcttcgc gatggtcgta gatggccttg gtggcggcct ccgtgtcgta cggatcgacg 126000
gccagcatgc aggaggcacg cccgcgcggg ttgttgggga tcttaaagta attaacgtcc 126060
atcgtcaccg gcgtaaggat tagttcgcac gcggcctttt gtccgtgcac cgtggcggcg 126120
gcattgcgct cggacatgct gccgaacgtc agcatggaga tggtctccgt gtctaacagt 126180
tgcggccgtt ctacgccggc cgcgtgccgg atccagcggt ccacctcgtc gtgccggtac 126240
acgttcatag ggaagacgcg aaagaggtcc tgcacgcgga cgcccatgtc ggttcgcacg 126300
cggtttacgt aggctacgca ggtatttgac gtgtaaccca gacccatgtc tacggtgtta 126360
atgttctgcg tgacgtggta cgtggtgctg atgtcgcgtt cctccttggt cacgataggg 126420
ttgttgatga taactgacgt gcatgatttg ccgctgtaga gcagcatgtc cacctcgaag 126480
gtgtcggtgc gtacggccgt gagtgcgaat cccgggtgga tgtgcgcctt ggtctgcagc 126540
accagtgaaa ctggtgagat tttgtataac atggcggcca gcgtcatgac tgagtgcaac 126600
acgttgggac aggtggccga gtaacgcgaa aagggcgagc gcagccagtt gtggtactcg 126660
tgcgcgaagg ctgtgggtag cgggaaacca ccgtcgtgac ggtgatagtg cgggaactcg 126720
gtcacgtagc gtttaatgtc gtcgctcaac gccgcgcaga tggtggggtt tgagtagaaa 126780
cggtggaaag gtacgggtag gctgtactcg atcaacgtct taggcgccgt cacgacgcag 126840
cagccgttgt aaagcacgtg ctgacgtgag ataaagtccg gcaggccctg acgctgcgcg 126900
tggtccagag gcgcgcgcac ttcgagcacc ttgacgtgct cgcccacgaa ttgcacggcc 126960
aaaaacagtt cacgacaggc ctgcagcagc ggcgtatgtg cgtcggtggc gacgtcctcc 127020
accagctcgg tcagcatctc gcctacggct tgacgttgcg ccgctatcga gtcttcgggg 127080
gtgacgccgc ttgtgctctc tttcgacgtc gtacctgacg tggagaccgc ggtggcggcc 127140
ggcatcagga gaaacgccgg tcggtaaaag aggtctacta gcagcgtctt gaggttgagt 127200
cccaggccgc aggcccggtt gttggtcatg gcgggcatga ggcagagata aaagaccttt 127260
tgtaacgtcc attcgtcgtc ggtggcacgg taatcgtcca caaacagcgg ctcgtcggca 127320
tccatggcgc ccaaacgcgg tacgtccgaa acgccgtggt gtcgcgcctc gatgttggcc 127380
gggttcaacg gttgccggtc ggccactacc tgtacgcctt ccatgttacg cggcaggtgc 127440
gtaacgaagg ggggccacag ccggtggtcg tgcagcgcgt tcacgtaagc cgatagcggt 127500
tcctcagcca gttgaccgtt gttaagtccc ggcagcgctg agatgcgcgt taccagacgc 127560
agcacggcga ccagattgcg gtagtgaaag agcaactgcg gtggtagggc gccatcagcc 127620
aggtgttcgg cgatcaacgt caccagcgcg tagctgtgcg caaaaaccag cagctgacgt 127680
gtgtgaaaca tgttgacgat acaacgtgct acgaaagtgc ggattagcaa aaaagcgtcg 127740
acgttgccgt gtaccagcac gtcgaccagg tagcaaagct cggggtaatt ggggcttgta 127800
acggtggttt tgaaaagtcg caacgtctct tcgtagtcgg gtggtggccg cagtcgcatg 127860
tgttccatga tctcccaggt gcgcagttcg tggaaggggc ccggtgccag tccatctggc 127920
aaattaccga tgacgatacg cggtgtacac agcgccaccg tttcgctgtt ttcctggcag 127980
tgcgtaaagt cgaagaaggg gtgcagctcg gtgtagagcg tgatgttgcc caccttgtag 128040
aagtcggtga ccacaaagtc ctgcttcatt tcgttcaccg tgcgcgggac ctcgcgtcgt 128100
acgcggtaaa aatgcggtat gcggcgcgcc gcaccgccca tgggttcctg ctgaaaacga 128160
cactcgagca gtcgttgcat ggcgggttcc gagggtggtc cgcgttccgt gaaggtctgt 128220
agacagggcg cgggctcgtg cagcaccggg tggcacagcg tcttgagcgc gtccacaaag 128280
tctatttttt gtacggcacg gtcccggttt agcaggtagg ccgtggtggg caacgcgttg 128340
cgaacggtgt cgttaagctt aactttgctt tccaccgtgg tgtaaccgcg atcctcgggc 128400
agatacagcc ctacggggaa gaaaaacgtc aggtccacgt tacgttctag cggatctttg 128460
gtatcggtgt ttttgtagac gcgccgcaag ttttccataa tcaccgtttt ttcgcccagt 128520
cggatcacgt ccatgctcag cggcgttaag ctgtgcgccc cggcctgcga aagcgagtcg 128580
ttgggcaaat gcggttggcc cgaagtcaga tgagccttgt acgagttgaa atcggccagg 128640
atcgagtgat aggatatggc agtgacggca ttttcgggac tgagtacaaa attgccgtag 128700
gtggccggcg ccgagaccgt ttctttggtg atgtggcttg agagcagcga catgatgatc 128760
tgcataacgt tggccgtgct taccatcacg ccactgatct tggcccccga gctcgtggtg 128820
tacgtggtgg ggttgtctag gatgctatcg gtggccgctt cggccagacg cgtgaggaac 128880
ttgagcacat agtcgcgatc gcgcgtgcga ttcagcaaaa agagcgtggc cagcattttg 128940
gccttgaagc tctgcaagat gttgcttcgc tggatgcggt tcagcgcctg tcgcgccagc 129000
gtggcgttct ctaccagcgt ctgcaccaca aagtacggcg gcgccttgcg tagcagtgtc 129060
tgtaaaaagc tgtgaatcaa gccgcgttcc atggcgtcgg ccgtgttttt gagcgcgcgc 129120
agcaccgtgt gcatagcttc cacgttgagg atcttgtcca ggatggtgcc ttcgaacgtc 129180
tcgcgcagat acgtgaggca ggctgcgctg agctcaaagg ggatggtgat gggggatttt 129240
tcactgtatt tggtgaccat aatggtggtc tgacgactgg taggcaaacc ggcgccgctg 129300
gccacccgcg gcacctgtac gtggaacagc atttttcccg tagtcagttt attgaggtcg 129360
tggaacttga tggcgtgcgc cgccgcggcc aagccgctgg tcaaaaaata aacccattcc 129420
aggcgattgc agaaggtgcc gaagatggct tcgaagtgaa tattgtaacg ctcggggtca 129480
tcgccgtagt agatgcgtaa ggcctcgaac atctcctcgc cggcgctggt cttgacgtgc 129540
gtcagaaagt cagtgggaat gcctacttta ggcaggagct cgagcgccga ccagttctcc 129600
atcgcggcgg cggcgtgagc gcgaggcgtc ggagctcggg gaaagcagcg cgacccggag 129660
aatggccggc gctgcgccgc gccgcctcgg ctgtgacgct ctaatagtcg tcggcggctc 129720
cgctatgccg cgccgggttt tacacgtccc cgtgcacgtt cgcgcctgca acctcaccca 129780
agagctatcg acgggcgagg acgcccgctt ctgtcgtccg cgacccgtta acgtcgaacg 129840
ggtgcgcgct gtttttgcgg ctctctaccg tgcctgtccg atacacgtga ggaccgaacc 129900
cgagcgtgtc aagctggtac tgggtcgtct gttactggga cccgtggccg taccctgttt 129960
ttgcgacggt gaagtggagg gccacggtga acatctggta cctacgacgc agttttgtcg 130020
cgggccgctg ctctacgtgc accgacgttg ttgttgcgga tccgtgaccg ccgggcgcgc 130080
gctgtcctac cacgttctcg aaaaccacgt ggccacgcat gtgctacgcg gattgctctc 130140
gctgacggaa tggaatcgag aattgccgag cctcttttgc gactgtcctg gcggcggtgg 130200
cgcctcggga accgaggaac gctacgctat ggcctgcctg ccgcgcgacc tcagcctgca 130260
cctggacgac tatccttacc tgatggtgga aatcggacgc gtactcagtg tcagcgaggt 130320
agacgactac gtaaccgccg tctccggcta cctgggcgag gccgcggcgc cgcgcatcca 130380
ggttcactac aagctgctct ttggactcaa cgtgcgtccg caagcgccgt gcgcgttgga 130440
cgctacacgc gactttttc tgctggagct gcaaaagctt tggctgggcg ttgaatatca 130500
ccacgaagtg acgtcggagt ttttcggtcg cgtgctggct cagctgcatc gcgaccgcgc 130560
ccgcgtcatg atggcgcttc gcttgcccga gcagacggtg tgccacctga gcaccttcgt 130620
tctcagtcgc ttcaagcgac aggtactgta cttcaagtta caggtgagct acggcaagtg 130680
ccggactggc cacgctgaca gaagtggggg agggggaaac ggtggaaatc agggacacca 130740
caacctgctg tgttatcgac gccttagcgt cacgtttgcc gacacggaca cggtgtggag 130800
aaaccttttc tacgtttatt atgaactagc tcgggatctg gggtcccatg ggacagagaa 130860
ccgacccgta aaccgcggtt acggtgtttc ttgcgctccg aggacgtcgc ggctatcacc 130920
gtcagaatcg acggtggttt cggcgaacgg acacgcgctg tcttccaccg cgctcccgac 130980
gacgagcgcg ggtcacaagc tgtcactgcc gcgcgacccg gccgccgatc gcgttcgacg 131040
ttacgtgtgc atcatctcgc gtctcatgta cgctcggtac ggggagagat ggcgtaaaca 131100
ccgtcaacgg cggtcggaga cgggagaaga ggaggaggaa gagacgctgg aatcggggga 131160
gactgacgcc acgccgccat ttgactttac ggggcagcag ctgcgccggg cctatcagga 131220
acaccgacgt cgtaaacatc tagccgtgca gcgttacgcg ccgtgtcgtc gtaagctcat 131280
cggcgggatg gagtttgccg aggtgacggg cgtgagtctg gaccgcatcg ccgtcaacgc 131340
tttcaacacc aaccgcgtta tcaatatgaa ggccgcgctc tcgtccatcg ccgcgtcggg 131400
tctcggcgtg cgcgcgccgc ggcttcccaa gaacatgacc cacagttttg tgatgtacaa 131460
gcacaccttt aaggagcccg cttgcaccgt cagcaccttt gtttccaacg acgccgtcta 131520
catcaactcg ctcaacgtca atattcgcgg ttcctacccc gagtttctgt actcgctggg 131580
cgtgtaccgg ctgcacgtta atatcgatca ctttttctg ccggccgtgg tgtgcaacag 131640
caactcctcg ctggacgtgc atgggctgga ggaccaggcg gtgatccgct cggagcgcag 131700
caaggtgtac tggaccacca actttccgtg catgatctcg catactaaca acgtcaacgt 131760
gggctggttc aaagcggcta cggccattgt gccgcgcgtc tcgggcgctg acctggaagc 131820
cattctgctc aaagaactct cgtgcatcaa gaacatgcgc gacgtgtgca tcgattacgg 131880
tctgcaccgc gttttcacgc aactagagct gcgcaattcg taccagatcc ccttcctggc 131940
caagcagtta gtgctgtttc tgcgtgcttg cctgctcaag ctgcacggtc gagagaagcg 132000
gctgcagttg gaccgcctag tatttgaggc ggcacagcgg ggtctctttg actacagcaa 132060
gaacctcacg gcgcacacca agatcaagca cacttgtgcg ctcatcggca gtcgtctagc 132120
caacaacgtg cccaagatcc tggcccggaa caaaaaagtc aaattggatc acctgggccg 132180
gaacgccaac gtgctgacgg tgtgtcggca cgtggaagcc cacaagatcc ctcgcacgcg 132240
cctcaaagtg ttagtcgagg tgctgggcgt gttgcagagt atcagcggta cgccgcacac 132300
gcgcgaagtg atccaccaga cgttgtttcg attgtgctcg gcggccgcag ccacatcggg 132360
cctgtgttca tcccctcccc cattgtgtgt gtcctcatct tcctccgtcc cttctgtccc 132420
aacctccgtc agcgttgacg gcagttctga acccacgtcg ccgcgagtgc ggtttgcatc 132480
acgatgatgg aagccgcggc cgctgccgcc gcggcgtttc gtccggagga gcgtccgacg 132540
ccgggttggc acgacgcggc gttgttaatg gacgacggta cggtgcgcga gcacgcgttt 132600
cgcaacggac cgttgtcgca actgattcgc cgtgtgttac cgccgccgcc cgacgccgaa 132660
gacgacgtgg tttttgcttc cgagctgtgt ttttattgca gcggtcgttt taaccgcagg 132720
tcgtccgtct tctccatcta ttggcagaag catagcgatc tggtgtacgc gcttacgggc 132780
attacccatt gcgccaagtt ggtggtggaa tgcggtcagt tggggagtag taggctacgg 132840
tggcgcgacg gtgatgcgag tggtgaggag cgccggggag acgacgacag cagggacgag 132900
ctgtacgacg tgccgggcat ttatatgatt cgcgtcaacg acggcggcag caccggcccc 132960
agacacgtta tttggccggg taccagcgtg ctgtgggcgc cggacgttgt gatcactacg 133020
gtgcagcgac gaatctcggc ggcgcgcgcc ctggtgaaca cgttccgcca atattttttt 133080
ttgctggaac ggcgctcgca cgaggagctg gttctttgtc cgcccgagat ggaggagcgt 133140
ctagcgccgt tgttgcagag tgccacgcga ggtgattcgg acatgtttga cggtgtggtg 133200
gccagcgctt atcaccgttt gcgaatgagt aatattccgc gttcatccgc ccgtctgctg 133260
gagcactgcg tggggctggc gggtgctaag aagctgctct tgctcgacgt gccgcgtctg 133320
gagaactatt ttctttgtca agtctgtctt tacgagttgg acgaggacga gatgggcgag 133380
gagatgctgg gcatgttggc cggaaagccc gaggatgccg ccgtctcggg cgcaagcggc 133440
ggttttctgc tacatcgcaa gacgatgaag ctggccgcct gtctgtgttt gttgctcaat 133500
tcgctgcatt tgcaccagga ggcgctggag gccttggatc ctccgccgcc gcgcgtcgag 133560
gagaacgacc ttgtcaacgt ggtgctgcgc cgttattatc gcagtcacgg cggcgtgcag 133620
gcgcggacgc tggcggcggc ccgggctttg ttagccgact acgctgaaac gttttcgcct 133680
ttggggagtt ttacgcgcct gggttacgat cgtctcgttt ctgccgatgc cggcgtcagt 133740
cgccggcacc tggtggctct gctgcgtgcc tagctgaccc tgaaacggat ggcgtgtata 133800
tcgtcacaca ggtaggtggc catgatgacg gcgatgataa gatcgtccga gatacgattc 133860
tggcgcttgg ccgagtagcg tgccgtcgtg ccttcggcca gcgtgacgcg gtgcaggttc 133920
tgaatctgct ccagaagata ctcgatgggg tcgtggctca gcttgatggt gtaggagacg 133980
agctcttgcg aggctttgat gtagcccgag ttgaaacgcg agatgaactg ttccacggcc 134040
agcgccttgt cgcggcccat gaggtagaag ggctgttcga tgtggttctg gtcgggcgtg 134100
tggtagaaga gcacgcggat gagcgtgctg ctctgcacgc tctgtcggat gaggcaggcg 134160
atgcgcacgg ccgccgcctg gttggtgttg ccctccacgg cgatacgcag ttcgtccagg 134220
taagggtgca ggctcagcac cgagatgatc atgtgcgccg cgcactcggc gatggctacc 134280
tcagaactct cggagaggtc gcgcaaaaag aaatgctcta ggccgtaaat gagaaactgg 134340
tgtcggtagg cgcctacggc cgccacgccc gtgcccgagg ccttgcggtt ggtggtgaag 134400
gccgggtcca gatacacgta aagcgtcttg ccgaaataat cgtaggcgtt ggtgttgagc 134460
gtgctgtaac gcaaaatatc gaactcttcg cggctctggt ccgtgatgag cacggtgttc 134520
tgcgagattt tattggtacc gccgatgatc tcgtccatga aagcgcccgg cataaacatg 134580
ttggccgtct tgcgcacctg cgagttgagg ctgatgaagg tgggcttgtg cagtcggtag 134640
caaggacacg ccgtggcgtc gcccttctcc gtgaagctgt gcaggtgctc ttcgcacacg 134700
taagagacca cgttgagcat gtcaaagggc gcattgttga ggcgcgtcaa gaaacacgtg 134760
gcgtcactgg tagtgttggt ggacgatatg aagatgatct tggtggtatt ctgggccagg 134820
aaccccagaa tggtgttgaa ggcctctttc ttgatgaagt gcgcctcgtc caccagcagc 134880
aaatggaagt tttgtcctcg gatgctctgt gtagagagga gacagaaaag ggactcttat 134940
gattacgcac gctcggctgg aagcctacag agtcggggtg gggccggaca ggtgagccag 135000
gtgagccgcc aggtgaggcg ggatcgccgt gtgccaaccg ggctgcgacc tgaaaaccgg 135060
aaccaatccg ccgacaccgg cgccgcgtga cgcgcgccca taaaaacgaa agtgtcgtcg 135120
tcgcgacccg ccacagccgc catgaactcg ttgctggcgg aactcaaccg actgggggtc 135180
gcgcacgcca ctacggagga tgtttttatc tttgtcgacc gcctctttca acacttttcc 135240

```
ttccttttcc aggccgagga gtcaggcccg cgccgcttgg aactggtcgc gtccgtgttc 135300
gagcacctga cggtggagtg cgtcaacgac atcctggacg cctgcagcca cccggacgtg 135360
aacgtcgtgg agacaagcaa cacctgtcgt ccctgccctt ctcctgttcc ctccgccccc 135420
aaaactgtca gcgacgctca gacgtcatgt gcgacgcctc gggcgcctgt gacatgaggc 135480
acgtccagaa cgcgtttacc gaggagatcc agttacactc gctctacgcg tgcacgcgct 135540
gctttcgcac gcacctgtgt gatctgggca gcggctgcgc gctcgtctcc acgctcgagg 135600
gctccgtctg cgtcaagacg ggcctggtat acgaagctct ctatccggtg gcgcgtagcc 135660
acctgttgga acccatcgag gaggccgcac tggacgacgt caacatcatc agcgccgtgc 135720
tcagcggcgt gtacagctac ctcatgacgc acgccggccg ttacgccgac gtgatccaag 135780
aggtggtcga gcgcgaccgc ctcaaaaagc aggtggagga cagtatttac ttcaccttta 135840
ataaggtttt ccgttctatg cataacgtca atcgtatttc ggtgcccgtc atcagccaac 135900
tttttattca gcttatcatc ggtatctact caaagcagac caagtacgac gcgtgtgtca 135960
tcaaggttag tcgtaagaag cgtgaggacg cgcttctgaa acagatgcgt tccgaatatg 136020
gaaacgcacc tgtattcgga tctggcgttt gaggcgcggt tcgctgacga tgagcaattg 136080
cctctacacc tggtgcttga ccaggaggtg ctgagtaacg aggaggccga gacgctgcgc 136140
tacgtctact atcgtaatgt agacagcgct ggccgatccg cgggccgcgt tccgagcgga 136200
gatgaggacg acgcaccggc ctccgacgac gccgaggacg ccgtgggcgg cgatcgcgct 136260
tttgaccgcg agcggcggac ttggcagcgg gcctgttttc gtgtactacc gcgcccactg 136320
gagttgctcg attacctacg tcaaagcggt ctcactgtga cgttagagaa agagcagcgc 136380
gtgcgcatgt tctatgccgt cttcactacg ttgggtctgc gctgccccga taatcggctc 136440
tcaggcgcgc agacgctaca cctgagactg gtctggcccg acggcagcta tcgtgactgg 136500
gagtttttag cgcgtgacct gttacgagaa gagatggaag cgaataagcg cgaccggcag 136560
caccagttgg ctacgaccac gaatcaccgt cggcggggcg gactgcgtaa taacttagac 136620
aatgggtcgg atcgccgttt gcccgaagcg gctgtggctt ctctggagac ggccgtcagt 136680
actccatttt ttgaaattcc gaacggagca ggaacctcct ccgcgaacgg cggcggcaga 136740
ttcagtaacc tggagcagcg ggtagcgcgt ttgttgcgcg gcgacgagga attcatctat 136800
cacgcgggtc cattggagcc gccttccaag atacgcggtc atgagttggt gcagctgcgc 136860
ctggacgtaa atccagacct catgtacgcc accgatccgc acgaccgcga cgaggtcgcg 136920
cgtacggacg agtggaaggg tgccggtgtc tcgcgtctcc gcgaggtctg ggatgtgcag 136980
catcgcgtgc gcctccgtgt gctgtggtac gtcaattcct tttggcgcag tcgcgagctg 137040
agctacgatg accacgaagt cgaactatac cgggcgttgg acgcttatcg ggcgcgcatc 137100
gccgtcgagt acgtgctgat tcgcgccgtg cgcgacgaga tctacgctgt actacgacgg 137160
gacagcggcg cgttgccaca gcgtttcgcc tgccacgtgc cacggaacat gtcctggcgc 137220
gttgtttggg aactttgccg tcatgccttg gcgctctgga tggatcgggc ggacgtgcgt 137280
agctgtatta ttaaggcgct aacgcctcgt ctgagccggg gtgccgccgc tgccgctcag 137340
cgagctcgtc gccagcgcga gcgctcggcg cccaaaccgc aggagctgct tttcggaccg 137400
cggaacgaga gcggtccgcc cgccgaacgg acttggtacg ctgacgtggt gcgctgcgtt 137460
cgcacgcaag tggatttggg cgtggaagtg cgcgcggcgc gttgtcctcg caccgggctt 137520
tggatcgtcc gtgatcgccg cggacgcctg cgacgttggc tctcgcagcc cgaggtgtgc 137580
gtgctctacg tcacgccaga cttggacttt tactgggtgc tgccgggcgg ctttgccgtc 137640
```

tcttcgcgcg tcactcttca tggcttggcg cagcgggctt tgcgagaccg attccagaac 137700
tttgaagcag ttcttgcaag aggaatgcat gtggaagctg gtcggcaaga gccggaaaca 137760
ccgcgagtat cgggccgtcg cttgccgttc gacgatcttt agtccggagg acgacggctc 137820
gtgtatcttg tgccaattgc tgttgttcta ccgcgacggc gaatggatcc tctgtctttg 137880
ctgcaacggc cgttatcaag gccactatgg cgtgggccac gtacatcggc gtcgtcgacg 137940
catctgtcat ttacctacct tgtaccaact gagcttcgga ggtcctttgg gtccagccag 138000
cattgatttc ttgccaagct ttagccaggt gaccagcagt atgacgtgcg atggtattac 138060
gcccgacgtg atttacgagg tctgcatgtt ggtgccccag gatgaagcca agcgcatcct 138120
ggtcaagggt cacggtgcca tggacctgac ctgtcagaag gcagtgacgc taggcggcgc 138180
cggcgcctgg ttgctgccgc gtcccgaagg ctacacgctt ttcttttaca ttctgtgcta 138240
cgacctgttt acctcatgcg gcaatcggtg cgatatccct tccatgacgc ggctcatggc 138300
ggcggccacg gcctgcgggc aggcgggttg cagcttttgc acggatcacg agggacatgt 138360
agatcccact ggcaattacg tgggttgcac ccccgatatg ggccgctgtc tttgttacgt 138420
gccctgtggg cccatgacgc agtcgctcat ccacaacgag gaacccgcga ctttttttctg 138480
tgagagcgat gacgccaagt acctatgcgc cgtaggttct aagaccgcgg cgcaggtcac 138540
actgggagac ggcctggatt atcacatcgg tgtcaaggat tctgagggcc gatggttgcc 138600
cgtcaagacc gatgtgtggg acctggtcaa ggtagaggaa cctgtgtcac gtatgatagt 138660
gtgttcctgt ccggtgctta agaacctagt gcactaacgg ggtctgacag ttcacgggga 138720
gaagaaacaa gaaacaacaa aaaaaaaaga ggacatggac tcgccacggt ttgtggcaag 138780
gcgtatatta tcatcatgga gctactcacg ttggtgttgt agcaactggc aaaaagcgcc 138840
gtgctcttgg cgccgcggtg gtcgatgctg atcacgttgt ccttgttctc gaccacgtag 138900
tcgcgcgcga aggtgtggcg gcagcggaac tcgacctctt tgagcacaaa ctgcgacacg 138960
tgcttttggt gcgccacgta gccgatgctg atgccgatca tgtgcttaag cagaaacgag 139020
ataatgggga tgatgaacca agtcttgccg tgacgtcgcg gcaccaggaa cacggtggct 139080
ttctgcttaa agatgtcgat ggaggtctgc gagaggaagt cgatctggaa ggcgtggatg 139140
aggtactgca gcacgcgatt ggccagcacg gggatcttgg tcacggctat aaaaaagatg 139200
acgtgtatca ataaattctt ttgaaacggt tcgagtcgga tggcttttgc gtcgccctcg 139260
acggcggtac tgaagccgcc gtcgagccac tttttaaagt cggtcatgaa gttgttgatc 139320
tgctgaaact gcggatcgcg gtagagctcg gtcaacgcgt ccagcttctg gtaggaggcg 139380
cgctgctcct cggagcacgg gcgaaacgtc agttcatcga gcgcactctt gaggcgctcg 139440
tgaaacagca gctcgcgctg gctttcctcg ggcgagttgt agtcgcggtg gcggccgcag 139500
aaggccatga gcggcaggaa ggcctcgttg cacgagtggg ccagcccgag ttcggggtgc 139560
atcatctggt agcgcttgcg gcacagcgcc gccacattgg tgaaggccgt ggagatgcag 139620
gaggtggggt ggctcttgcg cttctgcagc tccgcgtagc gctcctggat cttggcggcc 139680
gaatctccgc gcaacatgat ggcggcggcg gtggtgcgag cggaggttag gcggcagcgg 139740
cgagaggaga ggaaaaagat ggcgtccgcg aggacgacgg aggatccacc tgaaaaccac 139800
gttgtcgcgg acgtggcttg tgggacgggc gccgtcactc gttcgtcttc gtcgtcccta 139860
gtggtgtcgt cttcctcggc gtcaggctca gacgaatctt cctccgcctc tcctctcagt 139920
ttccccgtct cctctccctc aactgccgtc aggtctccgg ggtccgccgg ggtttcgacg 139980

```
tccctgtgct cggtggaacg gatggtcgag ctgtcggcgc agtctccggc cgccgatttc 140040
tcggtctccg aggcttggcg cttcgaggag gccgtaaata tggcgctggt ggcctgcgag 140100
gccgtgtcac cttacgatcg ctttcgtcta attgaaacgc ccgacgagaa tttcttgttg 140160
gtcaccaacg taattccgcg cgagtcggcc gaggtgccgg tgttggatag cagtagcagt 140220
ggtggcgata gcgggccgga ggacaaaaag aaaaacgtcg ggaataaaac cgcgggggaa 140280
aagaacggcg gtgggtctcg ggccaaacgc cgtcgtagac gacgcgctcc gaaaaacgac 140340
gccgccacgc cgtcttttct acgtcgacac gacgtgctgg agcgtttcgc ggccgcggct 140400
gagcctttgc cgtcgctttg tgtgcatgat tatgcgttac gcaatgctga ccgtgttacc 140460
tacgacggcg aattaatcta cggcagttac ctgttgtatc gcaaggctca cgtggagctg 140520
tcactctcca gcaacaaggt gcaacacgtg gaagccgtgc tgcgacaggt gtacacgccg 140580
ggcttgttag atcatcacaa cgtgtgcgac gtggaggccc tgttgtggct gctgtactgt 140640
ggaccgcgca gcttttgcgc gcgtgacacc tgtttcggtc gcgaaaagaa cggttgtcct 140700
ttccccgcgt tgttgcccaa actcttttac gaacccgtgc gggactatat gacctacatg 140760
aatctggctg agctgtacgt ctttgtttgg tatcgcggct acgaattccc tgcgccaacg 140820
ccgcaggcga cgacggcggg tggtggtggt ggtggtggta gtggtggcgg cggcggggcc 140880
ggcgcttgtg cggtcgagac gagcgcgtca gcaggccggg tcgatgacgc cggcgacgag 140940
gtgcatttgc ctttaaagcc cgtctcgctg gaccgtctca gagaggtgtt acaggcggtg 141000
cgcggccgct tctcggggcg cgaggtgccc gcctggccgg cctcgtcgcg cacctgtttg 141060
ttgtgcgcgc tctacagtca gaaccgtctc tgtttagatc tcgcgcgtga cgaggcgcgg 141120
accgtgagtt atagccccat cgtcatccaa gactgcgccg cggctgttac cgacgtcact 141180
ttgagccaca tcttgcccgg ccagagcacc gtctcgcttt tccccgtcta ccacgtcggc 141240
aagttgctgg acgctctctc gctgaacgac gcgggtctca tcacgttgaa tctatgacgt 141300
cggtcaacaa acagctctta aaggacgtga tgcgcgtcga ccttgagcga cagcagcatc 141360
agtttctgcg gcgtacctac ggaccgcagc accggctcac cacgcagcag gctttgacgg 141420
tgatgcgtgt ggccgctcgg gaacagaccc gatacagtca gcgaacgacg cagtgcgtgg 141480
ccgcacacct gttggagcaa cgggcggccg tgcagcaaga gttgcaacgc gcccgacagc 141540
tgcaatccgg taacgtggac gacgcgctgg actctttaac cgagctgaag gacacggtag 141600
acgacgtgag agccaccttg gtggactcgg tttcggcgac gtgcgatttg gacctggagg 141660
ttgacgacgc cgtctaacag gtatagcaat ccccgtcacg cctctgttca gattttatta 141720
aaaaaaaaac acaccataac gacagtgtcg gtgtggtagc tagtgcagcc ctaggaacag 141780
ggaagactgt cgccactatg tcctccgcac ttcggtctcg ggctcgctcg gcctcgctcg 141840
gaacgacgac tcagggctgg gatccgccgc cattgcgtcg tcccagcagg gcgcgccggc 141900
gccagtggat gcgcgaagct gcgcaggccg ccgctcaagc cgcggtacag gccgcgcagg 141960
ccgccgccgc tcaagttgcc caggctcacg tcgatgaaga cgaggtcgtg gatctgatga 142020
ccgacgaggc cggcggcggc gtcaccactt tgaccaccct gagttccgtc agcacaacca 142080
ccgtgcttgg acacgcgact tttccgcat gcgttcgaag tgacgtgatg cgtgacggag 142140
aaaaagagga cgcggcttcg gacaaggaga accagcgtcg gcccgtggtg ccgtccacgt 142200
cgtctcgcgg cagcgccgcc agcggcgacg gttaccacgg cttgcgctgc cgcgaaacct 142260
cggccatgtg gtcgttcgag tacgatcgcg acggcgacgt gaccagcgta cgccgcgctc 142320
tcttcaccgg cggcagcgac ccctcggaca gcgtgagcgg cgtccgcggt ggacgcaaac 142380
```

gcccgttgcg tccgccgttg gtgtcgctgg cccgcacccc gctgtgccga cgtcgtgtgg 142440
gcggcgtgga cgcggtgctc gaagaaaacg acgtggagct gcgcgcggaa agtcaggaca 142500
gcgccgtggc atcgggcccg ggccgcgttc cgcagccgct cagcggtagt tccggggagg 142560
aatccgccac ggcggtggag gccgactcca cgtcacacga cgacgtgcat tgcacctgtt 142620
ccaacgacca gatcatcacc acgtccatcc gcggccttac gtgcgacccg cgtatgttct 142680
tgcgccttac gcatcccgag ctctgcgagc tctctatctc ctacctgctg gtctacgtgc 142740
ccaaagagga cgatttttgc cacaagatct gttatgccgt ggacatgagc gacgagagct 142800
accgcctggg ccagggctcc ttcggcgagg tctggccgct cgatcgctat cgcgtggtca 142860
aggtggcgcg taagcacagc gagacggtgc tcacggtctg gatgtcgggc ctgatccgca 142920
cgcgcgccgc tggcgagcaa cagcagccgc cgtcgctggt gggcacgggc gtgcaccgcg 142980
gtctgctcac ggccacgggc tgctgtctgc tgcacaacgt cacggtacat cgacgtttcc 143040
acacagacat gtttcatcac gaccagtgga agctggcgtg catcgacagc taccgacgtg 143100
ccttttgcac gttggccgac gctatcaaat ttctcaatca ccagtgtcgt gtatgccact 143160
ttgatattac acccatgaac gtgctcatcg acgtgaaccc gcacaacccc agcgagatcg 143220
tgcgcgccgc gctgtgcgat tacagcctca gcgagcccta tccggattac aacgagcgct 143280
gtgtggccgt ctttcaggag acgggcacgg cgcgccgcat ccccaactgc tcgcaccgtc 143340
tgcgcgaatg ttaccaccct gctttccgac ccatgccgct gcagaagctg ctcatctgcg 143400
acccgcacgc gcgtttcccc gtagccggcc tacggcgtta ttgcatgtcg gagttgtcgg 143460
cgctgggtaa cgtgctgggc ttttgcctca tgcggctgtt ggaccggcgc ggtctggacg 143520
aggtgcgcat gggtacggag gcgttgctct ttaagcacgc cggcgcggcc tgccgcgcgt 143580
tggagaacgg caagctcacg cactgctccg acgcctgtct gctcattctg gcggcgcaaa 143640
tgagctacgg cgcctgtctc ctgggcgagc atggcgccgc gctggtgtcg cacacgctac 143700
gctttgtgga ggccaagatg tcctcgtgtc gcgtacgcgc ctttcgccgc ttctaccacg 143760
aatgctcgca gaccatgctg cacgaatacg tcagaaagaa cgtggagcgt ctgttggcca 143820
cgagcgacgg gctgtattta tataacgcct ttcggcgcac caccagcata atctgcgagg 143880
aggaccttga cggtgactgc cgtcaactgt tccccgagta acctggacgc ggaacgtgac 143940
ggttgccgag gggaaaggcg acagagaagg tacaaaccca ccggcgggga aaatactgag 144000
gcgccgccat catcatgtgg ggcgtctcga gtttggacta cgacgacgat gaggagctca 144060
cccggctgct ggcggtttgg gacgatgagc ccctcagtct ctttctcatg aacacctttt 144120
tgctgcacca ggagggcttc cgtaatctgc cctttacggt gctgcgtctg tcttacgcct 144180
accgcatctt cgccaagatg ctgcgggccc acggtacgcc agtagccgag gactttatga 144240
cgcgcgtggc cgcgctggct cgcgacgagg gtctgcgcga cattttgggt cagcggcacg 144300
ccgccgaagc ctcgcgcgcc gagatcgccg aggccctgga gcgcgtggcc gagcggtgcg 144360
acgaccggca cggcggctcg gacgactacg tgtggctcag ccggttgctg gatttggcgc 144420
ccaactatcg gcaggtcgag ctcttccagt tgctggaaaa ggaatcgcgc ggacagtcgc 144480
gcaactcggt gtggcatctg ttgcgtatgg acacggtctc ggccaccaag ttctacgagg 144540
ccttcgtcag cggctgtctg cccggcgccg cggcggcgga cggttcgggt ggcggcggct 144600
cgcactacac gggctcgcgc gccggcgtct cgccgggcat ccagttcggt atcaaacacg 144660
agggcttagt caaaacgctg gtggaatgtt acgtgatgca cggacgcgag ccggtgcgcg 144720
acggcctcgg tctgctcatc gaccccacgt cggggctgct gggcgcttcc atggacctgt 144780
gcttcggcgt gctcaagcag ggcagcggtc gcaccttgct ggtggaaccg tgcgcgcgcg 144840
tctacgagat caagtgccgc tacaaatatt tgcgcaaaaa ggaggacccc tttgtgcaga 144900
acgtgctgcg gaggcacgac gcggcggccg tggcctcgct gttgcagtca cacccggtgc 144960
cgggcgtgga gtttcgcggt gaacgcgaaa ccccgtcggc acgcgagttt ctgctttcgc 145020
acgacgcggc gctcttcagg gccacgctca agcgcgcgcg cccgctcaag ccgcccgaac 145080
cgctgcgcga gtacctggcc gatctgctgt atctcaataa ggccgagtgt tcggaagtga 145140
tcgtgtttga cgccaagcac ctgaatgacg acaacagcga cggggacgcc acgatcacta 145200
ttaacgcgag tctcggccta gccgcgggcg acgccgctgg cggcggcgct gatcaccacc 145260
tgcggggcag cccgggcgat tcgccgccgc cgataccttt cgaggacgaa aacacgcccg 145320
agctgctggg ccggctcaac gtgtacgagg tagcgcgctt ttcactgccg gcttttgtca 145380
atccgcgtca ccagtattac tttcagatgc tcattcagca gtacgtgctc agccaatact 145440
atataaagaa gcatccggac ccggagcgga tcgatttccg cgacctgcct accgtctacc 145500
tggtctcggc catcttccgc gagcgcgagg aaagcgaact gggctgcgag ttgctggccg 145560
gcggtcgcgt tttccactgc gaccacatcc cgctcctgct catcgtcacg cccgtggtct 145620
ttgaccctca gtttacgcgc catgccgtct ctaccgtgtt agaccgttgg agtcgcgacc 145680
tgtcccgcaa gacgaaccta ccgatatggg tgccgaactc tgcaaacgaa tatgttgtga 145740
gttcggtacc acgtccggtg agcccctgaa agatgctctg ggtcgccagg tgtctctacg 145800
ctcctacgac aacatccctc cgacttcctc ctcggacgaa ggggaggacg atgacgacgg 145860
ggaggatgac gataacgagg agcggcaaca gaagctgcgg ctctgcggta gtggctgcgg 145920
gggaaacgac agtagtagcg gcagccaccg cgaggccacc cacgacggcc ccaagaaaaa 145980
cgcggtgcgc tcgacgtttc gcgaggacaa ggctccgaaa ccgagcaagc agtcaaaaaa 146040
gaaaaagaaa ccctcaaaac atcaccacca tcagcaaagc tccattatgc aggagacgga 146100
cgacttagac gaagaggaca cctcaattta cctgtccccg cccccggtcc cccccgtcca 146160
ggtggtggct aagcgactgc cgcggcccga cacacccagg actccgcgcc aaaagaagat 146220
ttcacaacgt ccacccaccc ccgggacaaa aaagcccgcc gcctccttgc ccttttaact 146280
cataaacttt caggtctcgc gtacgattcg cgagtcggga atgggacacc cgtgggtgtt 146340
tctccgtgtg tatattattt tttttttttg tgtgtttgcg cccccgtgtg tctaatgtgc 146400
tgtttgaaac acgtaaagta gctggtggaa gaacagataa acctttaata aaaaaaaaag 146460
tatgtgctcc cgacccacgg tctgcgtgtc tctttttttat gtccatgtct ccaagtctgg 146520
tgcgggtggc ggcggggtta agcgtcctcg aagtcttcat catcgtcgtc ctcttcttcg 146580
cggaggcgac ggctttccaa gctgtcgtgg tgactgagcg cagcgacttc ttcgccggag 146640
gctgtggcca gcgcctggta cttgacactg ccgctaccgc gtccgcgaaa gtagcggacg 146700
gcgcgacacg tcgtaaacat ggcccatatg aaaaagagca tgccgaacga ccagctgatg 146760
ccggtgcggt attcgttgct gaggaaggta tcgtactgca cgatggggta gatgaggccg 146820
cagagtccaa agaaggcgcc caggtggtag ccgaattgca ccttgacgta ttgaaaaaag 146880
acggcctcga tcagtaaaaa gtagatgatg gagatgatag cgtagaccac gaagacggct 146940
aacaccatgt ggcctgtacg cacgaaaaag ttgtttccga agccgtagca cagggccatg 147000
gctaccacgg tggtgttgaa accaagcgct acctctacca ggttgacgat gagcgtgcgg 147060
aactgcaccg tacctttgag cttggggtgc agacgcgaga agaaaaagag tgagcgtttg 147120
tagctgcggt actgcgtgac catgctcacg ttgaaaatgg tcaggcagaa aaagtgtacg 147180
gcggccatga aggcgatcat gctgggcagc cgaaatgaca tggtcagtgt gaatagttgg 147240
aacgtgtcca tgctgagaat gaagaggaag gctgtgaggc tgtcgcccat gtacgaaatg 147300
tcgcgtgtcg actggtttag gctcatgcct ttgtccttgc gcatgctgat cttgatccag 147360
cataccaggt agtagatggt cacggctaaa aagacgagct gcatgaacac ggcgtagcac 147420
accaactgca ccgagtctaa gaaaagcata ggcgtgtgca ggtgcattac gttgtaggcc 147480
gacatgttga gcctttcaaa gtccacgacg tgatagtaga cgcaggggta gcccaggtgc 147540
ggaaaattgc tcagcactag atgcacgctg acgttgacaa aagtcagcac catgaaaacg 147600
atagaagcgc tccatgtccg tgtattcacc ttatccacgt gcgagggggc catggcgata 147660
gcggcggccc gctcgctcgg gaggcgatgg gggcgcgccg atgacgacag gctcgcgggt 147720
cgttaaatac tacgatggga gccgccgcgg ctcacgacgc ggtttgagca cgtccgggcg 147780
gtcggtgaaa aaagaccccg cgggccttcg cgactctctt ctgtccgagg atgaccgctc 147840
agccgccgct gcaccaccgc caccacccgt acaccctgtt cgggaccagc tgtcatctca 147900
gctggtacgg ccttctagag gcctcggtgc ctatcgtaca atgtctgttt ttggatctgg 147960
gtggcggccg tgccgagccg cggcttcaca cgttcgtggt gcgcggtgac cgtctgccgc 148020
cggctgaggt gcgtgctgtg catcgcgcca gctacgctgc gctggcctcg gccgtgacta 148080
cggacgccga tgagcgtcgg cgcggcctag agcagcgtag cgccgtgttg gcgcgcgtgt 148140
tgctagaagg cagcgcgtta atccgcgtgt tggcgcgcac cttcacgccg gtgcagattc 148200
agacggacgc tagtggcgtg gagattttgg aggccgcacc ggcactgggc gtggaaacca 148260
cagcgctgtc gaacgcgctt agtcttttcc acgtagccaa gctagtggtc atcggctcgt 148320
atcccgaagt gcacgagccg cgtgtggtca cgcatgccgc ggaacgcgtc tctgaagagt 148380
atggcaccca cgcgcataaa aaattgcgtc gcggttacta cgcctacgat ttggccatgt 148440
cgtttcgcgt cggcactcac aagtatgtgc tggagcgcga cgacgaggcc gtcctggcac 148500
gcctctttga ggtgcgcgag gtgtgttttt tgcgcacctg tctgcgtctg gtcacgcctg 148560
tcggtttcgt ggccgtggca gtgaccgacg agcagtgttg tttattgctg cagtcggcct 148620
ggactcacct ttacgacgtg cttttccgtg gtttcgctgg gcagccgccg ctacgcgact 148680
acctggggcc ggacctcttt gagacgggcg ccgcccgttc tttctttttt cccggtttcc 148740
cgcccgtgcc cgtctacgcg gtccacggtc tgcacacgtt aatgcgcgag acggcgttgg 148800
acgcggcggc tgaggtgctc tcgtggtgcg gcctgcccga catcgtgggc tcggccggca 148860
agctggaggt ggaaccctgc gcgctctcgc tcggcgtgcc cgaggatgag tggcaggtct 148920
tcggtaccga ggccggcggc ggcgccgtgc gtctcaatgc cacggctttt cgcgagcgac 148980
cggccggcgg cgatcgtcgc tggctgttgc cgccgctgcc gcgtgacgac ggcgacggtg 149040
aaaacaacgt cgtggaagtc agcagcagca ccggcggtgc gcacccgccg agcgacgacg 149100
ctactttcac cgtgcacgtt cgcgacgcca cgctacatcg agtgctcatc gtggatttgg 149160
tcgagcgcgt gctggccaag tgtgtacgcg cgcgcgactt caatccctac gtgcgttata 149220
gtcatcgact ccacacttat gcggtttgtg aaaagtttat tgaaaatctg cgttttcgct 149280
cgcgacgcgc cttctggcag atccagagtc tgctgggtta catctccgag cacgttacgt 149340
cagcctgcgc ttcggccggc cttttgtggg ttctgtcgcg tggccaccgc gagttttatg 149400
tctacgacgg ctattcgggt cacggacccg tctcggccga agtgtgcgtg cggactgtgg 149460
tcgactgtta ttggcgcaaa ctttttggcg gcgacgatcc gggtcccacc tgtcgtgttc 149520
aagagagcgc gcccggcgtg ctgttggtct ggggcgacga gcggttggtg ggtcccttca 149580
acttcttcta cggcaacggc ggcgccggtg gtagtccgct ccacggggtg gtgggtggtt 149640
tcgcggcggg acattgcggt ggcgcttgtt gcgcgggctg cgtcgtcact caccgccatt 149700
ctagcggcgg cggtggtagt ggcgtgggcg acgcggacca cgcgagtggc ggcggtctag 149760
atgccgctgc cgggagtggt cataacggcg gtagtgatcg ggtttctccc tccacgccgc 149820
ccgcggcgtt aggtggctgt tgctgcgcgg ccggtggcga ctggctctcg gccgtgggtc 149880
atgtcctggg ccggctgccg gcgctgttac gggagcgcgt gagcgtgtcc gagctggaag 149940
ccgtgtatcg cgagatcctc tttcgcttcg tggctcgccg caacgacgtg gacttttggt 150000
tactgcgctt ccagcccggt gaaaacgaag taaggccgca cgctggggtg attgattgcg 150060
cgcccttcca cggcgtgtgg gccgagcagg gccagatcat cgtacagtca cgcgatacgg 150120
cgttggcggc cgatatcggc tacggcgtct atgtggacaa ggcctttgcc atgctcacgg 150180
cttgcgtgga ggtctgggcg cgagagttat tgtcgtcctc caccgcttcc accaccactt 150240
gttcttcttc ttccgttctc tcctccgcct tgccgtccgt cacttcgtcc tcttcgggca 150300
cggcgacggt gtctcctccg tcttgttctt cttcgtcggc aacttggctc gaggagcgcg 150360
acgagtgggt gcgctcgctg gcggttgacg cgcaacacgc tgctaagcgg gtggcttccg 150420
agggcctgcg gtttttccgg ctcaacgctt aacgagtcac gtaggggaac tacgtgggta 150480
agtgacgtgg atactagtaa aaaaaagtgc gtcaaagttc tcagcgtgtg acgtggatac 150540
tagtaaaagg gacgtcaaag ctcactacgt gttgcgtgtt tttttttcta tgatatgcgt 150600
gtctagttcg cttctcactc ttcctctccc cgttcccagc gcggtggcag cttgggggt 150660 gagggcaaat tggggtagtt ggcgttgagc acgtctagca ggcccaggcc cacgggccaa 150720
ccgtccacgg tcttacgctc ggtcagcttg aggctaaacg agtgtgcctc gtcttgaccg 150780
gtaaggcgga aaaagaagcg tgctaccagc tgcaggcagg tatgccgcgt ctgctggaaa 150840
agcacgaagg tagcgggcac gtactgcaca atgtgcggtt ctttttcctc aaagagtagg 150900
tagagcgcgc tgcagatcag ccgccgggcg ctgtggtgca gcagccggcc gaagctttcg 150960
cgcacgttca ccgcgtctag gtactggagc aggtcgtgca ggcacttgcg cgttaagttg 151020
caattttcca cgcatgaaat aacggtacag agcgcgaagt gcagcaggtt gtcggccttg 151080
acgatgccgc agcggtgttt gagccgcaga tccgagagcc tcacctgcgt gacggcgtct 151140
tcggtctcga gcaaaaacac ggcggagtag cccagaaagg ccgaggtgca cagcaactcg 151200
ctgcggtact cggccatgga aaccagcagc ccgtgctccg tgtgcagcca cagcttgtcg 151260
ccgcgcaccg taaagtcgag cacttgcggc tccatgatca tcacattctg tctagtgaaa 151320
tccgtatgga cctccagcac gccgcggatc atcagggcct ccatttcgaa atcggccgac 151380
acgctctggg ccgcgccgct cctcgtctgc cgtgatcaag cggcgcggcg cggacctttc 151440
aagcgttcct gggccgccgc tcgaggcagt tccccttttct ggcactccgc ccgccgcttc 151500
gcggctcatt tggcgccggc gcgccttctc gcggctgcaa atcaactcca cgtatcggca 151560
aaacttgctg tcgtcgtagg cggcggctac gatctcgccg aaggagagct gcaggtaggc 151620
ctcgggtacg gggtccagcg tgcccagcgc caggatgtga cacagatagg gcagggtcac 151680
gcgctctacc gtgtaattgg agtatacgat ggcctcttcg gccccctgat gcgtgaccag 151740
acgccgcagg cgaaaggtgc ggaaatactc gttttcccac agctgcgtga ggaagcgttc 151800
cagcgactcg gtgccgggca cgaactgcga gaagaagctg ttggccacca ggcggttgtc 151860
ctccaccgcc agcggacgga agggcgccgc gtcgcgcgcc ttgcgcacgg cctccaacac 151920
gggcaggtgg tacagttcgg cgtcgcgcgc gcccaggctc atggagtcct cgcgccgcga 151980
ggcgtagcgc gtgagcaggt cgcgcagctc gcgcacgcga ttctcccagg tctggttgag 152040
cgtgcgcagg tcctggatct cgtccacctg cgactggatc tgctcctcca ggcacttgat 152100
gacctgcttc ttaaacaggt cgcggatgtc ccgctcgggc gccgccgggc cgggtggcgg 152160
cggcagcagc ccgacgtggc ccgcgggtcc tcccaccacg gcgccgccgg gtcccaccac 152220
gccgggtcca cccggaccac gcgcgggtag tagacggttt tggtccacca gcgagggggt 152280
caggtcctgc agaaaggact cgacgctgtc ctcgatgccg atgcgcgatt tgctgtccga 152340
gacgttaagc aaaaacttca taatggactt tttggcgtcg ctgccccggt cgtgctgctc 152400
catcatctcc accagcttct tgcagttgag ctcgtggcgg ctggcggtca ccactttcac 152460
aggaaaggta ttgagcaact ggcagatctt ttggtggcgg cagagcccgt cgtagcgcag 152520
aatctcctcg tgcaggtgtg ccaccggcgt ggtgaacagc agcttgtcgc gctcataagc 152580
cagcggttcg gccgccacgt acaagcggat gtgcttgccg cgcagctgcg cctccagccg 152640
ctccgagcgc accttcttga agacgcgtac ctcgggcgcg ttggctatgc gcacggcgcc 152700
caggcgctcg gccacctgca gcagtagcgc caggttagcc tgcagcaggt cctgcgccag 152760
cgggtgtgtc tcggtggccc gctgcacggc cgcgcgtaca aattgcgccc gctcggccgc 152820
ctcgctcggc ttggtcttca cgtccagcag cggtaccagt cccaccgtta cgcaccaatc 152880
cacgtagaga ccatagtcgt cgttatcggc gtactgatat aaaatgtcgc ggagcgcgcc 152940
cagcacgccc gtttgcacgc tctggcgcaa cgaggcgctc cacaccaaca gatactgctc 153000
caggtcctct tcgtccagcg cgcggtaggg aaacaacgcc gcgtgtaact tccactcctc 153060
ggccacgcgc cgcaccgtga tggtgtcaaa gagcgtcttg cacactccgt agagcagctg 153120
cttgcgcagc acgcacgggt cgcgcagcac ctggtgcatg ctctggccgc gacacgtccc 153180
cagaaagccg tgcagcaacc gcaggaagct catcgtctgg cccgtgggga aaatgtcgat 153240
gacggcctcg tcatccacgc cgcggcccac gcccaagtac gacgacgcct tgatcctcaa 153300
cctctcgtcg gccgccaaga tcgaacggat cgtcgacaag gtcaagtccc tctcgcgcga 153360
gcgctttgcg cccgaggatt tttcgttcca gtggtttcgc tccatcagtc gcgttgaacg 153420
aacgacagat aacaacccct ctgccgcaac taccgccgcg gcaacggcga ccgttcactc 153480
ctccgtctcc tcttctgccg ccgctgccgc ttcgtccgag gccggcggca cgcgcgtgcc 153540
ctgcgtcgac cgttggccct tctttccctt ccgcgcgctg ctcgtcaccg gcacggcggg 153600
cgccggcaag acttccagca tccaggtgct ggcggccaat ctagattgcg tgatcaccgg 153660
taccacggtg atcgccgcgc agaacctcag cgcgatcctc aaccgcactc gctcggcgca 153720
ggtcaagacc atctaccgcg tcttcggctt cgtcagcaag cacgtgccgc tggctgacag 153780
cgccgttagc cacgagacgc tggaacgcta ccgcgtgtgc gagccgcacg aggagaccac 153840
catccagcgc ctgcagatca acgatctgct cgcctactgg ccggtcatcg ccgacatcgt 153900
ggacaaatgc ttaaatatgt gggagcgcaa ggccgcttcg gcctccgccg cggccgcggc 153960
cgccgcctgc gaggacctct cggagctgtg cgagagcaat atcatcgtca tcgacgagtg 154020
cggccttatg ctgcgctaca tgctgcaggt ggtggtgttt ttttactact tttacaacgc 154080
cctgggggac acgcgacttt accgcgaacg ccgcgtgccc tgcatcatct gcgtcggttc 154140
gcccacgcag accgaggcgc tggagagccg ctacgaccac tacacgcaaa acaagagcgt 154200
gcgcaagggc gttgacgtgc tctcggcgct gattcagaac gaagtgctca tcaactactg 154260
cgacatcgcc gacaactggg tcatgtttat tcacaacaag cgttgcaccg acctggactt 154320
tggcgacctg ctcaagtaca tggagttcgg tatcccgctc aaggaggagc acgtggccta 154380
cgtggaccgc ttcgtgcggc cgcccagctc catccgcaac ccctcgtacg ccgccgagat 154440
gacgcggctt tttctctcgc acgtcgaggt gcaggcttac ttcaagcggc tgcacgagca 154500
gatccgcctg agcgagcgcc accgtctctt tgatctgccc gtctactgcg tggtcaacaa 154560
ccgcgcgtac caggagctct gcgagctggc cgacccgctg ggcgactcgc cgcagcccgt 154620
cgagctctgg ttccgccaga acttggcgcg catcattaac tactcgcagt ttgtcgacca 154680
caacctctcc agcgagatca ccaaggaggc gctgcgcccc gcggccgacg tcgttgccac 154740
caacaacccc tccgtccagg ctcacggagg gggaggatct gtaatcggga gcaccggcgg 154800
caacgacgag acggcgtttt tccaggacga tgataccacc accgcgcccg atagccgtga 154860
gacgctgctc accttgcgca ttacctacat caagggcagt tcggtgggag tcaactctaa 154920
ggtgcgggcc tgtgttatcg gataccaggg cacggtcgaa cgtttcgtgg acatcttgca 154980
aaaggacacg tttatcgaac gcacgccctg cgagcaggcg gcctacgcct actcgttagt 155040
ttcgggcctg ctcttctcgg ccatgtacta cttttacgtg tcgccctaca cgaccgagga 155100
gatgttgcgt gagctggcgc gcgttgagct gcccgacgtg agttcgctct gcgccgctgc 155160
cgccgccacg gccgccgctc ccgcttggag cgggggagag aatccgataa ataatcacgt 155220
cgacgcggat tcttctcagg gcggccagag cgtgccggta tctcaacgga tggaacatgg 155280
ccaagaggag acccacgaca tcccctgcct gtccaaccac catgacgact cggacgccat 155340
cacggacgcc gaactcatgg atcacaccag tctgtacgcg gatccctttt ttctcaaata 155400
cgtcaagcca cctagcctgg cgctgctttc tttcgaggag acggtgcaca tgtacactac 155460
cttccgcgac atttttctca agcgctacca gctcatgcag cgtctcacgg gcggtcgctt 155520
cgccacgttg ccgctcgtta cctacaatcg ccgtaacgtg gtgttcaagg ccaactgtca 155580
gatcagctcg cagaccggct ccttcgtggg catgctttcg catgtgtcgc cggcgcagac 155640
gtacacgctc gagggctaca ccagcgacaa cgtgctcagt ctgcccagtg accgccaccg 155700
catccacccc gaggtggtgc agcgcggcct ttcgcggctg gtgctacgcg atgcgctcgg 155760
gttcctcttt gtgctcgacg ttaacgtctc gcgcttcgtc gagtcggcgc agggcaagag 155820
tctgcacgtg tgcaccaccg tggactacgg cctcacttcg cgcacggcca tgaccatcgc 155880
caagagtcag ggcctgtcgc tcgagaaggt ggccgtggac tttggggacc atcccaagaa 155940
cctcaagatg agccacatct acgtggccat gtcgcgagtc acggaccccg agcacctcat 156000
gatgaacgtc aacccgttgc gacttcccta tgagaagaac accgctatca cccccctatat 156060
ctgtcgcgcg ctcaaagaca aacgcaccac gcttattttt tgacacaaca ccgtgtaagg 156120
aaaacgtgac tttattgagc agggtaaaaa ccacgtacaa gaaccacgtt gtctatcccc 156180
aaaaaacaca caccgtcagg gaacacatcg cctatagata gcggcacttc acataaaacc 156240
accgtacctg catcacggtg gctcgataca ctggaaattc aataaaaacc accgtgtctc 156300
cgtgacggta cttatcgggt cagcatcttt ctcttgagat ttttgttcgt aaacttatcc 156360
gtttccccgg tccgcggtgt ctcctcgtaa ggctgacagt ctacgagtgg tacctgcaag 156420
agaagaaacc cgggtgggag cgacgccgtc gctgggtatc aaccccgcgg ctgaccgtcg 156480
tccggtaaag gaacaacccg tcgtcgcaag ccgggttcga ccaagagaaa aacccgggtg 156540
cgggggggag acgggtcgtc ctttggttgt tcgcggacgg cgtacatccc gcgtgggtca 156600

```
gtcgacggcg tcgctccgtg cggtcggtca tcattctgct tcacatatat gggttgtttg 156660
tgtttttttt tttataatga atacgcactg atcctatccg tgactgcgcg tgtggcagag 156720
aggatgcctt ataacatgta ttttgaaaaa ttgccaacag ctataatttc tctcatgtag 156780
cagaatagag accttttgtc gtctttttgt ttgtcattac ttgttttcca gggaattaga 156840
gagagggaac cgcgcctccg gcggcggtgc ccgcggaccc cggccccttc tcgcgtgcgc 156900
ggtgtgactg gttgagcgaa tgagcagcta ggcttggtgg tgctccgcgt gcgggggaga 156960
agacgattaa caacaaaaaa taagtggaag tggccggtgg gtctttgtcc gcgtgcgcgc 157020
ccatccgtcg ccgggaccga gcagaaagtg atgtggtggt acattgattt tttccttgac 157080
aggaaagaaa aaaaaagagt tttgttttcc tatgtgagag gagaaaggta tgtgaggaga 157140
tgttcgatga tcgtatgtta cagttatgct gtaaggaagc ttttatcgtg cgtcctgttt 157200
ttcatttgat gtatatgaca caattgaaac ctatcgatag gcgtatatcg aggattcatc 157260
aattcttaga atcgtcgtct ttttggctaa ttggactttg cccatgttgg ttgtcattcg 157320
tggcctgagg tcatcgtcgt ccatgacgac gtgtctatag cgtgcggtgt gatcattgtg 157380
tcgagccaga gaaagcgcgc ctcgcacgac gtttgcggat cggctcgcgg gtgtgtggaa 157440
ttcctaagaa cataatcagc tggtcgtctt tctttgatgt gttgttgtcg tcgaggtctt 157500
gcttcgtttt ctttttcttt tttagtcgat ggaacttttc ttcggtacgg gttcttgtta 157560
tggaagcttg tgttttcgaa catgaattcg aaaaaataaa aaggcctatc ttcgtttcaa 157620
aaaaaggaca gatatcaatc ttcttaactt atatcatggt aaattcagaa tcctatggtg 157680
tcttattatc tctaaagtag tcaacattat ggtctaattt gtatttccct gacgagatat 157740
atatgatcct tataacctgg ctactatcat gaacaacaat atccttactt acagtcatct 157800
tcgtgagtta atgaagtata atatcggtca tctatcaact tatctgctat gtaacgtacc 157860
cttttaggta ttttgcgttt cttaacgagt gtacccgcct gtgtgaggcg aaactctgag 157920
aagtctaccg agtcgagtta caagtcacta aaacacttac acgagttatc tatactaaaa 157980
tcactatcta tgttgtttgc ttacctaatt attatcctac atgacgaagc tacctcccaa 158040
cgtaaggtag ggggagagga gacagaacaa taaaaagtaa ctaatgtttc ttagaactta 158100
cccgctaagg acttaccaaa ctatattcac caaaaaacaa cagctacgtg tttcatttgt 158160
tttaatctac cgaagtaaaa aaaaaaagat gattagctat ccagaaccta cttacttctt 158220
aatgttttaa ctaaggatgc ctatgggatt ggaaaaaaaa tcacagcaac ttgctactaa 158280
tcagttgaca gcgaagagac tcataacaaa gatttctggg taatacggtt ataataatgc 158340
ttatggacta aaggatactt ggaaaaaaag aatgggctat gactatagag attcgttgag 158400
atatcaaact tcaaataggc ggctatcatt catggttgtg gtgactatat cgtggagaaa 158460
aaatgtgatc gttagttagc taggtgagac ttacagctat ccatccgtct agtttttcgt 158520
tgtaatgatg atagtacgtc tatggtggtg atcgattttg gttagcaatt tgttcgttta 158580
aaggcttaat gtacttatgc tacatgatgt attattcttt gattcatcgt tcctcctaag 158640
ggggtgtatg tatgtatgta ctagtcgtat agtgttccta acatcatgac tattcagact 158700
atggcttcat ctatcgtgtc taaagttcac ctattctact attactatat atatgcacta 158760
ctatgtaact aggatatggt cctataaggt gtcttctatc acggtggctt gtttatcgct 158820
tggcggttac gagcaagagt tcatcacgga ccagccgtga ggcagggcac acgcgggtcg 158880
gcggcgatga tgttccccgc gaaggggaca acaaaaacaa gacaagaggc cgccggccgc 158940
```

ggccacggac gcgtagcggt tacacaatgt ttggttgagc gttttgtttc atcgtcgtgg 159000
tggtggtttt gttgttctct gtatatatcg tgtggtggct ttatcgtcat cattattatc 159060
atcattcttg tttccatcat cacgatgagt tttctccgtt ttcctctcct ccagtggtag 159120
tcgtgtatca tcatcaatca tcgtagtgac gtcgttgctg ctgctgctct tgccttcatg 159180
gcggtatttc tcttcctccc ccctaacccc atattaactc gtgagtgtga tggttagagt 159240
ggctgcttgt tttttttttc ttttctcttt ggaacaacaa aagaggataa agatggtcgg 159300
tgaatgtatt attattatca tcatcattat gatacggtcg cggtcttctt ctccgatgac 159360
gaaacctgcg cacatcgaag aaaagacgag cgcgcgaacc gatagccgtc cgtctgggac 159420
gaaggagaag atgatgggga gaggaggaga gccccagaag ccagagcgag aagggagacg 159480
acagacatac gtcgtcaccg tcctctggag gaggcacggc ggcgctgttt gttgtttgga 159540
tgcttgatta tatcctgttc tatggggtag attattatca ataggcttgg ttttcaaagg 159600
tcagcctgtg tattgtcgtg tctttttttt cgttctcatg atcgcggaga ccacacagac 159660
gtgcgcgtct cccaatggct aggcgttctt tttaggtagt aattttttga tctttttttt 159720
ttcttaacaa gtctggcttg atttctttta tctatgatcg attcttcttt ttctcggggg 159780
ttgcatcttc cgtgaaagta aagtgacact actctaaatg gtaaccatat tatctgttga 159840
ttaggagaaa aaataatttt ttcgcacgaa atcgatccta agtgaggtga tttacttgct 159900
atcacacgaa atgattatct tttgctgcta acgtactgaa tttttttaaca gaattgcttc 159960
tccgtaacta tttccgcaga ttcagacaga ttgtcaaaaa aaaaatacgg cacagaaata 160020
gtgggtctgt ggcttttggt tcgtgtacat tcgcgtttgc gtgtcgagat ttctacggta 160080
tgtttattct tcctgcgatg atgtagggtc cttggtgtaa gtaggatttc gagtatctct 160140
cttagagcga acaaaataat caaaaaaacaa cagctaggaa atcgagggtt actctacgat 160200
aaagtgtctc tacaaagtga agaatgttac gttgtggtgg aataataaga ctcgcgtgat 160260
cgatgagtga tcgagagcgg ctcgaacctt ctttaagagc tttgtttagt gcaactttaa 160320
attacaagga gtagaaagct gaaatgaatc tatgaaggtg ctattctttg aatatcttac 160380
tttgtacgct tcacattcgt tatttggata gagagttgtc tagagaaaat ctgtgattct 160440
ctatgagtgt tatttttatt atccttttgg ggactacgat ttttcttctt gttctacata 160500
ccactactac tcgtaatcac atacatggac gaaaaaaaaa ttcgtcaggc agtagatacc 160560
agattctccg acgttacggc gtcttttttt cttttgagag agtatctgct gagattgtcc 160620
gtggtgtatc tagtcgctat ttttgttgtt actagtagtt ttgcacacag tttattcagt 160680
atagtttttc ttcttgccat gatcaattga gcccaccacc ttttttttta gagaggagga 160740
atttcgtctt gatctccagc cggagacaac ggcggcggtg gtggtggtgg cgggagagac 160800
ttcaaggcaa tgaaaaaaaa atttcgtttt gccatcaagt ggtgacgata acccgtcaga 160860
ttgataattg gttcctacag aaactattct aaccgcggaa gaaagaaatt gaaaaaaaaa 160920
attgacaaaa acatcataac ataaaggacc acctacctgg gacgcgcagt tgggcggcgg 160980
attggggcgg catgctgcgg cgatgctgtc ggtgatggtc tcttcctctc tggtcctgat 161040
cgtctttttt ctaggcgctt ccgaggaggc gaagccggca acgacgacga cgataaagaa 161100
tacaaagccg cagtgtcgtc cagaggatta cgcgaccaga ttgcaagatc tccgcgtcac 161160
ctttcatcga gtaaaaccta cgttggtagg tcacgtaggt acggtttatt gcgacggtct 161220
ttcttttccg cgtgtcgggt gacgtagttt tcctcttgta gcaacgtgag gacgactact 161280
ccgtgtggct cgacggtacg gtggtcaaag gctgttgggg atgcagcgtc atggactggt 161340
tgttgaggcg gtatctggag atcgtgttcc ccgcaggcga ccacgtctat cctggactta 161400
agacggaatt gcatagtatg cgctcgacgc tagaatccat ctacaaagac atgcggcaat 161460
gcgtaagtgt ctctgtggcg gcgctgtccg cgcagaggta acaacgtgtt catagcacgc 161520
tgttttactt ttgtcgggct cccagcctct gttaggttgc ggagataagt ccgtgattag 161580
tcggctgtct caggaggcgg aaaggaaatc ggataacggc acgcggaaag gtctcagcga 161640
gttggacacg ttgtttagcc gtctcgaaga gtatctgcac tcgagaaagt agcgttgcga 161700
tttgcagtcc gctccgatgt cgttcaccca gttactttaa taaacgtact gtttaaccac 161760
gttgcgtcgt gacgttgttt gtgggtgttg ctaggcgggc tggaaagatg atgtataaat 161820
agagtctgcg acggggttcg gcgctctgcc ggctgcggcg gcactcgctc cacggcctcc 161880
gacgagcgtt gcgctcgcgc tttgcgccgc cgcgtcatgg atctgcctac taccgtcgtg 161940
cgaaaatact ggacttttac gaatcctaac cgcatcctgc atcagagcgt taatcagact 162000
ttcgacgtgc gccagttcgt ctttgacaac gcccgtctgg tcaactgcgt ggacggcgat 162060
ggcaaggtgc tgcacctcaa caagggctgg ctctgcgcta ccattatgca gcacggcgag 162120
gcttcggctg gcgccaagac gcagcagggc ttcatgtcca ttgacattac gggcgacggg 162180
gaacttcagg agcacctctt tgtacgcggc ggtatcgtct ttaacaaatc cgtctcctcg 162240
gtggtgggct ccagcggacc caatgagagc gcgctgctca ctatgatttc cgagaacggt 162300
aatttgcaag tgacttacgt gcggcattac ctgaaaaacc atggcgaatc ctccggcgga 162360
ggcggtggtt gcggcgccgc gtctaccgcc tccgccgtct gcgtgtcctc gttgggtggc 162420
agcggcggga ctcgcgacgg cccttctgcg gaggaacagc aacggcgaag gcaggaacag 162480
cgtcacgaag aacggcgcaa aaaatcgtcc tcgtctgccg gtggtggtgg aggcggcggc 162540
gctagtggtg gcggtggcgg cggcgggagc ggcggtcagc actcctcgga ctccgccaac 162600
ggactgctgc gggatccccg gttgatgaac cggcagaagg agcggcggcc gcctccctcc 162660
tccgagaacg acggtgagtc ccggccctcc tcgcgtcacg gtgctttccg agtggactcg 162720
tgagcccccc gtagcgcacg agcgagcagg cgagcggtgt tggtgcgctg gtggttgtgt 162780
ggatgataac catgtgcttt ttcgtgcgct atgtgtcgtc ccgtctgtag gctctcctcc 162840
cctccgggag gcgaagagac aaaagaccac cgcacagcac gaaggccatg gcggcggcgg 162900
caagaacgag acggagcagc agtccggtgg tgctggcggt ggtggtggcg gcggcagcgg 162960
ccgcatgtcg ctgccgctgg acacgtctga agcggtggcc tttctcaatt actcgtcctc 163020
atcctccgcg gtctcttctt cctccaacaa ccaccaccac catcatcacc accataacgc 163080
cgtgacggac gtggccgccg gcaccgacgg tgcgttactt ctacccattg agcgcggagc 163140
ggtggtttcg tcgccgtcgt cgacgtcgcc gtcgtcactt ctttcgctcc ctcgacccag 163200
cagcgcccac agcgcgggcg agacggtgca ggagtccgag gcggcggcga cggcggcggc 163260
tgcggggtta atgatgatga ggaggatgag gagggctccg gctgaggcgg cggaggcacc 163320
accgcagtcg gaggaggaga atgattccac cactccagtc tctaactgcc gtgttcctcc 163380
gaattcgcag gaatccgcgg cgcctcagcc tcctcgcagt ccgcgttttg atgacattat 163440
acagtcattg accaaaatgc tcaatgattg taaggagaaa agattgtgcg atctccccct 163500
ggtttccagc agactcttgc cagagacgtc gggcgggact gtcgtcgtca accacagcag 163560
cgtcgcgagg accgccgcag ctgtctccac agccggcgtt ggccccccag cagtcgcatg 163620
tccgccactc gtcaccaccg gtgttgtacc ctcaggttcc gtcgccggtg tcgcgcccgt 163680
tgccgccgca gtcgaaacac cagctgctcc tccccggccc gtgtgtgaaa tcaagcccta 163740
cgtggtaaac cccgttgtcg ccaccgccgc ggctgccagt aactcttcct cgtcttcttc 163800
ggctccactg ccgccgccac caccaccgcc gggcggacgt cggggtcggg cccggaacaa 163860
tacccgagga ggcggcggcg gtggtggcgg tggtagaaac agccggcggc aggccgcatc 163920
gtcgtcgtct tcctcctctc ggagatcgcg acggagaaac aaccgccatg aggacgagga 163980
caacgatcct ctgctccggt tgtcgcaagt cgccggcagc ggccgccggc gagggccctc 164040
gttcctcgag gacggactcg aaattatcga tcccagcgag gaggctgcga tcgccgccgc 164100
ctcgatcgcg gcgtttttcg acgattaaaa aacagagccg agaccggaaa aattatgaaa 164160
caggacgcgc ttggacattt gggtttccac ccctttcggt gtgtgtctat atatattgtg 164220
gtcactgatt ttttttaca ataaagtaga catcacagtt caccaccttg tctccccggt 164280
gtatctatta tcatcaatca cccacagagt cgccagtcca tggtctctcg gtaatgcgtg 164340
tccagatacg cgttggccag tataaagtgg tcgttgccca cgaaggcgcg ggtggtgttg 164400
cgcggcgacg ggtggcagga cttgagtacc aagtgccgcc gtcggtcgat caggtactcg 164460
caggtgtgcg cgtcggcgcc ccacagcatg aacaccagat gctcccggcg ctctgacagc 164520
ctccggatca catggttact cagcgtctgc cagcctaagt gacggtgaga tccaggctgt 164580
ccgtgcacca cggtgaacac ggtattgagc agcagcacgc cgcgtcgcgc ccaggcgtcc 164640
aggcaacccg aggccggacg ctgaaacccg tccaccgtac gcgccagttc gcgaaacacg 164700
ttgttgaggg agggcggcgg cggtcggccc gccagcgtgc cgaaggccag gccgctggcg 164760
ctgccgtcgc agtacgggtc ctggcccacg atcaccacgc gcacctgctc gggcggacac 164820
agatagctcc agcggtgtac gtgctcgggt gccgggtaca ccatctcgag ttgccgcgcg 164880
ccctccaccg ccgccaccgt gtcgcgcagc agcaccgtgt cgtggtcggg caagctgagg 164940
aagcggatcc agtcggcgct cagacaaaac acgcgagcct gctcgtcggg ggttaacaga 165000
gagcctttat tatcagcaat gttagcgagc atccactgct tgagggccat agcgcgagtg 165060
agccggcagg ttgacgcgcg tctgcttcag ctcgggcggc agtccggcgt agtatttatc 165120
taggtggcgt agcagcggcg ggtccagctg gtgacgcagg cagaattcct tcactgcgtt 165180
gtacaggccg taaaagagcg tgatgccctc gggcgcggca gcggtgctca cgggcagacg 165240
cacggcgcgg ttggtacgcg tggcttcgtt gcgtatggcc accaccacgt taaagagaga 165300
cggtggcacc agctcgaagc ctaacacgtg ttccgtgaag atgctgcgcc cgtatgacag 165360
tcgcgtgagg tcgtagccgc ggcacaggtc gtccacgcac gtgtacacgg ccggcgagcc 165420
atcgccgcac tcgctgtagc cgcgcatcac cgtcatccag cgcggcgctg tgtccgagct 165480
caacagcgtc agcagggccc gcaattgatc cggattgttg tacagcaggg ccagagtgtc 165540
caggaaagcc tcgtccaaca gcacggagtt ggcggcctcc ggcgtaacgg gacggtaacg 165600
gataagttgc gatagcgggc catcgcgccc ggtaacattc accaacgggc gcagccaact 165660
ttcatacttg tcaccctcaa acacctcacc caacaagcat cggcgcgtta gttcggggca 165720
ctccgcgggg actttctcgg cggcggtagg agcgacgctg acggcggctg aggaaacaat 165780
gggcagcaga aggcaacacc acagcagtat caccggtcca ggtgagaaag agaagccgca 165840
atccgggcgg cggcacatca agtctgcggc acgatgagag tgtgacggta aggagccagt 165900
tggcgccaaa agttggcact caggtcttcg atccctaaaa cgttatatat tgcatccagc 165960
aggtgagcca ggctaaacgg attcacgtac caggtttggt tacccgcgac gatgacggcc 166020
agaccgtggg cgctacagtt ggagaggttc ctgggtacga aggtaactga gtcgatgtcg 166080
cgccacgggg ggaatgagac agacgactgg cgcacgctgt aatcacaact gtgattgacg 166140
tattgtagcg tgtaatttag gttgcactca gcctcgaagt agagggggaa ccacagttcg 166200
tcgtactcgt cgtcgtcctc cagttctggc tcttcttcat ccaccgcaat gtctacgctg 166260
ctctgagatt cctcttcgta caggatgatt gacaggttat ggctacaaag gtcctgggcg 166320
ggaggacgcg tgggagcgcg ggtggtggta atgttttcca ggtcaaaagt tggagtgtag 166380
tcggatgtta catccccgtt gttggaggtg gtagaagtcg cggccggtgt cacggtggta 166440
agtatggata cagaagagga gggggaagta gcgttcgtac cgatggttgt ggtattatta 166500
ttccttgtat ttcttgttcc agaaaccgtt gacgttgaga tgagaatcga cgtggcgctg 166560
gacgtcagat tgctgaccga ggaaaccgtg gtgggagtgg tgacggtgtt actcgtggtt 166620
gaagtgacgt taggggaggt agtagtggta ccggtggtgg cgacggtagt gtttgtcgtg 166680
gcggcggcag cggtggtact ggtaacggtg gtcgcgttgg tttccaccgc ttcacacagt 166740
aagcaaaagc acagggccag gaaaagcaac cagccccgcc atcgccgccg ccgcttcatg 166800
aggtgggcag gcgaaagctg gtgaattcgt tgtacagcgg caagtggggc gccgcgatcg 166860
aagggtacgt caacaagctg acgttgatat taaatacgtc tggctgcttt tctacgatgg 166920
aagcgcacag ggttacggcg tcgaacaggt ctttcttggt ggcgcccgag acccacatct 166980
ggtatacacc cgtctcgtgg tacgaagtag agcgcggcac caccggacgg atgcagtcca 167040
gaacgcggtt gggatcctgg tgaaagaatt tgaacgtggc tacggcctgt ggcgtgtgcg 167100
gcatcgtctg cgtgatgagc tgctggcccg ctaacacggt gacgttgtgc aacttgagca 167160
gggcactctt gagggcctgg aaagcgttgc cgcacgaggc gctgatttgc agctgcacgg 167220
ccgtggagtc gtgcagccgc atgagacgtg acacctcttc gaagacgtac ttatacttac 167280
tggcaaagag tggcgcgtac cgacagtcgg ccggcaaaat gtaggtggcg ttgccgccgt 167340
tggtggccac ggcgggcgca gcggccgcgg aggccggcgt aaacagcgtc agcggccggt 167400
ggtggctggt aaggtcgatc atgggcggcg tggtgaccgt ggcggtggcg ggcatgacgg 167460
ggtttgcggc gacgggcact ccggccacag cggcggcagc ggcggccacg gcggcgctgg 167520
ccgagcccac acctgccggc agtcctccgc cacccatgac gccgccgggc agagcgtcgc 167580
ccagacagac ttccacagtg gcgggcgcgc tctcggcggt cagtacggtt tgccgatcga 167640
cctcgcgacg aaagctggtg aggaactcac tatgatccat ggccgcaggg cccgagatcc 167700
cgggattctg cgggtgctga ccgagtgcgg gccgagttat atggaagacg attagcttgg 167760
agcggagttt tgcgtcccta gctgacctgc ggatcagcga cgtgccatag ggatagactg 167820
tgagcggcgg ccgcaacggc ggggtcggcc gccgttcgtc gtcacggggc ggcgcgaggg 167880
aggaggaggt ggtggtgggt acgatcttga cgtggttaac gtcctgcccg tccgggggaa 167940
tacgcaaaaa accccgccgc ggcgctacca cgatggtgcg atgggtcttt ctcttgttgg 168000
ccggggccag ggacttgcag atgcgtgtgg agccgtagac gatctggacg tggtcctggg 168060
agaacatgac catcgccgcc aacgctcagc ggggggacgg gttgggaaca cagaggctga 168120
ggggaaaccc cgtagaagtc agcgaaataa aaacaacaca gcagccgctc ctctcgtttc 168180
gggccctacc actgcttgaa gtagggcacc gggtgtttct tttcttcaac gggctcctcc 168240
agtctcttat aggaccagtc ccgccggcgc gccagcatgt aggtcacgta caaaagaata 168300
attaccatga acaccaggaa agccagcacg ccgtaggcca gcagccggtc ctcgaacagc 168360
gggtcgctct tgataaacac gtaggtggtg gtaaaacttc ggcccgcgat ctggacgtgg 168420
agacgcacga cagtatacgt gccgttgagg tagaagacaa actcgcgtaa ccgttgtccg 168480
ttatacgtca cgttactaat attccacggc ggaatgagct ggtcgccctg atgcagatgc 168540
acggtgctgt tggggtgata gaggctgcta ccgttgagca agcagtgttc gtgttcctga 168600
agcagcacgc ggacccgcat agtggtagcg ttcaagcgag tcccgtacac ggcgtaaatg 168660
ggataggtga aaaggtccca agtggcgttg tgatggcggc cccagctgaa gaaagagcac 168720
gtgtactcag tggtctcctg cggcctgagt cccgagataa gcagctcttg agcagtagcg 168780
ttgtaggaga gatgtagttt tcctgtggaa aaaattaatg agttgtttat tttgttagca 168840
ggttggcgag ggaggaaggg gaacaaaaca gaaaggtacg tgttacttac ctttatcgtt 168900
ggagggaaaa gcgctaagat atcccacctg agtgaaggga cccttgcagt ctgtccgtgc 168960
ataacaagta actgataaaa tgtctggatt tttggtatta ttcaacagga taactttgca 169020
ggtggcgttt agagacactt ggtcgtagct gtagctggct tcgcaattca cagtatacag 169080
gtgcccctct ttctgcgtcg tggctatcac ggaggtggag gcggacgagg tagaggtttg 169140
taccgtggtg gtgacagcag aactgacgtt gttagaggta cttattgacg tagtagacgt 169200
gacggtggta ttactagggg aagtgacggc gcttgtggtg ctacttttca ctcccgggtg 169260
catgtcgccc aagagcgcaa ctacgagcgc gatcgccagc acggaacaca tgttgccgtg 169320
tgacgagacg gcgtgtggac gagctatatg tggcaggagg tcgcgtcacc tcttgtgacg 169380
cctaaacgtc cagctccaga taaaagaggc gttaataatg aacactacaa aaaccacttg 169440
cgtcaatatg acgatcataa aggctcggtg atcgctgcgc ctaaagtatg cgggattctc 169500
caccagctca ctatcttcga caaagtggat gaatgtgtta gtgttaccgg ccgttttgtt 169560
gaccatggat cgtactatga aagtcccggc gccaaaagtt ccattagagc cccagcaagt 169620
aacgctgccg ttcacgtagg ttcccggctc tcctgtcagc atgtgtgtca gttggtgggt 169680
ataattctgt ttaatgtttt ccatgtcctc gctgtaatta acttttctgg tgagaaactg 169740
tgtacggtgc gggagaacga tcatcatccc tgaggccaaa aagggcgaat cataagctgt 169800
tgtgttacaa aaaatagtca ggttagtatc attgtgctca tagatataag ccatttttac 169860
ttgaggttca taccaccacc ctaccctaat tgtagttgcc accgtcaccg agtcccatct 169920
cccgaaactt accaccgcca ccactaatag cgtcaccccc gcacggtaca tagttaccct 169980
ctcgacgtcg ccggctgtca atgacgtgcc tgcgtcagtg gctatgattt atagcttttg 170040
gacacaaccg caacggatct gtcgtaatct accttccaca gggccgccgt gacgatgctg 170100
aacgacagga tcagacagac ggcgtacagg agtcctaggt cggcgtcgac acggcaggtg 170160
cggatgtctc gcagggtggg tagatgggcg atgcacaact ctttctcccc ccgcccgtac 170220
atcccatctc gtatcagcag ccgtagcgtg gcattgatgg tcagcggggt aaccaaagaa 170280
atcacatagg gatgtgtaca ggaagtacag tgatgggtat ccgtgagatg tacgtcatca 170340
ccctcctcac cctcatcatg aaagaccagg actcgggtga gacgacccga tgaatactgg 170400
atctcccacc acagtctttg gtccaacacc gagagggcgc aagagattct aagtctccct 170460
gggttggggg agcagatgta agccccgtat gtgcctctcg ccatcagggc catacacatg 170520
aggaggagaa ggacaagtat ccgggaccac ccgcaccccc acatcaggag accagagacg 170580
gagatgtata aaaaagctac ttttattaaa cagcattctc accacacgtt aatactgtca 170640
cgggaaatca ctatgtacaa gagtccatgt ctctttccag tttctcactt actgagattt 170700
gttcctcagg tcctggatgg ctgcctcgat ggccaggctc agggtgtcca ggtcttcggg 170760
aggggtctcg gtgggcttct caaactgccc cacggcgtag gccttcgcgg ccgtctcgta 170820
gataggcagc atgaacccac cctggttggt ggagaagatg cgcaccatga cctgtttggg 170880
aaacttttgc atcaggggca ggcacaggtt gagagcgccc aacaggtcca cgggggtggc 170940
agcgtggata atcatgttgc ggtaatcaga agagcggggg cacaattggt gggtgtgcag 171000
ttctttgagg ttccacacgg ccttgacacc gtcgttacaa gcatcggccg tgcgctgcgc 171060
cacatcagga gggtgtgtca caggcatagt gtgctccatg aggaagggag tggagagggc 171120
caggttgcac atgctaccca ggcgacaccg tacctgatcc acctcattct tcacttcatg 171180
attgcgggtg tagatgatct gaatgccctt gttgttcacc tgcatggttt tgcaaacttt 171240
gatggcctct tctaacactt ggtgcatact agggatcatg aatggcagat tcttgtactc 171300
aagagaacga ttggtgtgac ggaacatgcg gctcacctcg tcaatcttga cgcgaccccg 171360
ccgagtctgc acgttgggtg tgcagaaggg ggtgttctta tctttcatga tattgcgcac 171420
cttctcgttg tccaactcgg agatgcgttt gctcttcttc ttgcgaggtc cggtgctcgc 171480
cccgccgctg ctctgatggc cgcagctcag cagagaggag gaggccgcgc caccaaaacc 171540
gccgcgccca tggtggctcg aggtcacgga tgctcctccg ccactgctgc atttcatctc 171600
ctcggactca ctctccgagt ccgaagccga actgcaggag gaggaagacg aagaggaact 171660
atcttcatcg ggccggccca aaggatcggg aagaggaggg tggttcatct gggagagcgg 171720
gtgcgtggga gaggtcactc gcggcgtgcc gctgccggtg gaaggggaag acgcggtagc 171780
accgcgggtc tcgacttctt caccctgttc ttcctcgcta tcagagatca cgatacagcc 171840
ggcggtatcg ataatcttgt tgcggtactg gatggtaaag tcgggctcgg gcttgatgtc 171900
ttcctgtttg atgaggggca gcatgatagg cgcgggaggc acgggcggtt taataatcac 171960
cttgaaagga cgcgtggttt tgcgcggttt cttacgcggg ctgagctcgg gagtagcgga 172020
tgccccgggg agaggagtgt tagtaaccgc gacgctggtg gggtcggct tgttaagagg 172080
ggcgctgcta acgctgcaag agtgggttgt cagcgtgggg ccggtgctac tggaatcgat 172140
accggcatga ttgacagcct gggcgaggat gtcacctgat ggtgataaga agacacggga 172200
gacttagtac ggtttcacag gcgtgacacg tttattgagt aggattacag agtataacat 172260
agagtataat atagagtata caatagtgac gtgggatcca taacagtaac tgatatatat 172320
acaatagttt actggtcagc cttgcttcta gtcaccatag ggtgggtgct cttgcctcca 172380
gaggcggtgg gttcctcagc accatcctcc tcttcctctg aggcaacttc ctctatctca 172440
gacactggct cagacttgac agacacagtg tcctcccgct cctcctgagc accctcctcc 172500
tgttcctcat cactctgttc actttcttcc tgatcactgt tctcagccac aattactgag 172560
gacagaggga tagtcgcggg tacaggggac tctggaggtg acaccagaga atcagaggag 172620
ctggcaccag cggtggccaa agtgtaggct acaatagcct cttcctcatc tgactcctcg 172680
gcgatggccc gtaggtcatc cacactagga gagcagactc tcaaaggatc ggcccccaga 172740
atgtactggg caaagacctt catgcagatc tcctcaatgc ggcgcttcat tacactgata 172800
acctcaggct tggttatcag aggccgcttg gccagcatca cactagtctc ctctaagaca 172860
tagcagcaca gcacccgaca gaactcactt aagagagaga tgccccccgta catggtcatc 172920
atacaagcgt cactagtgac cttgtactca ttacacattg tttccacaca tgtagtgagg 172980
atatccataa atatgtgatc aatgtgcgtg agcaccttgt ctctctcctc atccaaaatc 173040
ttaaagattt tctgggcata agacataatc tcatcaggag agcactgagg caagttctgc 173100
aatgccgcca tggcctgact gcagccattg gtggtcttag ggaaggctga gttcttggta 173160

```
aagaactcta tattcctgta gcacatatac atcatctttc tcctaagttc atccttttta 173220
gcacgggcct tagcctgcag tgcacccccc aacttgttag cggcgccctt gctcacatca 173280
tgcagctcct taatacaagc catccacatc tcccgcttat cctcaggtac aatgtagttc 173340
tcatacatgc tctgcatagt tagcccaata cacttcatgt cctcgaaagg ctcatgaacc 173400
ttatctaaga tatctaaggc attctgcaaa catcctccca tcatattaaa ggcgccagtg 173460
aatttttctt ccgtctgggt atatttttc agcatgtgct ccttgattct atgccgcacc 173520
atgtccactc gaaccttaat ctgtttgact gtagaggagg ataacaacac atataagtat 173580
ccgtcctcct gactcattta tcgctatctc gatgccccgc tcacatgcaa gagttaatct 173640
tcactctatc tgacatacac aagtaaatcc acgtcccatg caggttagta tatatcacat 173700
acatgtcaac agacttaccg agttctgtca ggacatcttt ttcggggttc tcgttgcaat 173760
cctcggtcac ttgttcaaag gttttgaggg attcttcggc caattctggg aacagcgggt 173820
ctcccaggct cagctgactg ttaacctcct tccttaacat agtctgcagg aacgtcgtgg 173880
ccttggtcac gggtgtctcg ggcctaaaca catgataaac aaagtcataa gcacatggat 173940
cacatacagg aaatatgtat ataacattaa agatataact ttttattaaa aaaaggggaa 174000
cacaagtccc gacacgtacc gtggcacctt ggaggaaggg ccctcgtcag gattatcagg 174060
gtccatcttt ctcttggcag aggactccat cgtgtcaagg acggtgactg cagaaaggat 174120
ccatggaaag gaacagtctg ttagtctgtc agctattatg tctggtggcg cgcgcggcag 174180
caacgagtac tgctcagact acactgccct ccaccgttaa cagcaccgca acaggagtta 174240
cctctgactc tcaacagaac acaactcagc tgcctgcttc ttctgctgct gccttaagtc 174300
ttccatctgc gtcagcggtg caagcccatt ccccgagctc attttcagac acataccta 174360
ccgccacggc cttgtgcggc acactggtgg tggtgggcat cgtgctgtgc ctaagtctgg 174420
cctccactgt taggagcaag gagctgccga gcgaccatga gccgctggag gcatgggagc 174480
agggctcgga tgtggaagct ccgccgctac cggagaagag cccatgtccg gaacacgtac 174540
ccgagattcg cgtggagatc ccacgctatg tttaataaaa actgcgggta ctggggacgg 174600
tgttgttgta tatgtgaatt tgtaaataat aaatgggacc ccatcctgta aaaatacaga 174660
gtccgtgtca gtctctgaag gacagagtat tggcatatag ccaataaaga gagttgtggc 174720
aaagagccat gttatggatt agtaatggaa agtatcgcca ccaatagagg agtggtcaat 174780
aatggtcaat aacccacacc tataggctaa gctataccat cacctatagc ataaggaagc 174840
gggggtgtat agaccccaag ccaaaaacag tatagcatgc ataagaagcc aagggggtgg 174900
gcctatagag tctataggcg gtacttacgt cactcttggc acggggaatc cgcgttccaa 174960
tgcaccgttc ccggccgcgg aggctggatc ggtcccggtg tcttctatgg aggtcaaaac 175020
agcgtggatg gcgtctccag gcgatctgac ggttcactaa acgagctctg cttatataga 175080
cctcccatag taaacgccta ccgcccattt gcgtcaatgg ggcggagtta ttacgacatt 175140
ttggaaagtc ccgttgaatt tggtgccaaa acaaactccc attgacgtca atggggtgga 175200
gacttggaaa tccccgtgag tcaaaccgct atccacgccc attgatgtac tgccaaaacc 175260
gcatcaccat ggtaatagcg atgactaata cgtagatgta ctgccaagta ggaaagtccc 175320
gtaaggtcat gtactgggca taatgccagg cgggccattt accgtcattg acgtcaatag 175380
ggggcgtact tggcatatga tacacttgat gtactgccaa gtgggcagtt taccgtaaat 175440
actccaccca ttgacgtcaa tggaaagtcc ctattggcgt tactatggga acatacgtca 175500
ttattgacgt caatgggcgg gggtcgttgg gcggtcagcc aggcgggcca tttaccgtaa 175560
```

gttatgtaac gcggaactcc atatatgggc tatgaactaa tgaccccgta attgattact 175620
attaataact agtcaataat caatgtcaac atggcggtca tattggacat gagccaatat 175680
aaatgtacat attatgatat agatacaacg tatgcaatgg ccattagcca atattgattt 175740
atgctatata accaatgact aatatggcta atggccaata ttgattcaat gtatatatat 175800
cgatatgcat tggccatgtg ccaacttggt atcgcctcta tcggcgatat ggcctcatat 175860
cgtctgtcac ctatatcgaa actgcgatat ttgcgacaca cagaatcgcc caagtcgcca 175920
aagtcgtcta tcgccatccc ccgtaaacga tataagcgtt atcgccagat atcgcatatg 175980
cccaaaaatc actttttaaa aaatggcgat atcagttaca cagaaactca catcggcgac 176040
attttcaata tgccatattt tcaaatatcg attcttccaa tatcgccatc tctatcggcg 176100
ataaacacca ctatcgcgcg acatgaattt agtcggcgac agaaatctcg aaacgcgtat 176160
ttcggacaaa cacacatttt attattcact gcagcatata gcccatttta gcgcggcaca 176220
catccagccg tttgtgtttc ttaacgctct ccaggtactg atccaggccc acgatccggg 176280
ttatcttgtc gtattccaga ttgatccatc aatagggaac gctgccagcg gcgcccagca 176340
ggtactgcgc cttgtcgttt actttgccgc agcgtattcg cccgtcagct tcgaggtata 176400
acctacaaca cggaggggaa ggggggtaca aaacgtgaaa ttagactttt ttttttaatg 176460
atgttttgtc cctctctgtc ttactctccc ataggctgta aggccctcag gaagagactt 176520
acggattgta gttgcagctc gtcagtttgt tgtgtacgac ctggcgtgtc aatgaatggg 176580
tcatggtggt gacgatcccg cgaatctcag ccgttttctc gggactgtag cagacttcgc 176640
cgtccggaca ccgcagcctg tggattcatg aaaatctact ctggcattcc cgaggatcgt 176700
cgatggaaca tggctatcag aaacgtcgag agacagatcc agacgcacca cagaacgcag 176760
acaatcatga aaatacgtac gcgacggtga agcgattgca cattttgaaa tcgtaacagc 176820
gttccggcgg gtggttgacg tttatgaatt cgcaacattc ttctgcgcgc acccgcggca 176880
cgcggctgtg acccaatagc agccacaacg ccgtcaagaa cggcgtcaga tctttgggac 176940
tcatgacgcg cggttttcaa aattccctgc gcgcgcgacg ggctcaaacg atgagattgg 177000
gatgggtgca gaaggtgtaa gtctggttat tggcctcggt gaacgtcaat cgcacctgaa 177060
aagacacgct gtagtcccgg aagacgtgag cccagctctc cagcttcatc acacacatct 177120
gataacgtgt gccatcgttg acgacgaagc gtagcagctt ggtctgcttg ggcaccatgt 177180
gcgctccaaa aatcttggcg tcttccacgc tgatctgcac gtttccgtcg ctcggtttcg 177240
aagccgttcg gggcatccgt tggaggatgg tttggttccg accgctcagg taccagatca 177300
cctttttcac ccaggtggag cttctctcca ccaaggtctg gccttcccgg ttgtacagca 177360
gatacagggt ctcgttgcga cactcgggac ccgttgatac ccgctggaac cccgagaatt 177420
gcaaggggga tcgtgggggc gagggataga gaaaaggaca gtaaaacgtc gccgcgtcat 177480
gcggtttgga atacgtcagt ttagaccatg gcggggacgg attctggttt gctgttagcg 177540
tcgaccacgg agacgccaga cagggcgttg cccaaaccgc gcacagaagc aggcagtgaa 177600
agtggtgacg aagcagaagc cgcagcatat tatttcccgt gacgcaggct agttggcaaa 177660
gagccgcacg ctgaactcga ggctccgggc gtgtggcgcc agcgaaccgg cggcgttgaa 177720
cgtggtcctt ttgttggtgc cgccgcgacg gttctgacgt ctaaagtcgc tgatgagcaa 177780
cgacacctcg gtcacgttga ttctgcaagc acaggttccg aacgtcattt catacccat 177840
gcggttactt acccgttacc cgttcgccct taccttcccg ttgtcatgca tctttagcgc 177900
gtaccctcac ctcttgagca cgtcaaagtt gtccaagccg tggctcgcat cgtagtggta 177960
gttcaacgtg aggtccacga gctgttccac atacttgtaa cgggtttggt cgggcagcgc 178020
gcgagagcac gcgtcccagt aatgcggtac tcggtaataa tcgttttttt ccgcggtttc 178080
ccgctggcac tgacccagca ccacggcgca cagacaaaca gacagccaca cccgacacag 178140
ccgcatgttg cagactgaga aagaaagctt tattatgaga catcatacac atagtatagg 178200
cgaggtgatg gggcggggaa agagttggaa ccgaaagaca aaaaaaaaag cctagtcgta 178260
ctcgggatct ctgagcgaga cgggttgcat ggcaactttc attagtttgg gaatctgcca 178320
gctggtgctg ttcgaaggtt cttccatttc cgaggcggtc agttcatcgt acaccgaaac 178380
gtagtacctg atggggtcct cctcattgtc cgagaggtga gattcgatgg tcaaaggcga 178440
gcctctccca taattgggat tcacgaacga cgtgtccaag ttgccatcct ttctgaaata 178500
gatgacgttc tcaggatcat gtttcatgcg ctcgcgggcc gcggacgcct cctcctcctc 178560
gtcccagtcc cgagtttcca accgctgata agggctcgag gaacaaaatc cggcggggat 178620
ctgagaacct cgtcgggaac cgctgccaaa cgggctgctg ccgccactgt cgtccgtgtc 178680
gtccaacagg ttgacggctt cttcgtcggc gaaacgaaag cgacccgggt gcttgcaaca 178740
cgaggagtaa actaccgcga ccagtaccgc tatgaagctg aaaatggagg tgcctgtcac 178800
gatgtagaag aggatagcca gcactttcat gatctcgtta ttgcgcacgt tgtgaacgga 178860
agactcgtgg gtggtggtca tgttgatccc ggtcgtgggt ccgctactcg tggcgttgtc 178920
gacgctattt ctgttgctgg tgctagtagg gacttttgtg ctgctggtca cattcgtaac 178980
gtcgctgagg tctatctgaa gcagcaaccc gaacgcgacc agggccagga atgttgcgcg 179040
aaggggaccc cgcggggccg gcattctcga gacgtggcga cgtggatttc ttgctatgtc 179100
cgcgaacgac gtgtgacgag gacgtggttt ccgcaagcct ctaccgacgc cgcgacacca 179160
ggtaggttat caaaacgcga gcccatatcg ccgccatcat tgtaatcagc aatgtgttga 179220
ggtactgcac gatgaatctg tctagtgaca ccagccaacc ctctgctttt gcgggcaagc 179280
gcgctttcgg tgacagggtg tatcgtacgt agccacgggt caggcgcgcg ttgtagcggt 179340
acacgcagaa atctatccac aagccaacgc ccggttgtag cttcggatgg tggataatag 179400
cgcggtgacg tacgccgcgg ggctttagaa tctccacctg taaggccatc tcctccaggt 179460
agtgggtctg actgcgacgc agcgtccagt tcatgtaaaa gtcggtctcg ccgtgtccgg 179520
ccacgaagag gctgcttact aaatcgggcg ccagagctag gtcaggcgta tcaaattcca 179580
ctgtcaggcg acctgattct aacggttcca cgatccggga gagcgtttct agatatagag 179640
caaagcgtac cacgtctacc tgcggtgtaa aaaactgttg tgggcgttca ccgtcgttga 179700
ccacgtaggc cacgtagagg ccaacatttt ccaccacggg ttctagctgc aggcggcacg 179760
taaagcttag aaacgacggc tgtacggttt ggttcccgtg aagctgaagc gtcacttcct 179820
tgccggggct caccgtgctg taacgccgca ccgagtcggt catctgctcc agatcggtag 179880
accagaaggg cgtgcaatgc atactgtccc agtcgcgaca cgcagcccag cctagctcgg 179940
tgaagggtcg acgcacaccc gagaaagtgt gcttgaagac cagggggtcg cctcggtagc 180000
tcagtagtcg aacatgcaca tagtcgcggc tagcgtcgac agacggtccg tagagggcca 180060
gcagtacgag cgtgaacagc aagcgcaaca tgctgcgcgg gttaggaaat gcggcgtgcc 180120
ggccaccgcc cgactcataa acgctaccag catgacgtct cagatcacac aagtgacgag 180180
gagcgtaccg caaatcacta gggaaaaggc cagcagagcc cgatagtctt gctcttcgcg 180240
aacgatctcg tccggttcct cgcaatcttc gtggtccaca gaagatgagg agcaggaatt 180300
ttcgttaatc tctgcgagga tactagtgct gtaccacacc agagcgctta gtgtgcccag 180360
agctaccgca cggtaaaata gggacatgat caccagcgca gtctaaagta gtggtaattc 180420
agtttcttgg cgtatttcca gagaaaggct ttgtaggccg tagggactgg ccaggcaccg 180480
aactcaatat ttgtagacac tacgtcgtaa atgcgttgtt cctcgtctaa gactaaccga 180540
aaaaatagcc ggttgatgtg acgacgcacg gcttgcgcgt taggattgag acacttggtg 180600
cccttgtcct ttaaaatagc cagcacttcc tgacgattgc agctttcgct cgctgcgatt 180660
ggcttaagca attcggttcc gaccggcagg gtattcaaca gaatttggtt attacagcga 180720
caccgcttgt cgtaatcttc tagttctaaa agacggacgg ctatgggaca tatggcaagt 180780
aacatatatg cggtcaatga caggtatcgt accgataaaa gtttaatgcg cgaattcaga 180840
atcggatgat gtaaccatgt tagcaacata ttgaaaacat gatattttct gctctaacaa 180900
acttgtctgt ttaaaatata tactaaatat tattccttca gacctactag ggttacagtt 180960
atttttcccg gccctcgttc cggttgtctt gttacattaa cattatacca cctgttatcg 181020
ttgcgtttgt ctagccattt tgaaaaaggg tgatggggcg ataaacatac tccaggtcca 181080
tgtttttttc ctccgcctag atacaagaaa tattcattgt tattgcatct gggaccacca 181140
gattcgcgat gaaaccaaaa attacccaac ataattgttt tgggcggcag ttttttacca 181200
tcaagacatt tgcagcgtaa ttccgttcca tgcacttcat aataatacat atacgttaaa 181260
gaaataatca acgcaccaaa aattaatcgc attataattt tattatttac gtcactacca 181320
ataattcgta atatccggta ttcccggaaa atcactcaaa actgcgtcca tgacacatca 181380
attcccgata agtacccccc tttgaaatcg gatcccccca cataccaatc aatcatacaa 181440
cacacaggtt taaaaatcga tcacacgtca attaggtttc aaaatcgata ccatttatta 181500
tcaggaatct agactaattc tacaatgaca gctctgaatt tctctctcgt ctttcttgtc 181560
aggttctcat catcaatctt cacttccacc catcggggag tcatcgtcgc tccaaaaccc 181620
tttggggtca ctggttggaa aagtctctga cacgatccag gcaccccgta cccagtccga 181680
ctgatctagc ctacggagca tctcaacagg catgagctgc agggccacgg ctgtcacggc 181740
actgtatcga tgtaacacta gggactttct ttgcgatgta gccatcaaca cggcgtatgc 181800
cccatagttc gcgtgatacg acgcatgatg ggttaaacgt tcccatccgg cagtgccgtc 181860
tcgggtccgt gcacacaaca gctgcacagc gttatgatgc ttaaaattaa ccataacgct 181920
gggactactg atgaaggagt agtaatgagc caggacgccg tacatcgaag gcaacaagaa 181980
agagtgacag cacgatagca ccgggctctt atgtaggcga cagcttattt ttcctgacgt 182040
cggcaaaaag tacctaaatt ccccacagat attcagacac ggttccgtaa agtgcttctt 182100
tttttagtgc aggaattgga aaaaataata aaaaatatga acagctcatc tgtaattatc 182160
tgtgtgactt catcgtaccg tgatgtaaaa acaacaacag gaagcttaca gggtgcggta 182220
gaaaatttttg ccgattgagc aacactgttg gcatctctca ctccgatagg cggctataag 182280
atagagaatt aaaagtatga tacccacaag aaagataaag agagacaacc aggctagagt 182340
atgacgaccg ctttttcctt gtttgacggt tatatgtgcg gtatgatttt gctgtcgttg 182400
cttgtgatgt tggacgcctg gagtggaaaa gtacgtatgg ttcttaggcg cgcatacggt 182460
attattggtg gaagtgcagt tacgaatcat gacttgagtg acgttacatt gagtgcaatc 182520
ggtacagttg taaagtcccg atacatacgt gccgttgggg caaggggtac acgttacgct 182580
ggtacgctcc gtgcatactt tagtaactct ttgtcccaaa ccacacggag gacagcattc 182640
gttgcccagt tgcacttcat tatgctgaca cactttagtc accccaagct gcaataatat 182700
cacaccgaag cagatgagca tcaccagagg cttcatgcct cctaccggaa gaataaaaat 182760
aactcatggg gccgaacggt gtcatcctct ccgcggtttg taatacgaga tcgtaaacgt 182820
aaataaatga cataacttca ctaacccgca tactacaaag tccacctacg acgctgaaag 182880
tttttccagg acagaacagg atagtcagcc atcttcacag tctacctctt aggccgtatc 182940
taggagcata ggtaatcagt ttgcagccac agtacagcga gcccaagaga ccgcacacgg 183000
tccctgctgg gaacacgtac caccacatcg attcgtcgtg ccgtataatc gtagagtttt 183060
ccgaactttt atacacgccg gtggcgttag ggccgtgtgt gctgctgtga ttggacgttt 183120
tgtgagctag gtaacagctg tgatttcacc tgtcgccaag actgacagcg attacccagg 183180
tggagcacaa tcacatagct gatagacgtt aattgatccg ttgattccca tggacatttt 183240
aacggtaaca atacagctcc cgttaaacat tagattaata gacgttagtg gataacagca 183300
tgttattcgc ccgtgatcgt ggttatgcac tttcttgttt tttgctcata tgctgtaagg 183360
tgttcgagaa tcgtggggag tatatgtgtt gaatcagagt catctttact gaccgcgcca 183420
tacttcgtat acgaacttaa ccggcgtaaa gtgtttcccg atatataaac cggcgcctat 183480
tgtagctgta gcgcccatag gtatggcata tacccacggt gatgttgtgt tattcgtttt 183540
ttgtgataaa acgtagctta tgtttagtgt gtgttccgtc acgttatgtg tgtcgttaaa 183600
agacggcgtc tgtacagtat ggctttgagt tgtatcttta attgttattg catttggagg 183660
tgttgtgtac agagttgtta ttgcgtgttc aggtgttacg ttttgaggta cagctgtggt 183720
gtacacgggc tccaaggtgt agttacggag tctttctatg caggtagtgt tgagatattt 183780
gtgaatgctg gttatgttcg attctgtgag gttaaagtgt gtactattta tggcggtgta 183840
atttagacgg tcttgccatc ctgaggatgt tagtgttagg taattcgtgt tgttcacgtt 183900
tgcttgatat gtataagtag gtgtactgtt tgtgaggtcg caagtgtgat tctcttgcag 183960
agattttatc catcttgtgt gaaaatattg agatacgcga tgaatgtttt cgctatctat 184020
attgtaaagc gtttcggtgg tacttagggg ttgtttgctg taactcttat tttggaccca 184080
gggtgtgaac catgactcca atgtttgtat agtaaggtgt cctattaata aagacgaact 184140
gattcctacc gtaatgttat atcgcacacc tagggtgccg tttacaaaca cggaaatgtt 184200
tccgttacaa accacgttgg cagatgaatt agattccagg tggtaacgat aggataatga 184260
ccgttcgctc ccaacggatg acacaaagta tccgaataac caacacgccc attcaatccg 184320
catattttaa tcacactatt cacatttcac acactgcatt ttttaacatc ttattttttt 184380
attttatgcg tgttctcacc tcttcatctt tttaacaccg gggtaactat cgtaagtcgg 184440
taggcgtcga tagccctcac cgcctcgtcg tccccttccc ggcgtggggc accagcgtcc 184500
acagcactgc aggtaacaca ggtagcatag gaaacatacg gtgaaaatac tccaaaatcc 184560
caaaaatgcc gcgattcccc gagtggccca gggagacatc ccggtgtcta tgtcggccgg 184620
cggtgctggc gtcaccggta aaaatttcgg cgggtgtggc tgcgaacggt agcagtcgcc 184680
ggggagccgg taacgctgta tcactgtcca acagcggtcg ggttcctcgt ccggacatgc 184740
gggtttccag caatcctcgg cgtcggcgcg gccgatatag aagtagttgc gttgaaaacc 184800
gcggtacatc ccgcagtcgt gattccgtag acgccagggc gtcggcgacc agatctggtc 184860
tcccagcgag tagcgaccta acgccggcgt gcagcaaggt tcgtcgggcc ggctgagcgt 184920
ctccagttgc gtcagaatta cgaagcgttg catgatgagg ccgtggctat agttgcgcag 184980
cacgcattcg tacatgccgg ccgtgtccgt cgatacgttg aaagtcagcg agaatatttg 185040
gccgagatgc aactgcgaga aattccaagt ggcgtacggc aggcggtatt gaagtccatt 185100
catcagccta tggcctttga cggcgtccag gatgagctcg tcgctgccgt cgtgggaacg 185160
acagaaacgt gcgcgaatgg aaaccatggg ccaggagtgt gtcatgaccg tgcaggggat 185220
ggtaacttgc tctccctcgg cgaccaacac cggcgccggc gacgtggtct catagttctc 185280
ggcccacatc ttttcggcga tgtcagcggt ggcgaagggg aacgaagagg aagaatattc 185340
gaggagtcgc gggcagctca acagcaccca gaacagccac ggcagagttc ggagcgactc 185400
ccggcggcac atgatgattc ttttcttccc tttttcgcag agacgctgcc cgcctgttcc 185460
tgctccgtgt gtcggccgct caaacgtcgg gccggcgtgg tggtgaccac cgtgcgacgc 185520
agcttctcgc ccgggatgcc cgcaactgag cgtccggttt ttttacaggt ctttttttgct 185580
gcctctccct cgccgtcgcg gccgacgtgg tggaccagca ccgcgcagga actctcgcgt 185640
cgccggcggt acgcgacctg tctcattgct acctcggatg tttaagaagg aacgtttatc 185700
tgcgtcacag ggtctgatga agctgccaag agtcgtggct gtggcgtagc gcgttttgta 185760
cagcgcgttt caccgctttc tgcatggccg ctaccacatc gggtgggagc ggctccggcg 185820
gaagctcgat gagcagttgc tgcgaatctc ggcgttcggt gtccgccgtt tcgtcggacg 185880
tggcgtaaaa aaccgaggtg gtcgcccagt cgtccacgct gtcgacggct tctgtcagtg 185940
ccgggttgtc aaaaccgcca tcggacgcgg gtgataaaag aacgtacgat gacacgctgt 186000
tagtacgact ctcgtcgtcg ctttgggaac gacgtgatgg acgacggtag atgacctcgt 186060
cttgccacgc gtcgaagcgg tcgcagcagc gctggatcca agcgcagcga agcagcttac 186120
ggaacacgtc gttgttccaa aagtagagca taaagagaaa gaaaagtagc gtaacgatga 186180
agccgaaaac gacgagggtc ggcagggcac taccgccgct gccgtttttt gcgccgtgcg 186240
ggtgcacggt ggtagtgccg ttagtctgag cgggggtcat gacaagtctg aagagatgag 186300
agcgcgggtg ctcatcagga acagttgagg tgtctcccta ccgaagcctt agcctctacg 186360
gtgttttatg atcaacgtgt ctacgaacgt cattgtgaaa gtgacgtctc aggctttccg 186420
aaaccgcgtc aagttcaacg ttggtttcgg tttagcctgc gtcaccgagg cggaggtgga 186480
aatgagccgt cctgtggggg agtgtacgac cctgtagtgc ccatgggtaa cgttgcatcg 186540
gaagaagtga atgcggcatt ggtgtacgcg tgagtggctt tgctctctga ctcggaggag 186600
ttgccgcagc agctgcagac tttacgtact agccaaaaac agcaaaggca gcaagtaaat 186660
atgagaagga gtccagataa tgtccagccg ctagcggcaa gtagcgcgag ctgtggcgcc 186720
cccaaatcac tgccgttaga agcattaata catgctgtcg atggtgtagt cgtgttagtg 186780
gtaccagcag aagtagattg actggaatta gagctggtac ctgtagtggt ttcactcgcc 186840
gatgcggcaa gtgcaaataa aactaatatc cacagcatgt tcgttactat ataattgata 186900
tacgaacccc tttgtcgtga caatcagcgt tatatacgct gtatcggcat cgttttaccg 186960
gaaagtttat cgtaatgtaa cccgcgttgt gtacattcgt actgaaaggg aacccccggt 187020
gatgtgcaca ttatactctt tcattctggg gtttcccaat gacgtaaaaa tttccactac 187080
acaataaaat tactgactca tgtgaaaagt gtgcttttta ttaacagagc agagggttta 187140
cagtagatat atgtttgcca gggccaccgt tttctaacac cgatcaccgc caccattacc 187200
acccgttgaa ctccacaccc gggagccgcc tgatcgccag ggactcctca ccgtccatcg 187260
tccgaacaag ctcccgtcac cgatgctgcc accatcaccg agagaaagaa ccgcttgctg 187320
cagatacgct tgggctcgcc tccgtgcgga cgccgtttcg tgcagacgct gagtagatcg 187380

```
agcagagaat gtcaaaacga cattaccgcg atccgctccc ctcttttttc tttttctcat 187440
tcacgtgtat tcttgatgat aatgtaccat ggctacggtg gtgaactgcg tcgcggatcc 187500
cgtcacgggt ttcaacagat cgacgtcggt cagcggcgcc gtcaccgcca tgtccggcgg 187560
aggcacgctg tttctctggt tagcgacgtg gaccgacgac gaagacgatg aacccgcgcg 187620
gcggtctgtt atccgcgacg acgcgtagct gcactgggaa gacacttcct cccaacggac 187680
caagatctca tcgggtcgtt cggagaaacg gtatcgtctg tccgactccc gccgtacggc 187740
gccgaggccc agcgacgaca ggtccgcgaa ccggcgctcg tattccccgt acagctcgca 187800
acagcggatc agccagcggt agctcaaaaa catgcgcacc agtttgaagg tgtcgtgcca 187860
atggtaagct agatagcaga gaatggccac gatcagcacg agcatcacgc cgatgatggg 187920
taacccgacg ttcagcggca gatcgtccat ggtgaccgtc ctctgtccgg atctacgtcc 187980
cagtctctct cttttgtaca gcactcgcgc gggaacggcc ccctcaaccc tcttacgtag 188040
cgggagatac ggcgttctcc cgcgggccac ttacttgcac ggtcgcttga acggcggctt 188100
ggaccgccac atgtaccgca tccatccatt ctggcagcag cgcgttcgac gacgtcgtac 188160
gagtcgcgga tgatgttacc ccgccagcac ctccgccggc aaccgcgtcg tcgttgctat 188220
cgtcgccggt ttcgggcgat gacagcgccg gcggcgcggg tctcgtctcg tccaccattt 188280
ccaccgtgtc gaagcgacag ccgctgccgt agtacatggc cccgttcaac ggccggcggg 188340
ccgggtcgcc gagttccggg tcgggcacat ccatggctcg ccgtctgctt ctctgccgct 188400
cgtggtgccg acggcacttc tcaggataat gacagccgca aaatagatcg tggagcatgt 188460
ctcgccaact gtcctggtgg taatatctta agtacgcgat gagcgcgccg atggccataa 188520
tcataagcgt aagcaaaacg gcacagataa cgtgaaacac cgcggtcatc caagtcgggc 188580
ggcgtcgggg acgcggtggg tcggtttctc ttacgccggc gtcactcagc caccacaccc 188640
gtagtcgaca ttcccagaac cggtgaatgc gactcaggac ctttcgacgc cgccatttat 188700
ttccaacgtc caagtcccac gtcatttctg gcatctccac gcccttgact gacatactct 188760
ctttctctct cttagctgcg gtgaaaaaga gggaaggcgt gtgctgctat acaactgtac 188820
aacggacgcg ctcgctgttt cggtctcagg tcatctgcat tgactcggcg tccttcatga 188880
cgctctgcac cgccttttcc aagagttcct cgatgtccga ccatcgagga ggcggggcta 188940
actcggaaac cgacacgata ggcagcgtgg tcggctccgt cggcgtgcgg ggtcggggac 189000
agggacacga gagtcccacc ttcgagagat tctccagccc gacggtgcgc ggcagtctcg 189060
gattccgcgg tggcttttgt ggcgtcggcg ttttcgggaa gggcctgggc gtcaccggcg 189120
gtgtccagcc gaccggcttg ggtttcgtgg gcggcggtgt tttcttggtg ggcggcgtgc 189180
tcaggttctt acgcggcgcg ggtatcggcg tcgggggcct gtgcgacgac agccgcgtgg 189240
tgggggcccg gaccggcggc gtaggcggcc gcttcttgcg cccgggcggc ggaggtggct 189300
tccaggatgg cggcggctga tgcagtaccg tgtcgacgct ggccgaggac gacaaagagc 189360
tcgacgagga gcaatgcgac ggagatcggc cgatgctggt cggcgttccc ggcgtggata 189420
cgtcggggat ctcgaatcgc gccggaggaa actcgggttt atctatcggc agaccatcct 189480
ctcctatgta gagcgacgta caccgcggca cctgcggcgt cggcgggtgg gtggccaccc 189540
gcatgagccc cagttccaga tccagcggct caacgacgtc ttctttcgga attcgatagc 189600
agcacgcgca ggcaccacgc ttatcagaag cagcacccgg gagccggcct cgcgacgaag 189660
tctcgtcgga tcgcttgcgg cctcggcgct gggtaaataa ggaaatggcc aggaccaggg 189720
aagccagtcc ggtaccgccg aggagcccga cgccgagcca cagccacacc atgatcttct 189780
```

```
ctcctgcttg gaatctcaaa ctccgtgtcg ggaagggccg gtgtacggac atttatgcct 189840
tggatttctg gaaacgtcat tttttggcaa ggaatgtgtt tattgtccaa acactgagga 189900
aggagatgtg agccaagtcg gaaaattcct tatcacaccg ggggcgggtt acgttccggt 189960
ctgatgctgc tgctgttgtt gtagagccgc ggccatggcc gcctgcacgg cagcttgtac 190020
cgcctcggcc acgccgggtg gcatctgcgg catggcgggg ggagacgcgt cgggcggacc 190080
gccgggcatc gccgtcggct gcgacggtgg ttgtgaactc accgtcggct cgcacggagg 190140
tttgttcttc ggtctaccct tcggtttgtc tttcgcccta cctttcttcg gtttgggttc 190200
cgatgtcggt gttggcggtt gcggtgggat gacgggctgg tgggactcct ccgacggcgg 190260
ggggacgaac accgtcggcg ccgaaaccgg gggactctcg actatctcgc agatcaccct 190320
gtcaggatcg tcgccgtgtc cgggacgccg tcgatgaccg tattggacca tgtcgtaaat 190380
catcgtctcc ttgtaacacg ctgaacagca gcggctacag gggcccgaga tgcatttgca 190440
gctgcactta cagctgcagc tgcagtagcg aacccatcgg caggtaagga ggtcgattac 190500
ggagtctttg aagaattccc ggtaacggat gagatacgcg cagaggaaaa tcatgaaaac 190560
agaacagccg actacggctg cgatgccggg tcccgaagag acatccgccg acgatcccgc 190620
caaacaccaa attcctaaag ccgcgcatgt tatccaggcc acaataatcg tgggaacgcc 190680
ccattggcat tgccacgaag gatcgtgcac gtcgcaaccc attgctactg cgttctccca 190740
caaacgccat cgcactattt atctctacag cggctgccga gtcacgtccg ccggcgccca 190800
tcggccgcgg cgatctccta gtaacactcg tccgacactt ccaccatctc cagctcggcc 190860
ggcggttcgg cgtcctccac cagcggcgtc gtctcatctt tgccacagca gcggacgcac 190920
accttctcca ggcagaacgc caccagctgc cgccgaacgt accacaggta cacgtgcaga 190980
cctgcgaaca ggactacgga ggtcatgacc accacgacac acacgggaat ccagggatca 191040
aaattgctat cggaactcat ggctatcgcc gccgacgtgc gcgcgtgtgt ctcaccgccg 191100
ctcgcccgtt gtcgcgcggc ttgttatacg ctagcccgtc gccgcctcgg ggcacggtgc 191160
cctcctaccc acgtaacttc ctccgtgact taaagtcgcg tgtggtagat ctcctgctcc 191220
gtggacgaac cgtccggcag gatagcggtt aaggattcgg tgctaaggcc gtgtcgccaa 191280
cgtcgaatgc tacgttgcaa cagcttcgac ggacggccat cctccctctc atcgcaataa 191340
taaaacacca gcagcgcgca cgacgcgatc acggtaaccc ccatgactag acccacgcag 191400
atagccagcc ccgctagcgt atccagcgcc atcccgttcg ctcccgtcgt cgtctcctga 191460
acaaagcaac aactccgcag tccccgtttt caaccgtttt tgtttccttc tccgcgagca 191520
aatgttaact cccgcggtct ttccggccgt gctctacctc ctggcgcttg tcgtctgggt 191580
tgagatgttc tgcctcgtcg ccgtagccgt cgtcgagcgc gagatcgcct gggcgctgct 191640
gttgcggatg ctggtcgttg gcctgatggt ggaagtcggc gccgccgccg cttggacctt 191700
cgtgcgttgt ctcgcctatc agcgttcctt ccccgtgctt acagccttcc cctgaaaccc 191760
acgttaaccg accgtcccga aaacgccggt gttaacacag gaaaaaaaga aaccacgcag 191820
gaaccgcgca ggaaccacgc ggaacatggg acactatctg gaaatcctgt tcaacgtcat 191880
cgtcttcact ctgctgctcg gcgtcatggt cagtatcgtc gcttggtact tcacgtgaac 191940
caccgtcgtc ccggtttaaa aaccatcatc gacggccgtt ataaagccac ccggacacgc 192000
gccgcggcac ttgcctacgg cgctgctcca gggaaactcc tcttccttct gctcttcctc 192060
cttcaccgca gggatcgttt ccctcggcca gggacatacc gaagcaacta ccggaacaac 192120
```

```
ctggaggagt cgcggcatga cggcgcccaa gtgtgtcacc accacgacct atctggtcaa 192180
gaccaaggag cagccctggt ggcccgacaa cgccatcagg agatggtgga tcagcgttgc 192240
catcgtcatc ttcatcggag tctgtctggt ggccctgatg tactttacgc agcagcaggc 192300
acgcaacggg agcggcagcg gctagacaag tcccaggcgg ctacagctcc aagcgccgta 192360
gccggcccgc ctgccgatcg cgacgtcgtg gaccatcgaa cagagagtca cgcgtacgag 192420
accccgaggt acgccacgcg gtgcctaacg cggtatacca cacccgtacg gtctgcagtg 192480
cggcgtacaa cgtgtggaaa acgcgttgcg tcgcagagtc cgccacgtcc ctgtcttgtc 192540
gctccccaat cgtctcccgc acaccccccg cggcacccag agggcgggtg aggcaagtat 192600
tcttaaggcc gttctccgtt ccatagccca taaattgttg attccggagc tcgttggcgc 192660
ggaaatagcc ggataagggg agcaacaacc gtcggcgaaa gccgtcccgg tcattcagtc 192720
cgggtttcgc gtccagtcgg acgtgtgacc gttgggcaac ggaacggcgt ttcactgcca 192780
aaattgtatc gggtagtgta cgagacgtcg gcggtgcaga atgcgactcg cggcgtagct 192840
cgccgtcgct atgcggctcg tcgccgtgtg gcgcggcctg gccggctgtc tgcgcccaga 192900
tctgttggcc ttttggttcc tctggctgct gctgcgtgtg tgctttggca gacgcggtgg 192960
cagtttgcgg tctgcggtaa gtgaggatgt tgccgagcaa gcgcacttgc ggcgcgtgat 193020
cggcacgcgt gttattgtag gttcgttgcc agatggcaag tgctgtcaac agcagacgtt 193080
gtgggcggtc ggtgtatttt tgtgggttgc ggtgagagtc ggcactcggt gttttgtgag 193140
tgatctcaac agtttgtgtt gcttttagca gcgtccaaaa cagcgacgcg actttgggga 193200
tggcctcgtg ctcaccgccg cggagagtgt cgccggacct gctcgtcagc agcgagctac 193260
gcagacggaa tatctggagg agagttacgt gtgtcacagg agagcgcggg tctccggcgg 193320
taacgacggc ggtgtcgtcg acacgtgtgc ggcctgctgt gctctgcgga aaagcgccgg 193380
tctcggagac cgtggacgaa aaagagaacg gagcagctac cgctggcggc ggcggcgtta 193440
atgctgccgt tgatgttaga cgttgtgagt actcggaaac agcggtgagg cagaagctcg 193500
atccttcagg gaacgacagt cgatgtgtgg tagccgcagc aggtgaggtt ggggcggata 193560
acgtgttgcg gatcgtggcg agaacgtcgt cctccccttc ttcaccgccc cacccaccct 193620
cggttggtgt ttcttttttc ttgtgtcctg cagatagttc cacggacagc gacggcaagt 193680
ccataatcgc cggtgtgcaa gtggtggacc acgacgaaga tatcatcgcg ccgcagagtt 193740
tgtggtgcac ggcgttcaag gaagccctct gggatgtggc tctgttggaa gtgccgcgtt 193800
gggcgtggca gggctggaag aggtggcgca acagcgagtc tgggcgtcga tggagtgctg 193860
ggtctgcgtc ggcttccagc ttgtctgact tggcgggcga ggccgttgga gaattggtgg 193920
gatcggtcgt cgcgtacgtg atccttgaac gtctgtggtt ggcagccagg ggctgggtgt 193980
gcgaaaccgg tgtggaagcc gaggaggcta tggcgcggcg gcgacagcgc atgctgtggc 194040
gtatgttctc tcgtggaggc gacggcgaat gcagcagacg gtgttcgatg gagatggcgt 194100
gcgaggaaga aagcgccgtg ttgtgagcag acgacgttgg atgcgggacg tcggagcaca 194160
tgggccatgt gtggtggcag atggcggtgt ccacttgtgc ttgtcgcggc agtgcacaga 194220
cgaagcaaca tgtcgctgtg aagagataga gtgtgagcat agctgtatgc agcgttgcgt 194280
gtagaagcgg ggggatgaag acgttaataa agagtagcgg cggttgtgat agggcgaccg 194340
ctgaggcgag ctgcgtgtgc gtgccgtctg tgttccccgt gtccgccgcg aaaggccccc 194400
gtccccgtcc ccgccgcaag agtcccccgt ccccgccacg caacagctcg ccatcccgca 194460
actccccgtc cccgccgcga aatgcccctg tccccgtcct caccaccgtc cccgccgcaa 194520
```

gagtcccccg tccccggcac gcaacagccc gccatcccgc gacgccccgt ccccgcacac 194580
cccccgtccc cgcacacccc ccgtccccgc acacccccg tccccgcaca ccccccgtcc 194640
ccggcgcaac ccccgtccct gtccccagcg taactcccgt taccggcgcc ggcgcccagc 194700
acgcccgaaa acaacgccgt cgccgccccg aaaagcgaag cgctgcgcaa aagctgcgta 194760
gaaacgccgc acaaacaccg tagaaacacc cgccgccaac ccccgagcgc ccgcaacacc 194820
ccgtccccgg cgctggtccg cgaaaaaaaa caccgcggga cgccacgcaa cggcagtgcg 194880
cacaaagcgc cggacacagc acgccgcaaa cgcgctgagg acgccgacgc gcttacttat 194940
gtcacgcaac actccctcag ccctgtccag tgtcggactg gcggaacgac aagtgctgtg 195000
gagccacacg caccggcagc gcgcagaaag cgccgtggac agcaagccgc agaagcggcg 195060
gagcgcttgc ggcgccataa aggcgcttag ccctgtcccg caccggcggc ggtcggggtg 195120
tgtcgggggc gcggcggggt gggtgtgtgc cgggtgtggc gggtgtgtca gggtgtgccg 195180
cgggtgtgtc gcgggcgtgt gccgggtgtg tcggggtgtg ttggccgggt gtgtcgcggg 195240
cgtgtgccgg gtgtgtcggg gtgtgttggc cgggtgtgtc gcgggcgtgt gccgggtgtg 195300
tcggcggggt gtgtcagggg tgtgtcgggg tgtgttggcg ggccgtgtct gcgtgtgtcc 195360
tcgacgcggg ttgtgcagtg tgccccgggg cccgcgactc ctcccttgcg cccgcgtctt 195420
gtctggccgt tgttttgcgt gtgtccccaa ggacccgcgc tgccgtcccc tggggactca 195480
aacagacaca gacgcgcgtc tgcttttcgc cgtgcgcgcc gcacgtcgct tttattcgcc 195540
gtcgccgtac ccaccgcagc acacgcaact agtcgccgtc gccgtccaca cacgcaactc 195600
caaatttcac ccccccgcag aaaacacccc cccgcccctc ggggacccag cacacggccc 195660
ggaatggatg tcgggcgtcc acctaggagg gtgcgcgctc ggggacccag tccgcggccc 195720
tgttgcgcgt gttcctccgg gttcctgcct tttccagtcg agtgcgtcgt cggctgccgg 195780
gtggttttcc acggccttcc agactgcacg gccccaaggc ggcgccagca agcgccatac 195840
acgtcgctgc ctataaaagc caggtgcgtg tctgccgtgg cacacggacg acggagccgt 195900
ccgcgtgtgt aaacggcgtg gtcgctgacg cgggtttgct tcctatatag tggacgtcgg 195960
aggtgtccgg cggccatggc ccagcgcaac ggcatgtcgc cgcgcccccc gcccctcggt 196020
cgcggccgcg gggccggagg gccttcgggg gttggttcct ctcctccttc ttcttgtgtg 196080
ccgatgggag cgacgtcaac agcgggcact ggtgcgagtg ctgcgcctac ggcgacgccg 196140
ggccacggcg tccaccgggt agaaccccgc gggccgccgg gcgcccctcc gagtagcggc 196200
aacaacagca acttttggca cggcccggag cgcctgttgc tgtctcagat tccggtggag 196260
cgccaggcgc tgacggagct ggaataccag gccatgggcg ccgtgtggcg cgcggcgttt 196320
ctggccaaca gcacgggccg cgccatgcgc aagtggtcgc agcgcgacgc gggcacgctg 196380
ctgccgctcg gacggccgta cggattctac gcgcgggtga cgccgcgcag ccagatgaac 196440
ggcgtgggcg cgacggacct gcgtcagctg tcgccgcggg acgcgtggat cgtgctggtg 196500
gcgaccgtgg tgcacgaggt ggaccccgcg gccgacccga cggtgggcga caaggccggc 196560
catcccgagg gtctgtgcgc gcaggacgga ctgtacctgg cgctgggcgc cgggttccgc 196620
gtgttcgtct acgacctggc gaacaacacg ctgatcctag cggcgcgcga cgcggacgag 196680
tggtttcggc acggcgcggg cgaggtggtg cggctgtacc gctgcaaccg gctgggcgtg 196740
ggcaccccgc gcgcgacgct gctgcctcag ccggcgctcc gacagacgtt gctgcgcgcc 196800
gaggaggcga cggcgctcgg acgggagctg cgccggcggt gggccggcac gacggtggca 196860

```
ctacagacgc cgggaaggcg actgcagccg atggtgctgc tgggcgcgtg gcaggagctg 196920
gcgcagtacg agccgttcgc gtcggcgccg caccccgcgt cgctgctgac ggccgtgcgt 196980
cggcacctga accagcgtct gtgctgcggc tggctggcgc tgggcgcggt gctgcccgcg 197040
cggtggctgg gttgcgcggc ggggccggcg acggggacga cgtcgccgcc agcggcgagc 197100
ggcacggaga cggaggccgc cggcggggac gcgccgtgcg cgatggcagg agccgtgggg 197160
tctgctgtga ctatacctcc gcagccgtac ggaggcgccg gcgggagcgc gatttgcgtg 197220
ccaaacgcgg acgcgcacgc ggtggtcggg gcggacgcga cggcggcggc agcggcagca 197280
gcggcggcgc cgacggtgat ggtgggtccg acggcgatgg cgggtccggc ggcgtcgggg 197340
accgtgccgc gcgccatgct ggtggtggtg ctggacgagc tgggcgccgt gttcgggtac 197400
tgcccgctgg acgggcacgt gtacccgctg gcggcggagc tgtcgcactt tctgcgcgcg 197460
ggcgtgctgg gcgcgctggc gctggggcgc gagtcggcgc ccgccgccga ggccgcgcgg 197520
cggctgctgc ccgagctgga ccgcgagcag tgggagcggc cgcgctggga cgcgctgcac 197580
ctgcacccgc gcgccgcgct gtgggcgcgc gagccgcacg ggcagtggga gttcatgttt 197640
cgcgaacaac gcggtgaccc catacatgat cccgtcgcat ttcgtctttc ggacgctcga 197700
actctcggtc tcgacctcac caccgtcatg acagagcgtc aaagtcaatt gcccgaaaag 197760
tatatcggtt tctatcagat taggaaacct ccttggctca tggaacaacc tccaccccca 197820
tctcgccaaa ccaaaccgga cgctgcaacg atgcccccac cgctcagtgc tcaggcaagc 197880
gtcagctatg cgctccgata cgatgatgag tcttggcgcc cgctcagcac agttgacgac 197940
cacaaagcct ggttggatct cgacgaatca cattgggtcc tcggggacag ccgacccgac 198000
gatataaaac aacgcagact gctgaaggcc actcaacgac gaggcgccga aatcgacaga 198060
cccatgcctg tcgtgcctga agaatgttac gaccaacgct tcactaccga aggccaccag 198120
gtcatcccgt tgtgcgcgtc cgaacccgag gatgacgacg aagatcctac ctacgacgaa 198180
ttgccgtcgc gcccacccca gaaacataag ccgccagaca aacctccgcg cttatgcaaa 198240
acgggccccg gcccacctcc gctgccgcca aagcaacggc acggttccac cgacggaaaa 198300
gtttctgcgc cccgacagtc ggagcatcat aaaagacaga cccgaccgcc aagaccgcca 198360
ccgcccaaat tcggggatag aaccgcggcc catctctcgc aaaatatgcg agacatgtac 198420
ctcgatatgt gtacatcttc gggccacagg ccacggccgc cagcacctcc gcggccgaaa 198480
aaatgtcaaa cacacgcccc tcaccacgtt catcattgaa agtctctcca gtccctatgt 198540
tgtcaggacg tgctgtcgtt cttcgcttgc tgcgaagccc gttcttccga gtcgtgtcgc 198600
tgcgtccagc gtcgcgccca agatgggaat ttgggtcttt tcacgcgtag cctcctccac 198660
cacggctgct gatcgccgtc actaaggacc gacacggagg atgacgagga gcttctcccc 198720
gactccgcgg tccgcgaccg gctacgtagc gcgtgtccct gccagtctcc gcagttacac 198780
cacacgtcgt gagcagcgtg cacctgctgc cgccactggg cctcggcgtg ctcaggccac 198840
ccgccggagc ccggtctgag ctccgacgca ggatgcgcgt actcaacgtg cgccttccag 198900
tccatacagc aacaccatag gtcgtgtgag tcgtcggcta cccgccgcca ggccagttcc 198960
cgcatgggaa ggctggacac gccgaccgag aggtcaccga gcccggacgc catctcttct 199020
tcctctccgt cgctgtcatt aagcagccag gtcacctcct ccgctccgcg gtccgccggt 199080
ctcgacggac cgcgccgccg tcggcaacac ggaaaacagc acgccagccc gagccgctaa 199140
ggccgcatgc ccctgccgcc caactgaaca cgcatacccc gctcaactgc gttttgccac 199200
ccctgccagt gctctcgctc gagcaccacc ccgtatctcc caaccttttt ccaataaacg 199260
```

aaaccgacat gacatacgta atgggtgctc gtggctacat ttattgaaac aaaccgcgat 199320
cccgggcgtc ttagcacacg aaaaaccgca tccacatcat agacaagtta cagtccacag 199380
tcacatacac gataaacaat accaacaggg taatgtttat ggagtaaaac actattgtcc 199440
aggccacatg cgtgtatgac ttccgcacca tcccgtactg catgttccac atgtacgcgc 199500
tagacgtgta atccactcgc agttcgggga cgcaacgcag ccagatcaca tccccttgca 199560
gtaccagacg cagggctagc gtctcgaaga tcggcatcac atctaagttc cgcacgttcc 199620
actttaacga ctccccggga acgaactcca cgtcgtcggc gtgtacgtac aggttctctc 199680
ccacgccgcc ataatcggcc ttcggatcga agacgaaccg actcatgttg cccacgatgc 199740
tcccccgagc aaacaacttg ccgttgtcaa tgtagcaccg gttgtcctcg atctcaaacc 199800
aggggtgctt ggccgtggac ttccagggcc ggagcgcgtc ttccccggct ttagtgatgc 199860
catcgggcag gcggatcaag ggacccatgg aggtccaaag acccacccag gctttccaga 199920
gattgttcat ggtgaaacag cgtgtggact gtacgctctt tcccaagtta tatcccagag 199980
tagtgacgtg agcccagcca cctcccagat tcctgacgtt ttggttagct ttcctgccaa 200040
ttcctcccgt agacttatga ttctcctagc ccattcccga taaaaataca cggagacagt 200100
agatagagtt acgaataaac cggtttattt attcaagtgt ctcaggagat tattgaacga 200160
gcgtggatac cacgccatcg tcagttcatg gtggcattga gcagccatag caccagagtc 200220
ccggcgcccg gtatcagaca tgctgaccta ccgggcgcct ccgagtccat atcccgcggc 200280
ctgggtgtta gagtccgtac ctggcagccc aggtaggttt caggtaccag ctggttcgta 200340
cctgttaaat aaatcgcaga cggcgctca ccccctacggt caggagcaca agaacaacca 200400
gagagaacag atatacgagc agggttctga acagcagacc ccaattgtcg tctctcatgc 200460
ttcgctgaag gtaccagttg atggtctgag agctatagtc catcctcacc tggggaacac 200520
acgcggcata tttcttgggg tctccccacc tcgtagacaa cgtgatgtcc accatatcca 200580
cggtgtgcga caccgggtac ccaccgatgt tccactcgaa ataggctccg cgctcatcat 200640
ggtggtactg ctcaccggac acttgcaatc tgtccatgta agattgagag acgataccca 200700
cgttcacaaa gtgtttcttg gtgaagttgc ccgacatcct cccccttgaag tacagcatgc 200760
ccatatggaa ccagcattgg ttctcctcca cccgaaagtg ggccgatttg atctccgata 200820
ccaccacatt caggggccgg ggcaccgagt ccgcgagtct caggaacagg acggccagga 200880
tcgcgagcac caacaccggc ttcatggctc cgaaggtccg ctgctcggct ccgctcaccg 200940
ctccggtctg gctgcagcag tgcttcgctg agaagtagcg tgtggactgc acggtgtttt 201000
tgaatatata gcgtttcttg gtgacgttgt ttcccctacg tagtaggcaa ctacgtgcca 201060
aaagaggcgt tacggtactt tccgtaccgg gatttccaaa ccgcgacttt ccacacggcg 201120
gtttcaacac cgggactttt cacacggtga tttcggcacc gggactttcc acacggcggt 201180
ttcgccaccg ctgacgttct catcgccgcc cacgtcaacg gtggcgacac cgtactttcc 201240
catgcggttt ataaacgtca agagtcacgt cagtcgccca cccccattac acggcgatat 201300
cccgataggg catgagggga cccgggtgtc gcgacatgtc gacgacaggt gcggattagt 201360
ggtcgtgtcg cgacatggac gtgcaggggg atgtctgtcg cgatagagtt gatgtgacag 201420
cccgctacac ctctctgtcg cgacatgcat acacaacggg ccggcttgtc ggcgattgtc 201480
gcgacatatc gttatcagtt agcgaccgga gttgtctatc gcgacatatc gtcgactatc 201540
gcgacagaaa aaataccgtt cgtagagaat gccgtgttga aggaacgcgc ttttattgag 201600
acgataaaac agcatcagga gccacaacgt cgaatcccac gtccagtcga ttcgtatgtt 201660
atgctgcaca gcaatgctag aataacaacc agcagggtaa tcccgcaaca taaatacaaa 201720
gtcacagcga agaatccgtg tcgttctatc aagcgaaacg cgttccaaac ggccccgtca 201780
cagacgcagt tattcataag cgttaacaac cggtggctag gatgaatatc caaatcacag 201840
ggcagtagcc gacggactcg ttgacaggtc agcctaccct caaggttcct atcgttcgga 201900
cgggatttgt gcgttttagg cctctttttc gccgcctgca agcattggtg cgcaaagtcc 201960
tcacccagct gtttccagct atcatctgca tctgtgcagt cccctgtatc gttgtaacaa 202020
acgggtctgt gcgactttgt tctcggaaca caagcttgtc gcggagacag agagagaagg 202080
gttttcgggt cacgcgaaga ccgctcaccg gggggtcggca acgcacacat caacagaaaa 202140
ccgagacgga tcaagaggtc catagtgaag aaggagcgat atcgacgtac ttacgaaacg 202200
gcgattatat atgttctcaa caataccgcc ctacgttgta tgatgtaacg tgtgacgtga 202260
gtctgatcca acactgaacg ctttcgtcgt gtttttcatg cagcttttac ggaccatgac 202320
aagcctgacg agagcgttca tcggggcatg aagtacgcat tacacaaact ccatatattt 202380
gttacgatag aatacggaac ggaggaggct ttcgccacac ctatcctgaa agcgttgcat 202440
tctttatgat aggtgtgacg atgtctttac cattcccacg gctgctttgc gtgatgatga 202500
cattcatcat gtatttccat tcacacatac cttttgtgca tacggtttat atatgaccat 202560
ccacgcttat aacgaaccta acagtttatt agcccttgac aggataggtc aaaagattat 202620
atgtaggttt tccggtaaac cgaattgtga tatttctctg caggaaatag aacagcctgg 202680
tacctataaa acggacaatg cagtactgta gcagcgtaac caagtaggtc cacatgaaca 202740
cgtacaaaat tatggtaagc catcgttttt cataccacag cctgtagctg tcgtacatga 202800
atgaggacgg tcgaggaacc cagggtagtt gtaattgggg gcgacattcg tactgtccag 202860
aagacaattg cacgggtttc agtgagatga gtactttagc gatgtcggcg ggggcgctac 202920
gtttcaccgt gacggtgaga acttgaccgt cgttttgtac ttcatgaggc acgttataca 202980
agccactggt atcatgaagg atgacctctg atgcgatgtg aggattaaat tgtccctcaa 203040
accgccaaac gctggtcatg tttccaccgt caattacgca gctgacggtg tgagatacca 203100
cgatgttgga cttaggtttg gggggctaatt gccttttttac aaattccctt ctgtattgca 203160
ggtcctgctg ccactgcttt tccgtgcgga aagtcgccat gtcttccaca cgtgtggcga 203220
cgatagacgc caccaaggta gataccagaa gcagctggat ccgcatggta ttaccgtatg 203280
tcaattagaa agttgagcgg acacggttat cgttcctggc ggatataagt atataaacgc 203340
gagttagcct ttcccgtccg ttttgtacac ccgttcccca cacaaatgac gaatacgacc 203400
ttttttttt ataaaaataa accacgtgta ttatagaaaa acatttacat agaaaagaga 203460
cacacggatc aacataagga cttttcacac ttttggggta cacaggcgtg ccaccgcaga 203520
tagtaagcgc tggatacacg gtatacagtc ctggccagca cgtatcccaa cagcagcacc 203580
atcgccatct gtatggcgat cacgaccccg agctctaagt gtctgtattc atagtgtagt 203640
cgtcgcaggt tatccactga attcccgtaa ctgaaataac gtatatggta ccgaggctgg 203700
caccacatgg gtttgcattt ggtgcacggc accaaatgca gagtgagatg gtccaagtcc 203760
gtgggcaccc actggcgcaa acggaatacg gcttcggtgg tctccacgag gcactccggg 203820
gcgtgcagac ggccccactt tcgtccgcga cggcccgacc agccgacccg agccactatc 203880
cctttctcgg gatagaacgt accctgtaca cgccacacag cgtccaacac gccgtccttg 203940
acgacgcagc tggcctgata gctggacacg ttgttaagcg gcggaaagcg aaactgacgt 204000
gccggcggag ccacatagtt cggttcaccg tgttgtcgcg gttcgtcctc cctatagtaa 204060
tagtagtcgt cgtcctcata ggggttgccg gcgtgagcca gcgttaccca acagcagccc 204120
aggccgacga ggaggcgcag ccaccgcctc atggcggctt cgccagtcaa tcgtctttag 204180
cctcttcttc ccgtgaagtc cttccggtgg cgcggtgccg acctcggacc cagggacgta 204240
tccacctcag gtacacacag caggctacct ggacaccgaa gctgaacaag gctacgtgtt 204300
tcacaaactg caccagtacc acatagagga atgtcaggta gcgtctctcc gcaaacagcc 204360
gttccaagtc tgagggcgtt acccgcagcg gcaaccaggg cagcctggac gccggccggc 204420
aatggagcac gctccggtta caggcactgc aggggtaaac ggttaacatc acgtaagaga 204480
gtcgtgcgtc cacctgtggg agctcagttt cgtaacgtag agccccgtca ttttccagct 204540
ggggtgcgcc gaccttgaaa tgggtcgcgc tccgctcgtt accccaggtg ccgtaggctc 204600
tcggggccgt atcggagaag ttgccacgca caagccaggc ggccacgagt accccgtgct 204660
ggacgtaaca ttcggacacg gaactggaga cacggtagcc ggacacgtcc ccaaacccgc 204720
gagggtactg ggcagacgga acggacttgc tatttgacaa cggacagata cgagacgacg 204780
aggacgcaga cgactcgtcg ctggaccacg acaaccggag cgactccttg gagcggctcg 204840
agagtacact tactgcgatc agacaccagt gccagaagaa ggaacaggtg gacggggacc 204900
acaggatcat agccgccggc accgcggccg gccgcaggaa gccgcccggc gcgtcgtctg 204960
tgtgcgggag ccgaaacacc gtgcctcttt atatcgtccc gacgtgacgc gagtattacg 205020
tgtcagggga aaccccgtc acgacgaacg tgatttgtaa gtgacgcggg gtgctgacgg 205080
ggttcggccc gagaggtgac ggagcgcctc acgtcagtat gatgtccgat ccgcgtcagc 205140
cccgacgtgg ttgtggtcac cgaaacccac gtttatatgg acgttgagag cagcgcctga 205200
ccacatgatt catcatacca tttctcggaa tcgggcccat gccgggaaag cacattcctt 205260
ttcagtaaac aacaatgaca tcataacaaa tcattttatt cgcgaggtgg ataataaccg 205320
catatcagga ggagggatcg ggtgatgacg caggccccgc agaacagtcc gaaataaatt 205380
tttagtattg ccccatagtc gcctagatac cagaggtacg tcaagttcat caaaacgccc 205440
atcggcgtcc cggaatcgta taccgggcac acgaagcgtt cataacaatc ccgggaggcg 205500
agtgttaggg tagcagagta gtttcggggt cggtttcctt ccggcgacga cagttccgtg 205560
ggcagcagaa tgtacagcgc ctcggtagct gtcgcggtgc cttccacgag gatgggctgc 205620
cggtgccttt cgtgattttc cccgtcgtgt agccaagccg aggcccgcaa agtcttaggc 205680
gaggggaatt gtccatagag tttcaccgca cccttcagta catggttctg aataacacag 205740
ccgcacgtga agtaggtagg ttctctcgtc tcctccgtgg ctgccgccac cactcccagc 205800
caccacaaca ggcagatcgc cagagggttc cggaggcttc cccggcgtag catggttttg 205860
ggttaaagca aaaagtctgg tgagtcgttt ccgagcgact cgagatgcac tccgcttcag 205920
tctatatatc accactggtc cgaaaacatc cagggaaaat gtcggtgcag ccaacctttc 205980
acatacagcc cccaaaacac ttgaatcact gccaccatca tcagcgtata ctgcgccgac 206040
ttaatcgtga gcgcgtagta cgccattaga cggcgatctt cgaacaatag tcgttcgatg 206100
tcctctaacg agctccacag gggaacccaa ggcacgaggc accggggttc gcactctaca 206160
taataagttt ggcattgatg acagggggaa aagtagaaca acacgagttt tgtgcgttgg 206220
ggaacacgat agtcccggag ccagtagcgt tttgcgacga ggctttcgga gatgtcctcc 206280
accggcgtcg gcactcgatc cgcgtagccc tccagcgtct ggtagtacac ccggggtgtc 206340

```
ggcgtgggca cggacaggtt cccgcgcagg gtccacagag cctccagtcg accgcccgat 206400
cggagcacgc agcgcgcctc ggaatactct actcggtact ccgaaacatc gggcagaggc 206460
ggtaacggct ccgtctccac caagggcgga ggttcatcga aaagagtcaa ggataattca 206520
ggcatactac ccgcgaccgg ggcccagagg gctagaataa gcattacaag attcattctg 206580
tcttacaagg gaaggctgtt cccctgtcta gactcaaaag ctgtaaggct atcttatagc 206640
atgtagtctt gcacgtcacg gggaacaggg tggtgatcta gtgacgtcgg gagaacacgg 206700
tgttttaggg tgcgggggac aaaggacagt acgacagatt aggtgataga aacgtttttt 206760
tttatttatg aaaaagccag tgtgccgtgc ggcctagggc cccggcgtag tttggatacc 206820
agatgggggc cgtcaggggt actaccacga gcagaaacat aatgacttgg tccatatata 206880
gcagcatagc ggtgcgcagc aggtcgccgt ccgtgtagca atttgacggt gagcgataaa 206940
gcaccgttaa tgtgtcgcgg ataagcacga tcttgaggcc gtagatgaag ctcacagtca 207000
gtgctaaaat gatgcgttgg tatggttccc aggactgcac ggcgatgaag agccagagta 207060
tgggaagcat gaaacttagc aaacagagga tggctaaccg tcgttgcatg ttccaggcca 207120
tgagccaggc taggcccgta caccagacgc agagcatgga tgacaggaca taggcctgga 207180
ttaccacggt gcgatcgaaa cacagcccga tggtggacac ggatatcgta gtgagggtgg 207240
tatataccat gaccagcatc agggtcccgg gtcggcgctg acgttccagc cagtacgcgt 207300
ggcaacgcag agcacagggt agcagtgtgc tccagaaggg cagtgtatcg cgcaggtagg 207360
gggttgtcac gcgccacggt atgagcatga aaaggatggt agtggctatg gtggcgctgg 207420
tctggaacac gacggtgccg tagagacgta ccatccagag aaagtgttga acgctccgca 207480
gggtgtcttc atctttggtg attacggtga ctcgacggat cggcggtggt gacggcggcg 207540
acacgggtgg gggtttctct ttcttatggc cgagtggctc gccttggtga aactggatct 207600
gtaccatgac gggtgctcga cgaacagtcg tcggggcttc aggtacccgg caagttttat 207660
agagaaaggg ggacgatggg tggtggctac gagccaccgc caccttcgca atacgaggat 207720
ctgaaggcgg caaagacggt cgtccagggc aggcgccaga ggttgggact gagcacgatc 207780
agcgtgattt taaacatggt caccagtcct acgtagatca gcagcgagcc gcgtaacgtc 207840
tgagcagccg gcagttcgtc gcggatgtaa cgcgtgccgt agaaagtcac ggtcatcata 207900
aggaagacga tggcgccgta gccgtagagt agaatacgct gatgatggaa cacggtctgg 207960
tcgccgataa cccagagcgt gatgaaaaaa acgctggtga gcacccgtga gcatatgagc 208020
tcccaacgct tagcgcgaaa actgtcccca accatgacag cgccggtgca agctatccac 208080
agcgtgagga ccagtgtgta gtcgatgagg atggcgggca ggtcggagca ccaggtgtag 208140
aaaaccgtgg taacggagag gaggcctacg tagcccatgg tcaataccac gtcgtcgggg 208200
tgcctttcgc cctgtatcaa gaccaaacac cagagaaggg agggggcaaa aaccagcagc 208260
agaggggaag attcatgttg acatatgttg tgggaatcgg ggatacccag ccaaatcatt 208320
ccgcagaaag ccgtactgat ggcgatgtga aagaccacta gggcgtagac ccggacgagg 208380
acagcaaaac ggcgcagcca cataaggccg tggtgcagct gcaggaggga agcccattgc 208440
ggcgaatgta gcgacggcag cggcgggtcc atgaggcggg tgatgcgccc gagtgaacgg 208500
gtgagcgtct cggtggagtc ttcttataaa ccagcgggtc tcaagcaacc ctgctctgga 208560
acgtcgcggt ggtgctgttg aggatgacgc tgagcgtgcc gttgtcaacc cggtaatgat 208620
gataggtgcc cagcttggcc aggtagctga acatttggtc ccagcgtgcc gaccacacca 208680
cgggcgtgag catcaggagt gtggtgtgat agatgagtgt ctcggtggcg taaagtacca 208740
```

```
gcgagctgcg gatgatgtgg ctcacgggca ttttggtggc gatgtagcgc acgtcttgga 208800
aaaggacggc caggatgcag cccacgaaca cggtgtagag acacagcaga gtcttatgca 208860
accaggtgta agtagaagcc aggacgctga ccatcaccgt caaaagtgtg gaggtgaaaa 208920
gcgcgtcacg ccacacagag ctgaggcggt gttcccaagc cacgccgttg caggccacga 208980
acaacgtcca cgttaggatg aggctggaaa cgccgatggg cgctgtggcg cacaggttga 209040
gcccggcggt ggtgaacgag agaagcgcca catacagtgc aaacaccagg ccgttgctgg 209100
ggtgtctgtg gtcggtgagc tccagcgcgc ccagaaccaa caccggtgtg cagctaagca 209160
atagcggcga gggatcgtcg cggcactcgt agcccagtga ggggtaaccc agccaaacca 209220
gcgcgctaat gagtacgctg aaagcggttt ccagcgtcag caatccgtag acacgcatga 209280
cgatcgcggt ccgacgtagc caacacaccg catcttcgga agctgtggac gctgtttccg 209340
aataccggga ggagatcgtg cttccctctt ccaaggatcg gaaagtagcg tccgtcgttt 209400
ccgcggacgc ggcttccctg gtacgctccg tttccgacga cgcggtttcc cgctgcgtgg 209460
aaactgtctc catgtcggga ccgcagcgcc cggcggcgta tccgcaaggt ctcgaagcta 209520
cagcttgtca gaggaaaagt aggtttgcaa aaaggtgcgc agggtcatga ttctcagcac 209580
catcagcaga gtgaaaacca ggctgagaaa caccttgacg gccgccaaaa gcgcgcgttc 209640
cagcggcgtc tcgtagcgta cagccagggc cgcttcgtgg aaatgcgaga cggctagaca 209700
ggtaatgagc acgctgaagg acaagacgat cttaaagcac caggaccaac cacgcctcaa 209760
gatgaccacc acgattgccg tgaaggtcaa cgtgatcaaa gcatggatga ccacgatctg 209820
acggcggacg gtacgttcgg gagccaacaa cgctacgccg gtgcagctga gaaaggccag 209880
taaggtgaac aacgcggccg agatgaccaa cgtaccgtcc aggcagagac atattacgat 209940
caacggcggc acgtgaagca gcgtgtaaaa gagcagaacg ccgatattgc tgggatgcga 210000
tgtttcgtaa cagtgaatga agatcaccga cgtgacgggt atgacaaaga cgaggctggg 210060
cgaggactcc gtgagacaca gacgggaatg gtgaaaccac gtcgcgggcg ccgcgtagca 210120
gaaggcgctc aacaacgcgg tcaagccggc cagctgccaa cccacggcgc cataggtgtg 210180
cagcgccacg cggcaacagt cgacccaagc cagactgcgg gtcgccagcc gggtctcttg 210240
gatcccgggg ggcacgtaga tgaccgtgcc atcggtgggt acttgaaacc ctttttctct 210300
tctcatggtg cgctgcgttc tctggaaacg gctgctctgt ccgaaaacca gttccgaacg 210360
aaaatctagg gcgagagggt ggacaacggc gttgacgacg aagcatggga caggtcgttc 210420
ggcgttaacg tcatcgcgtc ggacgacggt agttctaaga gacgtagatc gctcagcagg 210480
tcctgacagt tgcggattcg caagatcaga aaaaaaaggg aaatgaacgt aataaagagc 210540
tgtagcgacg tatgcgccac atcgcgtggc ataagaacgt gacggacgaa aaggacctgc 210600
tgcgaaaagt ggccggcgaa gataaggccc accgtgctgt agaagcccaa aagcagccgc 210660
aggggccaag tccagggccg cgtgaagacg atgagaacgt tagccagaaa gaccacgacc 210720
cagacgccgt tgatgagggc aaattgatcg gacagggtgc agttgtcgcg acagatgaag 210780
actacttccg cgcagagcaa ggtgatgacc aacgtgagca caaacgacgt caacacctcg 210840
cggggctcct ggcaggcaca cgtgacacct agcgccggga tgtgcgccag gaggccggcg 210900
agtaatagca ccagctgtcg gaacggacga cggcagcgcg ggtgccggtt tcgctgagcg 210960
agaaccggtc gctcatagcg gaaatacacg aagagcgcgg aggccacagg caccaggagg 211020
agcacctcgg gcgcccagac aacgtgacaa ggaaagcccg gacgcgactt gagagtcgct 211080
```

gtagggaaga ccagagagaa gctacccaag acggccaccg ccgtggagat ttggaagagg 211140
agcaagccgg cgattcggac gacaacctcg aagcgatgca cccagcccag cacggccacc 211200
acggccgctt catcatagtc gtcgttgttg ccgctgtcga acagccgccg aaacacgatc 211260
tgtcgctggg tcgcggtggg aaagcgcaga cccatgacag ccggaggcta tatgaccgcg 211320
cgtctaagac gcgagatccg tggggggact tttagatgtt tgggcggccc gcggttctaa 211380
caggcttgat tggtggagac ggccggcgcg gcgggtgggg gaaacgacga gtttttccgt 211440
tacgccatgg ttcgcgtgag gtttctctgt acctcccgca aaaggtcaca gcccgaaatg 211500
gaggccgcgt tggtggcccc ggtggcgcgt gacgataacc aggtcatcca agcgatgagt 211560
ttgtctaatg agtcctcggt ggtgaaaagg atgagaatga gcaggtacag gtacaccagg 211620
ttctcataga gacacaaggt gagcaggtcg gcctcggacc acgcgatctc aaacaggcgc 211680
gtggtgtcaa agaccgtgac gaccagcatg aagctgagcg ccatggcgta atagcccaaa 211740
aaaagtttgt gccccaacgg tacgggctgc aggtaaagtg cgatcaagaa cgcgataacg 211800
ccgatcacaa acagcgtgac gatgacctgc catcgacggt gattatggcc ggctagaccc 211860
gtgacgcagc tgcagaggct aaaaagcacg caagccaaga ggcccgagaa ggtcaccagc 211920
gtagaggagg agcaggcgct ggccacgatc accgaaagcg tcgtgagcac gctataaatg 211980
gtgagcaggc ccgggctcgg cggcgacgtg aacgatcctt catcgcgttt gccgtgcagc 212040
agggccaaac agatggtggg caccatcaaa ctcaagggcg gcataaagcc ggtgcaacag 212100
agaaagacgg tgcctttaag atgcggaaaa gccagcacca ggcccagaca gagcaagaag 212160
gtgcaggtgc cctgcacggc cacggtgctg tagacccgca tacaaagtaa aaagcgacgt 212220
acgtcgttcg tcgagacgga ggaaatcata atgactccgc gcgagggtcg cgggggtggg 212280
ggcgcccagg ccgtcccggt ggcctctgag ttcggagaca tgacggcggt ggctatcaaa 212340
aggcgcgtat gagaaaccgt ttatagagtg taatataatc accgtcattc ccacacggcg 212400
ttcccccata aagtcacgtc acactcgagt aagcgtgaaa aagctttatt gttgaataaa 212460
aaacacgagt acaacaccga gttgcggtgt tctgtctgtc tactgggtgg gggaggttca 212520
tcgtctgtct ctagagggaa ggtggggaac gtctaagcga gcgggagcgt gtcatctccc 212580
ccatcttttt acaacaagct gaggagactc acgccgtcga tgcgtccgcc gtgtttctcg 212640
gcgtactgct gcacccagac gtggccgcta aagatggcga cgctcatgtt taggagactc 212700
atgacgatgg tgtacaacac gacgctgaca cagacgctgt ttttagacaa cgttccacgc 212760
tggtagatga gatccagggt ctcgtaaata agcacggccg aagcggcggt caccaccagg 212820
acgtagagtc cgctgtagat cttgctgacc cacagcacgg gcgaaaagta aagcaatagg 212880
taaaagacga tgacggacca gccgtagcca atcccgatga ctttccagcg cgtgggattg 212940
ttgccggcca ggtaggtgag accgctgcag agaacgaaaa agaccatcac cagggcaaac 213000
gacagaccga tgacgcgcct ttctccgcaa aagcccgtgc acacggtgat gccggtgttg 213060
atcagcaagc acgccactgt gagatgagca aaattggtgg tgtgtgggcg aaactcggcg 213120
aaaccgcgta gcatagccag cgtggacacg ggtacgatgg aggatagggc tggcactatg 213180
ccgttggcgc actgtccctg cacatcgggg aaggcgagcc aagccagcaa gcagaccgtg 213240
agggtacaag ccagctgcca cacgagcccg tgatagacct ccatgagcag cttaaagcgt 213300
ttcaaccatt ggaagagctg ctgttcggcc accagcgcgt ggctgcgatg gagcggcacg 213360
atggtgaccg tcggcgactc atggtgttcg gaaaccgagg cggtgtcgcc catgctgccg 213420
cttacgaccg ctgtcggtct aaggtaggcg tcgatgaaac agtccgtctt atcagcaccc 213480
ggttaccgcg gatttgattg acgtcacgag tgtggtcaaa ccgtggcggc accctgtatc 213540
cgacccgtcg tcatgggctc cacaaccaga gcctcagaag atggtacatg ccgatgaata 213600
aagccacatt ttcgacatag aggcgtagcg agggctgaaa actctccggg aaagaactct 213660
gacaggtgat cagggacaga tcgtgaatta gcatcagcgt caccgtcaac agcgtcgtcg 213720
cgtgtaaacc gagaaagaac ggggccgcgg cccgcagcag ccaaagtccc agcgccgtag 213780
cgcagagcag agacaggacc gacggtagcc acagccgccg gagagacgcg ccaggatcgc 213840
aacccaaaag cgaggccccc aggcagctga gatctaccgc cagggcgaga agagccgcgc 213900
cgacaaaggc ctgcggcgac ggctggcaca tcagcaaggt cagaaaggct agcgcgtgcg 213960
gcaggcagta agccaacagg agtgggagtt tgcggggaca acggtcgatc gacggaccgc 214020
gtagcagcag gaacaggcag ccgacgggca cgacgaggct gagatgagaa agcgacggtg 214080
ggtcgtcgtc ccgtccccgc tcgcatagct cggccaccgg tggcggcatg agccaccagc 214140
tgagcacgct gagggcgacg gtggcggtaa gctggaaggc gacgaggacg gaggcgcgca 214200
gccataccgc cagcctctct aggtagggga ctacctcctc gacggtccat tctagcggga 214260
cgacatgaag catggcgaca agcgcggctg ctgtgaaaac gggcgcggtt ttataggcat 214320
taggacttcc ccgtcgtact ggcggctgtc aaagtcccgt tgtccaaagg cgcgccgtcc 214380
gaaagactaa tccaacgggg acccgagagc atgagcaaca acgtgagaaa gatggccatg 214440
ctgtccaggt agagacagac ggcgtgacgg atgcattggt taggtgggca gaaaaagatg 214500
accatgagac tgtcgtaggc cagaataccc aaaaagaagc tgatagagaa ggcgcacaac 214560
gtcaccacta tcttctgcag ccaatcggcg tcgcttagca gagcgagcgt gaggaacgaa 214620
agcagcatca ccacgtagac gcagctgatg catttccagc gacgtcggtc acggccacct 214680
agaaacgcca gccccgtaaa ggagataaac aacgccaggg tcatcacgta ggaacctact 214740
agtacgcggc tttcagagca catttggaag atggccgccg tcaggctgtt ggccaacaga 214800
tagatgaaaa gcaccgtggc gttactaggg tgttcgttgc ccaacgtgta cgtgatgaac 214860
atgcagacga tgggcacgag cacggtgaga aagaagctgt agttctcgac gcaaaagttg 214920
cggttttgtg ggaaccccaa ccaaaaaacg cttcccaagc cgaagctgaa agccagctga 214980
aagatgaaga tggcgtacac gcgcagccat acggtgaact ttttgaacca ctcgagagcc 215040
tccatgcggg agagcagcag cgcgttagcc tcctgcgcct gcatggtggc gacggtctcg 215100
gcacaaagcc gctgcggcgc acctaccctt ctcttataca caagcgagcg agtggggcac 215160
ggtgacgtgg tcacgccgcg gacacgtcga ttaggagacg aactggggcg acgccgctgc 215220
tgtggcagcg accgtcgcag cgaccgtcgt ctgagcagtg tgggcgctgc cgggctcgga 215280
aggcatgaag tagagcacgg agacaaagag gtacatgagg tccatgtaca agcagagcgc 215340
gcccgggata taactctcat actcgatgtc gtgcaggatg tcctgcgtat cgcacaccac 215400
cgaggtcacg atgacggcca aaccggctat catcaccagg atctcactta ccgcctcggg 215460
aaaaagagaa aatacggcga atagtaagag aatcagcgtg gatgcgcccg tcaataggga 215520
acgctgtaat tccacgtcgc gggcaaacag atacgtagcg agcgtgagga aacaaaatag 215580
cgtcactgtg gccaccatgg cataaatgac tgaacgatga ctaaagtgga agcctgacgc 215640
cgtgacagcc acgctggtaa gcaacgtgta cgtcagtaag atccatacgt tttgggaaa 215700 gttgggctcg gcccaacgca acagacctag gcacacgatg gagatcatta agcaagacag 215760
cgtcagacgc acgctggaaa agagctgctc cagccggtgc ggcaacacca gccagcaaaa 215820
ggcgcagacg ctcataagga tgaggcattg cacccagata aggatgtaga tgcgcaacag 215880
gaagaccgac cgggctatct ggacctgacc gcggagcgac atggcggcaa cgccggcggt 215940
tatcgccgag attcgtctaa atacacgaag cgaactagaa aacgcacaca cgtgatttgc 216000
aaaaagaaag cagctgccgg cttattattt tattaaaaat ttatctgtgc agaatcataa 216060
gtttatgatg aataaaaacg gggaaaggga atctgctttt agggacccgg gtctggtccg 216120
tcgtctccca tctggtcggg ttcggggatg gggacctgtt tcagcgtgtg tccgcgggcg 216180
tgcatggctt ttgctcgccg gccgcgctgt aaccaggcct ctttctctgt ggtcggcgag 216240
tcttccgacg ggtagggagc ctgggagtcc atcgcttcag gcccaccgct cgttccctcg 216300
accgtcgtgt cgtcctcgtt ttcgctatta cacggggttt ctggagtatc gcctatacgg 216360
ttggcaattc tccgggggcg gccgctttcg tcctcgtcgc tgctatcgcc gcccggtaat 216420
tcgacgccgc attcgttgta cggagcgcgg cacatgggcg gcggaaagaa cttgggcatg 216480
cgaaagcagc gttgtccatc cacggtctgc gtggtttcat cgttatcctc ccataatccc 216540
ccctgtagcg ccggcagcgt ttcgacgctg tgagagggga aggcccagtt ctggttgtct 216600
tgcagcgcgc ccgtgggcag taggtccgtg cggccccagg cgctgctgtt gttgggtacc 216660
ttgtcagtgc cgcgagtagg tcgcagaaac cagtccagag cgctctctag ctgcgagcgt 216720
gtgatggtgc ccagtgcgcc gtgccagcgc agcacgtctc ttttcagcgt gtggtgacag 216780
acgggcagct cctccaaccg acactcgccg cgcaatccgc ggtcgaagcg gcagagacca 216840
cgcagtttaa gcagaccgca cttgagaaac atgtgaaaat tatcggcaat gcgatacagg 216900
tctgagtcct cgatcttgtg taggtagacc acgccaaact tgtcgagcag caccatgccg 216960
ctgggcacaa aaggcccgta tgccaggtaa tagcccacga ggccgacgac gtaccactcg 217020
cagcacaagc gttgacgaat aaagttcaaa agatcgcgaa agtccgcggc cggcatgtgg 217080
tcaaaaggcc ggcaggcgcg caggccctcg atggagccca gcatgagcaa cggctccacc 217140
tcggtgcgac ccggcgtgcg gatgaccagg ttgagaccgt tcatttcgcg ggccgtcttg 217200
gccacggccg cagcgtcagt ggggtcggtg cagaggaatt tttgcacatg atagcgcggt 217260
tcggtggtgg cgaacggcgt ttgtgggtgc cgatacacat attcgcacca gagtaggccg 217320
ttcttggaaa aggctttgat atcactggcc acctcgtaga gcccgtcggt ctcccagtcg 217380
tagacgtaga cggtgccgta atgacttagc atgagcacgc agggcagttc ctgcgcctgc 217440
ttggtgtttc gtgttagatc gctgtcgggt ggacgtacgg ctagtacacc gacggcttcc 217500
agggtgtcat cgcagcagag atagtcggcg gccagagaac gtgcgtaaat ctgcgggata 217560
gcggcctgtt cgcgcatcac taggaaccag ttggcggggt tgcgcagtgc tacggtggtt 217620
ccctggtggc gctgcacgta ggttctcagc gccggaggat cgtactggcg cagatagagg 217680
ccttgcagca tcgataacgt cttttgaaag acggtgtttc taaattggaa aacgccgtag 217740
tcgcagcgga tagcatcttc gcagcgctcg tcgcgctgtc ggagataggt gccccaggct 217800
tcggcggcgg ctttggtgag tagggacatg ccggcaaagc cgtctcgaca gcgagtcgga 217860
taaagcgcgc tgcgcgaaag cttaatatag gagcagcgtc agacgaatcg cggctggtgg 217920
cccagggggt gggacgcgcc gcctacacaa agtgctcccg aaaatcgaaa ctcttgaccc 217980
actccggaga caaatccgta ttcagattga tgcgtcgcgc ttccacttcg gcttccgaaa 218040
cctcggcctc cgtccggtag gcgttaacga tacgctgacc caggtgccaa cgttctttct 218100
ctgccaaacg ccgttgctca aaccattcgt ctacgtcctt gaggtcaaag acagtgtcct 218160
cctcaaggtc aaagcctagg tcttcccact cgtcgtcatc gctctcgtgg ccggcggcca 218220

```
tacgcgcggc aaccgcgtct tcccctcctc ttctatcaac gttgggtacc acgttgtttt 218280
cttcgggttc cataggttct gcgccactgt cgtcatcatc ctctccctgc tcctcatcgt 218340
ccgccaaggc gtcgtggatc acctccaggt tctgattgtc gggtacgacg tggttatctt 218400
cgtcgtcgtc gcgtggcatg ggcggcggcc gacggcggac gaccggcatg gcgcggccgt 218460
cgtttccttc gtcttcctct tctccgtctc ccagggaacg cggtcgacgg cgttccgcga 218520
agtcgccgcg gaccacgcgc gcctgccaga tggtaaacgc gtcccaacca tcccagttat 218580
ttagcatttc ggcgcggaaa cggtcgcctc gacagagcca gcgaaactgc cgcgcgtagt 218640
cgcggtctac gccgctgtcg aacatggtaa agtgaagacg cgccgcctcg cccatgtgta 218700
cgcagcctcc gttgcgttcc agcctggccg cgcgccgcag accgtgttcg tagcggcgac 218760
gcacgtacac cttcatgagg ccggcgcgaa agagttcctc taggctgtcg gccagacggt 218820
agatttcacc ggctagacgc tgcaggggcg gcgagcggtc caggtgcgac ttgacgatta 218880
ccacgtaaaa acgacagaaa cggtcgaaga tgatgaggaa tgacgtgtca aaaaaaccac 218940
cggcgcggta ggagcccacg gcgcccagca ggtaccagcg gcaacgcagt tgcagcgtga 219000
cgtacatttc gcactcggcc aagcgggcgg ctggcgctac ctcgaagggc cagcagtccg 219060
tcaagcagcc gaaactggtc aggagtttca acgttttggc atggcgtcca ggtgtatgaa 219120
agttcacgtc gcgtccgtgg tgttcgccaa cgcaggcggc caacgcgtcg gtgtcatgac 219180
cgtgacgcag cagcatcgct accacgtcgt gcggtacccg cgtagcaaac ggcgtctgtg 219240
gctgacggta tacggcttcg gtgtacatca taccgtaacg cgccagttcg tccagatgac 219300
gcgcgcacag cagcagaatc tcttgcgagg gttcgtagat gtagaggcgc gtaccgccac 219360
ccatgcagag caccagctcc gtctcttcat agtgatcgtc caccatgatc acgcatttgc 219420
ctagcacgat aaggcgttcg gggcaacaaa ttacgtcgtc cagcagttgg tcgcgcagct 219480
ccggcatggt gctgccgggc cgcacctgca ggaaccagtt gtgcggaatg ccgagcgaca 219540
acacctggtc gacgtggtta cggacccagt cgcgaagcac gtcggcgctg tactggcact 219600
caaagatgcc ctgaaagtcg cccatgaccc gcagaaaagt ttcgtagcgc gtgtggcaat 219660
agaggaattc atcgtttcgc gtaaacgtgg gagctccgtc ttcccagcgt gtacgccaca 219720
tgtcaaaaga ggccgccagc tagacacccc agaaaagaag cagagaaaga gagttctttg 219780
tgcgacacgt tttattccgc gtcctccgct cgacgctcaa atctggatgt actcgcgcac 219840
acccgtcagg ctctttaagg gaaaagggtc cgagtacgtc actaaccgcg actgatgcac 219900
cagggcggta atcacccgct ctgcgccctc gcgcgtcgac gaacgcgtcg tcaccaggca 219960
gtgcagccgc gggcccgtat cgtcctgatg accagcggcc tcgcgctcgg ctgcttccac 220020
accgacaatg tcgggatcca acacgtagct ctgcgagttg gtgtcgtagc ggtgtagcac 220080
caacgtgttg gggtccagac gctcccacgc gccctcgtgc gggtcaaaac gctccgttaa 220140
acagagccag tcatactgct gctgcagaat acgccgctcg cgctcgcgtc gctcatcggg 220200
caacgcggcg tcttcgttga agagaatgtc ccgcttgtgg tctacggcac gctcgtggtg 220260
gtgcgggcac agatgacggt gttccatacg cgtctgacgt tgacgctcgc gctcaaaacg 220320
ccggtgtcga aagaccattt tcagcaaccc catgcggaaa aactccgtga tggtgttggc 220380
aacgcgccgc acgtagtggt tggggtcgtc catctggatg gcgtacacgg caccgaacca 220440
gtccaacagt accagcactt cggccacaaa actgcgtccc ggccgcggac gtcccgtcac 220500
gcctagcaca taccacggcg tggccagatt agcacggaca gcccaccacc aacgacggct 220560
```

-continued

```
ctccacctcg gtgagcgcac aaaagggcca aatgcggtgt aactgctgca ccgttttcat 220620
cagccgcata atcaccgtgc cgtaacccgg tgtatgcaac ttcacgtcgc aacccaggat 220680
tcgttcggcc gtggcgtacg agccctcagg cgttgtgtca ttgagaaaca aaacatgcat 220740
ggtacgcgcg cccttagggt atcgtcgcgg aacaggtacc gtcattctcc gcagagtggt 220800
gtgaatcacg tcgcgatacg caatctccga acgtgacaca ccgtaacgtg ccagttcgtc 220860
caggttgtgc gataccaaca ccatgtactt ttcacgagtg tcgtaggcgt agacgcgaga 220920
aaagcgaccc ataaaaacca cgtacggggt agccaccatg ccatcatggt gatcgcgacg 220980
tggctcgggc aacaaaataa cagcgtatcc caacggcgtc agcggctcgc ggcaacagat 221040
gagctttgac gccgcctgtt tggcggcggt aatgattccg tcctccgtac gtaacatcac 221100
atgccagccc ttggggggac ccaaggacag acagcgtccc tcgttacgat gaacgtaacg 221160
cgtgatttcc attggctcca ggcaaaagaa cagttcctta aaatcccgca acacttgtcg 221220
gtataacgcc atgggatcct cagccgccac aggcagcgcg gggagctccg gcggcacaac 221280
tgcagcgccg tcagggccag aacccgcagc cggatccatc attgcgcgac actctcagcc 221340
ggacaaccgg cgtcactgac agaagccgag ccaaatacag agaaagcaac gctacaccgt 221400
caccccgctc ccaagcgccg cggaaagtgc tccgattttt caccgtcgtt cgcgacgttg 221460
atttgcctcg gtctgagaac cgacctagcg ttcggaccgg tgcgcagaaa cagccggcgg 221520
tccgagccac tgagcggttc acagccccgg ccgccgatag ttaccggaga gacgttcgag 221580
ctgcaggtac atcggcgctc cccgctccgc caccccgcgc ccgccccagt ttatactctc 221640
cgacgccccg tccaacgcgc ctgtggaggg ccaatcggac cgcgggagct ctccaagtgg 221700
atgacaggca cagccgggtg cccgaccgtg aagagccctc atccacctga acagaccgct 221760
aaccgaagga ccccgaatcg cgtccgtcgg tcccgacgtc cgtcgccatc tggttccctg 221820
ctgttggcta cctctcggat ttcaaaaaag agcacgtgcc gatgacggtg cacaggaaag 221880
agccaaagtg tcacggcgtc tttttttatt tgtgttcctt tcctgttttg tactcgtaaa 221940
ctgttgacgt tgtttttaca tccaaaaggg caagtaagaa acaggatgag gcatggtagg 222000
tttgggcgtg gggcggccct ccagcacggc ggcccgggcc gcccggcggg tgagcacccg 222060
gcgttgcgcc gtatctatct tgtgtttctt ctgtgtcttt ttcctatctt gttccgcgac 222120
ggcctctttc atcacgttca gcatgcgttc ctcgacgccc tccagggatc ctggggagga 222180
gggagtccta gtgaggcttc caatgttgtt ttgtggattt tcggtttcct tttcttggtc 222240
gtcatcgtcg gacgtgtcgt cttcctcttg atcctcttct tcgtccgagt agtagacgca 222300
tagtccctgg ttcatcaggc tgggattcat caggttctga cggggaatcc gctgttgtag 222360
acgtttaacc gcccgttcca ggcgagagct catgccgcac cagacgctgt aacgccgcac 222420
gggcccgtag cgggctgttt gttcgcgtac atgatcgttg agctcttgcc aatattgttt 222480
ggcacactcc agatcggagg tttgtggata gtcgggtcgg atccgcggat cccaactgac 222540
atcggcggtg ccagagactt cgtccagact gttacgcata gagcaccagt cgggtcggac 222600
gataaacctg tccttgcgga ttaaccattt ataacgtagt tcgtgatggc gtgtagaggc 222660
ccgtacacgc tccacggtcc caaagcggtc ccagaaggga aagttttcgt gagggcagcg 222720
acccggcact tccagacgtt cggcgtcgtc cacggcgtag tgaaaacgcc ggccggcctg 222780
gtaaattttg agcagaccca cggttaacaa catatccacg ctgtcagcca accgccagat 222840
ctcgcgtcga gacacgtcaa aatagaaaaa ttcacaggct cggtcgacca ggatcacgaa 222900
atcggcgtga aagacgccgg agggtagcga ctcgcccacc acacccatta tcatggtttc 222960
```

gcagcataag cggtccacaa agaacttcaa caggtcgttg aattgctccg tctccataca 223020
gatgaagggc cagacgcctt tgaggttctc ggcctggccg cagagcagca acggacgcgt 223080
catctcgcct ggagtgcgca gaggcacgca ttcgccgcga taacgacagg tcacacgctg 223140
cagttcgctg atgctgttgt cgtgcaggcg aaggtcgcag ataatatgat ccggttgcgt 223200
ggttagcagc ggcgtgcgca tctgctcgcc gtagatggcc tcgcagtgca acagtccgtg 223260
tcgcgcaaaa tcatccagac tgtgcgccag gtagtaaagc accccgcaat cgcggtctaa 223320
acaccacacg gtttcgtaac gtcctagcag gagcaccaga cgggcctggc taggtggctc 223380
aatttcctct acatatacga aaaagtcgtc atcgtccgag tcctcgtcct cagaagagga 223440
ccgcggcccg tgtactctgg gcaacacggt ggtagagaac tgcaggacgc ccagagactc 223500
gagcgactct tcgcagcaga tgagctgacc ccagggcgtt tcgggcccgt cggtgacagc 223560
cgcgctgcca aagatgtcct caaactctac aaaatctaga cgccatccgg gtggcgctga 223620
aacgggaagg ctaatgttca tatcagcata gctacgaact aagtggcgga tgtcctgccg 223680
caagtcttgg cagagaatga gctttcgtaa acccttgagg gtcctccgaa caacggcccc 223740
agacgcgtag cgataggact ggcgcatggt gccgcggcgt ggagcggcac ttggcagcct 223800
attttatgga gtttcttcag tgacgtggct tgttcacgtc gttcgtgggc tgcggttggc 223860
agctccggtc tgtaaaccac ccgaaaagac tgacatcgac gtcaaagact cacgtaattt 223920
ggaacatgtg cgaccgcaaa gtgcgtcaga atagcacgtg gctttaggac ataaaaagta 223980
ccgtgaggtc tagacgtggt ttttgtgatt gacacttaca ccaggtaagc caagggacgg 224040
tgaaactgta tgtgaggaac ctgggtgctt agacaactaa cgtgtaatgc tttttacagg 224100
accgttcaac aggtgatact acctgcaagg taatgactac atctactaca actaccacta 224160
atatcatgct acaggtgagc aacgtaacga atcacacctt gaatagcacc gaaatttatc 224220
agttgttcga gtacactcgg ttcggggtat ggttgatgtg catcgtgggc acgtttctga 224280
acatgctggt gattaccacc atcctgtact accgtcgtaa gaaaaaatct ccgagcgata 224340
cctacatctg caacctggct gtagccgatc tgttgattgt cgtcggcctg ccgtttttttc 224400 tagaatatgc caagcatcac cccaaactca gccgagaggt ggtttgttcg ggactcaacg 224460
cttgtttcta catctgtctt tttgccggcg tttgttttct catcaacctg tcgatggatc 224520
gctattgcgt cattgtctgg ggtgtagaat tgaaccgcgt tcgaaataac aagcgggcta 224580
cctgttgggt ggtgattttt tggatactgg ccgcgctcat ggggatgcca cactacctga 224640
tgtacagtca taccaataac gagtgtgttg gtgaatttgc taacgagact tcaggttggt 224700
tccccgtctt tttgaacacc aaagtcaaca tttgcggcta cctggcgccc atcgtgctga 224760
tggcgtacac gtacaaccgt atggtgcggt ttatcattaa ctacgtgggt aaatggcaca 224820
tgcagacgct ccacgttctt ttagttgtgg ttgtatcttt tgccagcttt tggttcccct 224880
tcaatctggc actattttta gaatccatcc gtcttttatc gggaacgcaa aacgagactc 224940
tccaaaccgt tattactttc tgtctatacg tcggtcagtt tttggcctac gttcgcgctt 225000
gtctgaatcc tgggatctac atcctagtag gcactcaaat gaggaaggac atgtggacaa 225060
ccctaagggt attcgcctgt tgctgcgtga agcaggagat accttaccag gacattgata 225120
ttgagctaca aaaggacata caaagaaggg ccaaacacac caaacgtacc cattatgaca 225180
gaaaacatgc acctatggag tccggggagg aggaatttct gttgtaattc gatcctctct 225240
cacgcgtccg ccgcacatct atttttgcta attgcacgtt tcttcgtggt cacgtcggct 225300
cgaagaggtt ggtgtgaaaa cgtcatctcg ccgacgtggt gaaccgctca tatagaccaa 225360
accggacgct gcctcagtct ctcggtgcgt ggaccagacg gcgtccatgc accgagggca 225420
gaactggtgc tatcatgaca ccgacgacga cgaccgcgga actcacgacg gagtttgact 225480
acgatgaaga cgcgactcct tgtgttttca ccgacgtgct taatcagtca aagccagtta 225540
cgttgtttct gtacggcgtt gtctttctct tcggttccat cggcaacttc ttggtgatct 225600
tcaccatcac ctggcgacgt cggattcaat gctccggcga tgtttacttt atcaacctcg 225660
cggccgccga tttgcttttc gtttgtacac tacctctgtg gatgcaatac ctcctagatc 225720
acaactccct agccagcgtg ccgtgtacgt tactcactgc ctgtttctac gtggctatgt 225780
ttgccagttt gtgttttatc acggagattg cactcgatcg ctactacgct attgtttaca 225840
tgagatatcg gcctgtaaaa caggcctgcc ttttcagtat tttttggtgg atctttgccg 225900
tgatcatcgc cattccacac tttatggtgg tgaccaaaaa agacaatcaa tgtatgaccg 225960
actacgacta cttagaggtc agttacccga tcatcctcaa cgtagaactc atgctcggtg 226020
ctttcgtgat cccgctcagc gtcatcagct attgctacta ccgcatttcc agaatcgttg 226080
cggtgtctca atcgcgccac aaaggtcgca ttgtacgggt acttatagcg gtcgtgcttg 226140
tctttatcat cttttggctg ccgtaccacc tgacgctgtt tgtggacacg ttaaaactcc 226200
tcaaatggat ctccagcagc tgcgagttcg aaagatcgct caaacgtgcg cttatcttga 226260
ccgagtcgct cgccttttgt cactgttgtc tcaatccgct gctgtacgtc ttcgtgggca 226320
ccaagtttcg gcaagaactg cactgtctgc ttgccgagtt tcgccagcga ctcttttccc 226380
gcgatgtatc ctggtaccac agcatgagct tttcgcgtcg ggctcgccg agtcgaagag 226440
agacatcttc cgacacgctg tccgacgagg tgtgtcgcgt ctcacaaatt ataccgtaat 226500
aaaaaagcgc tacctcggcc ttttcataca aaccccgtgt ccgcccctct tttccccgtg 226560
cccgatatac acgatattaa acccacgacc atttccgtgc gattagcgaa ccggaaaagt 226620
ttatggggaa aaagacgtag gaaaggatca tgtagaaaaa catgcggtgt ttccgatggt 226680
ggctctacag tgggtggtgg tggctcacgt ttggatgtgc tcggaccgtg acggtgggtt 226740
tcgtcgcgcc cacggtccgg gcacaatcaa ccgtggtccg ctctgagccg gctccgccgt 226800
cggaaacccg acgagacaac aatgacacgt cttacttcag cagcacctct ttccattctt 226860
ccgtgtcccc tgccacctca gtggaccgtc aatttcgacg gaccacgtac gaccgttggg 226920
acggtcgacg ttggctgcgt acccgctacg ggaacgccag cgcctgcgtg acgggcaccc 226980
aatggagcac caactttttt ttctctcagt gtgagcacta tcctagtttc gtgaaactca 227040
acggggtgca gcgctggaca cctgttcgga gacctatggg cgaggttgcc tactacgggg 227100
gttgttgtat ggtgggcggg ggtaatcgtg cgtacgtgat actcgtgagc ggttacggga 227160
ccgccagcta cggcaacgct ttacgcgtgg attttgggcg cggcaactgc acggcgccaa 227220
aacgcaccta ccctcggcgc ttagaactgc acgatggccg cacagaccct agccgttgcg 227280
atccctacca agtgtatttc tacggtctac agtgtcctga gcaactggtt atcaccgccc 227340
acggcggcgt gggtatgcgc cgctgcccta ccggctctcg tcccaccccg tcccggcccc 227400
accggcatga cttggagaac gagctacatg gtctgtgtgt ggatcttctg gtgtgcgtcc 227460
ttttattagc tctgctgctg ttggagctcg ttcccatgga agccgtgcgt cacccgctgc 227520
ttttctggcg acgcgtggcg ttatcgccgt ccacttccaa ggtggatcgc gccgtcaagc 227580
tgtgtcttcg gcgcatgttg ggtctgccgc cgccaccgtc agtcgcacca cctggggaaa 227640
agaaggagct accggctcag gcggccttgt cgccgccact gaccacctgg tcactaccgc 227700
cgtttccgtc cacgcggata cctgacagtc cgccgccacc gtaccagctt cgtcacgcca 227760
cgtcactagt gacggtaccc acgctgctgt tatatacgtc atccgacatc ggtgacacag 227820
cttcagaaac aacgtgtgtg gcgcacgcta cttatgggga acccccggag cccgctcgat 227880
cgacggctac ggttcaggaa tgtaccgttc ttaccgcccc gaattgcggc atcgtcaaca 227940
acgacggcgc ggtctctgaa ggccaagacc atggagatgc ggttcaccat agcctggatg 228000
tggtttccca gtgtgctgct gatactgggg ttgttgacac ctccgagtaa cgggtgcacc 228060
gtcgatgttg gacgaaacgt atccattcga gaacagtgcc gccttcgaaa cggtgcgacg 228120
ttctccaagg gagacatcga aggtaacttc agtgggcccg tcgtcgtgga gttggactac 228180
gaagacatcg atattactgg cgaacggcag cgacttcggt tccatctcag cggactcggg 228240
tgtcctacaa aggaaaatat aagaaaagac aatgaaagcg acgtcaacgg tggaattcgc 228300
tgggctctat atatacaaac cggcgacgcc aagtacggta ttcgtaacca gcatttgagt 228360
atacggttaa tgtatcctgg ggaaaaaaat acacaacagc tgttgggttc tgatttcagt 228420
tgcgaacgtc accggagacc gtccacgccg ttgggaaaga acgccgaagt gcctcccgcg 228480
acccgcacgt cttctacata cggcgtcctc agcgcttttg tagtgtggat cggatccggc 228540
ctcaatatca tctggtggac cggcatcgtg cttctggcgg cggacgctct cggacttggc 228600
gagcgttggc tgaggttggc actgtcccac cgggataaac atcacgcatc gagaaccgcg 228660
gcgctccagt gtcaacgcga catgttactt cggcaacgtc gacgggctcg gcggctgcac 228720
gccgtttctg aaggcaaact gcaggaagag aagaaacgac agtctgctct ggtctggaac 228780
gttgaggcgc gaccctttcc gtccacacat cagctgattg tgctgccccc tcctgtagcg 228840
tcagctcctc ctgcggttcc ctcgcagccc cccgagtatt cgtctgtgtt tccgcctgta 228900
taaaaataaa gagacgggag gctgatcgcg gccttcagcg tctcatttgt ctttactctc 228960
gagtgcggtc ggtgtctcat cggtgagacg aggccgccgc ccgacaagtt cgatctcatg 229020
tcgctcttgg agcgcgaaga gagttggcgt cgcgtagtcg actactcgca caacctgtgg 229080
tgtacgtgcg gtaactggca aagccacgtt gagattcagg acgaggagcc caactgcgag 229140
cagccggagc ccgcacactg gctagaatac gtggcggtcc agtggcaggc ccgggttcgc 229200
gattctcacg atcgctggtg tctctgcaac gcctggcgtg atcacgcctt gcgcggccgt 229260
tggggtacgg cgtattcctc gggttcctcg gcctcttcct ccggtttcgt cgcggagagc 229320
aagttcacct ggtggaaacg actgcgccac agtacccggc gctggttgtt tcgccgccgg 229380
cgagctcgat acactccgtc taactgtggg gaaagtagca ctagcagcgg ccagagtagc 229440
ggtgacgaga gtaactgcag tctacgcacc cacggcgtgt acacacgggg tgaacaacac 229500
taatcgataa gtcgcgtgta ggcgactggc tacatcaacc ggatatctgc ggggatttaa 229560
aaagacgacc cgttgtcatc cggcttagag caaaccgtcc ttttatcatc ttccgtcgcc 229620
atggctatgt acacatccga atccgaacgc gactggcgtc gtgtaatcca cgactcgcac 229680
ggcctgtggt gcgattgcgg cgactggcga gagcacctct attgtgtgta cgacagccat 229740
tttcagcgac gacccacgac ccgagccgaa cggagggccg ccaattggcg gcgacagatg 229800
cggcggttac accgtctgtg gtgtttttgt caggactgga agtgtcacgc gttatacgcc 229860
gagtgggacg gcaaagaatc cgacgacgag tcgtcggcgt cttcctcggg cgaagcgcca 229920
gagcaacagg tccccgcttg gaagaccgtg cgagccttct cgcgggccta ccaccaccgc 229980
attaaccggg gtctgcgggg cacgccccca ccgcgcaact tgccgggata cgagcacgct 230040
tccgagggct ggcggttttg caatcgacgg gaacggcgag aggacgatct tcgcacgcgg 230100
gctgagccgg accgcgtggt gttccagtta gggggagtac ctcctcgccg tcaccgggaa 230160
acttacgtgt aagaacacgg cgtgacaata aacaacatag cgtaaatccc cgtgtgatgt 230220
gtgtgattga cgttcgggaa acatgtcccc atcatcagcg tcacaactga cgtgggttgg 230280
tcactgacgt gcaggatgtt acgcgagtca gagaatcgca taagaacggg gtggtgagcg 230340
ggttcccaca ggagtctctg gcgcaaaagc accatgagcc tcaggttccc cgagagggcg 230400
ggttacgaga aactgggata ccgcccgcat gccaaacgcg tgtgggtgca tgacccgttg 230460
ggattgacgc ggtttatcat gaggcaactc atgatgtacc cgctggtgtt gccgttcact 230520
tttccgtttt acgtgccgcg gtcctagcac gtcagtggtg acgctgataa ttgcaacatg 230580
gcccatgacg aacccgcttg ggacgaacgt caataccacg tcaaaccgcc gtgacttggc 230640
tgaacgttga aacataaagc caaagcgccg tcggcacttg gcttcagagc agcgcctcgg 230700
ggcgatgcga cggcgatgaa cttagagcaa ctcatcaacg tccttggtct gctcgtctgg 230760
attgccgctc gtgctgtcag ccgcgttggt ccgcatggct ccggactcgt ttatcgtgag 230820
cttcatgatt tctacgggta tctgcagctg gaccttctgg gaccagtggt ggcggggaat 230880
cgctcagtcc ggacctggag agagcaggcg gaccgagcca gagggacctt cgttcggcgt 230940
tcaggcctta atactagcca catcttacct gtcggcggcc tgtctggggg ctccggtacc 231000
ttacccgccg gcctgtatcg tcccgaagaa gaggtgttcc tcctcttgaa ccgctgccat 231060
gggccactgt caacgccgaa aagcgcttgt ctggctgagg ttggtgtcgc taatgccagt 231120
tttttatctc gcttcaatgt cggtgatttt cacggagcgt catgggaaaa cggtaccgct 231180
cccgatggag agcccggggt atgctgaaat tcttcttaaa attacgtaaa cgacgtcgtc 231240
cagtcgttgt gccgcgattc gtacggttca tcgtctacgt cgttttgttc accgtcgctg 231300
tgcaacgcgt gaaacaagag cgtgatgcgc accttcggcg gtatgaagaa cgattgcaga 231360
aaaaccgtgc acggcgtcgg cagagttttc cgtgacttgg ggcggtgggt ccgagctgcg 231420
gtatgggtca cggcggcgtg cgtcttattg acaaagatgc cgatgtgtga ctaaaaaacg 231480
tcccagcccc agagcgatgt gtttcaataa aaattatgta gtatcatatt atgcgtgtcc 231540
tggtttttca ttttttggat gtatttgtcg cataaaaggc ggtgggatgt ggggatgaaa 231600
tatatccaga tacgcagttt tgttatccta acaaaacccg tgtcatgcta aaaacggtaa 231660
tgcaggatga aagtcccgtg tggggggggg gggcatatag tagtcgcttt taccgctggg 231720
catacgctat gcttgtattt gtgactatac tatgtgcagt cgtgtgtcga tgttcctatt 231780
gggaagggtg tgaatgtagg aggtataaag aatggtggga cgcaggaaga catcgctaga 231840
cacagctgta ttgtgctagc cccgcttagc gtcatgggta aaacggtgat aaagcgtcaa 231900
aacaccatgg gggggggggg caggaagctt ggtggcggtg ttcattaaat gcattctgtg 231960
tatttattgg tacatttgca aatcgccgag tataccggta taatgtggca ataatcgtat 232020
tgtgtgtact atgcagcgaa gaggacaata tcagtgtaac gtgaagcaag tgtgggaaca 232080
atgccagtga agaatatata aaagccagaa acatacataa atgaattgct agatacaggg 232140
ttctttgtgt actagcccaa tcatgtcaat acaatgtgta cagaaaaaag acgcaacaac 232200
gacggggggg gggggggcgt acgattaatt ctacatatta cagtacaggc taccgcgtgg 232260
tgttgtgtat gttacgatgc ggtgtgcctg tcggtgtaat tggatgtatg ttacttatcc 232320
gtggcgttgt gatagtgttg tgaaaaataa ttgtcgtgag cataatgaca gctgcaatat 232380
aaaatcactt tattaagcat tgtaatgata atgcgtggct acattagaaa acgtgacgcg 232440
tcgcatgtcg cggcacaatc tggcagcggg gtcggggtag ggtacggtgg gaggcatgta 232500
cacagatgga acaaaagcag aagtaacgtg agacggagca tatagtccag tatccagcgg 232560
ttcctgagta gcaccaccca tcaactgaat gccctcatga gtaaaagtct gcgggcggca 232620
gcccttgggg accgttggca tgggacgatc aatctccaaa ccacagcgta acaccgtttt 232680
cttccaacgt cgttgataca cgtcgttttt acggttactc cccagaaccc agaaagtctc 232740
gtccaagtcg taccaggaat cttctccagg gacacgcgac ggtttccaat cctcgtcgtc 232800
tcgtctcaaa gcacgtccca aactggcttg aggagtcaac ggtggttctg tgggtcgggt 232860
gtagcgcgag tgctttccct tcatgaccga ttcgtcttcc ttgcctttag gctttttggt 232920
ctttttgtgt atcatctggc caccggcttc cataaccacc gtggccaagt ccagtcccag 232980
agcttgagcg tcggcgcggc gtctggcgtc ttgcagatag tcttccacat ttgcacagat 233040
gaccggatgt ttggtggcta gggtgagcac ctcagcctcg ccgcggcccg gacgtagcaa 233100
aaaagctaac tgcccgtgcg gctcgcgcgc ccacagcgcg gcgcgcgggt gcaggtgcag 233160
cgcgtcccag cgcggccgct cccactgctc gcggtccagc tcgggcagca gccgccgcgc 233220
ggcctcggcg gcgggcgccg actcgcgccc cagcgccagc gcgcccagca cgcccgcgcg 233280
cagaaagtgc gacagctccg ccgccagcgg gtacacgtgc ccgtccagcg ggcagtaccc 233340
gaacacggcg cccagctcgt ccagcaccac caccagcatg gcgcgcggca cggtccccga 233400
cgccgccgga cccgccatcg ccgtcggacc caccatcacc gtcggcgccg ccgctgctgc 233460
cgctgccgcc gccgtcgcgt ccgccccgac caccgcgtgc gcgtccgcgt ttggcacgca 233520
aatcgcgctc ccgccggcgc ctccgtacgg ctgcggaggt atagtcacag cagaccccac 233580
ggctcctgcc atcgcgcacg gcgcgtcccc gccggcggcc tccgtctccg tgccgctcgc 233640
cgctggcggc gacgtcgtcc ccgtcgccgg ccccgccgcg caacccagcc accgcgcggg 233700
cagcaccgcg cccagcgcca gccagccgca gcacagacgc tggttcaggt gccgacgcac 233760
ggccgtcagc agcgacgcgg ggtgcggcgc cgacgcgaac ggctcgtact gcgccagctc 233820
ctgccacgcg cccagcagca ccatcggctg cagtcgcctt cccggcgtct gtagtgccac 233880
cgtcgtgccg gcccaccgcc ggcgcagctc ccgtccgagc gccgtcgcct cctcggcgcg 233940
cagcaacgtc tgtcggagcg ccggctgagg cagcagcgtc gcgcgcgggg tgcccacgcc 234000
cagccggttg cagcggtaca gccgcaccac ctcgcccgcg ccgtgccgaa accactcgtc 234060
cgcgtcgcgc gccgctagga tcagcgtgtt gttcgccagg tcgtagacga acacgcggaa 234120
cccggcgccc agcgccaggt acagtccgtc ctgcgcgcac agaccctcgg gatggccggc 234180
cttgtcgccc accgtcgggt cggccgcggg gtccacctcg tgcaccacgg tcgccaccag 234240
cacgatccac gcgtcccgcg gcgacagctg acgcaggtcc gtcgcgccca cgccgttcat 234300
ctggctgcgc ggcgtcaccc gcgcgtagaa tccgtacggc cgtccgagcg gcagcagcgt 234360
gcccgcgtcg cgctgcgacc acttgcgcat ggcgcggccc gtgctgttgg ccagaaacgc 234420
cgcgcgccac acggcgccca tggcctggta ttccagctcc gtcagcgcct ggcgctccac 234480
cggaatctga gacagcaaca ggcgctccgg gccgtgccaa aagttgctgt tgttgccgct 234540
actcggaggg gcgcccggcg gcccgcgggg ttctacccgg tggacgccgt ggcccggcgt 234600
cgccgtaggc gcagcactcg caccagtgcc cgctgttgac gtcgctccca tcggcacaca 234660
agaagaagga ggagaggaac caacccccga aggccctccg gccccgcggc cgcgaccgag 234720
gggcgggggg cgcggcgaca tgccgttgcg ctgggccatg gccgccggac acctccgacg 234780

-continued

```
tccactatat aggaagcaaa cccgcgtcag cgaccacgcc gtttacacac gcggacggct 234840

ccgtcgtccg tgtgccacgg cagacacgca cctggctttt ataggcagcg acgtgtatgg 234900

cgcttgctgg cgccgccttg gggccgtgca gtctggaagg ccgtggaaaa ccacccggca 234960

gccgacgacg cactcgactg gaaaaggcag gaacccggag gaacacgcgc aacagggccg 235020

cggactgggt ccccgagcgc gcaccctcct aggtggacgc ccgacatcca ttccgggccg 235080

tgtgctgggt ccccgagggg cgggggggtg ttttctgcgg gggggtgaaa tttggagttg 235140

cgtgtgtgga cggcgacggc gactagttgc gtgtgctgcg gtgggtacgg cgacggcgaa 235200

taaaagcgac gtgcggcgcg cacggcgaaa agcagacgcg cgtctgtgtc tgtttgagtc 235260

cccaggggac ggcagcgcgg gtccttgggg acacacgcaa aacaacggcc agacaagacg 235320

cgggcgcaag ggaggagtcg cgggccccgg ggcacactgc acaacccgcg tcgaggacac 235380

acgcagacac ggcccgccaa cacaccccga cacacccctg acacaccccg ccgacacacc 235440

cggcacacgc ccgcgacaca cccggccaac acaccccgac acacccggca cacgcccgcg 235500

acacacccgg ccaacacacc ccgacacacc cggcacacgc ccgcgacaca cccgcggcac 235560

accctgacac acccgccaca cccggcacac acccaccccg ccgcgccccc gacacacccc 235620

gaccgccgcc ggtgcgggac agggct                                      235646
```

GENETIC VARIANT OF CYTOMEGALOVIRUS (CMV)

CROSS-REFERENCE TO RELATED APPLICATIONS

This application is a National Stage application under 35 U.S.C. §371 of International Application No. PCT/SE2012/050407, having an International Filing Date of Apr. 13, 2012, which claims the benefit of priority of U.S. Provisional Application Ser. No. 61/475,926, filed on Apr. 15, 2011.

SEQUENCE LISTING

The instant application contains a Sequence Listing which has been submitted electronically in ASCII format and is hereby incorporated by reference in its entirety. Said ASCII copy, created on Mar. 21, 2016, is named 107830105_SL.txt and is 326,341 bytes in size.

FIELD OF THE INVENTION

The present invention is directed to the field of a new genetic variant of Cytomegalovirus (CMV), shown e.g. to be present in patients suffering from a cancer disease. Accordingly, the present invention relates to the field of diagnostic methods for cancer, and more specifically for cancer forms involving the presence of an infection of Cytomegalovirus (CMV). The invention especially concerns the diagnosis of glioblastoma, medulloblastoma, neuroblastoma, colon cancer, breast cancer, prostate cancer, ovarian cancer, cervix cancer, sarcomas, kidney cancer, skin cancer and pancreatic cancer but is also applicable to other cancer forms.

BACKGROUND OF THE INVENTION

Cytomegalovirus (CMV) is a common virus that infects a majority of the world's population; 60-100% of the adult population has experienced this infection and are carriers of this virus. CMV establishes latency and persistence after a primary infection and most infections are subclinical. In healthy carriers, the virus is found preferentially as a latent virus in myeloid lineage cells and reactivation is dependent of cellular differentiation into mature macrophages or dendritic cells, often caused by inflammation. Until the 1970th, only severe cases of congenital infections were thought to represent human disease of this virus. With the escalation of immunosuppressive individuals in the society such as AIDS patients and transplant patients, reactivation of CMV became a major clinical problem causing high morbidity and mortality among these patients. Therefore, the importance and the interest of CMV have increased over the past decades, as CMV disease is common in this group of patients and may be life threatening. The virus is reactivated by inflammation, and increasing evidence suggests a frequent presence of the virus in tissue specimens of patients with inflammatory diseases. Recently, increasing evidence also imply a frequent presence of an active CMV infection in cancers of different origin. We define a novel genetic variant of CMV in cancer, and demonstrate a new mechanism of cancer development.

CMV Infection and Cancer

Recent reports reveal the frequent presence of the genome and proteins of CMV in certain malignant tumors, such as colon cancer, malignant gloria (1-7), medulloblastoma (8), EBV-negative Hodgkin's lymphoma, cervix cancer, prostate cancer and breast cancer (for review see (9, 10)). We have confirmed the presence of an active CMV infection in 99% of malignant glioblastoma tumors, in >90% of medulloblastomas (MB) and neuroblastoma (NB), malignant melanoma, colon, breast, pancreas, prostate, skin, ovarian and cervix cancer (1, 8). Importantly, the virus infection remains latent in non-cancer tissue specimens obtained from the same patient, and in healthy control individuals (1, 3).

CMV and Oncomodulation:

Already in the 1970th, Fred Rapp's group reported a frequent presence of CMV in prostate cancer, and isolated a virus strain from tumors that was oncogenic in animal models (11, 12). In several later studies, CMV failed to transform normal human cells, so this virus was not considered to be oncogenic. Instead, the term oncomodulation has been proposed to describe the indirect influence of CMV on tumourigenesis mediated by numerous viral proteins with specific effects on host cell functions (reviewed in (13, 14). During the evolution, CMV has developed sophisticated mechanisms that affect many different cellular and immunological functions (15, 16). The virus produces about 170 proteins in an infected cell, of which approximately only 50 are essential for virus production (17). Thus, the vast majority of the viral proteins are devoted to control important host functions that will assist the virus to co-exist with its host. These proteins may through control of host functions contribute to cancer development, and by modulating the immune response, virus infected tumor cells will be protected from discovery by the immune system (15). CMV mechanisms potentially involved in cancer pathogenesis are referred to as oncomodulatory mechanisms (10, 13).

Oncomodulation is defined as the ability to promote, in an appropriate genetic environment supplied by tumour cells, an oncogenic process characterized by disruptions in intracellular signalling pathways, transcription factors and tumor suppressor proteins. CMV can block cellular differentiation, interfere with oncogene expression, induce specific chromosomal breaks, inhibit DNA repair mechanisms, control important epigenetic functions, control cellular proliferation, inhibit apoptosis, induce angiogenesis and cellular migration that all provide oncomodulatory mechanisms (10, 13). More recent data also suggest that this virus may be oncogenic; one study has shown that the expression of the CMV protein US28 in fact, by itself, leads to tumour development in a murine model through induced COX-2 expression and VEGF production (18, 19). Expression of US28 targeted to the intestinal epithelium in transgenic mice results in intestinal hyperplasia, adenomas and adenocarcinomas (20). In collaboration with Smits group, we recently demonstrated that US28 also leads to phosphorylation of STAT3 resulting in IL-6 production and a proliferative phenotype. STAT3 phosphorylation, for example in glioblastomas was correlated to survival in glioblastoma patients (6). We have also recently found that the CMV protein IE72 induces high telomerase activity through an interaction with SP-1 binding sites in the promoter (7). Induction of telomerase activity is a common phenomenon of oncogenic viruses. Interestingly, we found that only CMV infected cells in GBM tumors exhibited increased hTERT expression (7). In further support of an important role of CMV infection in cancer, we recently found that the level of CMV infection is associated with prolonged survival in glioblastoma patients (1). Furthermore, the level of CMV infection in glioblastoma tumors is a strong prognostic factor for patient survival. Patients with low grade CMV infection (defined as less than 25% virus positive cells) in the tumor at diagnosis survive more than 2.5 times as long as patients with high grade infection (21). In vitro, ganciclovir treatment inhibits tumour growth by 80-95% and animal models demonstrate inhibition of tumour growth by 40-75% using drugs targeting viral replication (8, 22).

CMV Avoids Detection by the Immune System

CMV has developed sophisticated mechanisms designed to avoid recognition by the immune system. For example, CMV inhibits the expression of HLA class I and class II molecules and antigen presentation, it controls T cell activation, inhibits NK cell activation, protects cells from cytolytic peptides that are released from activated T and NK cells (16, 23). CMV also produces its own and controls cellular production of chemokines, cytokines and growth factors (15). These are examples of strategies that make infected cells invisible to the immune system, and may explain why CMV infected tumors are not controlled by the immune system or by immmunotherapies developed against them. Hence, infected tumour cells will be invisible to the immune system (reviewed in (16, 23), at the same time as the virus is dependent on inflammation (24). Our group was first to identify cells of the myeloid lineage as the major circulating carriers of latent virus (24), and that immune activation of T cells and the consequent production of TNF-α and IFN-γ, resulting in macrophage differentiation, is a key element in the reactivation of latent CMV (24, 25). Virus infection also induces COX-2 (18, 26-28) and we recently found that the virus also induces 5-LO expression (29) to induce inflammation and enhance virus replication, which has a high relevance in tumour biology.

CMV Gene Products Confer Resistance to Chemotherapy

Apoptosis, or programmed cell death, is the final step in the mechanisms for killing mediated by NK cells and cytotoxic T cells. Attenuated sensitivity of tumour cells to drug-induced death is one of the major reasons for the failure of anti-cancer therapy. At least five different CMV proteins (i.e., IE1, IE2, UL36 and UL37, UL38) inhibit apoptosis and may enhance the survival of CMV-infected tumour cells. These proteins may also prevent the desired effects of chemotherapy. In support of this hypothesis, UL36 expression in neuroblastoma cells confers resistance against chemotherapy (30).

A Pivotal Role of CMV Dense Bodies in Cancer

Increasing data demonstrate that CMV proteins frequently are detected in cancers of different origin. >90 of glioblastomas, neuroblastomas, medulloblastomas, colon, breast and prostate cancer from pancreatic tumors, sarcomas, malignant melanomas, squamous cell carcinoma, ovarian cancer, cervix cancer demonstrate high CMV protein expression in tumour cells, but consistently non-tumour tissues surrounding the tumour are virus negative. We have also examined patient biopsies and found them all to be highly positive for CMV protein expression. While CMV protein expression is wide-spread in the tumours and CMV RNA transcripts are easily detected, but in sharp contrast it has been difficult to detect CMV DNA in the same tissue samples. This has been a controversial issue, puzzled many of the researchers in the field, and concerns have been raised if this represents an artefact.

Hence, there has been a long-felt need and an extensive search in the art to reveal the strategies of CMV infection and how this impacts the initiation or progression of e.g. cancer. This due to the fact that such revelation could unveil potential diagnostic methods which would allow earlier treatments of patients in need thereof, as well as potential new therapeutic treatments.

SUMMARY OF THE INVENTION

The present inventors have now solved the problems posed herein by defining a new genetic variant of Cytomegalovirus (CMV), shown to lack intron 2 (SEQ ID NO:17) of the immediate early gene (IE) CMV genome, said genetic variant being designated the name CMV IEΔi2. The present invention also relates to methods and uses encompassing the novel genetic variant of CMV discovered, named CMV IEΔi2, representing a variant of a wild type CMV and/or a new viral strain by the lack of intron 2 (SEQ ID NO:17) in the major immediately early gene, as well as splice variants transcribed from said genetic variant and proteins translated from said genetic variants. Said methods have a use in e.g. diagnosing a pre-disposition for cancer or an already developed cancer disease.

BRIEF DESCRIPTION OF THE FIGURES

Figure 9:
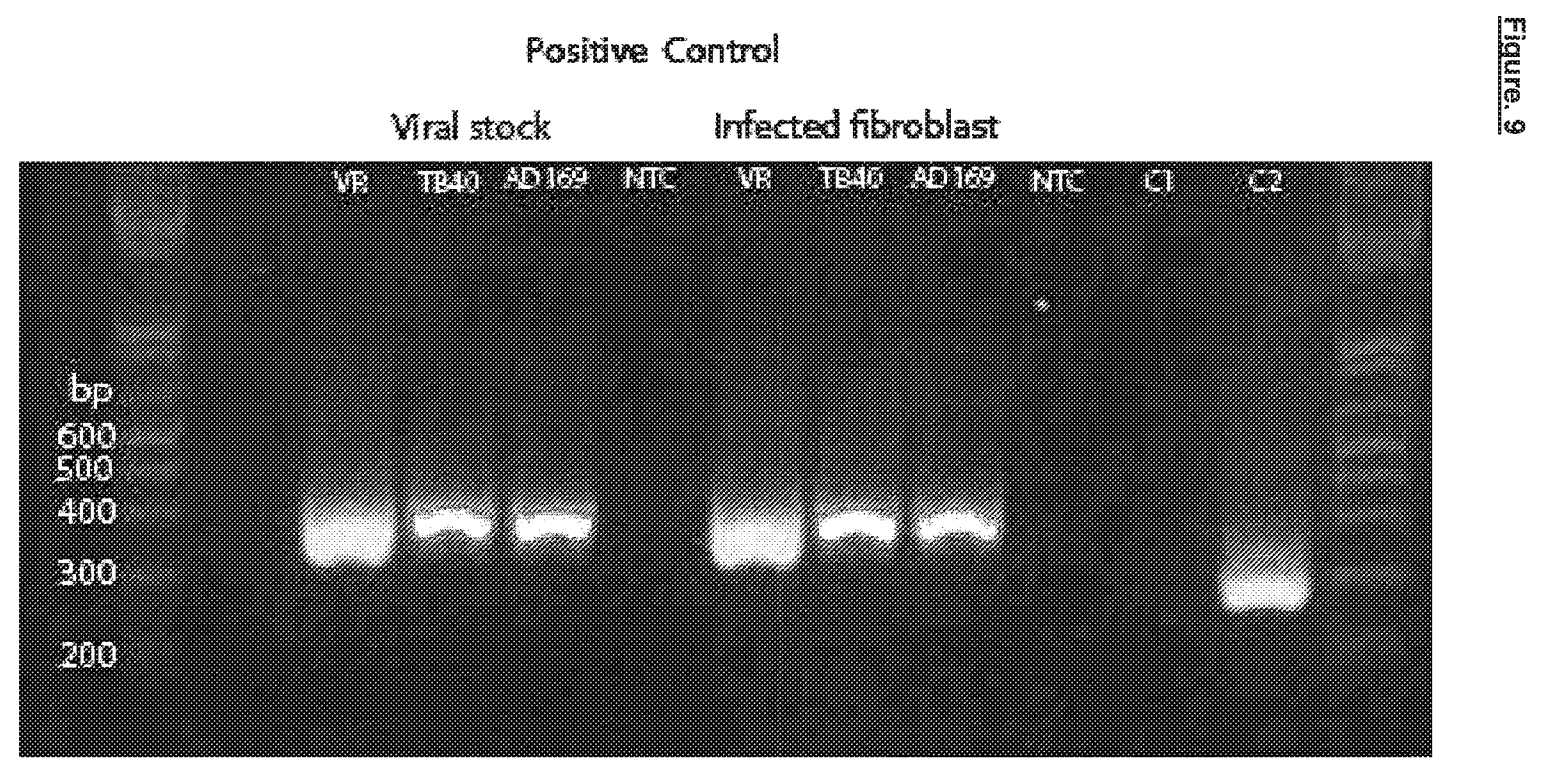

FIG. 9: Nested PCR of three different virus strains commonly used in laboratory research; VR1814, TB40, AD169 amplifying the wildtype fragment of 332 bp. Samples were prepared from viral stock or from—infected cells. NTC; negative control, C2; cDNA from an infected cell amplified a fragment of 218 bp.

FIG. 12: A and B) Sequence alignment of GBM RNA transcripts, i.e CMV DNA from glioblastoma primary cell cultures (harvested from 3 different flasks) depicting the deleted intron 2 of the immediate early (IE) gene (SEQ ID NOS 33 and 33-37, respectively, in order of appearance). The coding sequences of IE1, IE9, IE17.5 and IE19 are shown together with the Merlin reference sequence (gene bank AY446894.2) of exon 2 and exon 3.

FIG. 15: Western blot analyses of cell lysates from glioblastoma primary tumor cell cultures using a human cytomegalovirus (CMV) peptide antibody against IE86. Two exposures for demonstration of the positive control of virus-infected cells with the wildtype CMV strain VR1814. The CMV proteins IE55 and IE86 are very abundant in the primary cultures as well as a 40 kDa and a 20 kDa protein, whereas several of the unique proteins expressed in primary glioblastomas are lost. Only two samples express the 50, 53 kDa proteins (30, 46), three express the 28 kDa protein (42, 47, 48). Instead novel proteins re expressed size of 50, 53, 28, 24, 19, and 10 kDa.

FIG. 17: A) Fluorescent in-situ hybridization (FISH) analyses using a CMV probe containing the whole human cytomegalovirus (CMV) genome in a bacterial artificial chromosome (BAC) vector demonstrate integration of the CMV genome in chromosome 17 in a tumor cell from a glioblastoma patient. Two small dots representing the CMV DNA present in both chromatids of the chromosome 17 are visible in the higher magnification (B).

FIG. 18: A) Sequence alignment of RNA transcripts found in GBM patients (SEQ ID NOS 38-40, respectively, in order of appearance). Schematic drawings of known splice variants from Awasthi et.al. J Virol August 2004 p. 8191-8200 (31). Sequence alignment of immediate early (IE) 19, IE17.5 and IE9 from a published journal (Awasthi et.al. J Virol August 2004 p. 8191-8200(31) demonstrating amino acid alignments and splice variants of IE1 and IE2). B) The carton drawing shows the multiple splice variants derived from exon 2, 3, 4 and 5 of the IE gene.

DETAILED DESCRIPTION OF THE INVENTION

Definitions

An "intron" as referred to herein is any nucleotide sequence within a gene that is removed by RNA splicing to generate the final mature RNA product of a gene. The term intron refers to the DNA sequence within a gene, but is removed in the corresponding sequence in RNA transcripts transcribed from genes having an intron.

An "exon" as referred to herein is a nucleic acid sequence of DNA that codes for information for protein synthesis that is transcribed to messenger RNA.

Figure 5:
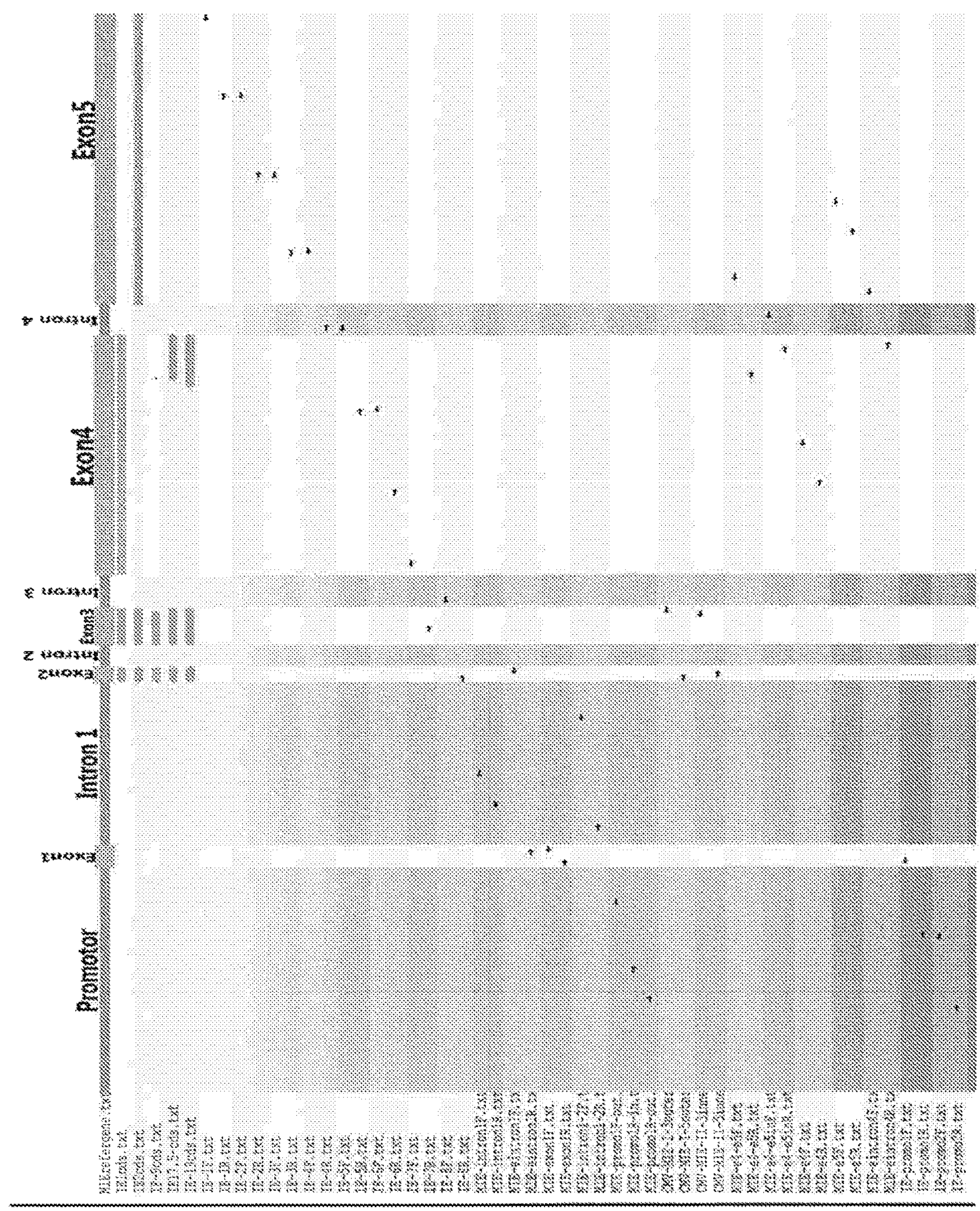
FIG. 5: Schematic illustration of the human cytomegalovirus (CMV) immediate early (IE) gene in wild type and location of the different primers used for PCR of the CMV IE gene region. In CMV IEΔi2, the intron 2 is missing, which is determined by a nested PCR using the major immediate early (MIE) outer and MIE inner primer pairs or a Taqman PCR with a probe spanning over exon 2 and 3 allowing only deleted variants to give a positive signal.
Figure 6:
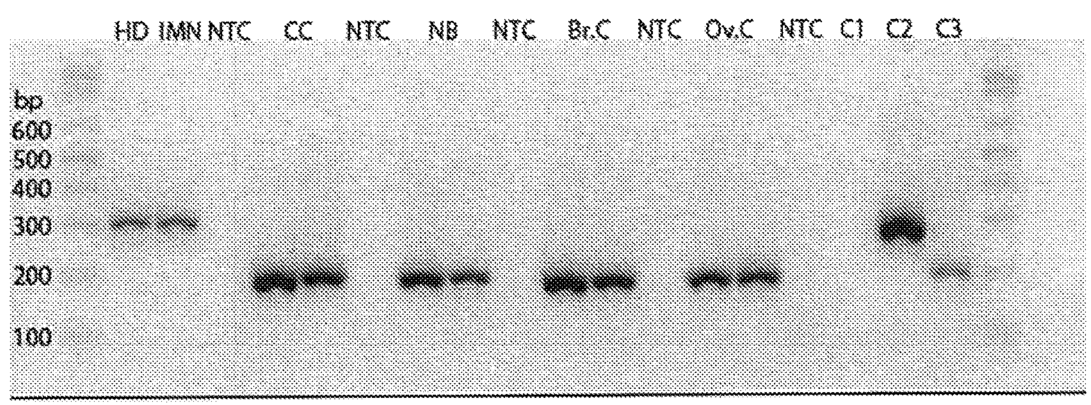
FIG. 6: Nested PCR amplifies a PCR DNA fragment of 218 bp in cancer patients; similar size as cDNA of an RNA sample of cells infected with a laboratory cytomegalovirus strain (CMV) (C3), while a DNA preparation of the same culture amplifies a PCR fragment of 332 bp (C2). A DNA fragment of wildtype was amplified from a healthy donor (HD) and a viremic patient with infectious mononucleosis (IMN). HD; healthy donor, CC; colon cancer, NTC; non-template control, NB; neuroblastoma, BrC; breast cancer, OvC; ovarian cancer, C1; uninfected fibroblast, C2; DNA from CMV-infected fibroblast, C3; cDNA from CMV-infected fibroblast.
Figures 7A, 7B:
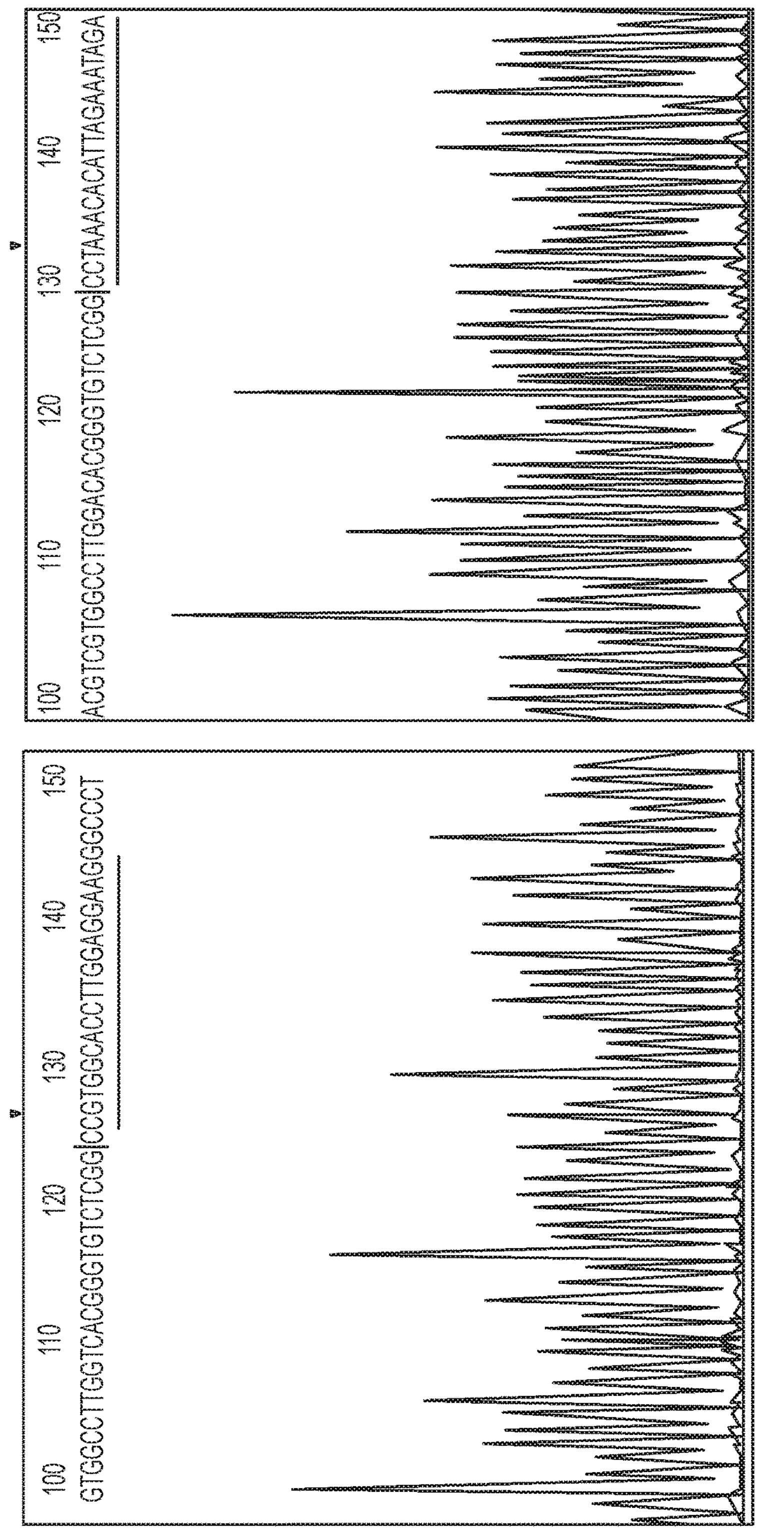
FIG. 7: Chromatogram demonstrating deletion of the intron 2 in a cancer patient carrying the CMV IEΔi2 variant (A) or the wildtype variant in a healthy donor (B). The figure demonstrates the site of intron 2 deletion in a cancer patient carrying the CMV IEΔi2 variant (A) (sequence: GTG GCC TTG GTC ACG GGT GTC TCG GCC GTG GCA CCT TGG AGG AAG GGC CCT (SEQ ID NO: 18)) or the wildtype variant in a healthy donor (B) (sequence: ACG TCG TGG CCT TGG ACA CGG GTG TCT CGG CCT AAA CAC ATT AGA AAT AG (SEQ ID NO: 19)).
Figure 8:
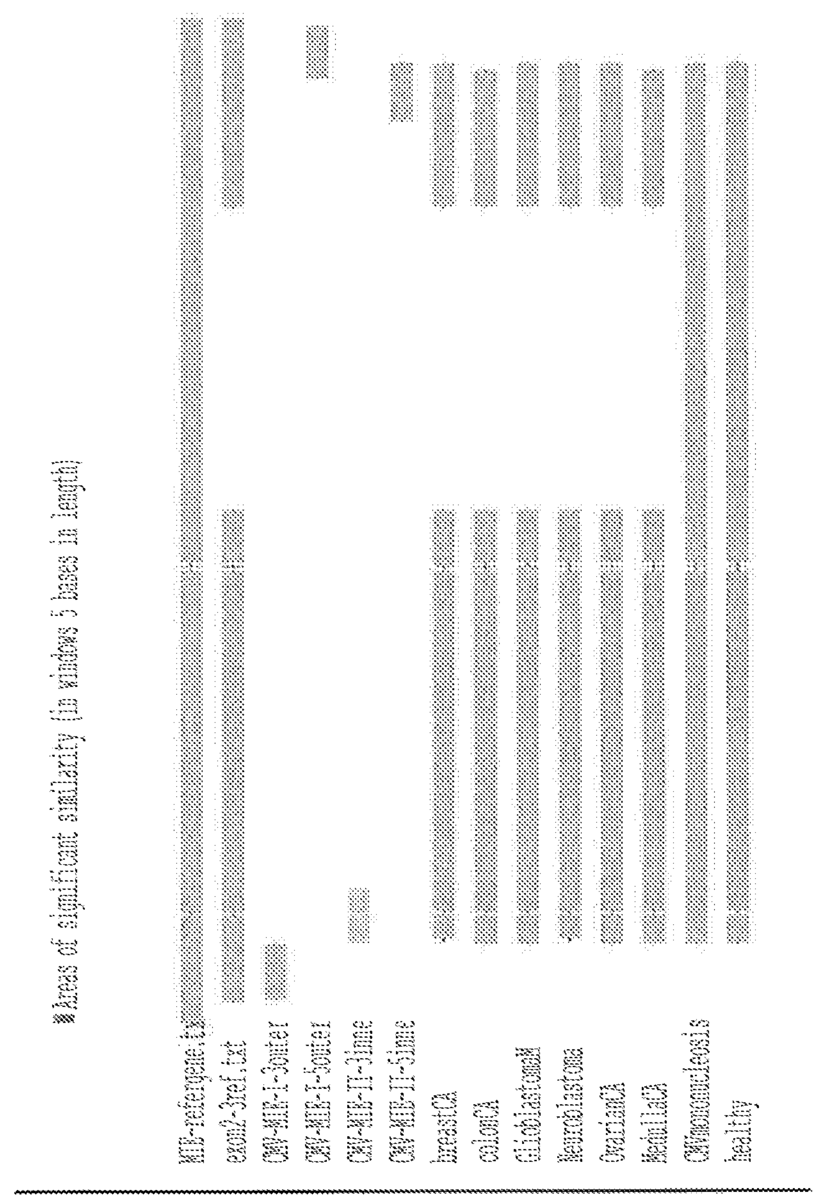
FIG. 8: A and B) Alignment of sequenced PCR products demonstrating the lack of intron 2 in the human cytomegalovirus (CMV) IEΔi2 strain found in cancers of different origin (SEQ ID NOS 21-32, respectively, in order of appearance). Exon 2 and exon 3 are indicated as well as location of primers used for the nested PCR. CMV IEΔi2 is found in e.g: breast cancer, colon cancer, medulloblastoma, neuroblastoma and glioblastoma, but a viremic patient or a healthy control carries the wildtype CMV strain.
Figure 10:
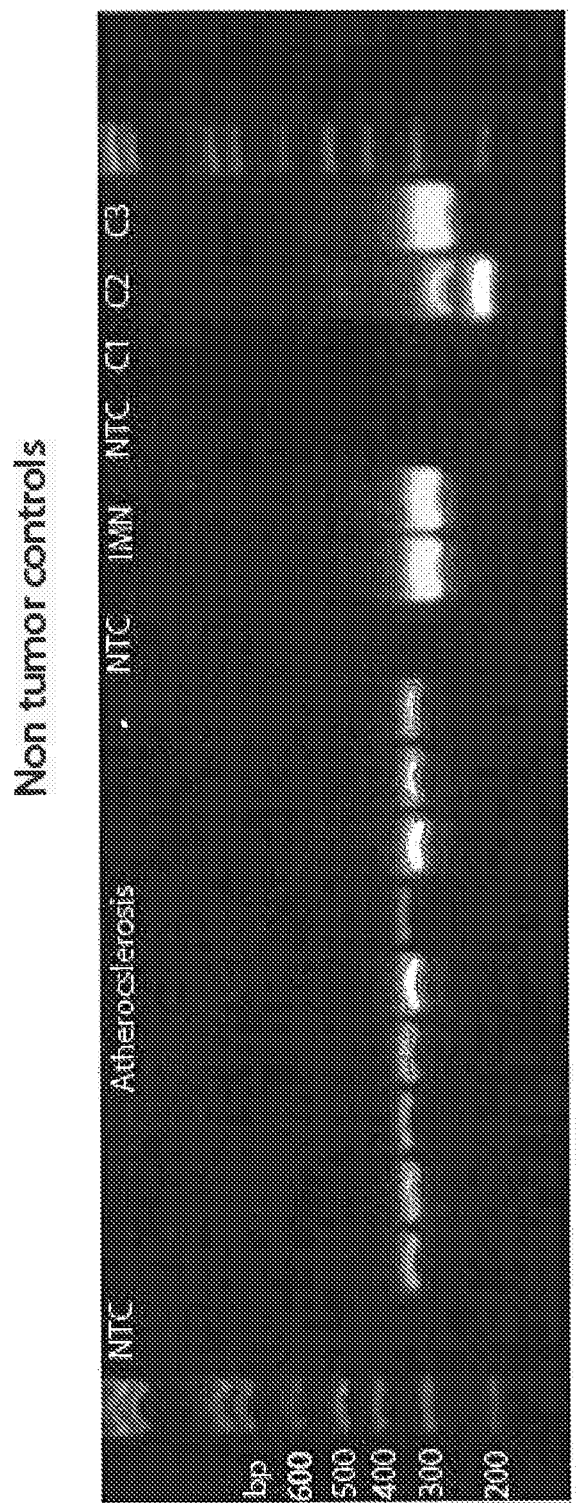
FIG. 10: Nested PCR amplifies the wildtype DNA fragment of 318 bp in serum samples from patients with atherosclerosis and infectious mononucleosis patients (IMN). C2; a cDNA sample of a CMV wildtype infected cell demonstrating also the wt DNA band (the sample was not DNAse treated), that is visible in the DNA preparation from the same cell (C3).
Figure 11:
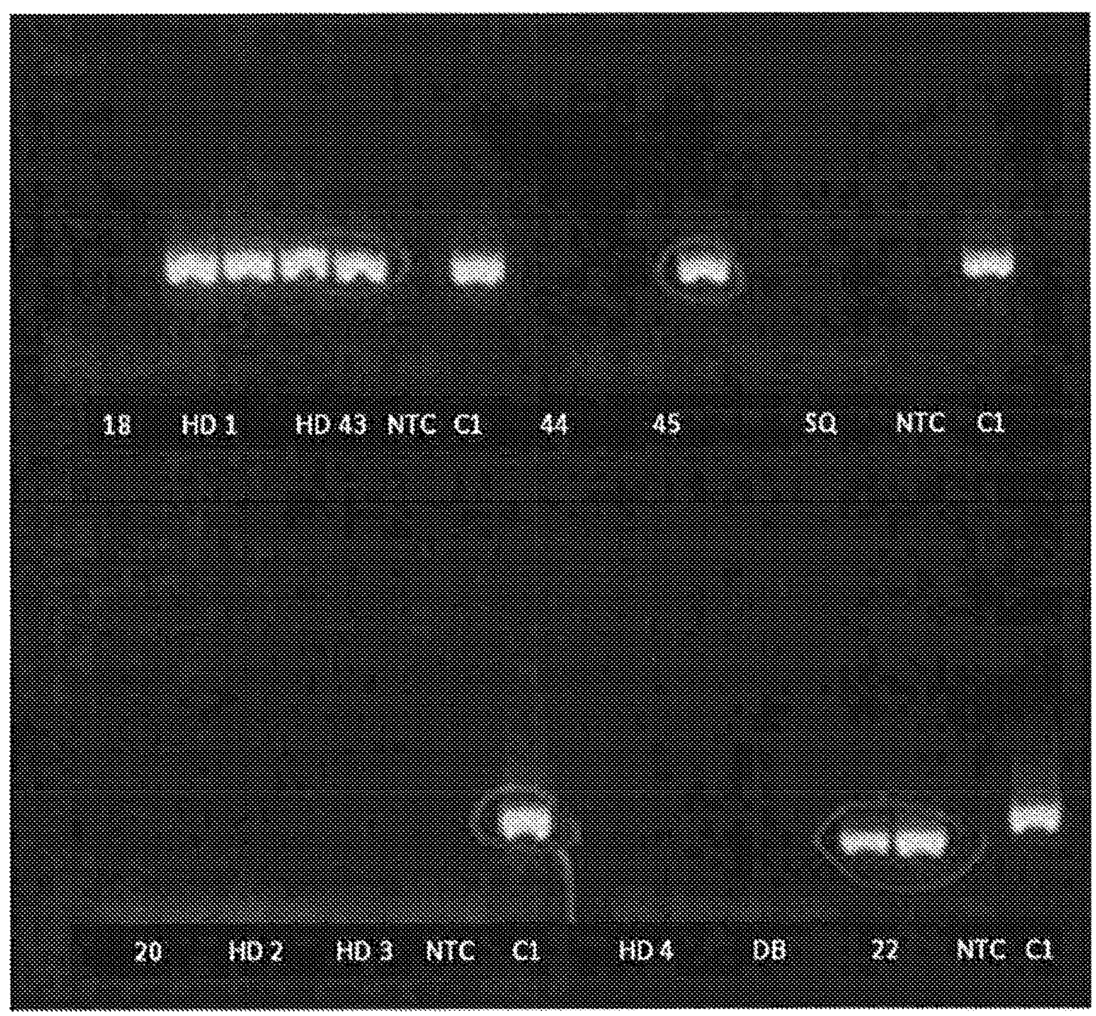
FIG. 11: Amplification of DNA in healthy blood donors. C2, positive control for DNA wildtype (wt) CMV. One individual (22) had the CMV IEΔi2 strain, found in 12-13% of controls examined.

The "CMV IEΔi2" as defined herein, also referred to herein as "CMVIEΔint2" refers to a genetic variant of CMV, being a separate strain of CMV, which corresponds in nucleic acid sequence to the CMV IE genome as shown in FIG. 5, but wherein the part corresponding to intron 2 of the region named Immediate Early (intron 2 of IE is provided in SEQ ID NO:17) is missing, lacking or deleted in the DNA as is demonstrated in FIGS. 6, 7, and 8. The wt CMV strain referred to in genebank (AY446894.2 Merlin), with the immediately early gene in base pair position 170689-176186 including the IE gene as referred to in FIG. 5 as a reference gene and FIG. 8 as reference to the CMV IEΔi2 lacking intron 2. Herein, said genetic variant is further characterized by that the nucleic acid sequence from position 173903 to position 174019 of Merlin reference sequence AY446894.2 (wild type CMV) is lacking in said genetic variant.

"Immediately early" (IE) genes are genes that are activated transiently and rapidly during acute infection and in response to a wide variety of cellular stimuli. They represent the first set of genes transcribed from the CMV genome during infection and are followed by early and late genes, which transcription they control. The IE genes represent a standing response mechanism that is activated at the transcription level in the first round of response to stimuli, before any new proteins are synthesized. The major Immediate early gene UL123/122 located in the viral unique long (UL) gene segment of the CMV genome, refers to a region situated in base pair position 170689-176186 of the wt CMV Merlin strain (gene bank AY446894.2). The major immediate early genes are transcribed under control of the major immediately early (MIE) promoter producing sense RNA transcripts encoding several IE proteins (IE1 or IE72, IE2 or IE 82-86, IE86, IE2-55 or IE55). These proteins share exon 2 and exon 3 and thus the same N-terminal of the protein. In addition to these major IE proteins, other IE proteins are produced by translation of transcripts of modified mRNA molecules (see below).

A "genetic variant" of Cytomegalovirus (CMV), as mentioned herein, refers to a CMV variant lacking only intron 2 or a new viral strain of CMV, which is a variant as compared to other CMV strains in the manner that the region commonly named as the Immediate Early region of the CMV genome (See FIG. 5) has been altered and does not comprise the region intron 2 (See FIGS. 6, 7 and 8). Hence, the variant is "genetic" or "genetically altered" due to that the variation occurs already on the DNA level of the CMV virus, and is thereafter multiplied in the events following the transcription and translation of CMV proteins from this genetic variant, which is further explained herein. The nucleic acid sequence of SEQ ID NO:1 define the characterizing DNA region of the genetic variant as defined herein, and as compared to the wildtype CMV. This region corresponds to exons 2 and 3 of wt CMV, which due to intron 2 having been lost, are now directly connected in the DNA of the genetic variant of the wt CMV. If a CMV virus has such a modified region, this can be used for identifying that such a CMV virus is a genetic variant of wt CMV. This can be performed e.g. by using a PCR method, or as further defined herein.

A "splice variant" is produced by a process sometimes referred to as alternative splicing (or differential splicing) by which the exons of the RNA produced by transcription of a gene (a primary gene transcript or pre-mRNA), such as in the present context the genetic variant CMV IEΔi2 are reconnected in multiple ways during RNA splicing. In molecular biology, "RNA splicing" is a modification of RNA after transcription, in which introns are removed and exons are joined. This is needed for the typical eukaryotic messenger RNA (mRNA) before it can be used to produce a correct protein through translation. For many eukaryotic introns, splicing is done in a series of reactions which are catalyzed by the spliceosome, a complex of small nuclear ribonucleoproteins (snRNPs), but there are also self-splicing introns.

The resulting different mRNAs may be translated into different protein isoforms and are all produced by transcription from the 5 primer end in wild type CMV infection. In the major IE gene, six known splice variants are known to produce variant IE proteins, such as that contain exon 2 and exon 3 (see FIGS. 5 and 8); IE9 (AY445661.1; exon 2 and 3 and 2 amino acids of exon 4; protein predicted to be of 10 kD but not observed in infected cells), IE19 (AY436380.1; exon 2,3 and a fragment of exon 4 producing a 38 kD protein), IE17.5 (AY445660.1; exon 2,3 and a smaller fragment of exon 4, shared with IE19, producing a 31 kDa protein), IE18 (SEQ ID NO: 2; exon 2, 3 and 5 producing an 18 kDa protein). Two IE proteins are made from exon 5; IE40 (SEQ ID NO: 3; 40 kDa protein) and IE60 (SEQ ID NO: 4; 60 kDa protein). Thus, thereby a single gene may code for multiple proteins. Accordingly, herein different "splice variants" are produced by different splicing events taking place during the transcription of the genetic variant CMV IEΔi2 to produce novel IE RNA transcripts and IE proteins.

Accordingly, the present invention relates to a genetic variant of Cytomegalovirus (CMV), herein referred to as CMV IEΔi2 or CMV IEΔint2, said genetic variant lacking intron 2 in the IE gene of the CMV genome. The present genetic variant of CMV has been shown to be present in high prevalence in patients suffering from a cancer disease, which is further shown herein.

CMV IEΔi2 has been found to be highly prevalent in patients with different cancer forms (72/86, 84%), while being detected less frequently in viremic patients (1/19, 10%) and in the healthy population (15/100; 15% tested 2010, or 0/285 tested in 1995) (32). Tumour cells infected with this genetic variant of CMV expresses splice RNA variants and novel CMV IE proteins further aiding in the establishment and progression of cancer. This novel CMV strain is detected as an active virus infection producing viral proteins in tumour cells of different tissues/organs, while non-tumor tissues surrounding the tumour remain CMV protein negative.

The CMV IEΔi2 has been isolated from 3 of 100 clinical isolates. In all three cases, the CMV IEΔi2 virus was isolated with a wt CMV virus, and appears to have a slower growth rate and lower replication efficiency.

It is presently not known what the life time risk of carriers of the CMV IEΔi2 strain is for developing a cancer or a CMV positive tumour, only that 84% carry the CMVIEΔi2 strain. Hence, it is not known how many of the 10-15% of individuals that are infected with the CMV IEΔi2 strain will develop cancer, but there is still a need to identify the carriers of this CMV IEΔi2 strain for many reasons, which is further presented herein.

It is presently not known how transcription of the genetic variant CMV IEΔi2 is regulated. In tumour tissue specimens, the presence of CMV IEΔi2 is associated with high expression of the splice CMV variant IE proteins.

Hence, in one aspect of the present invention, it is possible to detect a predisposition for cancer and/or diagnose a cancer form in mammal, by identifying carriers of the CMVΔIEi2 strain, such as by searching for the variant identification marker disclosed in SEQ ID NO:1, and by using various commonly used techniques. This information can be useful to avoid transfer of the CMVΔIEi2 strain between individuals through biological samples, such as via a blood donation, organ and stem cell transplantation as well as breast feeding.

About 70% of the adult population are carriers of Cytomegalovirus (CMV). CMV proteins and nucleic acids have recently been found in >90% of tumors of different origin including glioblastomas, neuroblastomas, medulloblastomas, breast, colon and prostate cancer. Increasing evidence suggest that numerous CMV proteins are oncogenic or oncomodulatory, but only few CMV carriers develop cancer. It has been found that a hitherto unknown virus strain of CMV was detected in 84% of tumor patients, primary tumor cultures (89%) or cell lines, whereas this strain was found in 0-15% of healthy blood donors and in 10% of CMV viremic patients. The virus strain was identified by a lack of intron 2 in the immediately early region of the CMV genome. Splice RNA variants and unique virus proteins were produced by CMV IEΔi2 strain in tumor cells. The penetrance of the oncogenic capacity of CMV IEΔi2 strain to cause cancer in individuals is still to be revealed. Still, spread of this virus by blood transfusions can be prevented by the methods for determining the presence of such a CMV strain in a mammal, such as exemplified by aspects of the present invention.

The present invention discloses decisive evidence that CMV infection in tumors describes a novel variant of CMV (CMV IE Δi2) highly associated with different cancer forms. Infection of cancer cells with this CMV variant represent a new entity of infection, producing defective particles "dense bodies" from cancer stem cells thereby proposing a novel model for cancer diagnosis and development. As support thereof, a new genetic variant of CMV has been revealed, consistently lacking intron 2 in the major immediate early region of the CMV genome.

Novel RNA transcripts and CMV IE proteins are produced by CMV infected tumor cells in primary tumors, primary tumor cultures and cell lines. RNA transcripts and proteins are delivered by dense bodies or exosomes from a CMV DNA positive cell to surrounding cells resulting in CMV protein expression in cells that will not replicate the virus, thereby allowing for transformation of cells, as they will not undergo lytic infection.

Without being bound by a specific theory, in which tissue/organ the tumor will develop will likely depend on recruitment of latently infected cells carrying the CMVΔIEi2 strain to the tissue and reactivation of the virus resulting in oncogenic transformation of cells and cancer development in the targeted tissue through delivery mainly of CMV proteins and RNA in defective virus particles; i.e: dense bodies or by exosomes. As inflammation is a driving force for reactivation of latent CMV, this initial step of cancer initiation will likely depend on inflammation, a well-known risk factor of cancer. When active, the CMV IEΔi2 will produce novel RNA transcripts from the CMV IE region (both sense and anti-sense RNA as described to be produced by CMV IEΔi2 in FIG. 12). IE proteins transferred between cells in CMV dense bodies providing a primary cause of many cancer forms.

In light of the fact that the CMV IEΔi2 strain is so prevalent in established cancers, further strengthen the suspicion of its potential high malignancy potential. Detection of the variant CMV strain (CMV IEΔi2) could therefore be performed before transfusion of blood or stem cell grafts, before organ transplantation to avoid transfer of this seemingly oncogenic CMV strain, and to prevent disease from developing in patients later in life. This could be performed as illustrated aspects of the present invention.

Furthermore, more than 90% of CMV seropositive breast feeding mothers have reactivated latent CMV in their breast milk, and the prevalence of CMV in children at one year is 30-40%, mainly due to virus transmission via breast milk. Thus, nursing mothers could choose to test whether they are carriers of the CMV IEΔi2 strain to avoid breast feeding and transfer of this seemingly oncogenic CMV strain to their children, and thereby lower their risk of future development of cancer. The test method should also be applied to fresh and banked semen that may contain the virus to avoid transfer of it by insemination. Accordingly, the present invention also relates to a method for identifying and/or detecting a genetic variant as defined herein in a biological sample obtained from a breast feeding mother.

The presence of CMV IEΔi2 in a human sample (tissue, or bodily fluids such as blood, plasma, serum, breast milk, semen, urine and saliva, or a stem cell sample) is diagnosed with PCR techniques specifically detecting the lack of intron 2 of the immediately early gene, and novel proteins are detected with Western blot or ELISA methods. It is disclosed herein examples of three diagnostic PCR methods to demonstrate the feasibility of detection of the CMV IEΔi2 strain from the wild type CMV strain in biological samples obtained from patients with different common cancer forms, encompassed by the present invention and described in detail in the materials and methods section.

Novel proteins produced by the CMV IEΔi2 strain are detected in cell lysates of tumor cells by Western blot using different CMV specific antibodies.

ELISA using antibodies specific to these proteins are used to catch the proteins for further detection in a sandwich ELISA set up. Accordingly, this could be utilized in aspects of the present invention. Furthermore, proteins of the novel sense and anti-sense transcripts transcribed from the 5 prime end or the 3 prime end, respectively are used in ELISA to detect antibodies produced against these unique proteins as screening of their presence in serum or plasma to define carriers of the CMV IEΔi2 strain, and used as biomarkers of disease. In other aspects of the invention, antibodies to CMV in intravenous immunoglobulin or specific monoclonal or polyclonal antibodies to CMV proteins present in the envelope of dense bodies produced by the CMV IEΔi2 strain are used to enrich these particles in human samples e.g: serum or plasma to detect the active form of the CMV IEΔi2 strain. PCR, Western blot or ELISA techniques are used to confirm the presence of nucleic acids or novel proteins.

Accordingly, in one aspect, the present invention relates to a genetic variant of Cytomegalovirus (CMV), said genetic variant being characterized by lacking intron 2 of the Immediate Early (IE) gene, the sequence of intron 2 of IE being illustrated in SEQ ID NO:17, of the CMV genome (CMV IEΔi2). Said genetic variant can hence be further characterized by lacking the nucleic acid of SEQ ID NO:17, i.e. the nucleic acid sequence in position 173903 to position 174019 of Merlin reference sequence AY446894.2. Wherein said sequence (SEQ ID NO:17) has been removed or deleted in said genetic variant CMV IEΔi2 as compared to the wildtype strain, in that area of the genome a DNA sequence is generated as specified in SEQ ID NO:1, i.e. wherein exons 2 and 3 have been adjoined due to the absence of intron 2.

SEQ ID NO:1 is generated by using the primers as specified in SEQ ID NO:7 and 8 and is used to amplify CMV DNA. Primer positions are from positions 173741 to 174073 of Merlin sequence AY446894.2 (SEQ ID NO:41).

In other aspects herein, it is encompassed an RNA splice variant obtained by transcription of a genetic variant as defined herein. In another aspect, the present invention relates to an RNA splice variant obtained by transcription of a genetic variant CMV IEΔi2. In one aspect, said RNA splice variant is composed of exons 2 and 3, and/or a part thereof, of the CMV IE gene.

In the context of the present invention, an RNA splice variant comprising one or more part(s) of an exon refers to an RNA splice variant which is composed of e.g. a part of one exon and a full other exon, e.g as exemplified in FIG. 12*b*.

In another aspect, said RNA splice variant is composed of exons 2, 3 and 4 or a part thereof of the CMV IE gene. In another aspect, said RNA splice variant is composed of exons 2, 3 and 5 and/or a part thereof of the CMV IE gene. It is to be understood, that in all aspects of the present invention as exemplified herein, said genetic variant (CMV IEΔi2) and/or the RNA splice variants and/or the proteins mentioned herein can be used, such as in any of the methods or uses or kits of the present invention, for identifying the CMVIEΔi2 strain, and hence carriers thereof.

In yet another aspect of the present invention, it is related to a protein encoded by an RNA splice variant as defined herein, said protein being selected from the group consisting of the CMV proteins having a size of approximately 150, 125, 86, 72, 55, 53, 50, 40, 38, 36, 32, 31, 24, 20, 19,18, 14, 12 and 10 kDa.

Another aspect of the present invention relates to a method for detecting the presence or absence of a genetic variant of CMV (CMV IEΔi2) and/or one or more RNA splice variant(s) transcribed therefrom as defined herein, and/or one or more protein(s) translated from said splice variant as defined herein, in a biological sample, said method comprising the steps of: a) providing a biological sample from a mammal, b) determining by a technical analysis of said sample obtained in step a) if a genetic variant of CMV and/or one or more splice variant(s) transcribed therefrom and/or one or more protein(s) translated from said one or more splice variant(s) as defined herein is present in said biological sample.

Another aspect of the invention relates a method for detecting the presence or absence of a genetic variant of CMV (CMV IEΔi2) and/or a RNA splice variant transcribed therefrom and/or one or more protein(s) translated from said splice variant in a biological sample, said method comprising the steps of: a) performing a technical analysis of said sample, and thereafter, b) detecting the presence or absence of a genetic variant of CMV and/or one or more splice variant(s) transcribed therefrom and/or one or more protein(s) translated from said splice variant(s) in said biological sample.

In a further aspect, the invention relates to a method for detecting a predisposition for developing cancer in a mammal, said method comprising the steps of: a) providing a biological sample from said mammal, and b) determining by a technical analysis of said sample obtained in step a) if a genetic variant of CMV and/or one or more splice variant(s) transcribed therefrom and/or one or more protein(s) translated from said RNA splice variant(s) as defined herein is/are present in said biological sample, and c) determining a predisposition for developing cancer on the basis of the presence or absence in said mammal of a genetic variant of CMV (CMV IEΔi2) and/or one or more splice variant(s) transcribed therefrom and/or one or more protein(s) translated therefrom as defined herein in said biological sample.

In yet an aspect, it is defined herein a method for detecting a predisposition for developing cancer in a mammal comprising the steps of: a) determining by a technical analysis of a biological sample if a genetic variant of CMV as defined herein and/or one or more splice variant(s) transcribed therefrom and/or one or more protein(s) translated from said splice variant(s) is present in said biological sample, and b) determining a predisposition for developing cancer on the basis of the presence or absence in said mammal of a genetic variant of CMV (CMV IEΔi2) and/or one or more splice variant(s) transcribed therefrom and/or one or more protein(s) translated therefrom in said biological sample.

In a further aspect, the present invention relates to a method for diagnosing a Cytomegalovirus (CMV) related cancer form in a mammal, said mammal carrying a CMV infection, said method comprising the steps of: a) providing a biological sample from said mammal, b) determining by a technical analysis of said sample obtained in step a) if a genetic variant of CMV and/or one or more splice variant(s) transcribed therefrom and/or one or more protein(s) translated therefrom as defined herein is present in said biological sample, and diagnosing, on the basis of the presence or absence of a genetic variant of CMV and/or one or more RNA splice variant(s) transcribed therefrom and/or a protein translated therefrom as defined herein, in said biological sample, if said mammal suffers from a CMV related cancer disease.

In yet a further aspect, it is defined herein a method for diagnosing a Cytomegalovirus (CMV) related cancer form in a mammal, said mammal carrying a CMV infection, said method comprising the steps of: a) determining by a technical analysis of a biological sample if a genetic variant of CMV as defined herein and/or one or more splice variant(s) transcribed therefrom and/or one or more protein(s) translated therefrom is/are present in said biological sample, and b) diagnosing, on the basis of the presence or absence of a genetic variant of CMV as defined herein and/or a splice variant transcribed therefrom and/or a protein translated therefrom in said biological sample, if said mammal suffers from a CMV related cancer disease.

In a method as defined herein, the presence or absence of a genetic variant of CMV (CMV IEΔi2) as defined herein and/or one or more splice variant(s) transcribed therefrom and/or one or more protein(s) translated from said splice variant(s) may be determined by the presence or absence in said mammal of antibodies directed thereto.

In addition, in a method as defined herein the presence or absence of a genetic variant of CMV (CMV IEΔi2) as defined herein and/or one or more splice variant(s) transcribed therefrom and/or one or more protein(s) translated from said splice variant(s) may be determined by the presence or absence in said mammal of T cells directed against a genetic variant of CMV as defined herein, one or more splice variant(s) transcribed from the genetic variant of CMV and/or one or more protein(s) translated therefrom in said biological sample.

Said biological sample for use in a method as defined herein may be any biological sample as defined herein, from which sample viral particles can be isolated for detection. If said biological sample comprises cells, these cells may be lysed before detection of the viral material and the viral material is thereafter isolated therefrom. Said biological sample may also be a plasma sample in addition to cell samples. Accordingly, said biological sample may in the context of the present invention be selected from the group consisting of a blood sample, a plasma sample, a tissue sample, a stem cell sample, an organ transplant graft sample, a semen sample, a urine sample, a saliva sample and a breast milk sample, but is not limited thereto.

In a method as defined herein, said technical analysis may be performed by a DNA detection method, such as ISH (In Situ Hybridization).

In one aspect, the present invention relates to a method as defined herein, wherein said technical analysis of said method is performed by a method comprising Polymerase Chain Reaction (PCR), such as TaqMan® real time PCR, or Sequence capture PCR. In one aspect, said PCR may be performed by amplifying at least a part of exon 2 and 3 of the IE gene of CMV to determine the presence of SEQ ID NO: 1, i.e. detecting CMV IEΔi2 in said sample. This is performed by using primers as exemplified in FIG. 5 and FIG. 8 and Table 1. This method is also used to detect CMV IEΔi2 in stem cells carrying the latent form of CMV IEΔi2 in for example CD34 positive hematopoietic stem cells, in circulating or tissue resident CD133 positive stem cells and in circulating or tissue resident endothelial progenitor cells identified by their expression of Vascular endothelial cell growth factor 2 (VEGFR2).

In another aspect, the technical analysis of a method according to the present invention is performed by using a FISH technique (Fluorescent in-situ hybridization). FISH is a technique that is used to detect and localize the presence or absence of specific DNA sequences on chromosomes. FISH uses fluorescent probes that bind to only those parts of the chromosome with which they show a high degree of sequence similarity. Fluorescence microscopy can be used to find out where the fluorescent probe bound to the chromosomes. FISH is often used for finding specific features in DNA for use in genetic counselling, medicine, and species identification. FISH can also be used to detect and localize specific mRNAs within tissue samples. In this context, it can help define the spatial-temporal patterns of gene expression within cells and tissues. In other aspects, the FISH technique can comprise DNA or RNA probes for analysis detecting the specific pattern of DNA location in cells infected with the genetic variant CMV IEΔi2, as well as identifying integration of CMV IEΔi2 DNA into human chromosomes. The pattern of DNA location is distinctly different in CMV positive tumour cells compared to latent wt CMV or active replication of wt CMV.

In other aspect, the technical analysis of a method according to the present invention is performed by using antibodies. Such antibodies may e.g. be directed against exon 2 and exon 3, i.e proteins encoded thereby, of the Immediate early (IE) region of the CMV genome, and will hence determine if a genetic variant of CMV is present in the biological sample that is being analyzed. In other aspects, antibodies directed against other regions can also be used, such as antibodies directed to non-infectious CMV particles i.e. dense bodies or exosomes from blood, plasma or serum of cancer patients. In other aspects of the present invention, different technical analysis methods as disclosed herein can be combined to identify the presence or absence of the genetic variant CMV IEΔi2 and/or one or more RNA splice variants thereof and/or one or more proteins expressed from said RNA splice variants, such as antibody detection followed by PCR or Western blot, or any other combination. Antibodies can also be used to detect the presence of non-infectious or defective CMV particles, including dense bodies translated from the genetic variant CMV IEΔi2.

In the context of the present invention, said methods as exemplified herein can be used for diagnosing cancer, wherein said cancer is selected from the group consisting of: glioblastoma, medulloblastoma, neuroblastoma, colon cancer, breast cancer, prostate cancer, ovarian cancer, cervix cancer, malignant melanoma, skin cancer, and sarcomas, kidney cancer, pancreatic cancer and metastases thereof. Other cancer forms not mentioned herein can also be diagnosed if said cancer forms involved the infection of a genetic variant of CMV as defined herein.

In a method as disclosed herein, the genetic variant of CMV (CMV IEiΔ2) as defined herein and/or one or more splice variant(s) transcribed therefrom and/or one or more protein(s) translated from said splice variant(s) may detected by using the nucleic acid comprised in SEQ ID NO:1, such in a PCR method by amplifying said region.

Any method as disclosed herein, may also be an in vitro method.

In another aspect, the invention also relates to the use of a genetic variant of CMV (CMV IEΔi2) and/or one or more RNA splice variant(s) transcribed therefrom as defined herein and/or one or more protein(s) translated therefrom as defined herein for detecting a pre-disposition for cancer in a mammal.

In another aspect, the invention relates to the use of a genetic variant of CMV (CMV IEΔi2) and/or one or more RNA splice variant(s) transcribed therefrom and/or one or more protein(s) translated therefrom as defined herein for diagnosing a Cytomegalovirus (CMV) related cancer form in a mammal. The cancer forms that can be diagnosed can be selected from the group consisting of: glioblastoma, medulloblastoma, neuroblastoma, colon cancer, breast cancer, prostate cancer, ovarian cancer, cervix cancer, malignant melanoma, skin cancer, sarcomas, basal cell carcinomas and pancreatic cancer. Other cancer forms not mentioned herein can also be diagnosed if said cancer forms involved the infection of a genetic variant of CMV as defined herein. It is also related to herein the use of a genetic variant of CMV (CMV IEΔi2) and/or one or more splice variant(s) transcribed therefrom and/or one or more protein(s) translated from said splice variant(s), wherein said variant is detected by using the nucleic acid comprised in SEQ ID NO:1, such as by using SEQ ID NO:1 in a PCR method by amplifying said region.

In the context of the present invention, said mammal as mentioned herein can be any mammal, such as a human being.

In one aspect, the invention also relates to a kit comprising reagents for diagnosing, and/or detecting the presence of a genetic variant of CMV (CMV IEΔi2) and/or one or more RNA splice variant(s) transcribed therefrom and/or one or more protein(s) translated therefrom as defined herein, in a biological sample obtained from a mammal, also including cells carrying latent CMV IEΔi2 for example CD34 and VEGFR2 positive cells. In one aspect, said reagent comprises reagents for performing a Polymerase Chain Reaction (PCR). In another aspect, said reagent comprises antibodies.

In one aspect, the invention also relates to a diagnostic method/kit comprising reagents for diagnosing, and/or detecting antibodies to proteins made against splice variant IE proteins of the CMV IEΔi2 strain in a patient serum or plasma sample using methods to detect antibodies specific to the CMV IEΔi2 strain related peptides, and higher levels of these antibodies; e.g using ELISA plates, membrane or beads coated with IE splice variant proteins, but not limited to those, as a biomarker of cancer or risk of developing cancer.

In one aspect, the invention also relates to a diagnostic method/kit comprising reagents for diagnosing, and/or detecting T cells reactive against peptides made from the CMV IEΔi2 strain in patients as biomarker of cancer or risk of developing cancer.

Furthermore, cells infected by CMV IEΔi2 strain represent malignantly transformed cells in common human cancer forms. Identification of novel IE CMV proteins, as defined herein, produced in higher abundance in tumor cells allows for immunotherapy and therapeutic vaccination targeting the novel CMV proteins and thereby efficient elimination of CMV IEΔi2 strain infected cells. It is shown that stem cells within the tumour are both expressing these CMV proteins as well as high levels of MHC class I and class II molecules demonstrating the feasibility to target them for specific immunotherapy.

Antigen presenting cells, e.g dendritic cells enriched by plasmapheresis from a cancer patient will be fed ex vivo with CMV IEΔi2 DNA, RNA in vectors to produce proteins in cells, or purified proteins from tumours or recombinant proteins to exon 2 and exon 3 will be used to be presented to autologous T cells from the patient. Reactive T cells expanded in culture are given back to the patient as adoptive therapy to obtain cure from cancer. Alternatively, the dendritic cells are given back in serial injections to the patient in a dendritic cell vaccination strategy to stimulate T cell expansion in vivo to CMV IEΔi2 related peptides. Both strategies aims to kill virus infected tumour cells and tumour stem cells in a cancer patient.

The CMV IEΔi2 strain proteins are used to induce production of antibodies including apoptosis inducing antibodies aimed to be used to be transferred to cancer patients to find and kill virus infected tumour cells and tumour stem cells. Accordingly, in one aspect the invention is related to such a treatment method as presented herein.

In other aspects, a CMV IEΔi2 genetic variant as presented herein will be used to develop a protective vaccine to eliminate this virus strain from the society. Protein based expression vectors and techniques are used to express the novel CMV IEΔi2 IE proteins to be used to produce a subunit vaccine against the CMV IEΔi2 strain for preventive and therapeutic vaccines. A DNA vaccine to the novel CMV IEΔi2 strain will be developed for expression of novel IE proteins to be used for preventive and therapeutic vaccines targeting the CMV IEΔi2 strain. Accordingly, in other aspects of the present invention, it is related to a vaccine vector for use as a therapeutic or preventive vaccine, encoding a CMV IEΔi2 strain. In other aspects, the present invention relates to a genetic variant of CMV (CMV IEΔi2), or the usage of SEQ ID NO:1, and/or one or more RNA splice variant(s) transcribed therefrom and/or one or more protein(s) translated therefrom as defined herein for preparing a vaccine vector for therapeutic or preventive vaccination against CMV infection. In some aspects, RNA transcripts can be used to express novel CMV proteins, as disclosed herein, from the IE region of CMVIEΔi2 to be used as vaccine vectors for therapeutic or preventive vaccination. In other aspects, IE proteins produced from the IE region of CMVIEΔi2 can be used to stimulate T cells (ex vivo) for adoptive therapy. Additionally, the transcripts and proteins presented herein can be of further use as targets for immunotherapy and for use in the development of preventive and therapeutic vaccines, as exemplified herein. In some aspects of the invention, particles may be selected out from blood and be used as biomarker for primary cancer or metastatic disease. Such particles may also be isolated from tumor cell cultures and used for the purpose of vaccination. Circulating tumor cells carrying the genetic variant CMV IEΔi2 can be detected with PCR as e.g. a biomarker of cancer and metastatic disease.

In other aspects of the invention, transfer of the CMV IEΔi2 strain by human tissue or cell transplantation; including blood transfusions, stem cell or organ transplant grafts, or from nursing mothers to children, can be avoided to eliminate transfer of cancer risk by detecting the presence of the genetic variant CMV IEΔi2 and/or one or more RNA splice variant(s) transcribed therefrom and/or one or more protein(s) translated therefrom in a biological sample obtained from a mammal, such as a human being. The method can also be used to match CMV IEΔi2 organ and blood donors to recipients carrying the same strain.

EXPERIMENTAL SECTION

Abbreviations

5-LO 5-lipoxigenase
BrC Breast cancer
CC Colon cancer
CDS Coding sequence
CK Cytokeratin
CMV Cytomegalovirus
COX Cyclooxygenase
CTLs Cytotoxic T lymphocytes
EBV Epstein barr virus
FACS Flow cytometry
FISH Fluorescence in-situ hybridization
GBM Glioblastoma multiforme
HCMV Human cytomegalovirus
HCMV-IEA Human cytomegalovirus immediate early gene antigen
HD Healthy donor
HHV Human herpes virus
HLA Human leukocyte antigen
HSV Herpes simplex virus
IE Immediate early gene
IEΔi2 Immediately early gene with deleted intron 2
IHC immunohistochemistry
IMN Infectious mononucleosis
MB Medulloblastoma
MHC Major histocompatibility complex
MIE Major immediate early gene
NB Neuroblastoma
NK Natural killer cells
NTC Non template control
OvC Ovarian cancer
PBS Phosphate buffered saline
PCR Polymerase chain reaction
pp65 poly peptide 65
RNA Ribonucleic acid
SnRNPs Small nuclear ribonucleoproteins
STAT Signal transducer and activator of transcription
UL Unique long
US Unique short
VEGFR Vascular endothelial cell growth factor
RT room temperature

Methods

Clinical Samples

We obtained over 400 samples from fixed paraffin embedded tumour specimens of the following tumours: glioblastoma (n=120), medulloblastoma (n=37), neuroblastoma (n=49), colon (41), breast (69), prostate (n=17), ovarian (25), cervix (40), pancreas (n=10) as well as lymph node metastases (n=35) of breast cancer and 89 brain metastases of colon and breast cancer were analysed for CMV protein expression. We obtained fresh or frozen tumour samples of 33 glioblastoma, 23 neuroblastoma, 2 medulloblastoma, 18 colon cancer, 20 breast cancer, 10 ovarian cancer, 10 pancreatic cancer specimens and primary tumour cell cultures from 24 GBM patients for DNA and when possible RNA preparations.

Detection of CMV Proteins

Immunohistochemistry (IHC)

Sections were stained with immunohistochemistry for CMV proteins using 3 different CMV specific antibodies for the CMV IE, pp65 and late proteins. All paraffin embedded tissue sections were de-waxed and rehydrated through alcohol series and stained by sensitive immunohistochemistry as described (1, 3). Primary antibodies used were antibodies against CMV-IEA (anti-IE1-72 and IE1-86, IgG 2a, Chemicon International, US), antibodies against HCMV-LA (IgG 2a, Chemicon), antibodies against CMV-pp65 (IgG1, Novo-Castra, US), and antibodies against smooth muscle cell alpha actin (IgG2a, Biogenex, San Ramon, Calif.) and von Willebrand factor (IgG1, DakoCytomation, Denmark) served as isotype controls.

Flow Cytometry

For single-cell suspensions of GBM tissue, the tumour was cut in small pieces with a sterile scalpel-blade in a petri-dish containing Accutase (Sigma-Aldrich). The tumour was incubated for 15 min at 37° C. During this time, the tumour was removed once from the incubator and dissociated through a pipette. After incubation, the tumour was further dissociated by pipetting and transferred to a cell strainer (75 μm) (Falcon, BD Biosciences Pharmingen, Stockholm, Sweden) on a 50-ml tube. A 2-ml syringe plunger was used to mince the tumour through the cell strainer. PBS was used to rinse the strainer and thereafter centrifuged for 8 min at 1200 rpm.

The cells were permeabilized using the kit Perm 2 (BD Biosciences) according to manufacturers instructions. The following antibodies were used: CMV-IEA (mouse monoclonal IgG M0854, Dako Cytomation), CMV-IEA (mouse monoclonal 11-003 Argene, Parc Technologique), CMV-IEA (mouse monoclonal MAB810R (810), Chemicon, Temecula, Calif., USA) and CMV-pp65 (mouse monoclonal, Novocastra). The cells were incubated with the primary antibody for 30 minutes at 4° C. Cells were washed with PBS and thereafter incubated for 30 minutes at 4° C. with the secondary antibody; polyclonal rabbit anti-mouse IgG FITC or PE conjugated (Dako Cytomation). After incubation cells were washed with PBS and fixed with 1% paraformaldehyde. Cells were analyzed using CyAn (Beckman Coulter) and the Summit 4.3 software.

Primary cell cultures of glioblastoma tumours were analyzed for CMV proteins using flow cytometry. The following commercially available cell lines were examined for CMV proteins; pancreas cells (ASPC1, Bxcp3, panc1, MiapaCa2, capan 2, capan 1, patu 8902), prostate cancer cells (LWG, PC3), colon cancer (CACO2), Lung cancer U1810, H23), breast cancer cell lines (skf3, MCF7, MDA231). Resected fresh GBM tumor tissue specimens from patients with glioblastoma multiforme (ethical permission no 2008/628-31 from Stockholm Regional Ethical Committee) were cut into small pieces and dissociated enzymatically (using 0.5% trypsin-EDTA) and mechanically into single cell suspensions. The isolated cells were propagated either in DMEM/F12 (Invitrogen) supplemented with 7% fetal calf serum, 100 U/ml penicillin and 100 μg/ml streptomycin. Cells grown in serum containing medium were named GBM cells.

FACS Sorting of VGEF-2 and CD34 Expressing Cells

Buffy coats from healthy donors (ethical permission 01/420) were received and kept shaking o/n at RT before isolating peripheral blood mononuclear cells (PBMC) using Lymphoprep (Axis-Shield, Oslo, Norway) according the manufacturer's instructions. Red blood cells were removed by lysis with RBC buffer [pH 8.0] for 10 min. 25-30×$10^6$ purified PBMC were diluted in 200 μl each of antibodies VGEF R2/KDR-FITC (R&D, FAB357F) and CD34-PE (Biolegend, 343506), PBS added up to final volume of 5 ml and incubated dark at 37° C. for 1 h. Cells were spun down (5 min, 1500 rpm), washed once with PBS and passed through a 40 μm cellstrainer (BD Falcon). Cells were kept on ice until sorting with a MoFlo Cytomation instrument. Cells positive for either antibody or double positive were collected separately after sorting and together with non-labelled cells as a control, DNA extracted using DNeasy Blood & Tissue DNA extraction kit (Quiagen) according the manufacturers instructions. Viral content was verified using the purified DNA in the herein mentioned Taq Man PCR.

PCR and Sequencing of the MIE Gene

DNA Extraction

DNA was extracted from tumor tissues, tumor cells and blood cells by using QIAGEN kit (Valencia, Calif.) according to the manufacturer's instructions, by the salting out technique or by Trizol extraction to obtain DNA, RNA and protein from the same sample.

Nested PCR for Detection of Deletion of Intron 2 in the IE Gene

DNA samples extracted from tumor tissues, tumor cells and blood cells were amplified by nested PCR using forward and reverse primers from exons 2 and 3 of the MIE-gene (SEQ ID NO: 5-8; Söderberg et al 1993, American Society of Microbiology). This method has been used extensively and has never previously detected an CMV IE genome variant lacking intron 2 in healthy controls, in CMV viremic patients or in experimental studies of multiple CMV strains infecting cell types of different origin (fibroblasts, endothelial cells, epithelial cells, cancer cells).

The in-house nested PCR was performed as described previously in our lab (Reference: Soderberg et. al in J. Viral 1993, 67(6), 3166-3175 (33)) with minor modifications. Briefly, approximately 50-300 ng of DNA or cDNA was amplified with 1.25 U of Taq Polymerase (Invitrogen) in a total of 40 cycles in the first step of PCR. In the second step of PCR, 1 μl of the 1st PCR products was used before subject to 30 cycles of amplification. Both controls, positive and negative samples were amplified as described and the final amplicons were run on a 1.5% GelRed-stained agarose gel. The bands were excised, purified (Qiagen Gel purification kit) and sent for sequencing (Sequencing Core Facility at Karolinska Institutet). The sequencing results were analyzed using free software Chromas and align with EMBOSS pair-wise alignment.

Taq Man PCR for Detection of Intron 2 Deletion Variant (CMV

A one-step PCR was developed by using primers covering the whole CMV MIE-gene. Briefly, approximately 70-200 ng of DNA was used in PCR reaction mixture consisting of PCR buffer (Applied Biosystem). Amplification cycles were carried out in a PCR machine (Applied Biosystem). 50 amplification cycles consisted of UNG activation at 50° C. for 2 minutes, hot start at 95° C. for 10 minutes, denaturation at 95° C. for 10 seconds, annealing and extension at 60° C. for 1 minute. DNA and RNA were extracted from uninfected or CMV (AD169 or VR1814 or TB40) infected MRC-5 cells. cDNA was prepared with a SuperScript III First-Strand Synthesis System for RT-PCR with Oligod$T_{20}$ (SEQ ID NO: 20). Amplified PCR product containing GelRED NucleicAcid Gel Stain (Biotium, Hayward, Calif.) were run on 1.5-2% agarose gel and visualized in UV light. PCR amplified bands were cut out and purified and analyzed by automated sequencing (ABI 3730 DNA analyzer). National Centre for Biotechnology Information BLAST search was used for confirmation of CMV genome. All sequenced data were aligned against reference CMV-IE genome (MERLIN) by using alignment software.

The Taqman PCR was performed using TaqMan® Fast Universal PCR Master Mix on the Applied Biosystems 7900HT Fast Real-Time PCR System with Fast 96-Well Block Module according to the manual. The default thermal profile setting was used with 50 cycles and 10 μl of the sample volume using the following primers/probes:

```
IEcDNA:
SEQ ID NO: 9:
Forward: 5'-TGACGAGGGCCCTTCCT-3',

SEQ ID NO: 10:
reverse: 5'-CCTTGGTCACGGGTGTCT-3',

SEQ ID NO: 11:
probe, 5'FAM-AAGGTGCCACGGCCCG-NFQMGB-3'

SEQ ID NO: 12:
IEDNA: Forward: 5'-GTGACCCATGTGCTTATGACTCTAT-3',

SEQ ID NO: 13:
reverse: 5'-CTCAACATAGTCTGCAGGAACGT-3',

SEQ ID NO: 14:
probe, 5'FAM-TTGGTCACGGGTGTCTCNFQMGB-3'
```

The specificity of the Taqman PCR has been tested with three closely related herpesviruses, i.e., HHV-6, HSV-1 and HSV-2. No amplification was noted with both primers/probes. Each sample was run in triplicates, along with the reagent control and non-template control as negative controls. The positive control for DNA was AD169-infected MRC-5 fibroblast cells and VR1814-infected macrophage serves as a cDNA control. Results were only considered valid if the positive and negative controls worked well. Occasionally, the PCR products were ran on 1.5% (w/v) high resolution GelRed-stained (Sigma) agarose gel, purified and sent for DNA sequencing to further confirm the amplicon.

Single and Nested PCR Utilizing IE Primers Spanning the Whole IE Gene and 2 Sets of Primers for the MIE Promoter Region Primers used are described in FIG. 5. The PCR was performed using Applied Biosystem Veriti 96-well Thermal cycler and the PCR profile was 94° C. for 2 mins, 35 cycles of 94° C., 30 sec; 55° C. or 60° C. (as indicated in the table), 40 sec; 72° C. for 50 sec, final extension at 72° C., 7 mins and hold at 4° C. DNA or cDNA samples were amplified and revealed a highly sensitive and specific method for detection of CMV IE gene segments. The PCR products were ran on 1.5% GelRed-stained agarose gel and visualized with Biorad gel documentation system.

Sequence Capture PCR

DNA Extraction

DNA was extracted from 3 ml whole blood by using Omega bio-tek kit (GA, U.S.A) according to the manufacturer's instructions and eluted in 100 ul $H_2O$.

Sequence Capture PCR (Method Modified from Mangiapan et al. 1996 (34))

DNA was denatured by heating the DNA for 10 min at 95° C. The sample was cooled on ice for 10 min to keep the strands separate. Then, 36.4 μl of 3.75 M NaCl containing 0.125 pmol of each biotinylated capturing primer was added.

Following capturing primers, (also used in nested PCR and hybridizing outside the binding area of the mentioned Taqman primers) were labelled 5' with biotin and HPLC purified (Cybergene):

```
SEQ ID NO: 15:
MIE II 5'-biotin: GAG AAA GAT GGA CCC TGA TAA T
(23-mer)

SEQ ID NO: 16:
MIE II 3'-biotin: CTC GGG GTT CTC GTT GCA AT
(21-mer)
```

Primers were hybridized with the DNA by incubating the tubes in a waterbath at 60° C. for 3 h. Two μl of M-280 Streptaviding Dynabeads (Dynal, Oslo, Norway) was washed according manufacturers' instructions before added to the tube and incubated for another 2 h at RT during gentle rotation. The magnetic beads with the biotin-labelled capture primers and hybridized DNA were fished out using a Dynal magnet and washed according manufacturers instructions before finally resuspend in 50 μl TE buffer (10 mM Tris-HCl, 0.1 mM EDTA [pH 8]).

Three μl of the bead suspension was directly used as template in the previously described Taqman PCR.

Protein Extraction and Western Blot Analysis

Cell pellets or tissue samples were solubilized in radioimmunoprecipitation assay (RIPA) protein extraction buffer (50 mM Tris-HCl, 150 mM NaCl, 0.1% sodium dodecyl sulfate (SDS), 0.5% sodium deoxycholate, 1% Triton X-100 and 2 mM EDTA) supplemented with Complete Protease Inhibitor Cocktail (Roche), phosphatase inhibitor cocktail (Sigma) and 1 mM phenylmethylsulfonyl fluoride (PMSF). From tumor tissues, proteins were extracted following TRIZOL-isolation of DNA and RNA according to the manufacturer's protocol (Invitrogen). Protein concentration was quantified using the micro BCA protein assay kit (Pierce). Samples were prepared in Novex Tricine SDS Sample Buffer (Invitrogen) with 0.1 M dithiothreitol (DTT) and boiled for 5 minutes. Equal amounts of proteins (25 μg/lane) were loaded on NuPAGE® Novex® 4-12% Bis-Tris Gels (Invitrogen), separated by sodium dodecyl sulphate-polyacrylamide gel electrophoresis (SDS-PAGE), and electrically transferred onto polyvinylidene fluoride (PVDF) membranes (Amersham) with a transblot apparatus (Bio-Rad). The membranes were blocked for 45 minutes with 5% non-fat dry milk dissolved in Tris-HCl-buffered saline supplemented with 0.05% Tween 20 (TBST). Immunelabeling was performed with the following primary antibodies at specified dilutions: mouse monoclonal anti-immediate early antigen (IEA) (1:1000; Argene) and rabbit polyclonal anti-IE72 (1:2000) and anti-IE86 (1:1000; kindly provided by Prof. Jay Nelson, Oregon Health and Science University, USA). Equal loading of proteins was verified by immunolabeling with mouse monoclonal anti-β-actin (1:3000). Following three TBST washings, the membranes were incubated with either anti-mouse (1:3000) or anti-rabbit IgG (1:3000) coupled to horseradish peroxidase (HRP). Bound antibodies were detected by ECL-plus kit (Amersham).

Fluorescence in Situ Hybridization (FISH)

For probe preparation, a plasmid containing whole CMV genome (kindly provided by Dr Nelson, Portland) was labelled by using Nick Translation Kit (Vysis, Downers Grove, Ill., USA) according to the manufacturer recommendations. For slide preparation, cells were treated with colcemid (Gibco) and washed with HBSS. The cell pellet was resuspended in cold 4% KCl and incubated for 14-16 hours at 37° C. Cells were collected by centrifugation and resuspended again in 4% KCl. Cold fixation solution (3:1 methanol:acetic acid) was slowly added to the cell suspension and incubated on ice for 1 h. Fixed cells were washed, resuspended in fixation solution, and stored at 20° C. before use. 20 ul of cell suspension was used for slide preparation. Approximately 200 ng of probe was added to 8 ul of hybridization mixture (2 ul Hybrizol, 2 ul of Cot-1 DNA, both from Invitrogen, and in 0.5 Mol Na acetate, pH 5.2, Sigma Aldrich) and 30 ul ethanol (95%) and incubated on dry ice for 15 min. After centrifugation, supernatant was discarded and 70% ethanol was added to the pellet (probe) and centrifuged again to purify the probe. Probe was dissolved in 8 ul hybridisol and 2 ul distillate water and was added to slides and denatured at 72° C. for 8 min followed by an overnight incubation at 37° C. Slides were washed in 2× Saline Sodium Citrate (SSC) for 3 min at 70° C., and dehydrated, before mounting with Vectashield (Vector, Vectashield).

Results

Figure 1:
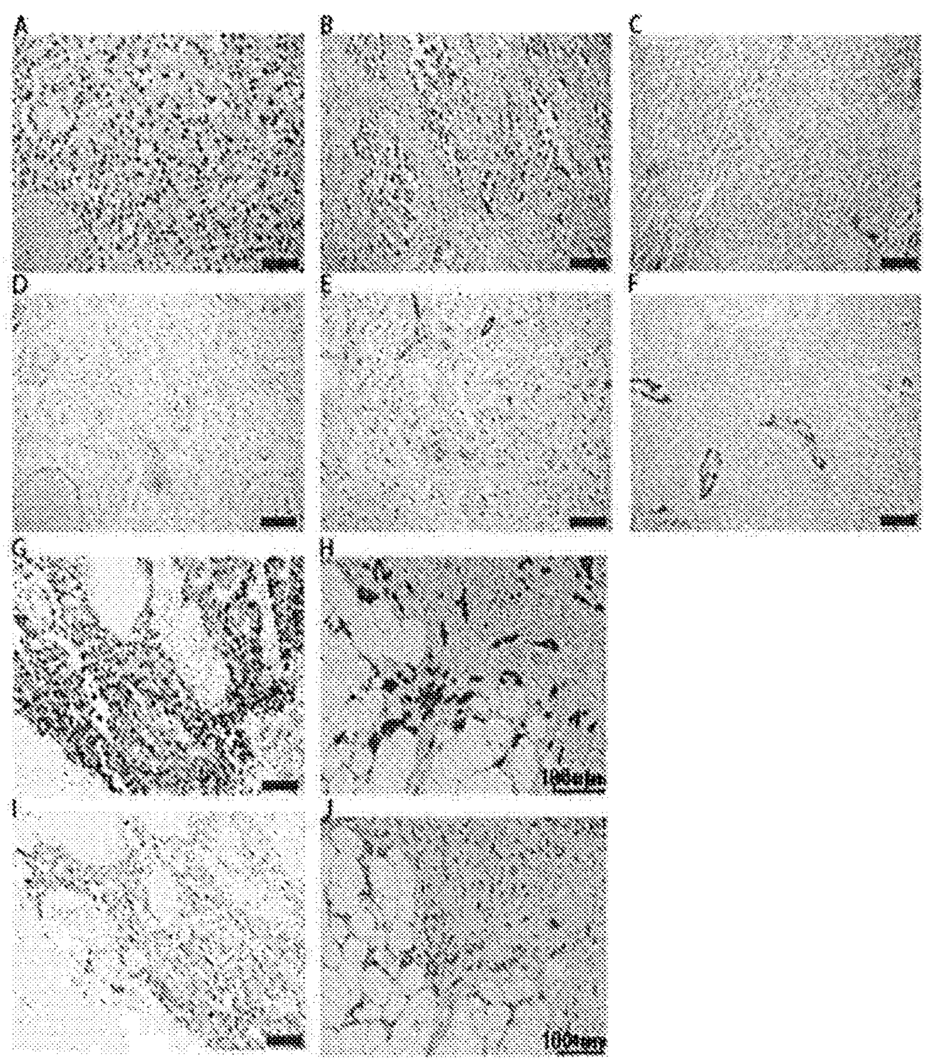
FIG. 1: Detection of human cytomegalovirus (CMV) proteins by immunohistochemistry. CMV immediate early antigen (CMV-IEA) was detected in brain tumor tissue obtained from GBM (glioblastoma multiform) patients (A), in neuroblastoma, NB (B) in medulloblastoma, MB (C), and in colon cancer tissue (G) and in breast cancer tissue (H). Antibodies against smooth muscle cells alpha actin (D, E, F) and antibodies against keratin 20 (I) and cytokeratin (J) served as controls. Unspecified bar=50 μm.
Figure 2:
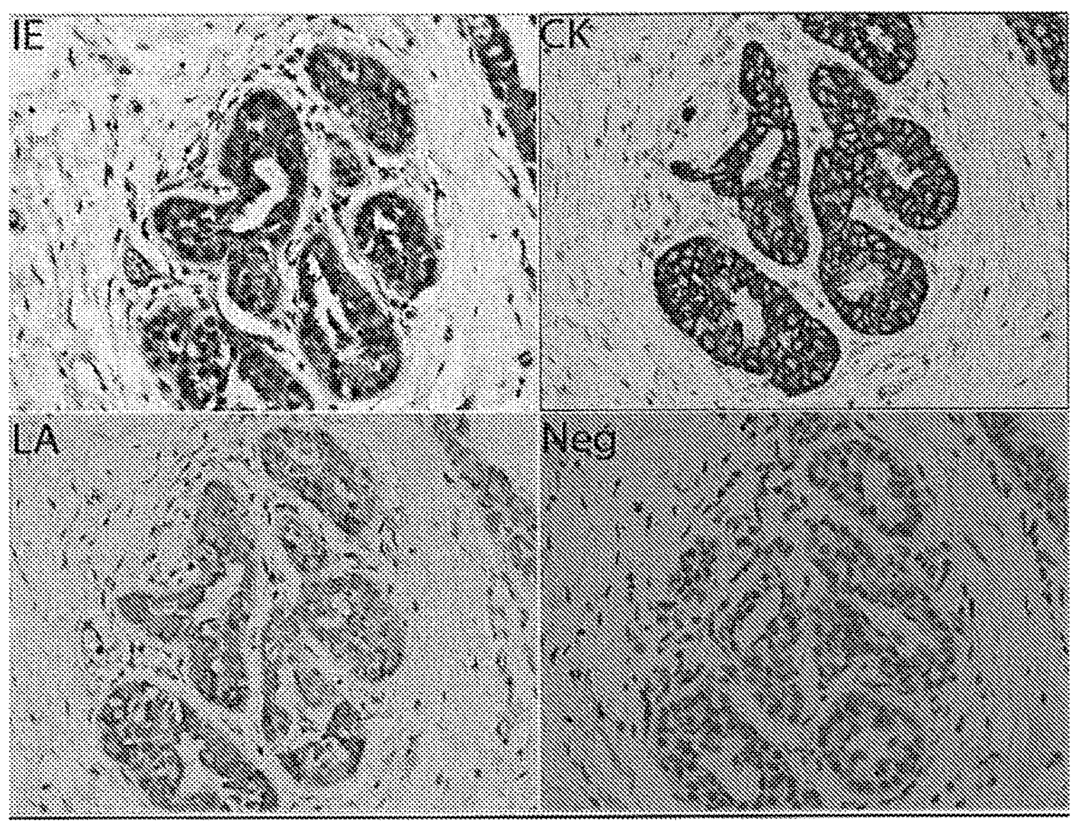
FIG. 2: Immunohistochemistry staining of human cytomegalovirus immediate early (CMVIE) and late (LA) proteins in a breast cancer sample. CK represents cytokeratin staining of tumor cells as positive or staining control, negative (Neg) control represent an isotype control antibody. The photo illustrates the restricted expression of CMV, i.e. CMV proteins in tumor cells.
Figure 3:
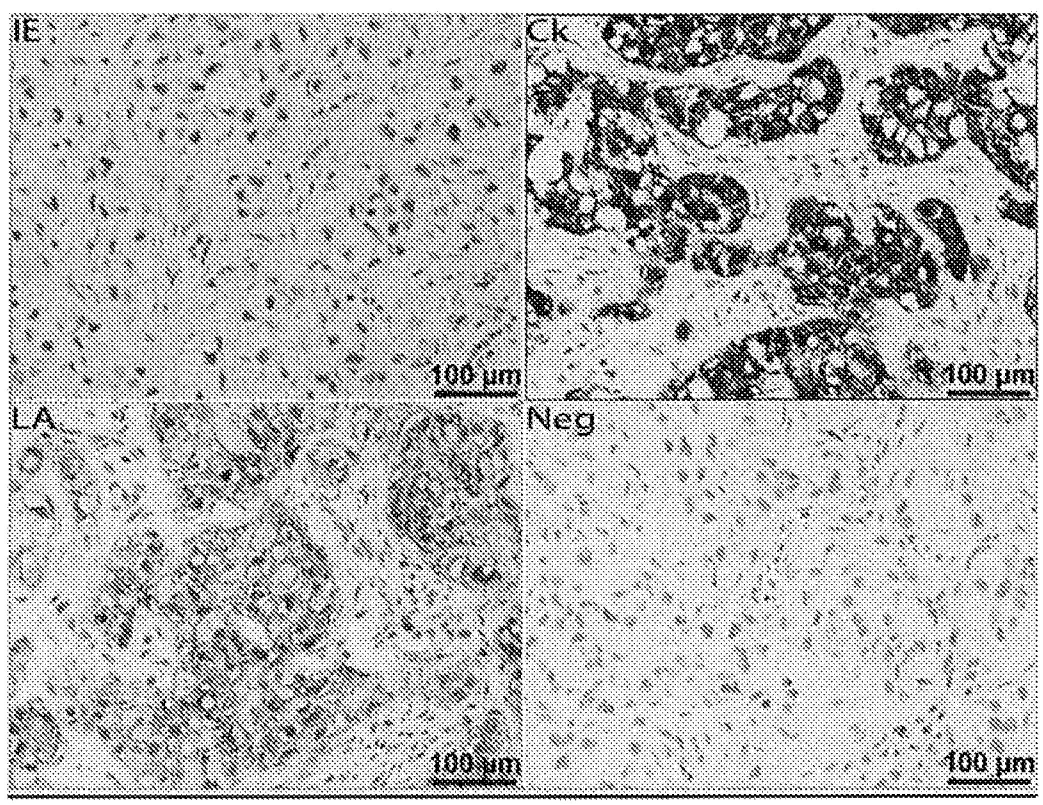
FIG. 3: Immunohistochemistry staining of human cytomegalovirus immediate early (CMVIE) and late (LA) proteins of lymph node macro-metastases of a breast cancer tumor in a lymph node. CK represents cytokeratin staining of tumor cells as positive, i.e staining control, negative control represents an isotype control antibody. The photo illustrates the restricted expression of CMV proteins in tumor cells also in a metastasis of the tumor.
Figure 4:
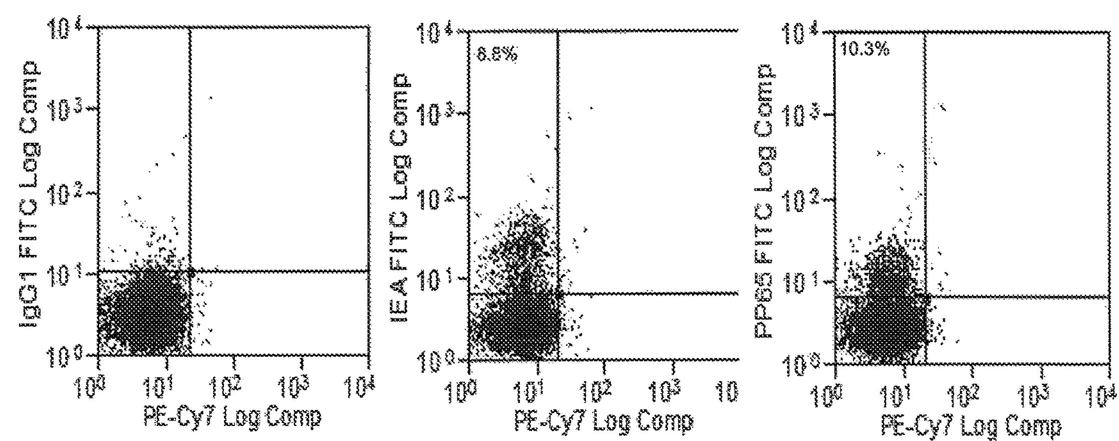
FIG. 4: Flow cytometry staining of a cell line (medulloblastoma D283) for human cytomegalovirus immediate early antigen (CMV IEA) and pp65. CMV protein expression is very often detected in tumor cell lines of different origin at various levels of protein expression (n=40; CMV positive cells varies between 0.5-69%, and are variable at different sampling occasions in the same cell line).

Over 90% of all examined tumor specimens and all examined metastases were CMV protein positive by immunohistochemistry or flow cytometric analysis (FIG. 1A, B, Table 1). Furthermore, flow cytometry revealed that 21 primary cell cultures of glioblastoma expressed CMV IE, pp65 and late proteins (FIG. 1). The number of CMV protein positive cells varied among the cell lines and between different sampling occasions of the same cell line (FIG. 4 and varying from 4-69%). However, rather consistent results were obtained of the number of positive cells using four antibodies against the IE, pp65 and late CMV proteins at the same sampling occasion (exemplified in FIG. 4). Samples of malignant melanoma, skin cancer, sarcomas, kidney cancer and pancreatic cancer were found to be CMV positive in all examined samples (n=18). In spite of the fact of high protein expression in tumour cells, we were unable to obtain infectious virus from fresh tumour tissues (n=21) of medulloblastoma, neuroblastoma, and glioblastoma tumours by co-culturing tissues specimens or cell lysates from tumour tissues with fibroblasts or endothelial cells (not shown). The CMV IEΔi2 variant was isolated from a one year old boy with upper respiratory infection and from two bone marrow transplanted patients with CMV syndrome (CMV infection due to reactivation of latent CMV after transplantation).

As the IE proteins play central roles in regulating the expression of early and late genes, we hypothesized that specific genetic variants may exist in tumors that may lead to non-productive infection due to loss of expression of essential viral proteins. This scenario may be dangerous as the splice variant proteins may act in cells not undergoing a lytic infection. We designed primer pairs spanning over the whole CMV IE gene; 2 primer pairs in the promoter region, and primer pairs for the IE gene according to FIG. 5. All sets of primers amplified PCR products of expected sizes, and DNA sequencing of PCR products confirmed IE DNA in in vitro infected cells and in DNA samples of CMV viremic patients. No PCR products were amplified from DNA extracted from HSV-1, HSV-2 or HHV-6 infected cell cultures used as specificity controls. DNA of 12 CMV viremic patients (10 mononucleosis and 2 transplant patients) and in vitro infected cells (AD169, TB40 and VR1814 strains) were tested; one mononucleosis patient had the CMV IEΔi2 variant, all others the wild type variant of CMV. DNA sequencing of 4 PCR products confirmed the presence of the normal full length DNA in samples of mononucleosis patients, and the deleted variant lacking intron 2 in 60/60 (100%), of cancer patients and in one mononucleosis patient.

We used a nested PCR assay with primer pairs in exon 2 and exon 3 of the IE gene that we designed in 1993. This nested PCR assay amplified a shorter PCR product of about 218 base pairs (bp) from 72/86 (84%) of DNA of specimens of malignant tumors (glioblastoma, neuroblastoma, colon, breast, ovarian cancer), cell cultures (12/15; 80%), and blood (9/33; 27%) of tumour patients. DNA sequencing of the PCR product revealed that intron 2 was absent in the PCR product (FIG. 6-8 and table 1). Furthermore, 12/15 of primary cultures of glioblastoma tumors from patients carried the CMV strain lacking intron 2. The strain was named CMV IEΔi2.

We prepared DNA from blood cells of 100 healthy blood donors, from enriched monocytes of 100 donors, from serum of 12 CMV viremic patients (mononucleosis and transplant patients), and 24 patients diagnosed with myocardial infarction (cardiovascular patients) and from 100 clinical CMV isolates. While 15/100 (15%) of the healthy blood donors enriched for monocytes were CMVIEΔi2 positive for CMV IEΔi2, 15% had the wild type, later shown to be 52/100 (52%), none of DNA samples of blood cells not enriched for monocytes was positive for CMV. Furthermore, none of the cardiovascular patients or healthy control DNA prepared from whole blood had the CMVIEΔi2 strain. DNA of 9 viremic patients as well as from in vitro infected cells infected with CMV laboratory strains VR1814, TB40 and AD169 had the wild type strain.

In later analysis, 2/24 (8%) of the cardiovascular patients, 20/100 (20%) of healthy control and 1/11 (9%) of the viremic patients had the CMV IEΔi2 strain. DNA of 11 viremic patients as well as from in vitro infected cells infected with CMV laboratory strains VR1814, TB40 and AD169 had the wild type strain. One mononucleosis patient carried the CMV IEΔi2 strain; this patient was also diagnosed with prostate cancer. 100/100 (100%) clinical isolates were positive for the CMV wt virus; three of these 3/100% also had the CMV IEΔi2 strain. Of note; in 1995, we examined 285 blood CMV donors (145 seropositive and 140 seronegative) using the nested PCR; only one of them carried the CMV strain lacking intron 2.

Next, we developed a Taq Man PCR assay to detect cDNA but not the normal DNA IE variant using cDNA and DNA specific probes. A cDNA probe spanning over exon 2 and 3 was used to distinguish the cDNA from the DNA variant in DNA samples prepared from blood and tissues of tumour patients and controls. This method was highly specific only recognizing cDNA of RNA preparations from in vitro infected cells, but not DNA prepared from the same infected cultures. DNA preparations of HSV-1, HSV-2 and HHV-6 infected cell cultures were negative in this assays.

30/32 (94%) DNA samples of primary tumor tissues and 16/21 primary glioblastoma cell culture specimens were positive by Taqman PCR using the cDNA probe. Again, DNA prepared from glioblastoma patients were negative using this method, while cDNA prepared from 3 in vitro infected cell cultures (strains AD169, TB40E and VR1814) were positive. DNA preparations from in vitro infected cells (strains AD169, TB40E and VR1814) or from 7 CMV viremic patients with mononucleosis were negative using the cDNA probe. However, in one viremic patient with prostate cancer and mononucleosis of CMV related to reactivation of latent virus, we detected a the CMV variant lacking intron 2.

Later analysis showed that 81/106 (76.4%) DNA samples of primary tumour tissues and 19/24 (79%) primary glioblastoma cell culture specimens were positive by Taqman PCR using the cDNA probe. cDNA preparations from in vitro infected cells (strains AD169, TB40E and VR1814) or from 7 CMV viremic patients with mononucleosis were positive using the cDNA probe. DNA prepared from 3 in vitro infected cell cultures (strains AD169, TB40E and VR1814) were negative using the cDNA probe.

To increase the sensitivity and specificity of the detection of the CMV IEΔi2 variant, we developed a Sequence capture PCR method. The CMV IEΔi2 DNA was successfully captured using this method and used for amplification of the biotinylated captured DNA by the nested PCR method or the TaqMan PCR assay (Table 1).

TABLE 1

Table 1: Summary of TaqMan PCR results using DNA from fluorescent-activated cell sorting (FACS) sorted healthy donors' peripheral blood mononuclear cells as template. Human cytomegalovirus, either wild type or IEΔi2 is mainly carried by cells expressing CD34, VGEF2R or both.

| | CD34 | | | VGEF2R | | | CD34 & VGEF2R | | | PBMC | | CD34− & VGEF2R− | |
|---|---|---|---|---|---|---|---|---|---|---|---|---|---|
| Donor | DNA | cDNA | % of pop. | DNA | cDNA | % of pop. | DNA | cDNA | % of pop. | DNA | cDNA | DNA | cDNA |
| 1 | Positive | Positive | 0.02 | Positive | Positive | 0.005 | n/a | n/a | n/a | Negative | Negative | n/a | n/a |
| 2 | Positive | Positive | 0.07 | Positive | Positive | 0.25 | n/a | n/a | n/a | n/a | n/a | n/a | n/a |
| 3 | Positive | Negative | 1.4 | Positive | Negative | 0.2 | Positive | Positive | 0.01 | Positive | Negative | Negative | Negative |
| 4 | Positive | Negative | 0.03 | Positive | Positive | 0.04 | Positive | Negative | 0.00 | Positive | Negative | Positive | Negative |
| 5 | Positive | Negative | 0.11 | Positive | Positive | 1.15 | Positive | Negative | 0.05 | Positive | Negative | n/a | n/a |
| 6 | Positive | Negative | 0.29 | Positive | Positive | 3.68 | Negative | Negative | 0.05 | Positive | Negative | n/a | n/a |

Latent CMV is known to be carried by CD34 positive cells in the bone marrow; these stem cells give rise to hematopoietic cells; mature blood cells as well as endothelial cells. We therefore selected out these cells by sorting them from blood samples of patients or healthy carriers by flow cytometry or magnetic beads (MiniMACS, Miltenyi Biotec Inc, CA) using antibodies directed against CD34 or Vascular endothelial growth factor 2 (VEGFR2, for circulating endothelial cells). We found that the CMV IEΔi2 DNA was present in CD34 positive cells and in VEGFR2 positive cells in the blood; which imply that the CMV IEΔi2 DNA is contained within a stem cell population of hematopoietic stem cells or endothelial cells We also identified the CMV IEΔi2 DNA in CD133 positive cells in glioblastoma; CD133 is a postulated stem cell marker for glioblastoma and medulloblastoma.

Hence, these two methods selecting the latently infected cells as well as the sequence capture PCR method can be used to optimise the detection of the CMV IEΔi2 DNA in healthy carriers or in cancer patients.

Figure 13:
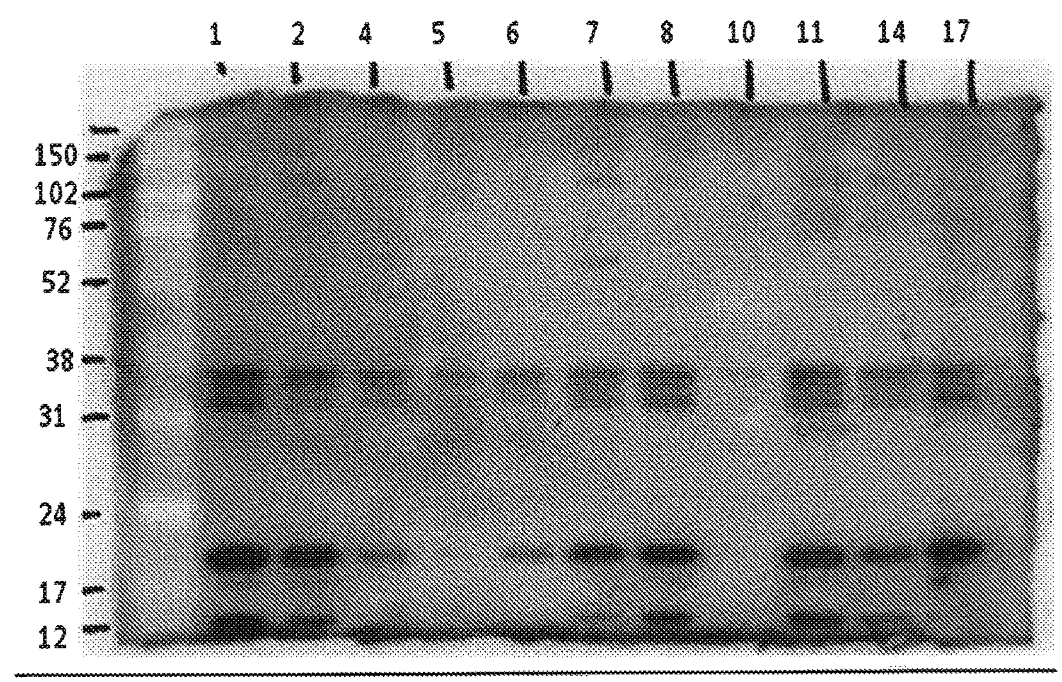
FIG. 13: Western blot analyses of cell lysates from neuroblastoma (NB) primary tumors using a human cytomegalovirus (CMV) monoclonal antibody (clone 810R). The CMV proteins immediate early (IE) 55, IE72 and IE86 are not abundant; only one sample demonstrates IE55 (NB7). Instead novel proteins re expressed sizes of 38, 31, 20 and 10 kDa. Positive control shown in FIG. 14.
Figure 14:
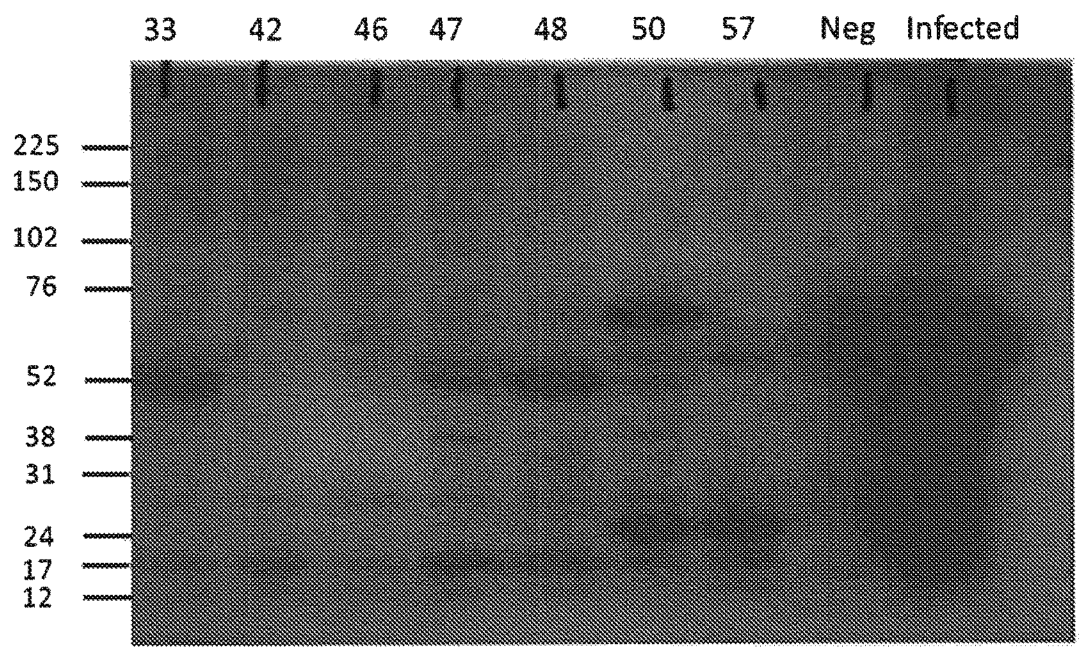
FIG. 14: Western blot analyses of cell lysates from glioblastoma primary tumors using a human cytomegalovirus (CMV) monoclonal antibody (clone 810). The CMV proteins immediate early IE55, IE72 and IE86 are not abundant; only two samples demonstrate IE72 (42, 50). Instead novel proteins were expressed with approximately a size of 50, 53, 28, 24, 19, and 10 kDa. Negative control is uninfected fibroblast, MRC-5; Positive control is infected MRC-5 at 15 days post-infection.
Figure 16A:
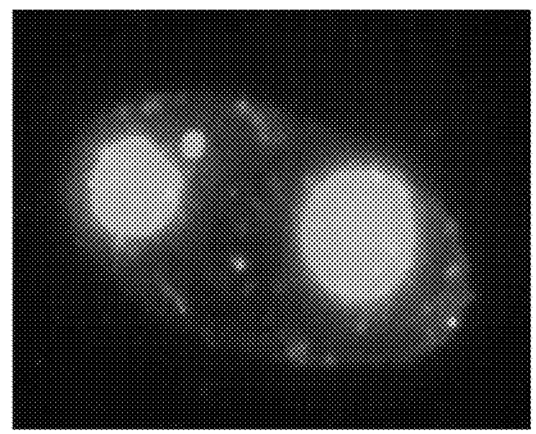
FIG. 16: Fluorescent in-situ hybridization (FISH) analyses using a CMV probe containing the whole human cytomegalovirus (CMV) genome in a bacterial artificial chromosome (BAC) vector. A) CMV wildtype infected cells (AD169) at 7 days post-infection. B) a healthy carrier of the CMV wildtype virus. C) an imprint from a glioblastoma tumor demonstrating a peripheral location of the CMV genome, which is sometimes amplified as depicted in D) another glioblastoma patient. The pattern of a peripheral location of CMV genome is very distinct and reproducible (n=40; 100%) in cancer patients carrying the CMV IEΔi2 strain in cancer cells.
Figure 16B:
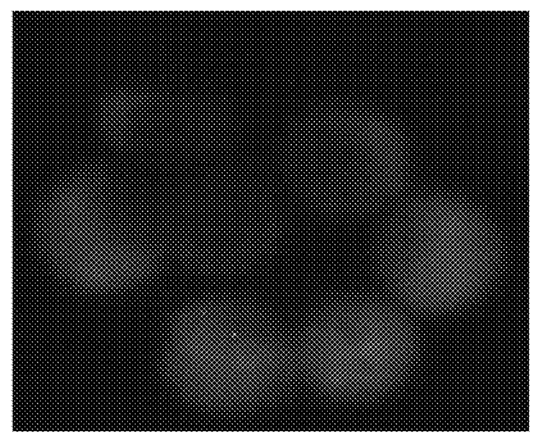
Figure 16C:
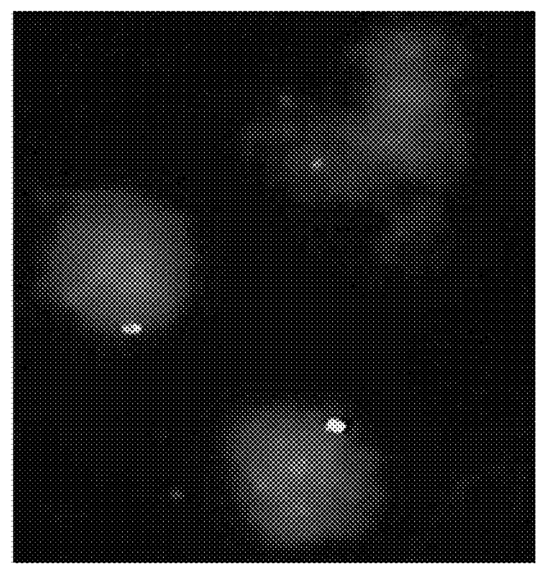
Figure 16D:
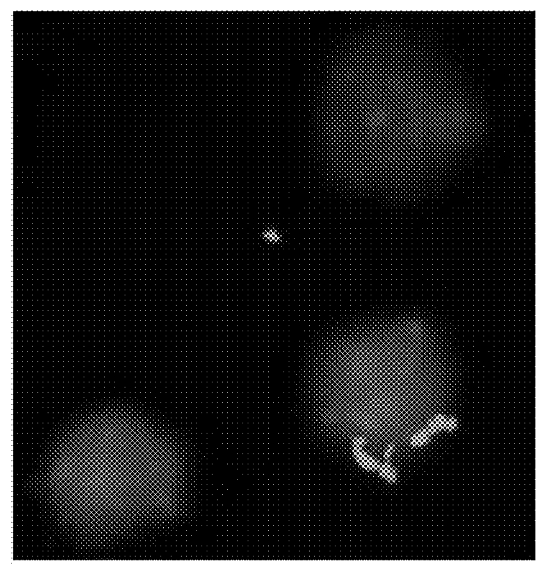

Cell lysates of 20 primary glioblastoma, 11 glioblastoma cell cultures, 11 neuroblastoma, 4 ovarian cancer, 6 breast cancer and 5 colon cancer tumor samples were examined by western blot and detected CMV IE proteins of various sizes (FIG. 13, 14, 15). IE proteins of various sizes were detected with monoclonal and polyclonal antibodies to the IE CMV proteins both in the tumour and cell culture specimens of primary cultures of glioblastoma patients. CMV specific antibodies recognized IE proteins of the following weights; 150, 125, 86, 76,72, 55, 53, 50, 40, 38,36, 30, 31, 26, 25, 19,18, 14,12,10 kDa in tumour cells and proteins of 125, 86, 72, 55, 47, 38, 18 kDa in vitro infected fibroblasts. The protein patterns differed between the different tumor types, but were fairly similar within different tumours, and among primary cell cultures of glioblastoma tumours (FIG. 13, 14, 15). The abundance of the most common IE proteins IE86, IE72 and IE55 were generally very low in tumour samples as compared to other CMV proteins identified in tumours of 125, 53, 50, 40, 38, 31, 25, 18, 14, 10 kDa. These results demonstrate that tumour cells produced IE proteins of different sizes compared to cells infected with wild type CMV in vitro. The most common IE reactive proteins were smaller size proteins of about 53, 50, 38 and 25, 19 and 14 and 10 kD that appeared to be the most common IE proteins produced by tumours. The proteins may be synthesized from the novel IE transcripts observed in glioblastoma primary cells subjected to primer extension using different IE primers as designed in FIG. 5 and demonstrated in FIG. 18.

A Fluorescence in situ hybridisation (FISH) method was developed using the whole CMV genome as a probe. Rare colcemide treated primary glioblastoma cells in passage 1 cultures (n=5) demonstrated integration of the viral genome into different chromosomes (17). The viral DNA appeared to be integrated into different chromosomes (we observed integration into chromosome 1, 3 9,17). In cells not undergoing mitosis we observed that CMV DNA was localized to the periphery of the cell nucleus in tumor cells, in contrast to the central location often in formation of owls eyes observed in in-vitro infected cells (FIG. 16). Thus, cDNA and or DNA variants of CMV were integrated into chromosomes and produced defective virus particles.

These observations demonstrate that:

1) A novel genetic variant of CMV lacking intron 2 of the immediate early gene (CMV IEΔi2) is the most common variant of CMV in cancer patients, being present in 84% of examined samples. This strain is present in 15% of healthy donors and in plasma of 10% of viremic patients, and its prevalence among clinical CMV isolates is 3%.
2) Multiple CMV proteins were produced from the CMV IEΔi2 variant in tumour cells.
3) The CMV IEΔi2 variant is detected in CD34 positive cells in humans
4) The CMV IEΔi2 variant is detected in endothelial growth factor-2 (VEGFR2) positive cells in humans.
5) The CMV IEΔi2 variant is detected CD133 positive cells in humans.
6) The CMV IEΔi2 DNA was located in the periphery of the nucleus of cancer cells, in contrast to central location in wt infected cells or in healthy donor carrying the wild type CMV DNA, as demonstrated by FISH.
7) CMV IEΔi2 infection in cancer cells was non-permissive in tumour cells but resulted in production of defective virus particles similar as exosomes/microparticles/dense bodies that mediated the transfer of viral RNA and proteins to target cells.

REFERENCES

1. Rahbar A, Stragliotto G, Orrego A, Peredo I, Taher C, Willems J, et al. Low levels of Human Cytomegalovirus Infection in Glioblastoma Multiforme associates with patient survival; —a case-control study. Herpesviridae. 2012 Mar. 16; 3(1):3.

2. Ranganathan P, Clark P A, Kuo J S, Salamat M S, Kalejta R F. Significant Association of Multiple Human Cytomegalovirus Genomic Loci with Glioblastoma Multiforme Samples. J Virol. 2011 Nov. 16.

3. Cobbs C S, Harkins L, Samanta M, Gillespie G Y, Bharara S, King P H, et al. Human cytomegalovirus infection and expression in human malignant glioma. Cancer Res. 2002 Jun. 15; 62(12):3347-50.

4. Mitchell D A, Xie W, Schmittling R, Learn C, Friedman A, McLendon R E, et al. Sensitive detection of human cytomegalovirus in tumors and peripheral blood of patients diagnosed with glioblastoma. Neuro Oncol. 2007 Oct. 19.

5. Dziurzynski K, Wei J, Qiao W, Hatiboglu M A, Kong L Y, Wu A, et al. Glioma-associated cytomegalovirus mediates subversion of the monocyte lineage to a tumor propagating phenotype. Clin Cancer Res. 2011 Jul. 15; 17(14): 4642-9.

6. Slinger E, Maussang D, Schreiber A, Siderius M, Rahbar A, Fraile-Ramos A, et al. HCMV-encoded chemokine receptor US28 mediates proliferative signaling through the IL-6-STAT3 axis. Sci Signal. 2010 Aug. 3; 3(133):ra58.

7. Straat K, Liu C, Rahbar A, Zhu Q, Liu L, Wolmer-Solberg N, et al. Activation of telomerase by human cytomegalovirus. J Natl Cancer Inst. 2009 Apr. 1; 101(7):488-97.

8. Baryawno N, Rahbar A, Wolmer-Solberg N, Taher C, Odeberg J, Darabi A, et al. Detection of human cytomegalovirus in medulloblastomas reveals a potential therapeutic target. J Clin Invest. 2011 Oct. 3; 121(10):4043-55.

9. Johnsen J I, Baryawno N, Soderberg-Naucler C. Is human cytomegalovirus a target in cancer therapy? Oncotarget. [Research Support, Non-U.S. Gov't]. 2011 December; 2(12): 1329-38.

10. Soroceanu L, Cobbs C S. Is HCMV a tumor promoter? Virus Res. 2011 May; 157(2):193-203.

11. Geder L, Rapp F. Evidence for nuclear antigens in cytomegalovirus-transformed human cells. Nature. 1977 Jan. 13; 265(5590):184-6.

12. Geder L, Sanford E J, Rohner T J, Rapp F. Cytomegalovirus and cancer of the prostate: in vitro transformation of human cells. Cancer Treatment Reports. 1977; 61(2):139-46.

13. Michaelis M, Doerr H W, Cinatl J. The story of human cytomegalovirus and cancer: increasing evidence and open questions. Neoplasia. 2009 January; 11(1):1-9.

14. Cinatl J, Scholz M, Kotchetkov R, Vogel J U, Doerr H W. Molecular mechanisms of the modulatory effects of HCMV infection in tumor cell biology. Trends Mol Med. 2004 January; 10(1):19-23.

15. Soderberg-Naucler C. Does cytomegalovirus play a causative role in the development of various inflammatory diseases and cancer? J Intern Med, 2006 March; 259(3): 219-46.

16. Soderberg-Naucler C. Human cytomegalovirus persists in its host and attacks and avoids elimination by the immune system. Crit Rev Immunol. 2006; 26(3):231-64.

17. Murphy E, Yu D, Grimwood J, Schmutz J, Dickson M, Jarvis M A, et al. Coding potential of laboratory and clinical strains of human cytomegalovirus. Proc Nati Acad Sci USA. 2003 Dec. 9; 100(25):14976-81.

18. Maussang D, Langemeijer E, Fitzsimons C P, Stigter-van Walsum M, Dijkman R, Borg M K, et al. The human cytomegalovirus-encoded chemokine receptor US28 promotes angiogenesis and tumor formation via cyclooxygenase-2. Cancer Res. 2009 Apr. 1; 69(7):2861-9.

19. Maussang D, Verzijl D, van Walsum M, Leurs R, Holl J, Pleskoff O, et al. Human cytomegalovirus-encoded chemokine receptor US28 promotes tumorigenesis. Proc Nati Acad Sci USA. 2006 Aug. 29; 103(35):13068-73.

20. Bongers G, Maussang D, Muniz L R, Noriega V M, Fraile-Ramos A, Barker N, et al. The cytomegalovirus-encoded chemokine receptor US28 promotes intestinal neoplasia in transgenic mice. J Clin Invest. [Research Support, N.I.H., Extramural Research Support, Non-U.S. Gov't]. 2010 Nov. 1; 120(11):3969-78.

21. Rahbar A, Stragliotto G, Peredo I, Orrego A, Willems J, Söderberg-Naucler C. Low levels of Human Cytomegalovirus infection in glioblastoma multiforme associates with high patient survival; —a case control study Submitted. 2011.

22. Wolmer-Solberg N, Baryawno N, Odeberg J, Fuchs D, Rahbar A, Taher C, et al. Frequent detection of human cytomegalovirus in neuroblastoma; a novel therapeutic target? Submitted. 2011.

23. Powers C, DeFilippis V, Malouli D, Fruh K. Cytomegalovirus immune evasion. Curr Top Microbial Immunol. 2008; 325:333-59.

24. Söderberg-Nauclér C, Fish K N, Nelson J A. Reactivation of latent human cytomegalovirus by allogeneic stimulation of blood cells from healthy donors. Cell. 1997; 91(October 3):119-26.

25. Soderberg-Naucler C, Fish K N, Nelson J A. Interferon-gamma and tumor necrosis factor-alpha specifically induce formation of cytomegalovirus-permissive monocyte-derived macrophages that are refractory to the antiviral activity of these cytokines. J Clin Invest. 1997 Dec. 15; 100(12):3154-63.

26. Zhu H, Cong J P, Yu D, Bresnahan W A, Shenk T E. Inhibition of cyclooxygenase 2 blocks human cytomegalovirus replication. Proc Natl Acad Sci USA. 2002 Mar. 19; 99(6):3932-7.

27. Hooks J J, Chin M S, Srinivasan K, Momma Y, Hooper L C, Nagineni C N, et al. Human cytomegalovirus induced cyclooxygenase-2 in human retinal pigment epithelial cells augments viral replication through a prostaglandin pathway. Microbes Infect. 2006 July; 8(8):2236-44.

28. Speir E, Yu Z X, Ferrans V J, Huang E S, Epstein S E. Aspirin attenuates cytomegalovirus infectivity and gene expression mediated by cyclooxygenase-2 in coronary artery smooth muscle cells. Circ Res. 1998 Jul. 27; 83(2): 210-6.

29. Qiu H, Straat K, Rahbar A, Wan M, Soderberg-Naucler C, Haeggstrom J Z. Human CMV infection induces 5-lipoxygenase expression and leukotriene B4 production in vascular smooth muscle cells. J Exp Med. 2008 Jan. 21; 205(1):19-24.

30. Cinatl J, Jr., Cinatl J, Vogel J U, Kotchetkov R, Driever P H, Kabickova H, et al. Persistent human cytomegalovirus infection induces drug resistance and alteration of programmed cell death in human neuroblastoma cells. Cancer Res. 1998 Jan. 15; 58(2):367-72.

31. Awasthi S, Isler J A, Alwine J C. Analysis of splice variants of the immediate-early 1 region of human cytomegalovirus. J Virol. 2004 August; 78(15):8191-200.

32. Taher C, Yaiw K-C, Rahbar A, Mohammad A-A, Assinger A, Khan Z, et al. High Prevalence of a Novel Genetic Variant of Cytomegalovirus in Cancer Patients submitted. 2011.

33. Soderberg C, Larsson S, Bergstedt-Lindqvist S, Moller E. Definition of a subset of human peripheral blood mononuclear cells that are permissive to human cytomegalovirus infection. J Viral. 1993; 67(6):3166-75.

34. Mangiapan G, Vokurka M, Schouls L, Cadranel J, Lecossier D, van Embden J, et al. Sequence capture-PCR improves detection of mycobacterial DNA in clinical specimens. J Clin Microbiol. [Comparative Study Research Support, Non-U.S. Gov't]. 1996 May; 34(5):1209-15.

The invention claimed is:

1. A method for determining the presence or absence of a substance associated with a genetic variant of human cytomegalovirus (CMV) in a biological sample from a mammal suffering from or suspected of having cancer, wherein said genetic variant lacks intron 2 of the Immediate Early (IE) gene loci of the CMV genome (CMV IEΔi2), comprising:
   performing a technical analysis of a biological sample from a mammal suffering from or suspected of having cancer, to determine if the sample comprises a substance associated with said genetic variant selected from the group consisting of (i) said genetic variant, (ii) one or more RNA splice variants transcribed from said genetic variant, and (iii) one or more proteins translated from said one or more splice variants.

2. The method of claim 1, wherein the presence or absence of said substance is determined by the presence or absence in said sample of antibodies directed thereto, or by the presence or absence in said sample of T cells directed against said substance.

3. The method of claim 1, wherein said biological sample is selected from the group consisting of a blood sample, a tissue sample, a stem cell sample, an organ transplant graft sample, a semen sample, a urine sample, a saliva sample, a cell swab, and a breast milk sample.

4. The method of claim 1, wherein said technical analysis comprises a DNA detection method.

5. The method of claim 1, wherein said technical analysis comprises polymerase chain reaction (PCR) or fluorescent in-situ hybridization.

6. The method of claim 5, wherein said technical analysis comprises PCR, and wherein said PCR is performed by amplifying at least a part of exon 2 and 3 of the IE gene of CMV.

7. The method of claim 1, wherein the technical analysis comprises using one or more antibodies.

8. The method of claim 7, wherein said one or more antibodies are directed against one or more proteins translated from exon 2 and exon 3 of the IE region of the CMV genome.

9. The method of claim 1, wherein the presence or absence of said substance is determined using the nucleic acid sequence set forth in SEQ ID NO:1.

10. The method of claim 1, wherein said genetic variant lacking intron 2 lacks SEQ ID NO:17.

11. The method of claim 1, wherein said substance is said genetic variant, wherein said genetic variant lacks the nucleic acid sequence from position 173903 to position 174019 of Merlin reference sequence AY 446894.2 (wild type CMV) (SEQ ID NO: 41).

12. The method of claim 1, wherein said substance is said genetic variant, wherein said genetic variant comprises nucleic acid sequences encoding exon 2 (residues 1-29 of SEQ ID NO:38) and exon 3 (residues 30-85 of SEQ ID NO:38) of CMV.

13. The method of claim 1, wherein said substance is an RNA splice variant obtained by transcription of a CMV IEΔi2 nucleic acid that lacks SEQ ID NO:17.

14. The method of claim 1, wherein said substance is an RNA splice variant that consists of exons 2 and 3 of the CMV IE gene.

15. The method of claim 1, wherein said substance is an RNA splice variant that consists of exons 2, 3 and 4 of the CMV IE gene.

16. The method of claim 1, wherein said substance is an RNA splice variant that consists of exons 2, 3 and 5 of the CMV IE gene.

17. The method of claim 1, wherein said substance is a protein encoded by said genetic variant, wherein said protein is selected from the group consisting of CMV proteins having a size of approximately 150, 125, 76, 75, 72, 55, 53, 50, 40, 38, 36, 32, 31, 30, 25, 19, 18, 14, 12 and 10 kDa.

18. The method of claim 1, wherein said substance is a protein encoded by said RNA splice variant, wherein said protein is selected from the group consisting of CMV proteins having a size of approximately 150, 125, 76, 75, 72, 55, 53, 50, 40, 38, 36, 32, 31, 30, 25, 19, 18, 14, 12 and 10 kDa.

* * * * *